United States Patent
He et al.

(10) Patent No.: US 10,717,720 B2
(45) Date of Patent: Jul. 21, 2020

(54) MODIFIED COMPOUND OF ANDROGRAPHOLIDE

(71) Applicants: Heilongjiang Zhenbaodao Pharmaceutical Co., Ltd., Heilongjiang (CN); MEDSHINE DISCOVERY INC., Nanjing, Jiangsu (CN)

(72) Inventors: Haiying He, Shanghai (CN); Zhigan Jiang, Shanghai (CN); Jianhua Xia, Shanghai (CN); Jing Wang, Shanghai (CN); Lixia Han, Shanghai (CN); Lihong Lan, Shanghai (CN); Hui Zhou, Shanghai (CN); Kunmin Lai, Shanghai (CN); Shuhui Chen, Shanghai (CN)

(73) Assignees: Heilongjiang Zhenbaodao Pharmaceutical Co., Ltd., Heilongjiang (CN); Medshine Discovery Inc., Nanjing, Jiangsu (CN)

(*) Notice: Subject to any disclaimer, the term of this patent is extended or adjusted under 35 U.S.C. 154(b) by 0 days.

(21) Appl. No.: 15/778,785

(22) PCT Filed: Nov. 22, 2016

(86) PCT No.: PCT/CN2016/106820
§ 371 (c)(1),
(2) Date: May 29, 2018

(87) PCT Pub. No.: WO2017/088738
PCT Pub. Date: Jun. 1, 2017

(65) Prior Publication Data
US 2018/0346438 A1    Dec. 6, 2018

(30) Foreign Application Priority Data

Nov. 26, 2015    (CN) .......................... 2015 1 0843708
Nov. 10, 2016    (CN) .......................... 2016 1 0990566

(51) Int. Cl.
| C07D 405/06 | (2006.01) |
| C07D 405/12 | (2006.01) |
| C07D 319/08 | (2006.01) |
| A61K 31/436 | (2006.01) |
| A61K 31/357 | (2006.01) |
| A61P 19/02 | (2006.01) |
| A61P 11/00 | (2006.01) |
| A61P 29/00 | (2006.01) |
| C07D 211/44 | (2006.01) |
| C07D 405/14 | (2006.01) |
| C07D 409/12 | (2006.01) |
| C07D 413/06 | (2006.01) |
| C07D 413/12 | (2006.01) |

(52) U.S. Cl.
CPC .......... *C07D 319/08* (2013.01); *A61K 31/357* (2013.01); *A61K 31/436* (2013.01); *A61P 11/00* (2018.01); *A61P 19/02* (2018.01); *A61P 29/00* (2018.01); *C07D 211/44* (2013.01); *C07D 405/06* (2013.01); *C07D 405/12* (2013.01); *C07D 405/14* (2013.01); *C07D 409/12* (2013.01); *C07D 413/06* (2013.01); *C07D 413/12* (2013.01)

(58) Field of Classification Search
CPC .............................. C07D 405/12; C07D 405/06
USPC ........................................................ 546/197
See application file for complete search history.

(56) References Cited

FOREIGN PATENT DOCUMENTS

| CN | 101012211 A | 8/2007 |
| CN | 101371832 A | 2/2009 |

(Continued)

OTHER PUBLICATIONS

The Extended European Search Report issued in European Patent Application No. 16867961.1 dated Dec. 11, 2018.
(Continued)

*Primary Examiner* — Patricia L Morris
(74) *Attorney, Agent, or Firm* — Harness, Dickey & Pierce, P.L.C.

(57) ABSTRACT

The present disclosure discloses a modified compound of andrographolide, and particularly discloses a compound shown in formula (I) and (II) or a pharmaceutically acceptable salt thereof.

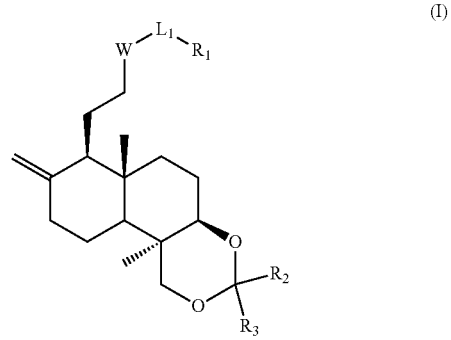

(I)

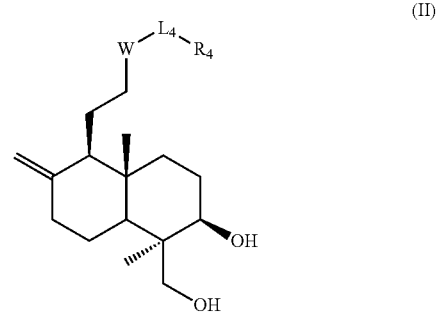

(II)

13 Claims, No Drawings

(56) References Cited

FOREIGN PATENT DOCUMENTS

| CN | 106800551 A | 6/2017 |
|---|---|---|
| WO | 0185709 A3 | 5/2002 |
| WO | 2015135606 A1 | 9/2015 |

OTHER PUBLICATIONS

Lixia Chen et al: "ent-labdane Diterpenoid Lactone Stereoisomers from Andrographis paniculata", Journal of Natural Products.,vol. 71,No. 5,May 1, 2008, pp. 852-855.
Berge et al., "Pharmaceutical Salts", Journal of Pharmaceutical Scoence 66: 1-19 (1997).
Maehr, J. Chem. Ed. 1985, 62: 114-120. 1985 , 62: 14-120.
Remington: The Science and Practice of Pharmacy, 21st Ed., Lippincott, Williams & Wilkins (2005).
Dai, Guifu et al. "Modulation of the Proliferation of Mouse Spleen Lymphocytes by 3, 19-Ketal Andrographolide Derivatives", Chinese Journal of New Drugs, vol. 16, No. 5, Dec. 31, 2007, pp. 378-381.
Nanduni S. et al. "Novel Routes for the Generation of Structurally Diverse Labdane Diterpenes from Andrographolide", Tetrahedron Letters, vol. 45, No. 25 Dec. 31, 2004.
Feb. 21, 2017 International Search Report of PCT/CN2016/106820.
Feb. 21, 2017 Written Opinion of PCT/CN2016/106820.
Priority application CN 201610990566.2 filed on Nov. 10, 2016 (without publication).

MODIFIED COMPOUND OF ANDROGRAPHOLIDE

CROSS-REFERENCE TO RELATED APPLICATIONS

This application is a National Stage of International Application No. PCT/CN2016/106820, filed on Nov. 22, 2016, and published in Chinese as WO2017/088738 A1 on Jun. 1, 2017. This application claims the priority to Chinese Patent Application No. 201510843708.8, filed on Nov. 26, 2015 and No. 201610990566.2, filed on Nov. 10, 2016. The entire disclosures of the above applications are incorporated herein by reference.

FIELD

The present disclosure relates to a modified compound of andrographolide, and particularly relates to compounds represented by formula (I) and (II) or pharmaceutically acceptable salts thereof.

BACKGROUND

This section provides background information related to the present disclosure which is not necessarily prior art.

*Andrographis paniculata* (burm.f) Nees (Acanthaceae) is known as *Chuanxinlian* in China, also known as *Chunlianqiuliu, Jinxiangcao, Yijianxi, Zhanshecao, Kucao, Ganlanlian*, etc. It is native to India and is also widely cultivated in areas such as Guangdong and Fujian in China. As a common traditional Chinese medicine, *Andrographis paniculata* has clearing heat, cooling blood, detumescence and other effects, and is clinically used for the treatment of upper respiratory tract infection and other diseases. Its main active ingredient is a group of lactone compounds known as total lactone of *andrographis paniculata*, among which andrographolide and dehydroandrographolide (14-deoxyl-11,12-didehydro-andrographolide) are the monomer components with the highest content in total lactone of *Andrographis paniculata*.

Andrographolide is an effective ingredient extracted from *Andrographis paniculata*. Its monomer purity is high, and its product quality and pharmacological effects are more advantageous than *Andrographis paniculata*. The disadvantage is that andrographolide is a diterpene lactone compound which is hardly soluble in water and is usually only administered orally.

Aiming at the clinical needs of acute viral infections, the prevailing approach is to introduce different hydrophilic groups in its structure to enhance its water solubility to prepare injections to improve efficacy. At present, the main products of andrographolide derivatives are *Chuanhuning, Yanhuning* and *Xiyanping*, and have been widely used in clinical treatment of respiratory infections, pneumonia and other diseases, but their adverse reactions occur from time to time.

SUMMARY

This section provides a general summary of the disclosure, and is not a comprehensive disclosure of its full scope or all of its features.

The present disclosure provides compound represented by formula (I) or (II), pharmaceutically acceptable salt or tautomer thereof,

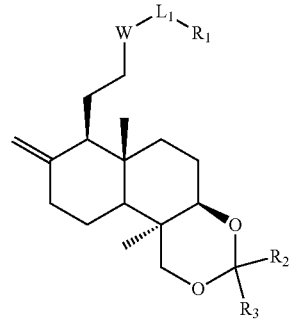

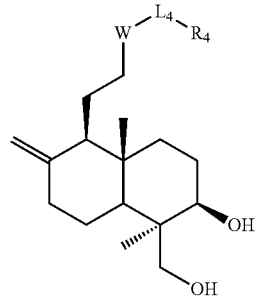

wherein,
W is O, $N(R_5)$ or a ring;

$R_5$ is selected from H, or from a $C_{1-3}$ alkyl optionally substituted by halogen, OH, $NH_2$, COOH, NHMe, or $N(Me)_2$, the number of substituent is selected from 1, 2 or 3; $L_1$ and $L_4$ are selected from a single bond and —$(CRR)_{1-3}$—;
$R_1$ and $R_4$ are selected from H, COOH, or are each independently selected from the group consisting of $NH_2$, a $C_{1-6}$ alkyl, a $C_{1-6}$ heteroalkyl, a 5-10 membered aryl, and a 5-10 membered heteroaryl, which is optionally substituted with 1, 2, or 3 R or R';
$R_2$ and $R_3$ are each independently selected from H, or are each independently selected from the group consisting of a $C_{1-6}$ alkyl, a $C_{1-6}$ heteroalkyl, a $C_{3-6}$ cycloalkyl, and a 3-6 membered heterocycloalkyl, a 5-6 membered aryl or heteroaryl, which is optionally substituted with 1, 2, or 3 R or R';
optionally, $R_2$ and $R_3$ can be linked together to form a 4-7 membered ring;
the ring

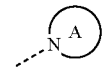

is selected from a 4-10 membered ring which is optionally substituted with 1, 2, or 3 R';
R is independently selected from F, Cl, Br, I, OH, $NH_2$, CN, C(=O)OH, or from the group consisting of a $C_{1-6}$ alkyl, a $C_{1-6}$ heteroalkyl, a -L-$C_{36}$ cycloalkyl, and a -L-3-6 membered heterocycloalkyl, which is optionally substituted with 1, 2 or 3 R';

L is selected from a single bond, —O—, —S—, —C(=O)NH—, —NH—, —C(=O)O—, —C(=O)—, —C(=S)—, —S(=O)—, —S(=O)$_2$;

R' is independently selected from halogen, CN, OH, N(CH$_3$)$_2$, NH(CH$_3$), NH$_2$, CHO, C(=O)OH, C(=O)NH$_2$, S(=O)NH$_2$, S(=O)$_2$NH$_2$, trihalomethyl, dihalomethyl, monohalomethyl, aminomethyl, hydroxymethyl, methyl, methoxy, formyl, methoxycarbonyl, Boc, methylsulfonyl, methylsulfinyl, ethyl, n-propyl, isopropyl, C$_{3-6}$ membered cycloalkyl, and 3-6 membered heterocycloalkyl;

"hetero" refers to a heteroatom or a heteroatomic group selected from the group consisting of —C(=O)N(R)—, —N(R)—, —C(=NR)—, —S(=O)$_2$N(R)—, —S(=O)N(R)—, —O—, —S—, =O, =S, —C(=O)O—, —C(=O)—, —C(=S)—, —S(=O)—, —S(=O)$_2$— and —N(R)C(=O)N(R)—;

in above cases, the number of heteroatom or heteroatomic group is independently selected from 1, 2 or 3.

In some embodiments of the present disclosure, R' is each independently selected from the group consisting of F, Cl, Br, I, OH, NH$_2$, CN, Me, CF$_3$, Et, N(CH$_3$)$_2$, C(=O)OH, Boc,

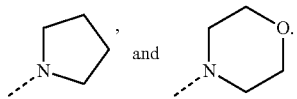
and

In some embodiments of the present disclosure, R is selected from F, Cl, Br, I, OH, NH$_2$, CN, C(=O)OH, or is selected from the group consisting of Me, Et, OMe, OEt,

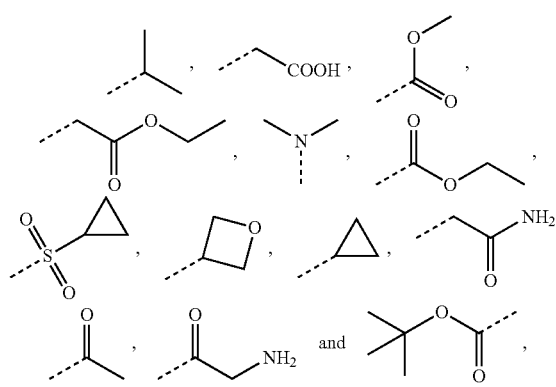

which is optionally substituted with 1, 2 or 3 R'.

In some embodiments of the present disclosure, R is selected from the group consisting of F, Cl, Br, I, OH, NH$_2$, CN, C(=O)OH, Me, Et, OMe,

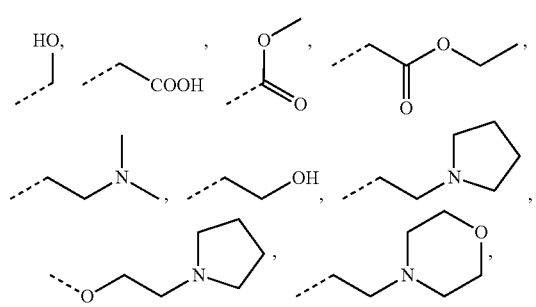

-continued

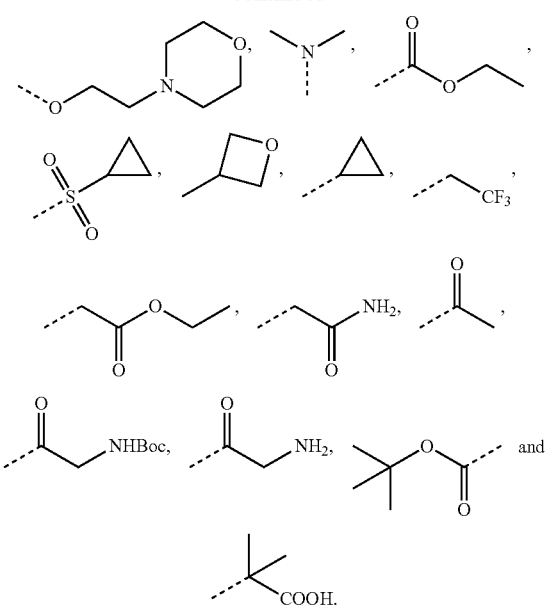

In some embodiments of the present disclosure, R$_5$ is selected from H,

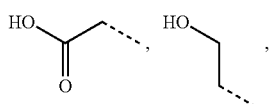

In some embodiments of the present disclosure, the compound, pharmaceutically acceptable salt, or tautomer thereof, wherein the ring

is selected from the group consisting of 4-6 membered heterocycloalkyl, 5-6 membered aryl or heteroaryl, 7-10 heterospirocycloalkyl, which is optionally substituted with 1, 2 or 3 R'.

In some embodiments of the present disclosure, the ring

is selected from the group consisting of

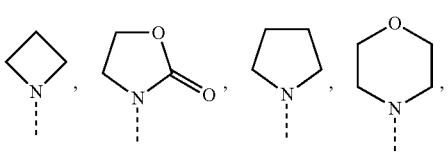

-continued

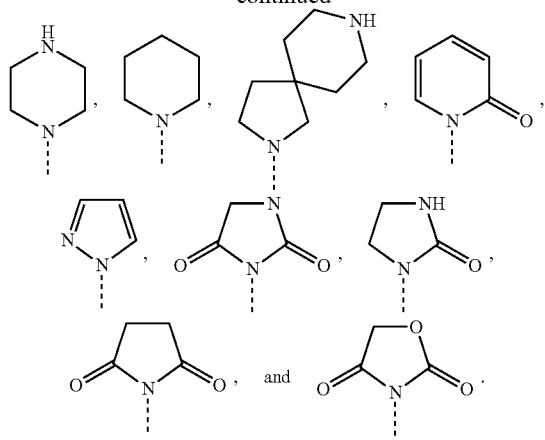

In some embodiments of the present disclosure, $L_1$ and $L_4$ are selected from a single bond and a methylene.

In some embodiments of the present disclosure, $R_1$ and $R_4$ are selected from H, COOH, or are selected from the group consisting of $NH_2$, $C_{1-4}$ alkyl, $C_{1-4}$ heteroalkyl, azetidinyl, pyrrolidinyl, tetrahydropyranyl, piperidinyl, cyclohexyl, phenyl, pyridinyl, pyridine-2(1H)-keto, pyrimidyl, pyrazolyl, thiazolyl, benzothiazolyl, imidazo[1,2-b]pyridazinyl, isoxazolyl and thienyl, which is optionally substituted with 1, 2 or 3 R.

In some embodiments of the present disclosure, $R_1$ and $R_4$ are selected from H, COOH, or are selected from the group consisting of $NH_2$,

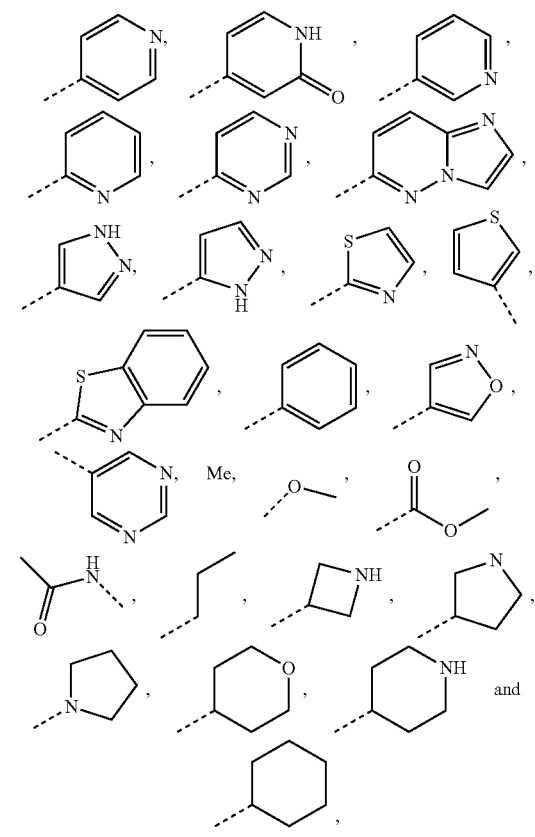

which is optionally substituted with 1, 2 or 3 R.

In some embodiments of the present disclosure, $R_1$ and $R_4$ are selected from the group consisting of

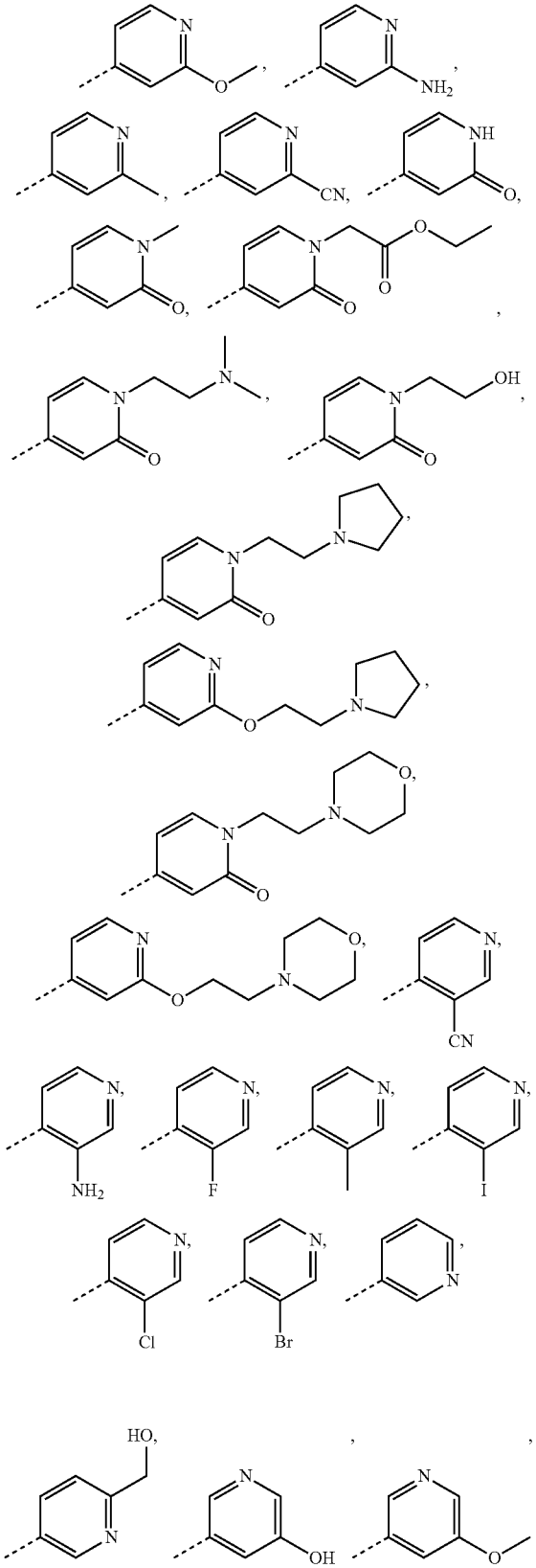

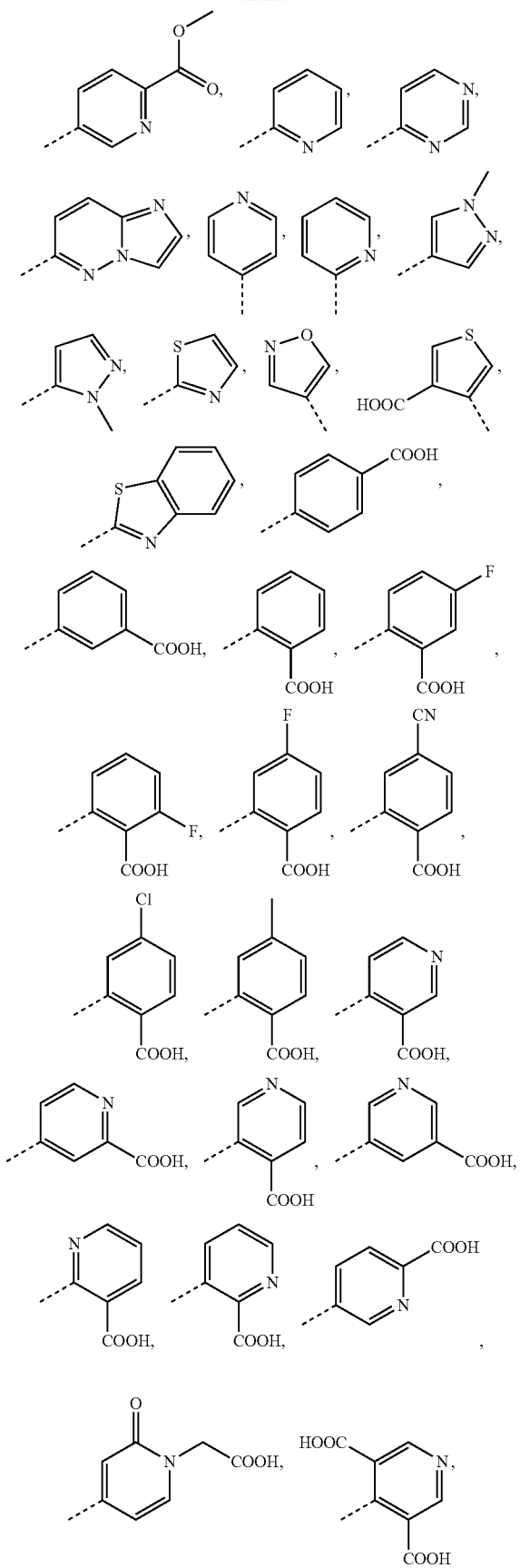
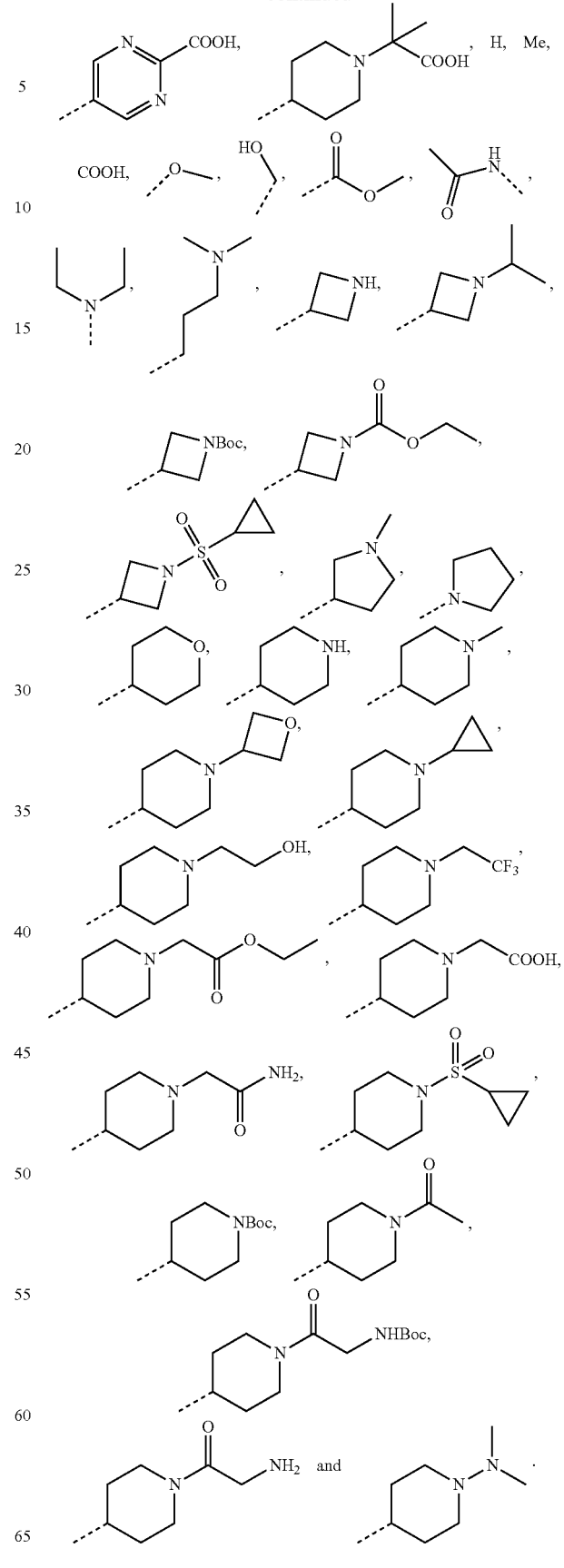

In some embodiments of the present disclosure, $R_2$ and $R_3$ are independently selected from H, or independently selected from the group consisting of Me, Et, n-propyl,

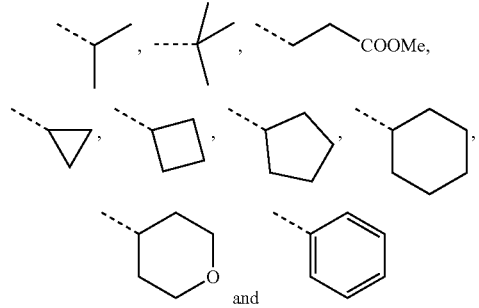

which is optionally substituted with 1, 2 or 3 R.

In some embodiments of the present disclosure, $R_2$ and $R_3$ are independently selected from H, Me, Et,

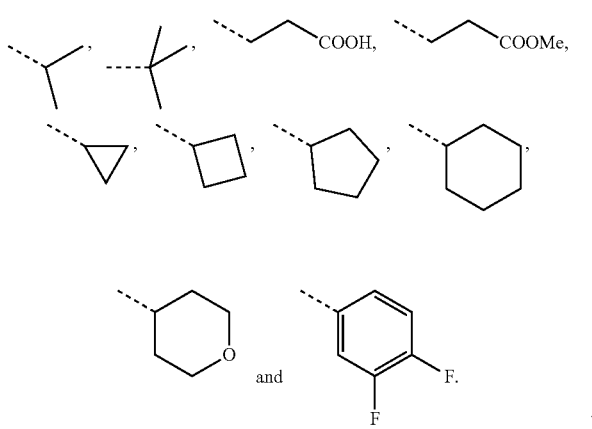

In some embodiments of the present disclosure, $R_2$ and $R_3$ can be linked together to form

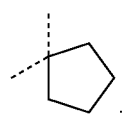

In some embodiments of the present disclosure, $R_2$ and $R_3$ can be linked together, the structure unit

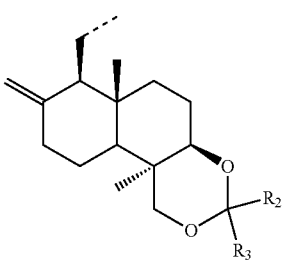

is selected from

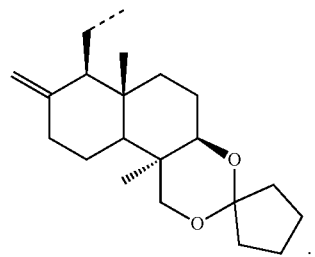

The compound of the present disclosure is selected from the group consisting of

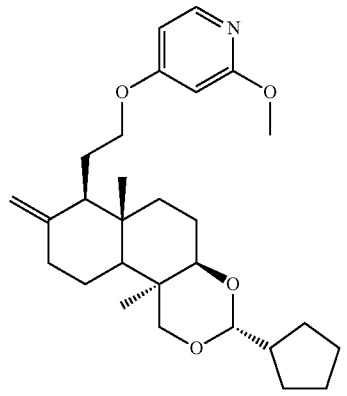

420

321

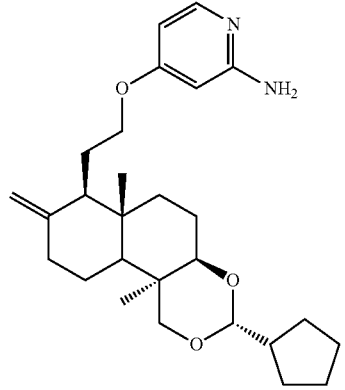

319

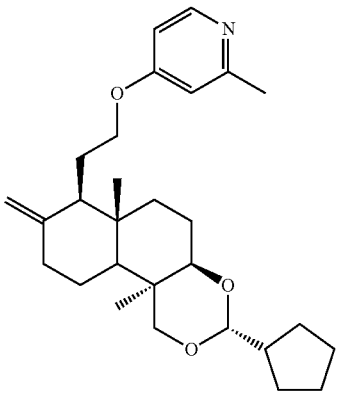

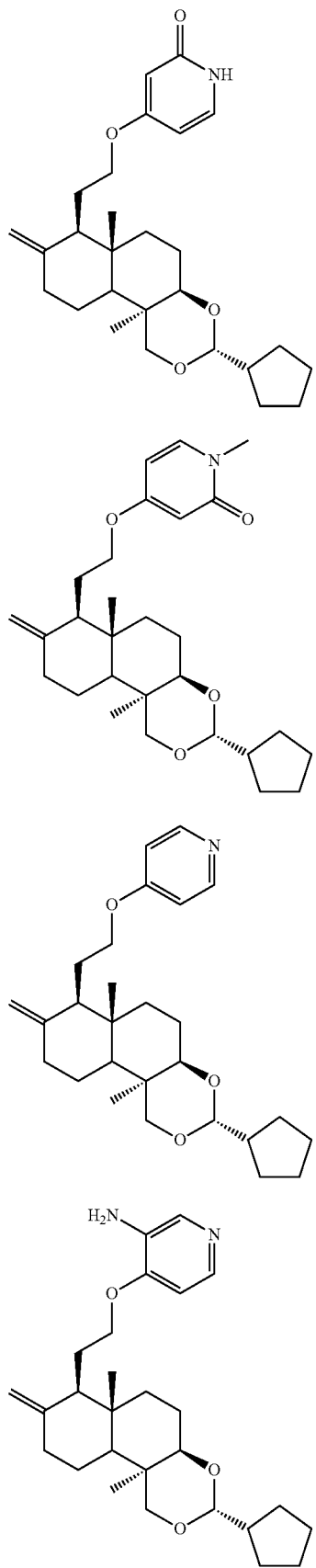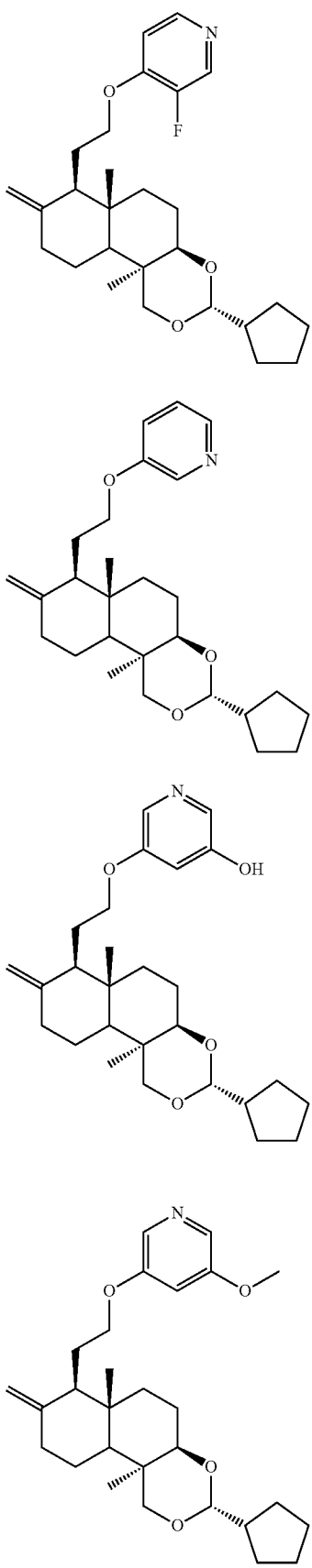

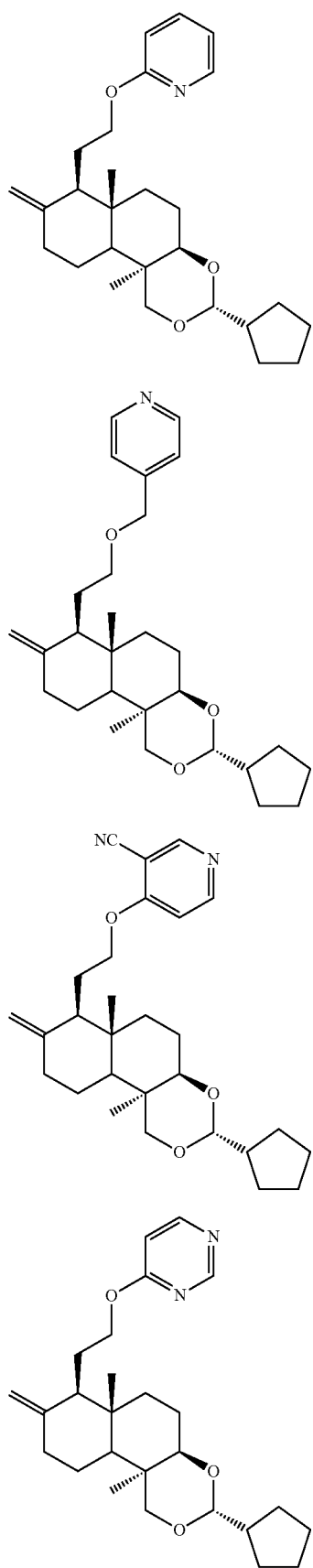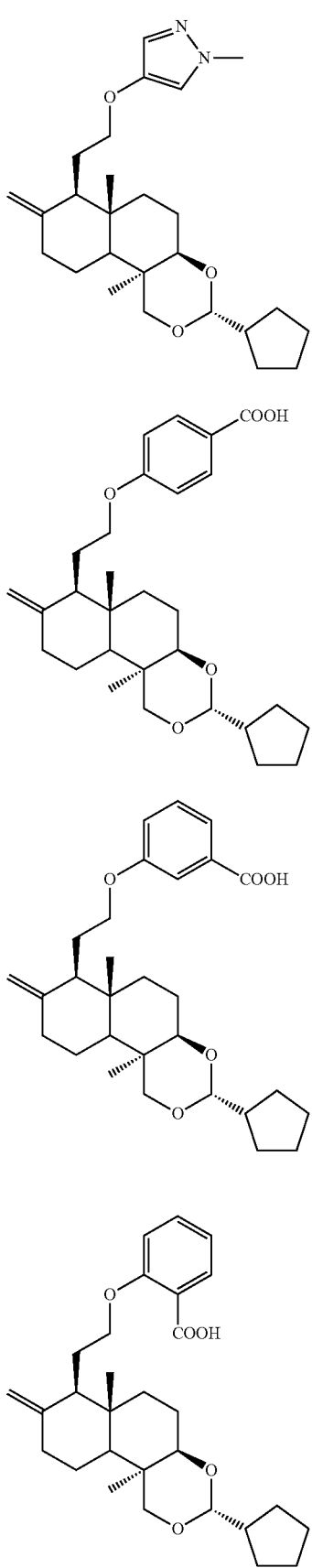

409
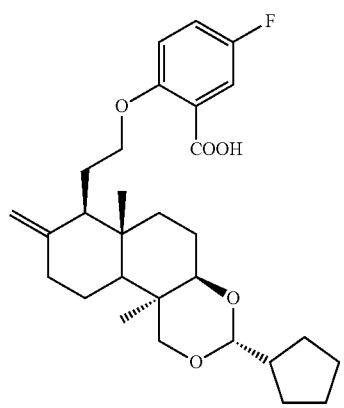
441
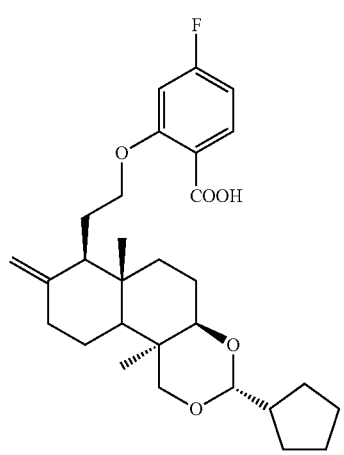
445
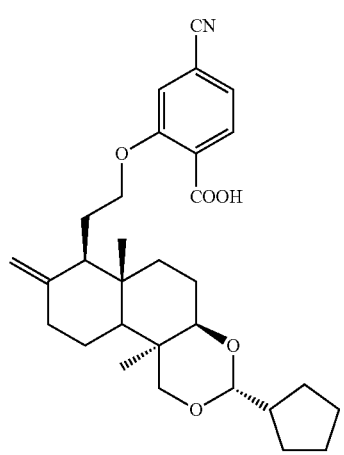
448
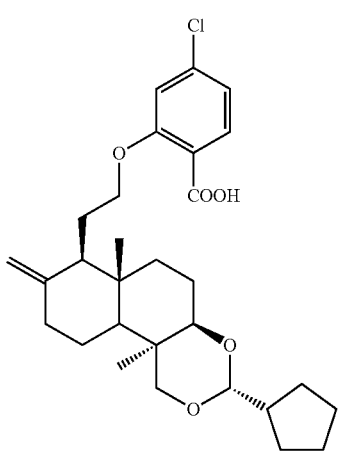
447
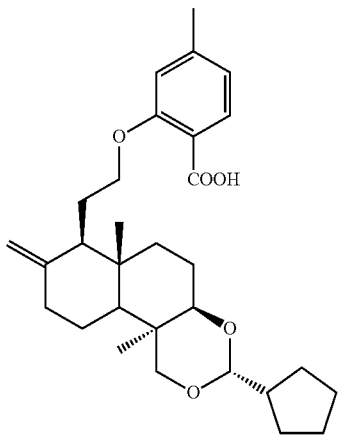
452
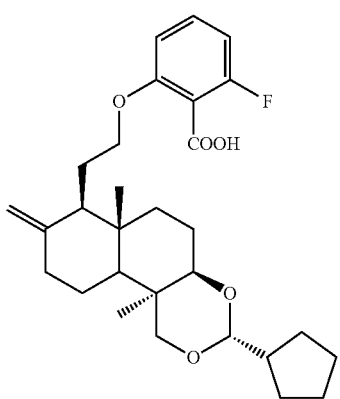

-continued
397
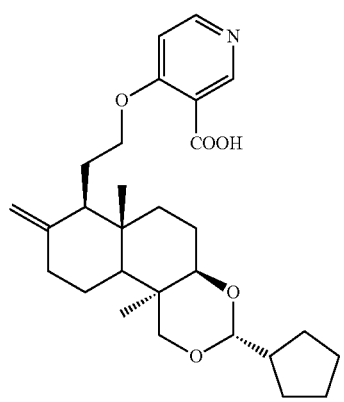
410
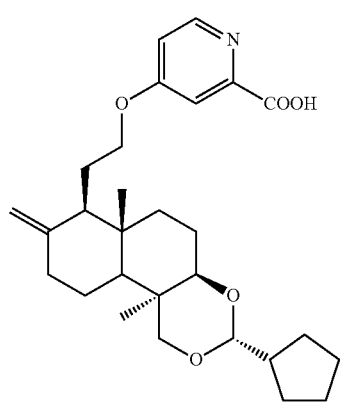
415
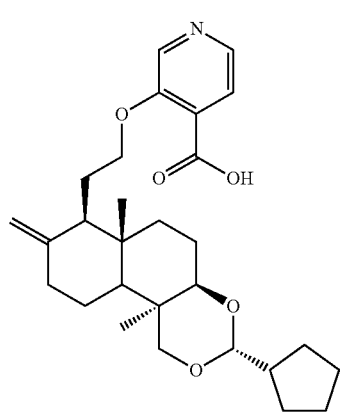
406
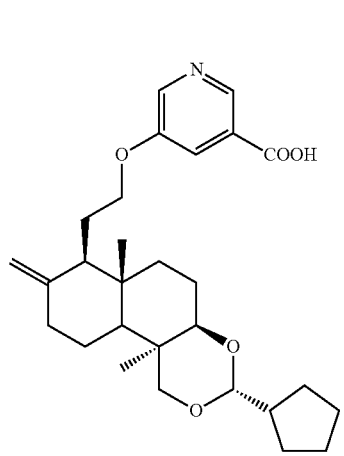
-continued
436
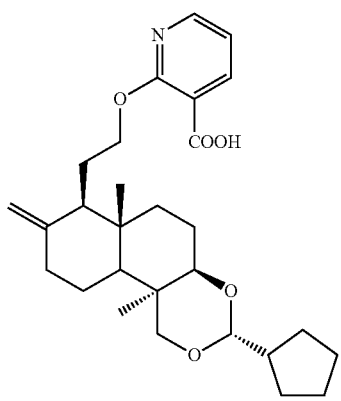
431
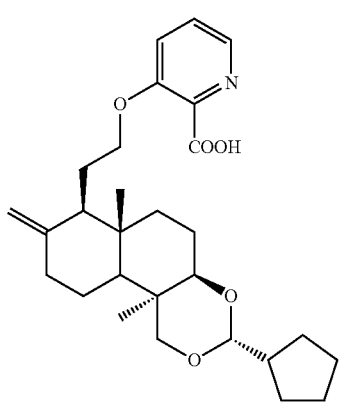
432
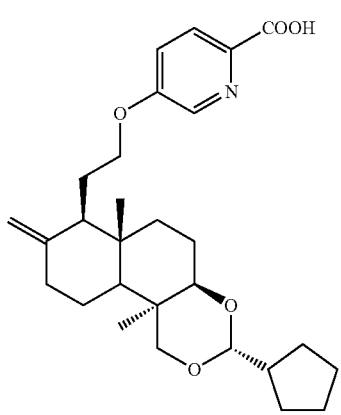
428
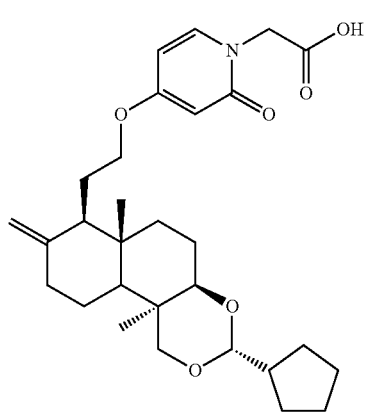

-continued
417
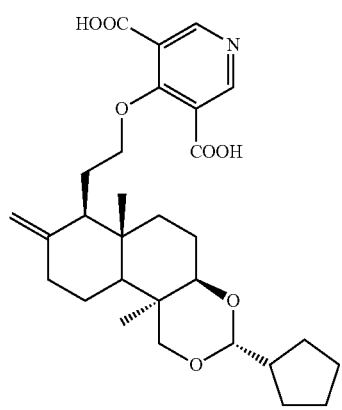
454
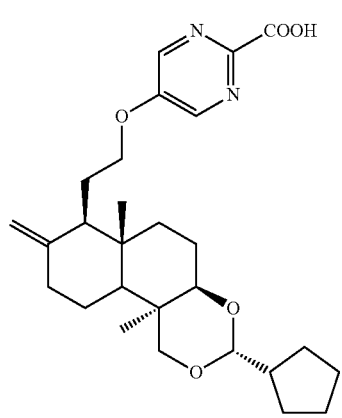
453
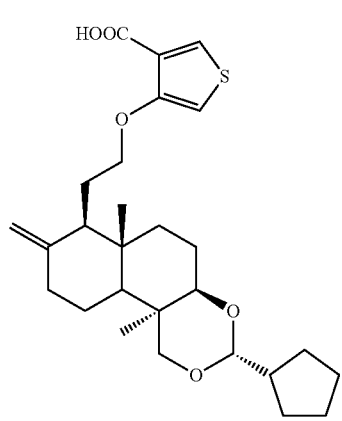
385
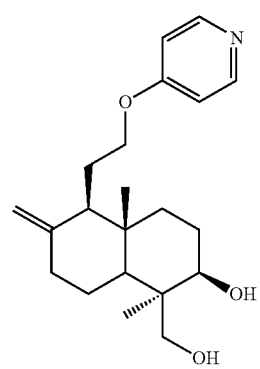
-continued
402
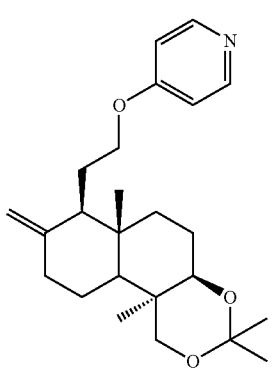
416
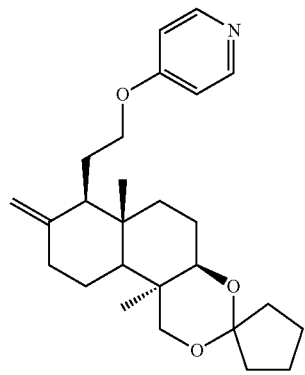
400
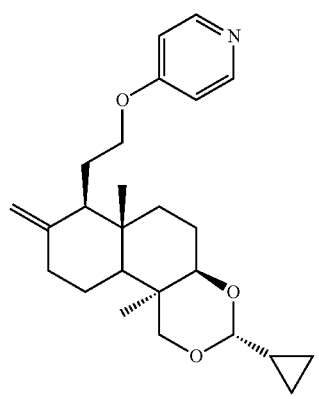
411
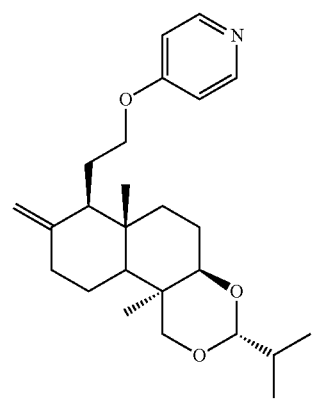

| | |
|---|---|
| 412 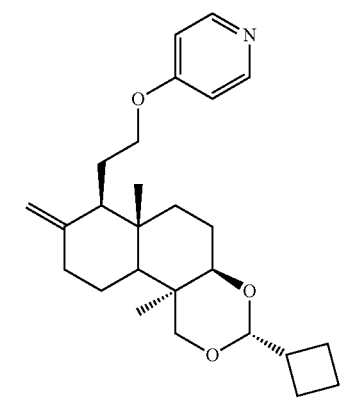 | 405 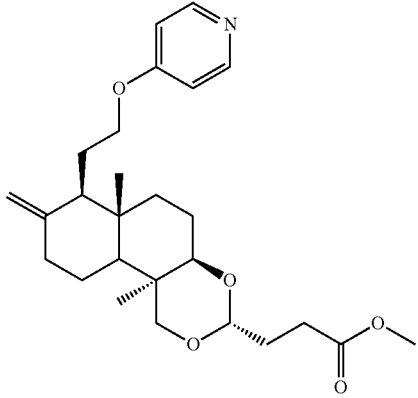 |
| 429 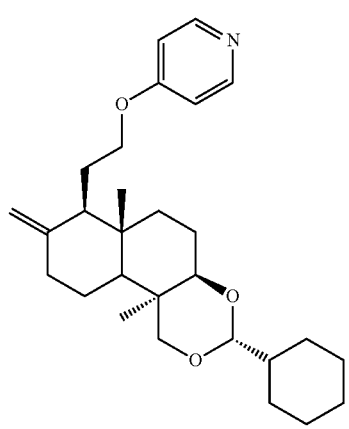 | 399 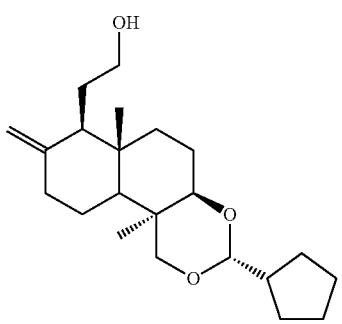 |
| 446 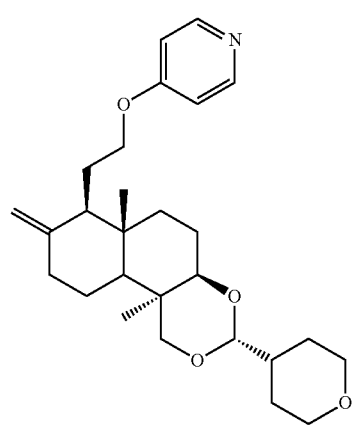 | 281 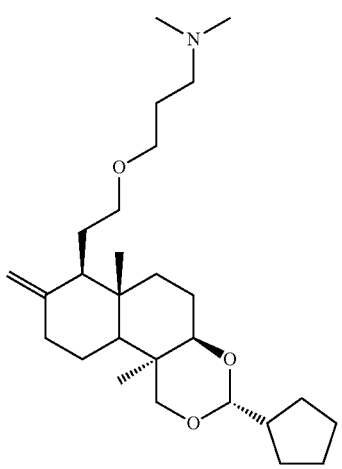 |
| 408 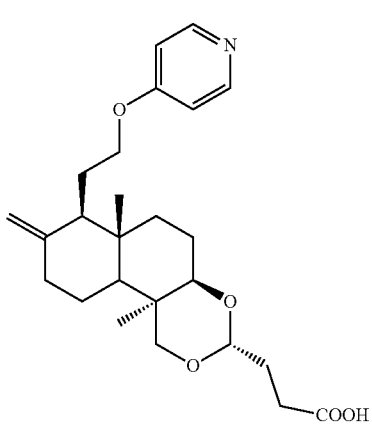 | 313 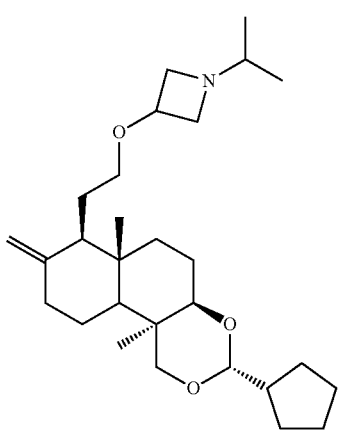 |

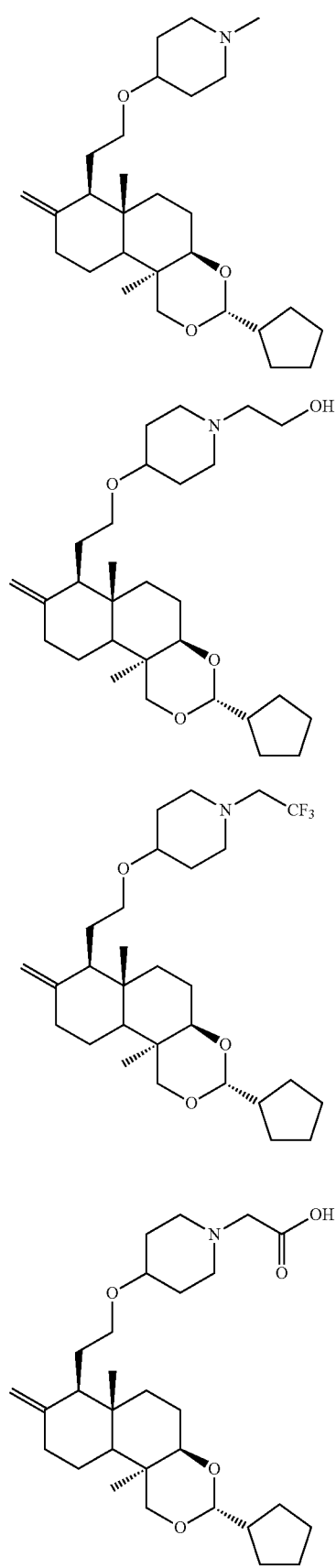
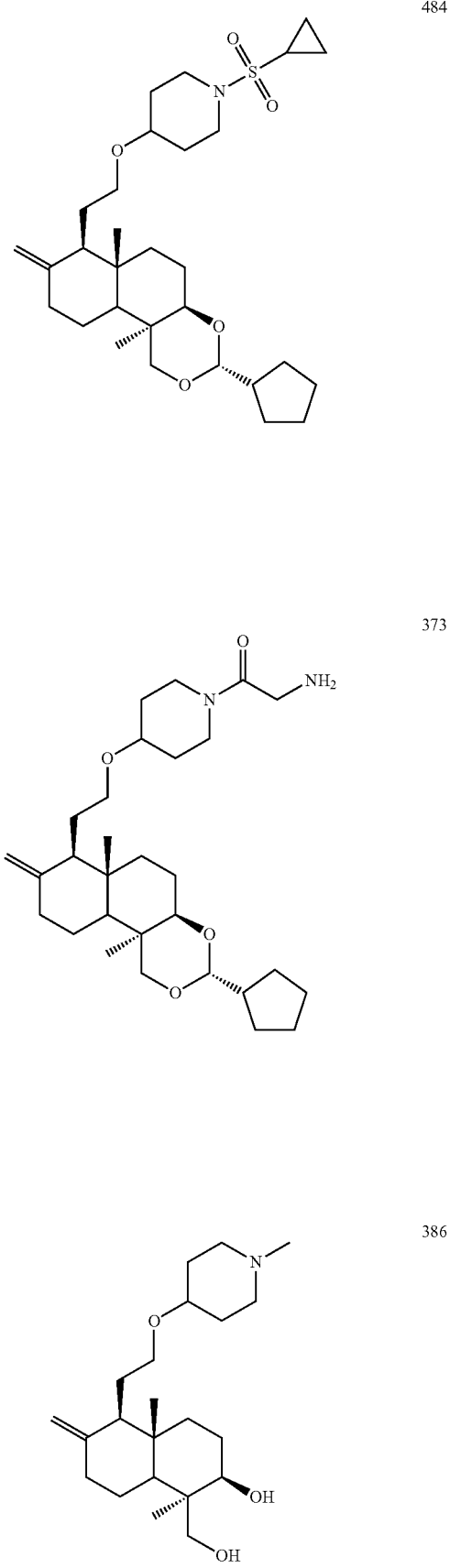

403
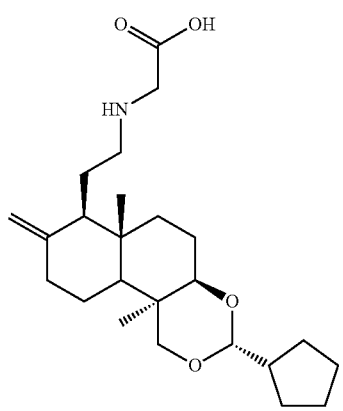
404
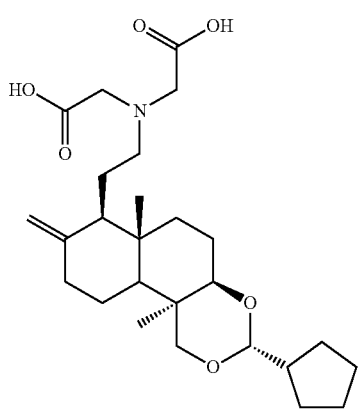
191
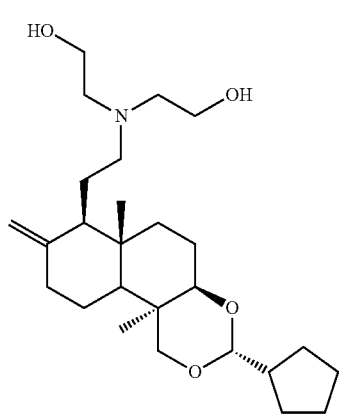
284
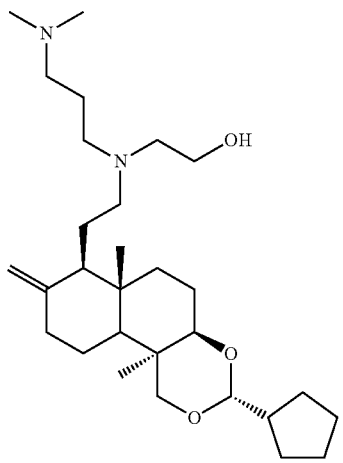
207
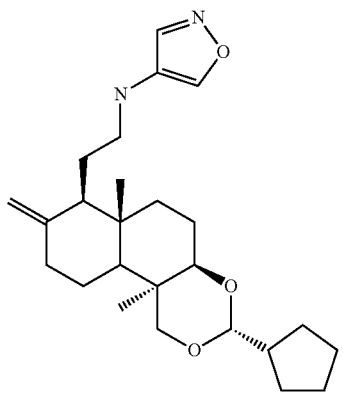
345
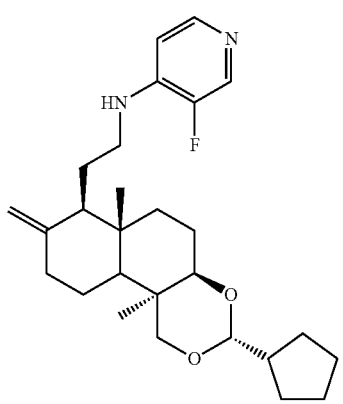

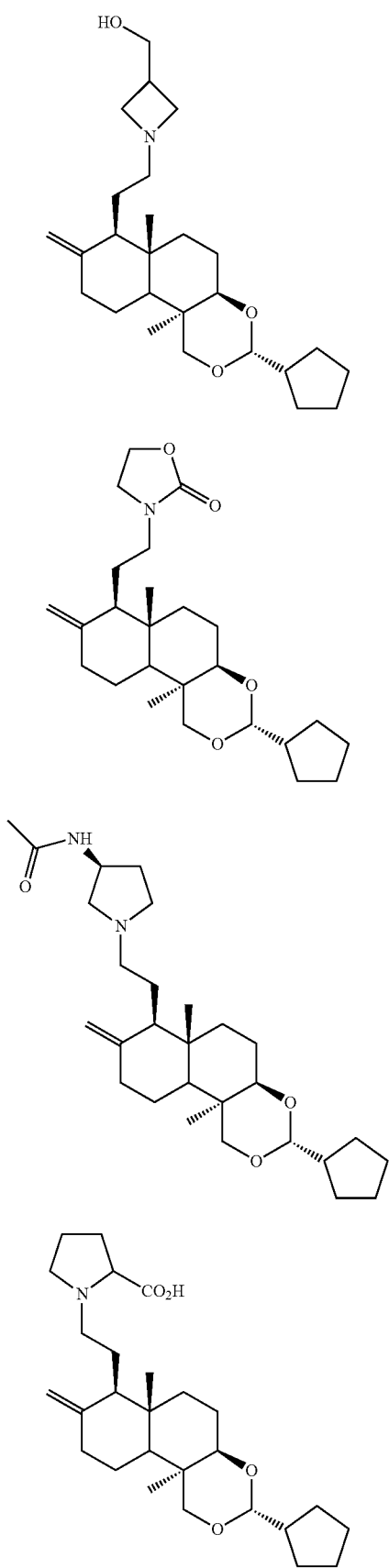
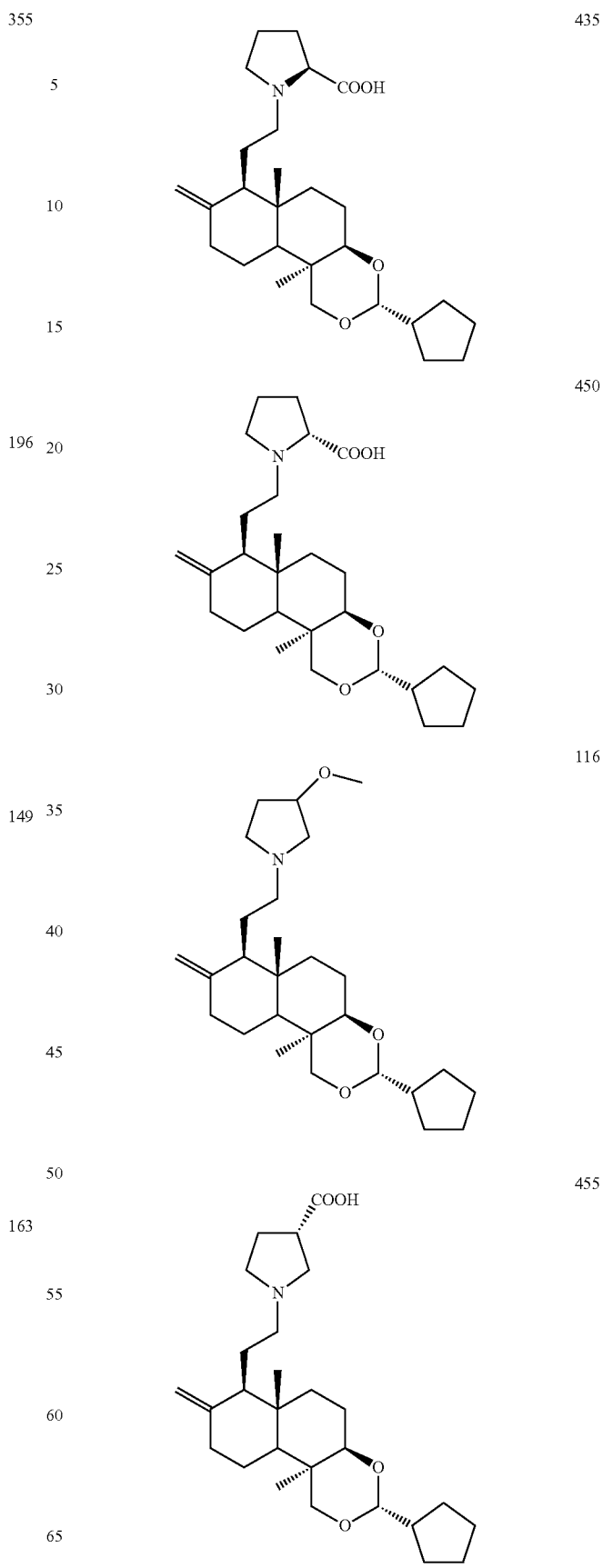

147
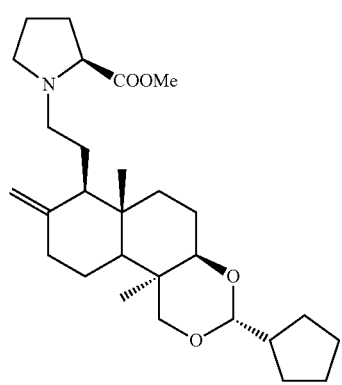
181
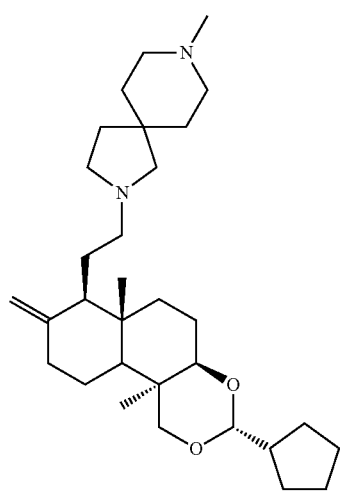
361
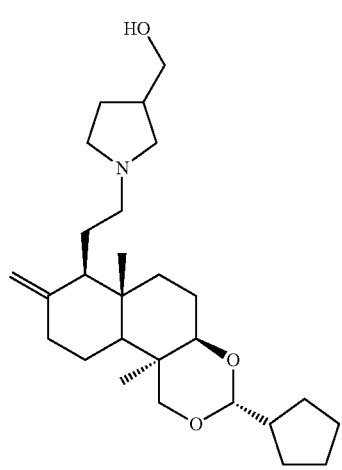
123
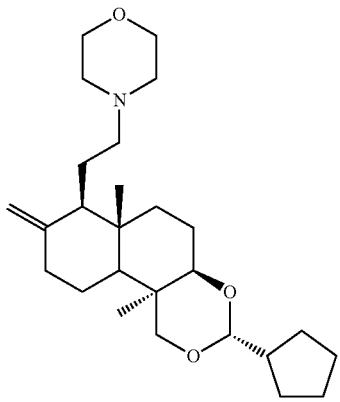
433
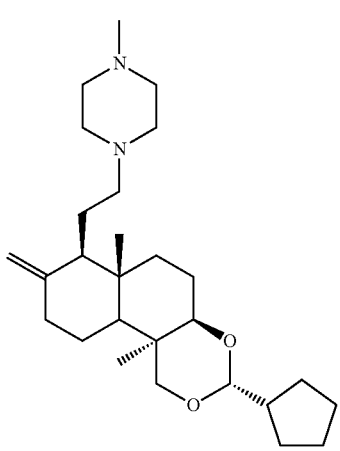
160
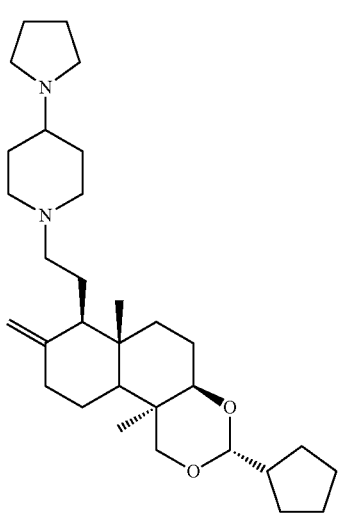

31
-continued
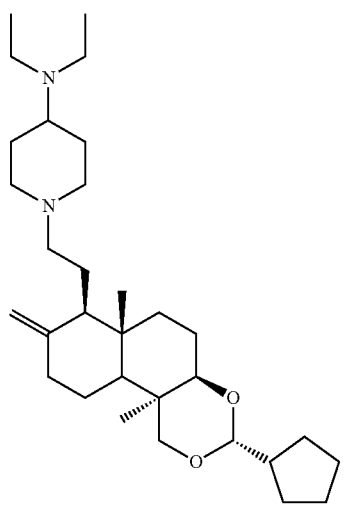
150
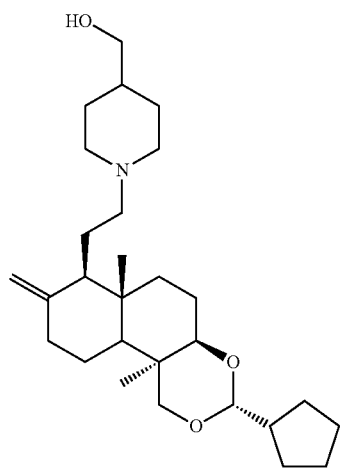
002
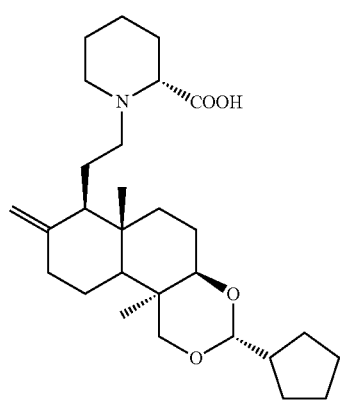
451
32
-continued
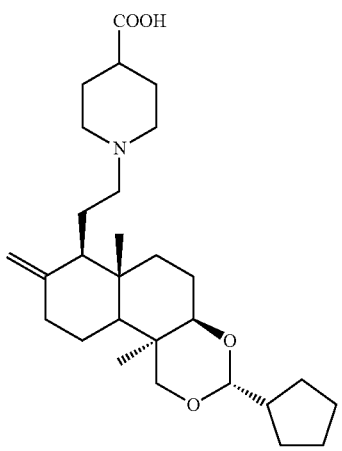
256
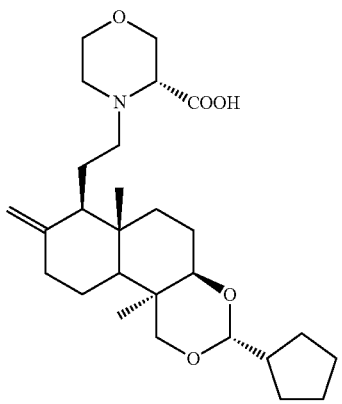
456
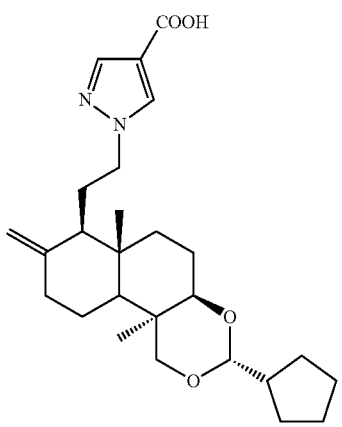
458

457
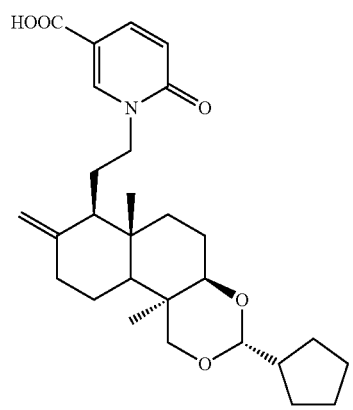
230
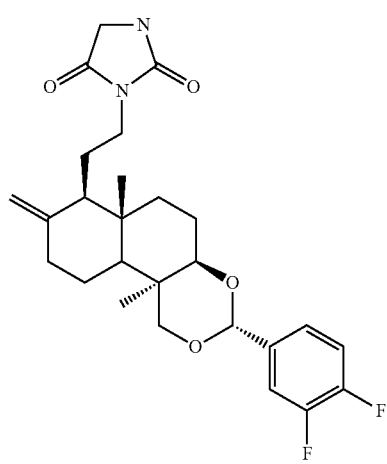
212
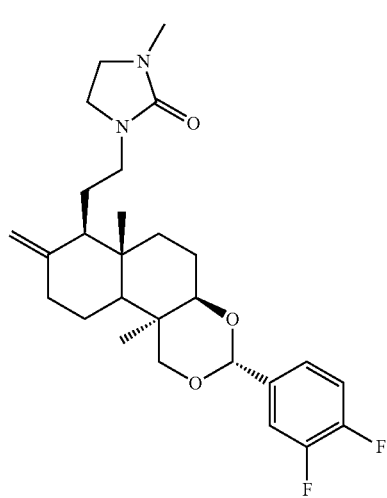
214
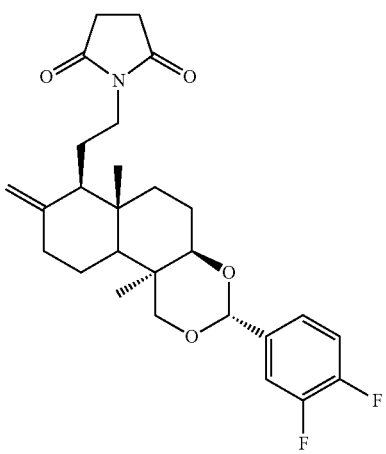
215
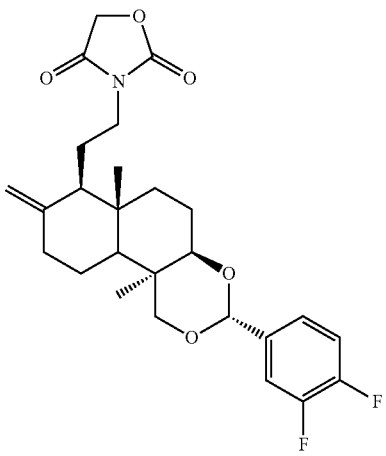
130
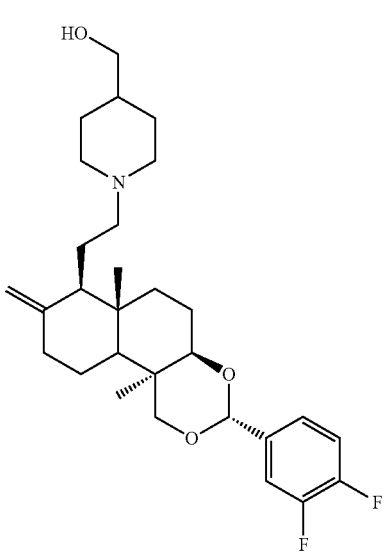

-continued

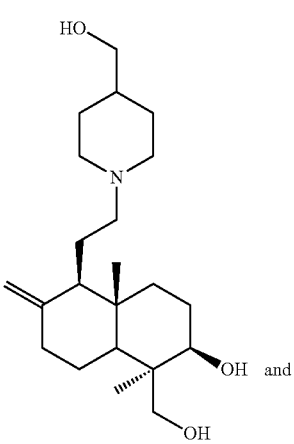

In some embodiments of the present disclosure, $R_1$ is selected from H, COOH, or selected from the group consisting of $NH_2$, $C_{1-4}$ alkyl, $C_{1-4}$ heteroalkyl, azetidinyl, pyrrolidinyl, tetrahydropyranyl, piperidinyl, cyclohexyl, phenyl, pyridyl, pyridine-2(1H)keto, pyrimidinyl, pyrazolyl, thiazolyl, benzothiazolyl, imidazo[1,2-b]pyridazinyl, isoxazolyl and thienyl, which is optionally substituted with 1, 2 or 3 R; other variants are as defined above.

In some embodiments of the present disclosure, $R_1$ is selected from H, COOH, or selected from the group consisting of $NH_2$,

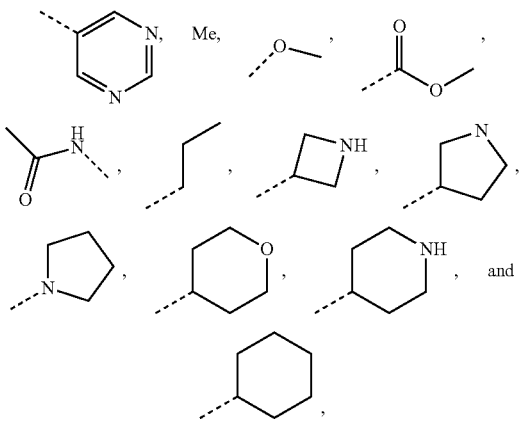

which is optionally substituted with 1, 2 or 3 R; other variants are as defined above.

In some embodiments of the present disclosure, $R_1$ is selected from the group consisting of

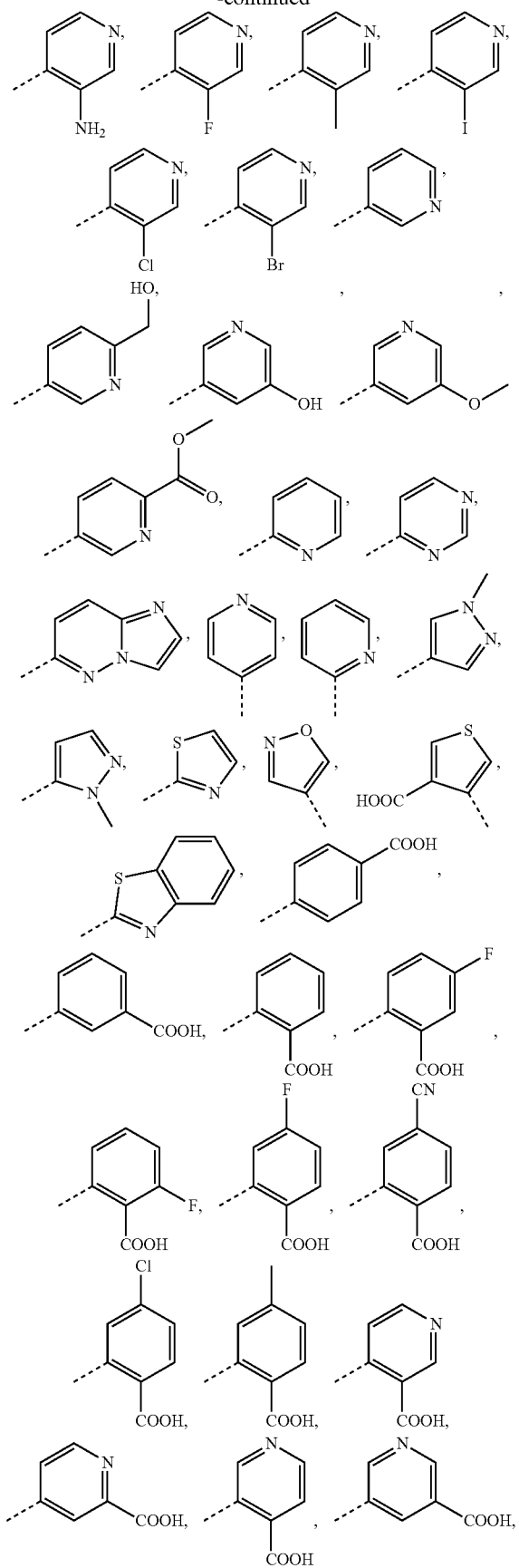
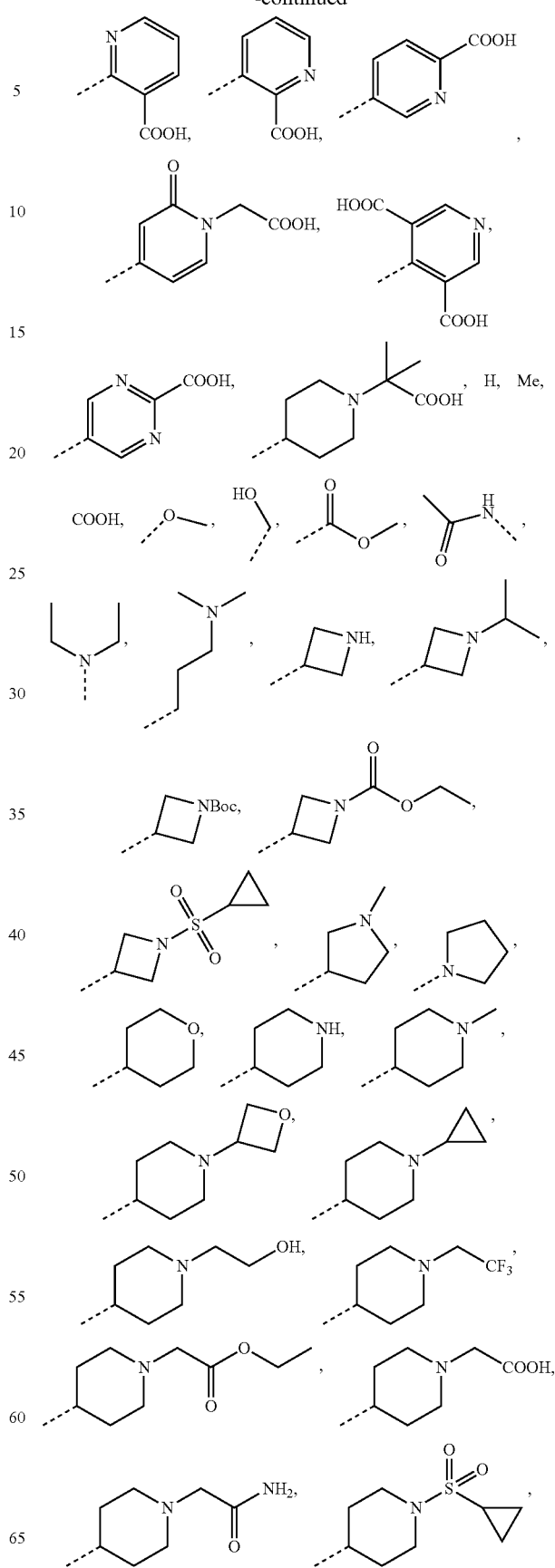

39
-continued

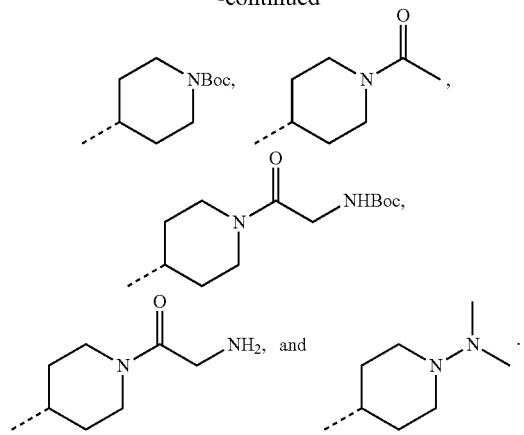

other variants are as defined above.

In some embodiments of the present disclosure, R$_4$ is selected from the group consisting of H and pyridyl; other variants are as defined above.

In some embodiments of the present disclosure, R$_4$ is selected from the group consisting of H and

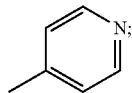

other variants are as defined above.

In some embodiments of the present disclosure, R$_2$ is selected from the group consisting of C$_{1-6}$ alkyl, C$_{1-6}$ heteroalkyl, C$_{3-6}$ cycloalkyl, and 3-6 membered heterocycloalkyl, 5-6 membered aryl or heteroaryl, which is optionally substituted with 1, 2 or 3 R or R'; other variants are as defined above.

In some embodiments of the present disclosure, R$_2$ is selected from the group consisting of Me, Et,

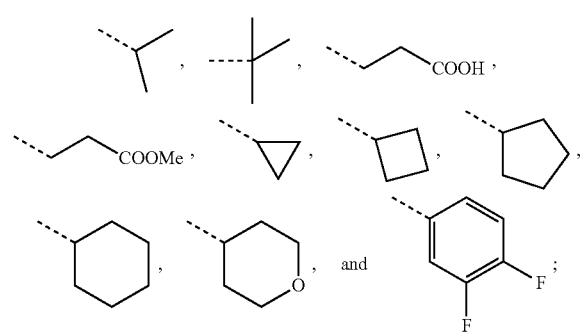

other variants are as defined above.

In some embodiments of the present disclosure, R$_3$ is selected from H and Me; other variants are as defined above.

In some embodiments of the present disclosure, the structure unit

40 is selected from the group consisting of

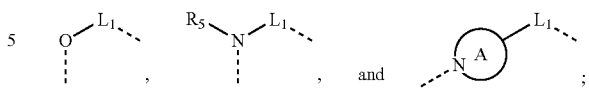

other variants are as defined above.

In some embodiments of the present disclosure, the structure unit

is selected from the group consisting of

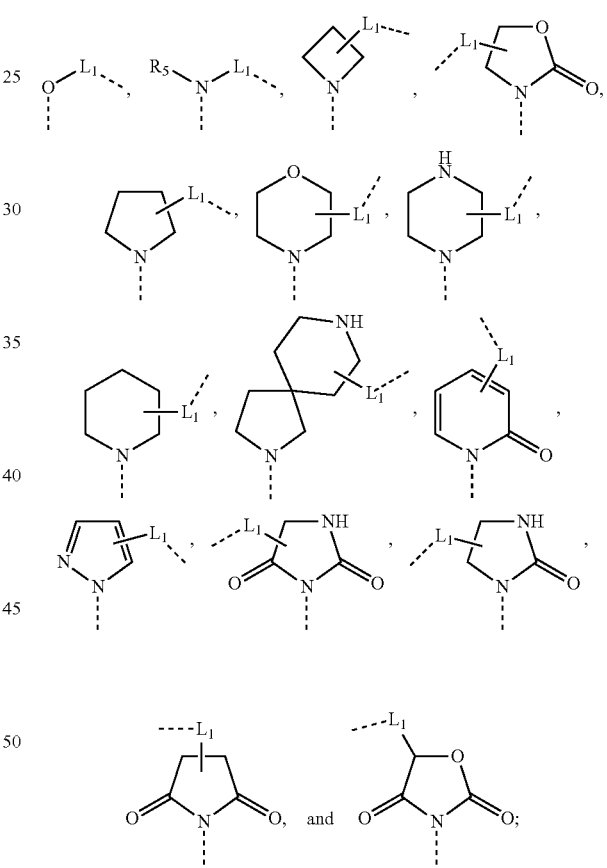

other variants are as defined above.

In some embodiments of the present disclosure, the structure unit is selected from the group consisting of
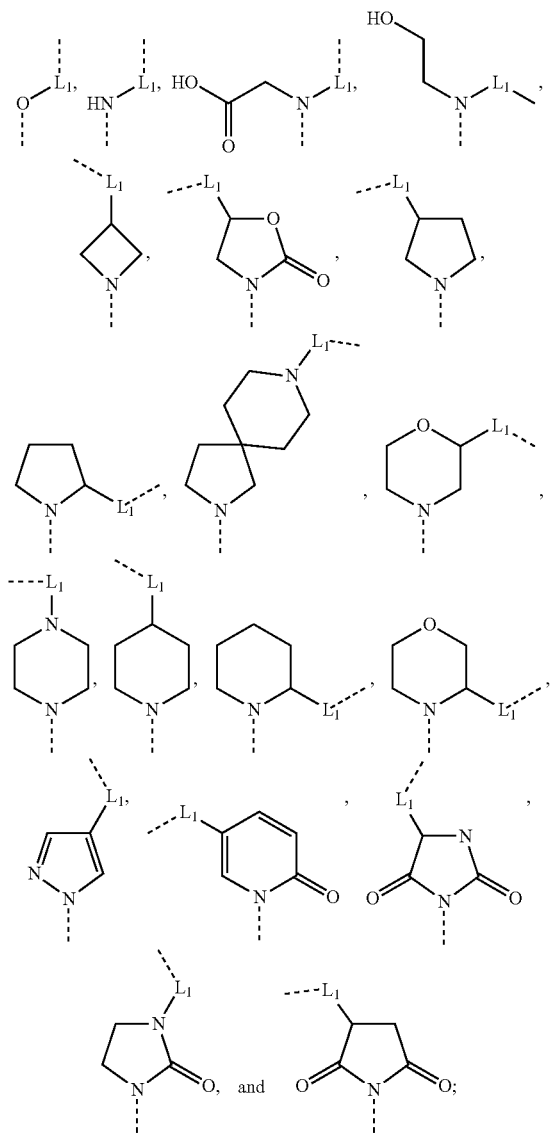
other variants are as defined above.
In some embodiments of the present disclosure, the structure unit
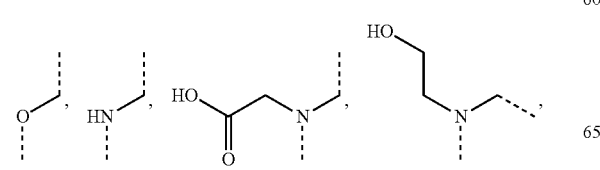
is selected from the group consisting of
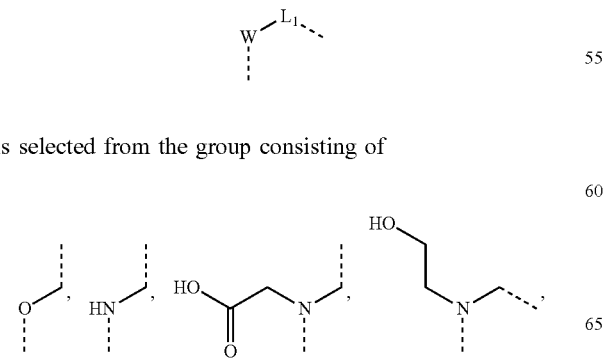
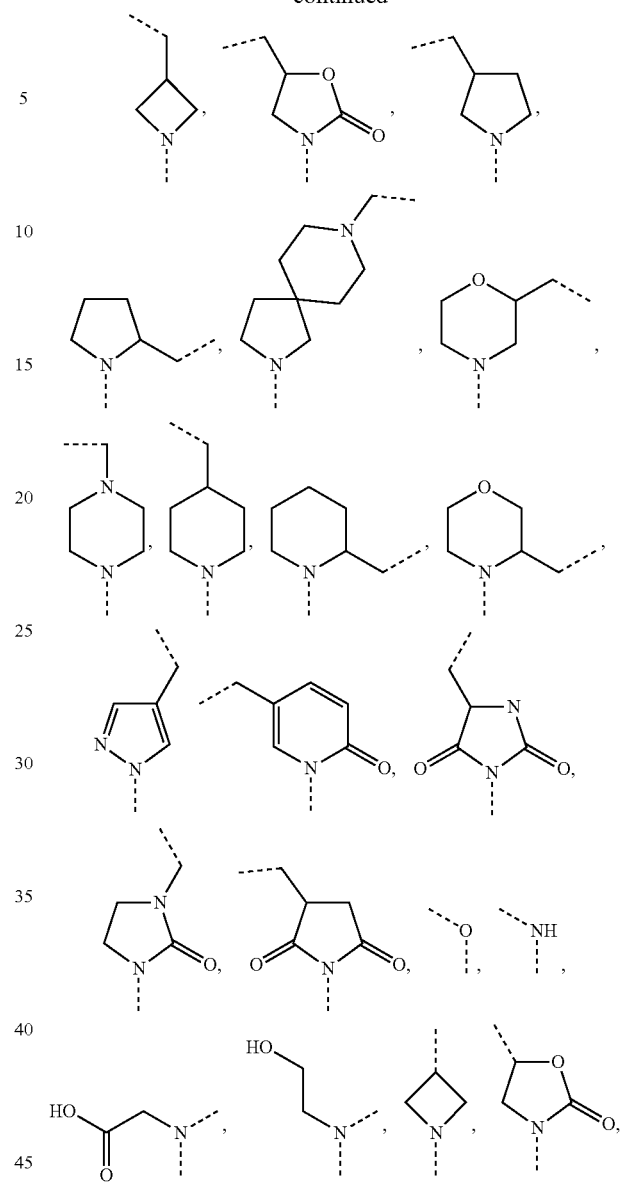
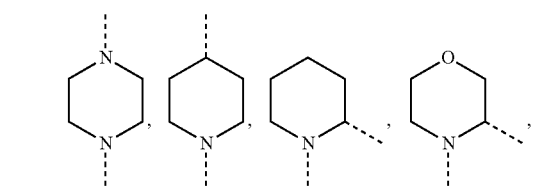

-continued

[chemical structures: pyrazole-L1, pyridinone, hydantoin, imidazolidinone, and succinimide]

other variants are as defined above.

In some embodiments of the present disclosure, the structure unit

W—L4— is selected from the group consisting of

[structures: O-L4 and N-A ring with L4]

other variants are as defined above.

In some embodiments of the present disclosure, the structure unit

W—L4— is selected from the group consisting of

[structures: O-L4 and piperidine-L4]

other variants are as defined above.

In some embodiments of the present disclosure, the structure unit

W—L4— is selected from the group consisting of

[structures: piperidine-L4 variant and O-L4]

other variants are as defined above.

In some embodiments of the present disclosure, the structure unit

W—L4— is selected from the group consisting of

[structures: O, O-CH2, piperidine, and piperidine variants]

other variants are as defined above.

In some embodiments of the present disclosure, the above compound, pharmaceutically acceptable salt or tautomer thereof is selected from the group consisting of (I-1), (I-2), (I-3), (II-1) and (II-2):

(I-1)

[steroid-like structure with O-L1-R1, R2, R3 substituents]

(I-2)

[steroid-like structure with R5-N-L1-R1, R2, R3 substituents]

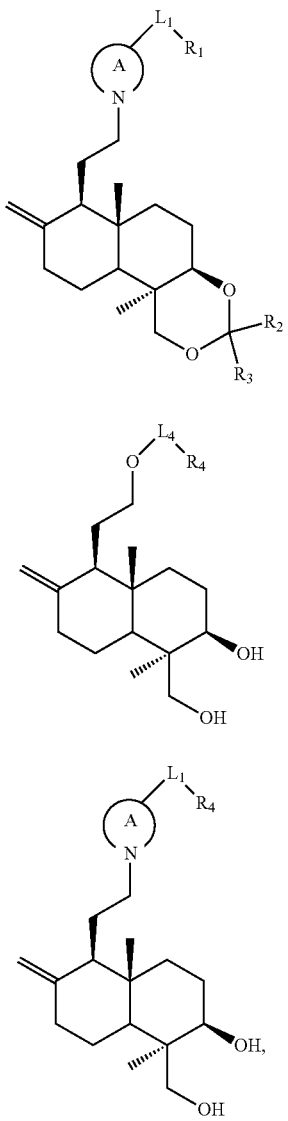

(I-3)

(II-1)

(II-2)

wherein, $L_1$, $L_4$, $R_1$, $R_2$, $R_3$, $R_4$, $R_5$ and the ring A are as defined above.

In some embodiments of the present disclosure, the compound, pharmaceutically acceptable salt or tautomer thereof is selected from the group consisting of (I-4), (I-5) and (I-6):

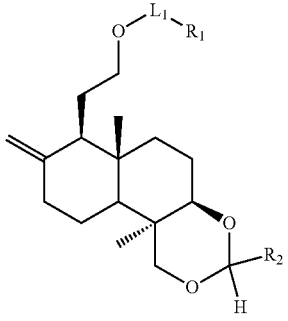

(I-4)

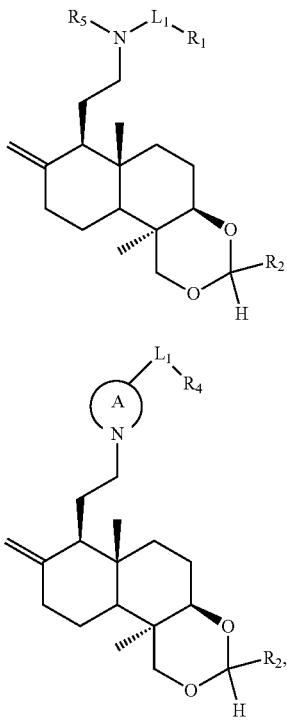

(I-5)

(I-6)

wherein, $L_1$, $R_1$, $R_2$, $R_5$ and the ring A are as defined above.

Some other embodiments of the present disclosure are provided through arbitrarily combining the above variants.

The present disclosure also provides a use of the compound or pharmaceutically acceptable salt in manufacturing a medicament for the treatment and prevention of inflammatory diseases. Specifically, the disease is selected from the group consisting of pneumonia, upper respiratory tract infection and arthritis; more specifically, the pneumonia is selected from the group consisting of viral pneumonia and bacterial pneumonia.

Further areas of applicability will become apparent from the description provided herein. The description and specific examples in this summary are intended for purposes of illustration only and are not intended to limit the scope of the present disclosure.

Unless otherwise specified, the following terms and phrases used herein are intended to have the following meanings. A particular term or phrase should not be considered indefinite or unclear when not specifically defined, but should be understood in the ordinary sense. When a trade name appears in this document, it is intended to refer to its corresponding article or the active ingredient thereof.

$C_{1-12}$ is selected from the group consisting of $C_1$, $C_2$, $C_3$, $C_4$, $C_5$, $C_6$, $C_7$, $C_8$, $C_9$, $C_{10}$, $C_{11}$, and $C_{12}$; $C_{3-12}$ is selected from the group consisting of $C_3$, $C_4$, $C_5$, $C_6$, $C_7$, $C_8$, $C_9$, $C_{10}$, $C_{11}$ and $C_{12}$.

$C_{1-12}$ alkyl or heteroalkyl, $C_{3-12}$ cyclic group or heterocycloalkyl, $C_{1-12}$ alkyl or heteroalkyl substituted with $C_{3-12}$ cycloalkyl or heterocycloalkyl include, but are not limited to:

$C_{1-12}$ alkyl, $C_{1-12}$ alkylamino, N,N-di($C_{1-12}$ alkyl)amino, $C_{1-12}$ alkoxy, $C_{1-12}$ alkanoyl, $C_{1-12}$ alkoxycarbonyl, $C_{1-12}$ alkylsulfonyl, $C_{1-12}$ alkylsulfinyl, $C_{3-12}$ cycloalkyl, $C_{3-12}$ cycloalkylamino, $C_{3-12}$ heterocycloalkylamino, $C_{3-12}$ cycloalkoxy, $C_{3-12}$ cycloalkylacyl, $C_{3-12}$ cycloalkyloxycarbonyl, $C_{3-12}$ cycloalkylsulfonyl, $C_{3-12}$ cycloalkylsulfinyl, 5-12 membered aryl or heteroaryl, 5-12 membered arylalkyl or heteroarylalkyl;

methyl, ethyl, n-propyl, isopropyl, —CH$_2$C(CH$_3$)(CH$_3$)(OH), cyclopropyl, cyclobutyl, propyl methylene, cyclopropionyl, benzyloxy, trifluoromethyl, aminomethyl, hydroxymethyl, methoxy, formyl, methoxycarbonyl, methylsulfonyl, methylsulfinyl, ethoxy, acetyl, ethylsulfonyl, ethoxycarbonyl, dimethylamino, diethylamino, dimethylaminocarbonyl, diethylaminocarbonyl;

N(CH$_3$)$_2$, NH(CH$_3$), —CH$_2$CF$_3$, —CH$_2$CH$_2$CF$_3$, —CH$_2$CH$_2$F, —CH$_2$CH$_2$S(=O)$_2$CH$_3$, —CH$_2$CH$_2$CN, —CH$_2$CH(OH)(CH3)$_2$, —CH$_2$CH(F)(CH$_3$)$_2$, —CH$_2$CH$_2$F, —CH$_2$CF$_3$, —CH$_2$CH$_2$CF$_3$, —CH$_2$CH$_2$NH$_2$, —CH$_2$CH$_2$OH, —CH$_2$CH$_2$OCH$_3$, —CH$_2$CH$_2$CH$_2$OCH$_3$, —CH$_2$CH$_2$N(CH$_3$)$_2$, —S(=O)$_2$CH$_3$, —CH$_2$CH$_2$S(=O)$_2$CH$_3$; and phenyl, thiazolyl, biphenyl, naphthyl, cyclopentyl, furyl, 3-pyrrolinyl, pyrrolidinyl, 1,3-dioxopentyl, pyrazolyl, 2-pyrazolinyl, pyrazolidyl, imidazolyl, oxazolyl, thiazolyl, 1,2,3-oxazolyl, 1,2,3-triazolyl, 1,2,4-triazolyl, 1,3,4-thiadiazolyl, 4H-pyranyl, pyridinyl, piperidinyl, 1,4-dioxanyl, morpholinyl, pyridazinyl, pyrimidinyl, pyrazinyl, piperazinyl, 1,3,5-trithianyl, 1,3,5-triazinyl, benzofuranyl, benzothiophenyl, indolyl, benzimidazolyl, benzothiazolyl, purinyl, quinolinyl, isoquinolinyl, cinnolinyl, or quinoxalinyl;

As used herein, the term "pharmaceutically acceptable" refers to those compounds, materials, compositions, and/or dosage forms that are within the scope of reliable medical judgment and are suitable for use in contact with human and animal tissues without excessive toxicity, irritation, allergic reactions or other problems or complications, being commensurate with a reasonable benefit/risk ratio.

The term "pharmaceutically acceptable salts" refers to salts of the compounds of the present disclosure that are prepared from the compounds having particular substituents of the present disclosure and relatively non-toxic acids or bases. When the compounds of the present disclosure contain relatively acidic functional groups, base addition salts can be obtained by contacting the neutrality form of such compounds with a sufficient amount of a base in pure solution or in a suitable inert solvent. Pharmaceutically acceptable base addition salts include salts of sodium, potassium, calcium, ammonium, organic ammonia or magnesium or similar salts. When compounds of the present disclosure contain relatively basic functional groups, acid addition salts can be obtained by contacting the neutrality form of such compounds with a sufficient amount of the acid in pure solution or in a suitable inert solvent. Examples of pharmaceutically acceptable acid addition salts include inorganic acid salts including, for example, hydrochloric acid, hydrobromic acid, nitric acid, carbonic acid, bicarbonate, phosphoric acid, monohydrogen phosphate, dihydrogen phosphate, sulfuric acid, bisulfate, hydroiodic acid, phosphorous acid and the like; and organic acid salts including, for example, acetic acid, propionic acid, isobutyric acid, maleic acid, malonic acid, benzoic acid, succinic acid, suberic acid, fumaric acid, lactic acid, mandelic acid, phthalic acid, benzene sulfonic acid, p-toluene sulfonic acid, citric acid, tartaric acid, methanylulfonic acid and the like; also includes salts of amino acids (e.g., arginine, etc.) as well as salts of organic acids such as glucuronic acid (see Berge et al., "*Pharmaceutical Salts*", *Journal of Pharmaceutical Science* 66: 1-19 (1977)). Certain specific compounds of the present disclosure contain basic and acidic functional groups so that they can be converted to any base or acid addition salt.

Preferably, the salt is contacted with a base or acid in a conventional manner and the parent compound is isolated, thereby regenerating the neutrality form of the compound. The parent form of a compound differs from its various salt forms in certain physical properties, such as solubility in polar solvents.

As used herein, "pharmaceutically acceptable salts" belong to derivatives of the compounds of the present disclosure, wherein the parent compound is modified by salt formation with an acid or by salt formation with a base. Examples of pharmaceutically acceptable salts include, but are not limited to: inorganic or organic acid salts of base radicals such as amines, inorganic or organic salts of acid radicals such as carboxylic acids, and the like. Pharmaceutically acceptable salts include the conventional non-toxic salts or quaternary ammonium salts of the parent compound, such as the salts formed by non-toxic inorganic or organic acids. The conventional non-toxic salts include, but are not limited to, salts derived from inorganic and organic acids which are selected from the group consisting of 2-acetoxybenzoic acid, 2-hydroxyethylsulfonic acid, acetic acid, ascorbic acid, benzosulfonic acid, benzoic acid, bicarbonate, carbonic acid, citric acid, edetic acid, ethanedisulfonic acid, ethanesulfonic acid, fumaric acid, glucoheptonose, gluconic acid, glutamic acid, glycolic acid, hydrobromic acid, hydrochloric acid, hydroiodide, hydroxy, hydroxynaphthyl, isethionic acid, lactic acid, lactose, dodecyl sulfonic acid, maleic acid, malic acid, mandelic acid, methane sulfonic acid, nitric acid, oxalic acid, pamoic acid, pantothenic acid, phenylacetic acid, phosphoric acid, polygalactanaldehyde, propionic acid, salicylic acid, stearic acid, acetic acid, succinic acid, sulfamic acid, sulfanilic acid, sulfuric acid, tannins, tartaric acid and p-toluenesulfonic acid.

The pharmaceutically acceptable salts of the present disclosure can be synthesized from the parent compound containing acid radicals or base radicals by conventional chemical methods. In general, such salts are prepared by the reaction of these compounds in free acid or base form with a stoichiometric amount of the appropriate base or acid in water or an organic solvent or a mixture of the two. In general, non-aqueous media such as ether, ethyl acetate, ethanol, isopropanol or acetonitrile are preferred.

In addition to salt forms, the compounds provided herein also exist in prodrug forms. The prodrugs of the compounds described herein are readily chemically altered under physiological conditions to be converted into the compounds of the disclosure. In addition, prodrugs can be converted to the compounds of the present disclosure by chemical or biochemical methods in the in vivo environment.

Certain compounds of the present disclosure may exist in unsolvated or solvated forms, including hydrated forms. In general, solvated forms are equivalent to unsolvated forms and both are included within the scope of the present disclosure.

Certain compounds of the present disclosure may have asymmetric carbon atoms (optical centers) or double bonds. Racemates, diastereomers, geometric isomers and individual isomers are all included within the scope of the present disclosure.

The graphical representation of racemic, ambiscalemic and scalemic or enantiomeric pure compounds herein is from Maehr, *J. Chem. Ed.* 1985, 62: 114-120. Unless otherwise specified, the absolute configuration of a stereocenter is represented by a wedge bond and a dashed bond. When the compounds described herein contain olefinic double bonds or other geometric asymmetry centers, they include E, Z geometric isomers, unless otherwise specified. Likewise, all tautomeric forms are included within the scope of the present disclosure.

The compounds of the disclosure may exist in specific geometric or stereoisomeric forms. The present disclosure encompasses all such compounds, including cis and trans isomers, (−)- and (+)-pair enantiomers, (R)- and (S)-enantiomers, diastereoisomers, (D)-isomer, (L)-isomer, and the racemic mixtures and other mixtures thereof, such as enantiomeric or diastereomeric enriched mixtures, all of which are within the scope of the present disclosure. Additional asymmetric carbon atoms may be present in the substituents such as alkyl groups. All these isomers and their mixtures are included within the scope of the present disclosure.

Optically active (R)- and (S)-isomers and D and L isomers can be prepared by chiral synthesis or chiral reagents or other conventional techniques. If an enantiomer of a certain compound of the disclosure is desired, it can be prepared by asymmetric synthesis or derivatization with a chiral auxiliary, wherein the resulting mixture of diastereomers is separated and the ancillary groups are cleaved to provide pure desired enantiomer. Alternatively, when the molecule contains a basic functional group (such as an amino group) or an acidic functional group (such as a carboxyl group), a diastereomer salt is formed with a suitable optically active acid or base, and then the diastereomeric resolution is performed by conventional methods known in the art, and then the pure enantiomer is recovered. In addition, the separation of enantiomers and diastereomers is generally accomplished by the use of chromatography using a chiral stationary phase and optionally in combination with chemical derivatization (e.g., forming carbaminate from amines).

The compounds of the present disclosure may contain unnatural proportions of atomic isotopes at one or more of the atoms that comprise the compound. For example, the compounds can be labelled with radioactive isotopes such as tritium ($^3$H), iodine-125 ($^{125}$I) or C-14 ($^{14}$C). The variants of all isotopic compositions of the compounds of the present disclosure, whether radioactive or not, are all included within the scope of the present disclosure.

The term "pharmaceutically acceptable carrier" refers to any agent or carrier medium capable of delivering an effective amount of an active agent of the present disclosure without interfering with the biological activity of the active agent and having no toxic side effects on the host or patient. Exemplary carriers include water, oil, vegetables and minerals, cream bases, lotion bases, ointment bases, etc. These bases include suspending agents, tackifiers, transdermal enhancers and the like. Their formulations are well known to those skilled in the cosmetic area or topical medicine area. For additional information on carriers, reference may be made to *Remington: The Science and Practice of Pharmacy, 21st Ed.*, Lippincott, Williams & Wilkins (2005), the contents of which are incorporated herein by reference.

The term "excipient" generally refers to the carrier, diluent, and/or medium required to formulate an effective pharmaceutical composition.

For a drug or pharmacologically active agent, the term "effective amount" or "therapeutically effective amount" refers to a sufficient amount of drug or agent that is nontoxic but can achieve the desired effect. For an oral dosage form in the present disclosure, an "effective amount" of an active substance in the composition refers to the amount needed to achieve the desired effect when used in combination with another active substance in the composition. The determination of the effective amount varies from person to person, depending on the age and general condition of the recipient, and also on the specific active substance, and the appropriate effective amount in an individual case can be determined by a person skilled in the art according to routine experimentation.

The terms "active ingredient", "therapeutic agent", "active substance" or "active agent" refers to a chemical entity that can effectively treat a target disorder, disease or condition.

The term "substituted" means that any one or more hydrogen atoms on a particular atom are replaced with substituents, including deuterium and hydrogen variants, as long as the valence of a particular atom is normal and the substituted compound is stable. When the substituent is a keto (i.e., =O), it means that two hydrogen atoms are substituted. Ketone substitution does not occur on aromatic groups. The term "optionally substituted" means that it may or may not be substituted. Unless otherwise specified, the type and number of substituents may be arbitrary on the basis of being chemically achievable.

When any variant (e.g., R) occurs more than once in the composition or structure of a compound, its definition in each case is independent. Thus, for example, if a group is substituted with 0-2 R, the group may optionally be substituted with up to two R, and R in each case has an independent option. In addition, combinations of substituents and/or variants thereof are permissible only if such combinations result in stable compounds.

When the number of a linking group is 0, such as —(CRR)$_0$—, it means that the linking group is a single bond.

When one of the variants is selected from a single bond, it means that the two groups which it connects are directly linked. For example, when L represents a single bond in A-L-Z, the structure is actually A-Z.

When a substituent's bond can be cross-linked to two atoms on a ring, the substituent can be bonded to any atom on the ring. When the recited substituents do not indicate by which atom they are attached to a compound included in the general formula of the chemical structure but are not specifically mentioned, such substituents may be bonded through any of their atoms. Combinations of substituents and/or variants thereof are permissible only if such combinations result in stable compounds. For example, a structure unit

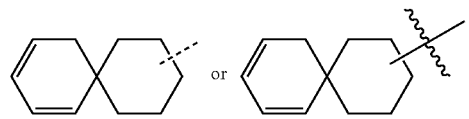

signifies that it may be substituted at any position on the cyclohexyl or cyclohexadiene.

Unless otherwise specified, the term "halo" or "halogen" by itself or as part of another substituent denotes a fluorine, chlorine, bromine, or iodine atom. In addition, the term "haloalkyl" is meant to include monohaloalkyl and polyhaloalkyl. For example, the term "halo(C$_1$-C$_4$)alkyl" is meant to include but not limited to trifluoromethyl, 2,2,2-trifluoroethyl, 4-chlorobutyl, 3-bromopropyl, and the like.

Examples of haloalkyl include, but are not limited to, trifluoromethyl, trichloromethyl, pentafluoroethyl, and pentachloroethyl. "Alkoxy" represents an alkyl group as defined above with a specified number of carbon atoms attached through an oxygen bridge. C$_{1-6}$ alkoxy includes C$_1$, C$_2$, C$_3$, $C_4$, $C_5$ and $C_6$ alkoxy groups. Examples of alkoxy include, but are not limited to, methoxy, ethoxy, n-propoxy, isopropoxy, n-butoxy, sec-butoxy, tert-butoxy, n-pentoxy, and S-pentoxy. "Cycloalkyl" includes saturated cyclic groups such as cyclopropyl, cyclobutyl or cyclopentyl. 3-7 cycloalkyl includes $C_3$, $C_4$, $C_5$, $C_6$ and $C_7$ cycloalkyl groups. "Alkenyl" includes a linear or branched chain hydrocarbon chain in which one or more carbon-carbon double bonds, such as vinyl and propenyl, are present at any stable site on the chain.

The term "halo" or "halogen" refers to fluorine, chlorine, bromine, and iodine.

Unless otherwise specified, the term "hetero" denotes a heteroatom or a heteroatom group (i.e., an atom group containing heteroatoms), including atoms other than carbon (C) and hydrogen (H), and atom groups containing these heteroatoms, for example, including oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O), —S(=O)$_2$—, and optionally substituted —C(=O)N(H)—, —N(H)—, —C(=NH)—, —S(=O)$_2$N(H)—, or —S(=O)N(H)—.

Unless otherwise specified, "ring" refers to a substituted or unsubstituted cycloalkyl, heterocycloalkyl, cycloalkenyl, heterocycloalkenyl, cycloalkynyl, heterocycloalkynyl, aryl, or heteroaryl. The so-called ring includes a single ring, a bicyclic ring, a spiro ring, a ring system having two rings sharing one bond, or a bridged ring. The number of atoms on the ring is usually defined as the number of members of the ring. For example, a "5-7 membered ring" refers to that 5 to 7 atoms are arranged in a circle. Unless otherwise specified, the ring optionally contains 1 to 3 heteroatoms. Thus, a "5-7 membered ring" includes, for example, phenyl, pyridinyl, and piperidinyl; in another aspect, the term "5-7 membered heterocycloalkyl ring" includes pyridyl and piperidinyl, but does not include phenyl. The term "ring" also includes ring systems containing at least one ring, wherein, each "ring" independently meets the above definition.

Unless otherwise specified, the term "heterocycle" or "heterocyclyl" means stable monocyclic, bicyclic, or tricyclic rings containing heteroatoms or heteroatom groups, which may be saturated, partially unsaturated, or unsaturated (aromatic), and contain carbon atoms and 1, 2, 3, or 4 heterocyclic atoms independently selected from N, O and S, wherein any of the above heterocycles may be fused to a benzene ring to form a bicyclic ring. The nitrogen and sulfur heteroatoms can be optionally oxidized (i.e. NO and S(O)p, p is 1 or 2). The nitrogen atom may be substituted or unsubstituted (i.e. N or NR, where R is H or other substituents as already defined herein). The heterocycles may be attached to the pendant groups of any heteroatom or carbon atom to form a stable structure. If the resulting compound is stable, the heterocycles described herein may be substituted at the carbon or nitrogen position. The nitrogen atom in the heterocycle is optionally quaternized. A preferred embodiment is that when the total number of S and O atoms in the heterocycle exceeds 1, these heteroatoms are not adjacent to each other. Another preferred embodiment is that the total number of S and O atoms in the heterocycle does not exceed 1. As used herein, the term "aromatic heterocyclic group" or "heteroaryl" means a stable 5, 6 or 7 membered monocyclic or bicyclic or 7, 8, 9 or 10 membered bicyclic heterocyclyl aromatic ring, which contains carbon atoms and 1, 2, 3, or 4 heterocyclic atoms independently selected from N, O, and S. The nitrogen atom may be substituted or unsubstituted (i.e., N or NR, where R is H or other substituents as already defined herein). The nitrogen and sulfur heteroatoms can be optionally oxidized (i.e., NO and S(O)p, p is 1 or 2). It is worth noting that the total number of S and O atoms on the aromatic heterocycle does not exceed 1. Bridged rings are also included in the definition of heterocycles. A bridged ring is formed when two non-adjacent carbon or nitrogen atoms are connected by one or more atoms (i.e., C, O, N or S). A preferred bridged ring includes, but is not limited to, one carbon atom, two carbon atoms, one nitrogen atom, two nitrogen atoms, and one carbon-nitrogen group. It is worth noting that a bridge always converts a single ring into a three ring. In the bridged ring, substituents on the ring can also appear on the bridge.

Examples of heterocyclic compounds include, but are not limited to, acridinyl, azocinyl, benzimidazolyl, benzofuranyl, benzosulfydrylfuranyl, benzosulfydrylphenyl, benzoxazolyl, benzoxazolinyl, benzothiazolyl, benzotriazolyl, benzotetrazolyl, benzisoxazolyl, benzisothiazolyl, benzimidazolinyl, carbazolyl, 4aH-carbazolyl, carbolinyl, chromanyl, chromene, cinnolinyldecahydroquinolinyl, 2H, 6H-1,5,2-dithiazinyl, dihydrofuro[2,3-b]tetrahydrofuranyl, furanyl, furazanyl, imidazolidinyl, imidazolinyl, imidazolyl, 1H-indolyl, indolylalkenyl, indolinyl, indolizinyl, indonyl, 3H-indolyl, isobenzofuranyl, isoindolyl, isoindolinyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, hydroxyindolyl, pyrimidinyl, phenanthridinyl, phenanthrolinyl, phenazinyl, phenothiazinyl, benzoxanthinyl, phenoxazinyl, phenazinyl, piperazinyl, piperidinyl, piperidinone, 4-piperidinone, piperonyl, pteridyl, purinyl, pyranyl pyrazinyl, pyrazolidinyl, pyrazolinyl, pyrazolyl, pyridazinyl, pyridooxazole, pyridoimidazole, pyridothiazole, pyridyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthienyl, thiazolyl, isothiazolylthiophenyl, thienooxazolyl, thienothiazolyl, thienoimidazolyl, thienyl, triazinyl, 1,2,3-triazolyl, 1,2,4-triazolyl, 1,2,5-triazolyl, 1,3,4-triazolyl, and xanthene. Also included are fused-ring and spiro compounds.

Unless otherwise specified, the term "hydrocarbyl" or its 1 subordinate concept (such as alkyl, alkenyl, alkynyl, phenyl, and the like) by itself or as part of another substituent means linear, branched, or cyclic hydrocarbon radicals, or combinations thereof, which may be fully saturated, unitary or polyunsaturated, may be mono-substituted, di-substituted, or poly-substituted, and may be monovalent (such as methyl), divalent (such as methylene), or polyvalent (such as methine), may include divalent or polyvalent radicals, and have a specified number of carbon atoms (e.g., $C_1$-$C_{10}$ represents 1 to 10 carbons). "Hydrocarbyl" includes, but is not limited to, aliphatic and aromatic hydrocarbyl, wherein the aliphatic hydrocarbyl includes chain and cyclic structures, including but not limited to alkyl, alkenyl, alkynyl, and the aromatic hydrocarbyl includes but not limited to 6-12 membered aromatic hydrocarbyl such as benzene, naphthalene, and the like. In some embodiments, the term "hydrocarbyl" refers to linear or branched chain radicals or combinations thereof, which may be fully saturated, unitary or polyunsaturated, and may include divalent and polyvalent radicals. Examples of saturated hydrocarbon radicals include, but are not limited to, methyl, ethyl, n-propyl, isopropyl, n-butyl, tert-butyl, isobutyl, sec-butyl, isobutyl, cyclohexyl, (cyclohexyl)methyl, cyclopropylmethyl, and homologues or isomers of n-pentyl, n-hexyl, n-heptyl, n-octyl and other atom groups. Unsaturated alkyl has one or more double or triple bonds, examples of which include, but are not limited to, vinyl, 2-propenyl, butenyl, crotyl, 2-prenyl, 2-(butadienyl), 2,4-pentadienyl, 3-(1,4-pentadienyl), ethynyl, 1- and 3-propynyl, 3-butynyl, and more advanced homologues or isomers.

Unless otherwise specified, the term "heterohydrocarbyl" or its subordinate concept (such as heteroalkyl, heteroalkenyl, heteroalkynyl, heteroaryl, etc.) by itself or in combination with another term means stable, linear, branched or cyclic hydrocarbon radicals or combinations thereof, consisting of a certain number of carbon atoms and at least one heteroatom. In some embodiments, the term "heteroalkyl" by itself or in combination with another term means stable, linear, branched hydrocarbon radicals or combinations thereof, consisting of a certain number of carbon atoms and at least one heteroatom. In a typical embodiment, the heteroatom is selected from the group consisting of B, O, N, and S, wherein the nitrogen and sulfur atoms are optionally oxidized and the nitrogen heteroatoms are optionally quaternized. The heteroatom or heteroatom group may be located at any internal position of the heterohydrocarbyl (including the position where the hydrocarbyl is attached to the rest of the molecule). Examples include but are not limited to —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, S(O)—$CH_3$, —$CH_2$—$CH_2$—S(O)$_2$—$CH_3$, —CH=CH—O—$CH_3$, —$CH_2$—CH=N—$OCH_3$ and —CH=CH—N($CH_3$)—$CH_3$. Up to two heteroatoms may be continuous, such as —$CH_2$—NH—$OCH_3$.

The terms "alkoxy", "alkylamino", and "alkylthio" (or thioalkoxy) are conventional expressions and refer to those alkyl groups that are attached to the rest of the molecule through an oxygen atom, an amino group, or a sulfur atom, respectively.

Unless otherwise specified, the terms "cyclohydrocarbyl", "heterocyclohydrocarbyl" or subordinate concepts such as aryl, heteroaryl, cycloalkyl, heterocycloalkyl, cycloalkenyl, heterocycloalkenyl, cycloalkynyl, heterocycloalkynyl, etc.) by itself or in combination with other terms mean cyclized "hydrocarbyl", "heterohydrocarbyl" respectively. In addition, for heterohydrocarbyl or heterocyclohydrocarbyl (such as heteroalkyl, heterocycloalkyl), heteroatoms may occupy the position at which the heterocycle is attached to the rest of the molecule. Examples of include, but are not limited to, cyclopentyl, cyclohexyl, 1-cyclohexenyl, 3-cyclohexenyl, cycloheptyl and the like. Non-limiting examples of heterocyclic groups include 1-(1,2,5,6-tetrahydropyridinyl), 1-piperidinyl, 2-piperidinyl, 3-piperidinyl, 4-morpholinyl, 3-morpholinyl, tetrahydrofuran-2-yl, tetrahydrofuranindol-3-yl, tetrahydrothiophen-2-yl, tetrahydrothiophen-3-yl, 1-piperazinyl, and 2-piperazinyl.

Unless otherwise specified, the term "aryl" refers to a polyunsaturated aromatic hydrocarbon substituent, which may be mono-, di-, or poly-substituted, and may be monovalent, divalent, or polyvalent, and may be monocyclic or polycyclic rings (such as 1 to 3 rings; at least one of which is aromatic), being fused together or covalently linked. The term "heteroaryl" refers to an aryl group (or ring) containing one to four heteroatoms. In one illustrative example, the heteroatom is selected from the group consisting of B, N, O, and S, wherein the nitrogen and sulfur atoms are optionally oxidized and the nitrogen atom is optionally quaternized. A heteroaryl can be attached to the rest of the molecule through a heteroatom. Non-limiting examples of aryl or heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolinyl, 5-isoquinolinyl, 2-quinoxalinyl, 5-quinoxalinyl, 3-quinolinyl, and 6-quinolinyl. The substituents for any of the above aryl and heteroaryl ring systems are selected from the acceptable substituents described below.

Unless otherwise specified, aryl groups, when used in combination with other terms (e.g., aryloxy, arylthio, arylalkyl) include aryl and heteroaryl rings as defined above. Thus, the term "aralkyl" is intended to include those groups (e.g., benzyl, phenethyl, pyridylmethyl, etc.) where the aryl group is attached to the alkyl group, and including those alkyl groups where the carbon atom (e.g., methylene) has been substituted by an atom such as oxygen, for example, phenoxymethyl, 2-pyridyloxymethyl 3-(1-naphthyloxy)propyl and the like.

The term "leaving group" refers to a functional group or atom that can be substituted by another functional group or atom through a substitution reaction (e.g., an affinity substitution reaction). For example, representative leaving groups include triflate; chlorine, bromine, iodine; sulfonate groups such as mesylate, tosylate, p-bromobenzenesulfonate, p-toluenesulfonates and the like; acyloxy such as acetoxy, trifluoroacetoxy and the like.

The term "protecting group" includes but is not limited to "amino protecting group", "hydroxy protecting group" or "sulfhydryl protecting group". The term "amino protecting group" refers to a protecting group suitable for blocking a side reaction at the amino nitrogen position. Representative amino protecting groups include, but are not limited to, formyl; acyl, such as alkanoyl (e.g., acetyl, trichloroacetyl, or trifluoroacetyl); alkoxycarbonyl, such as tert-butoxycarbonyl (Boc); arylmethoxycarbonyl such as benzyloxycarbonyl (Cbz) and 9-fluorenylmethyloxycarbonyl (Fmoc); arylmethyl such as benzyl (Bn), trityl (Tr), 1,1-bis-(4'-methoxyphenyl)methyl; silyl such as trimethylsilyl (TMS) and tert-butyldimethylsilyl (TBS) and the like. The term "hydroxy protecting group" refers to a protecting group that is suitable for blocking the side reaction of hydroxyl groups. Representative hydroxy protecting groups include, but are not limited to, alkyl such as methyl, ethyl, and tert-butyl; acyl such as alkanoyl (such as acetyl); arylmethyl such as benzyl (Bn), p-methoxybenzyl (PMB), 9-fluorenylmethyl (Fm) and diphenylmethyl (benzhydryl, DPM); silyl such as trimethylsilyl (TMS) and tert-butyl dimethylsilyl (TBS) and the like.

The compounds of the present disclosure may be prepared by a variety of synthetic methods well-known to those skilled in the art, including the embodiments set forth below, combinations thereof with other chemical synthesis methods, and equivalent alternatives well-known to those skilled in the art, preferred embodiments include but are not limited to embodiments of the present disclosure.

The solvents used in the present disclosure are commercially available. The present disclosure uses the following abbreviations: aq for water; HATU for O-(7-azabenzotriazol-1-yl)-N,N,N',N'-tetramethyluronium hexafluorophosphate; EDC for N-(3-dimethylaminopropyl)-N'-ethylcarbodiimide hydrochloride; m-CPBA for 3-chloroperoxybenzoic acid; eq for equivalent, equal; CDI for carbonyldiimidazole; DCM for dichloromethane; PE for petroleum ether; DIAD for diisopropyl azodicarboxylate; DMF for N,N-dimethylformamide; DMSO for dimethyl sulfoxide; EtOAc for ethyl acetate ester; EtOH for ethanol; MeOH for methanol; CBz for benzyloxycarbonyl, an amine protecting group; BOC for tert-butoxycarbonyl, an amine protecting group; HOAc for acetic acid; NaCNBH$_3$ for sodium cyanoborohydride; r.t. for room temperature; O/N for overnight; THF for tetrahydrofuran; Boc$_2$O for di-tert-butyl dicarbonate; TFA for trifluoroacetic acid; DIPEA for diisopropylethylamine; SOCl$_2$ for thionyl chloride; CS$_2$ for carbon disulfide; TsOH for p-toluenesulfonic acid; NFSI for N-fluoro-N-(phenylsulfonyl) phenylsulfonyl amide; NCS for 1-chloropyrrolidine-2,5-dione; n-Bu$_4$NF for tetrabutylammonium fluoride; iPrOH for 2-propanol; mp for melting point; LDA for lithium diisopropylamide.

Compounds are named by hand or ChemDraw® software, and commercially available compounds are named after supplier catalog names.

DETAILED DESCRIPTION

Example embodiments will now be described more fully.

Compound 297

4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)pyridine

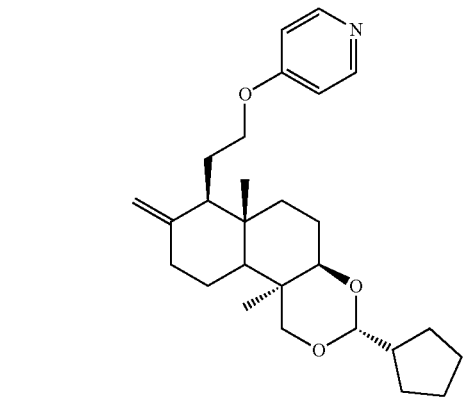

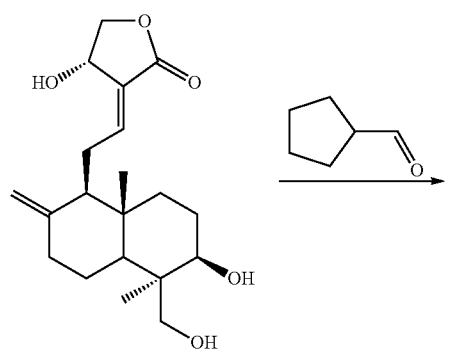

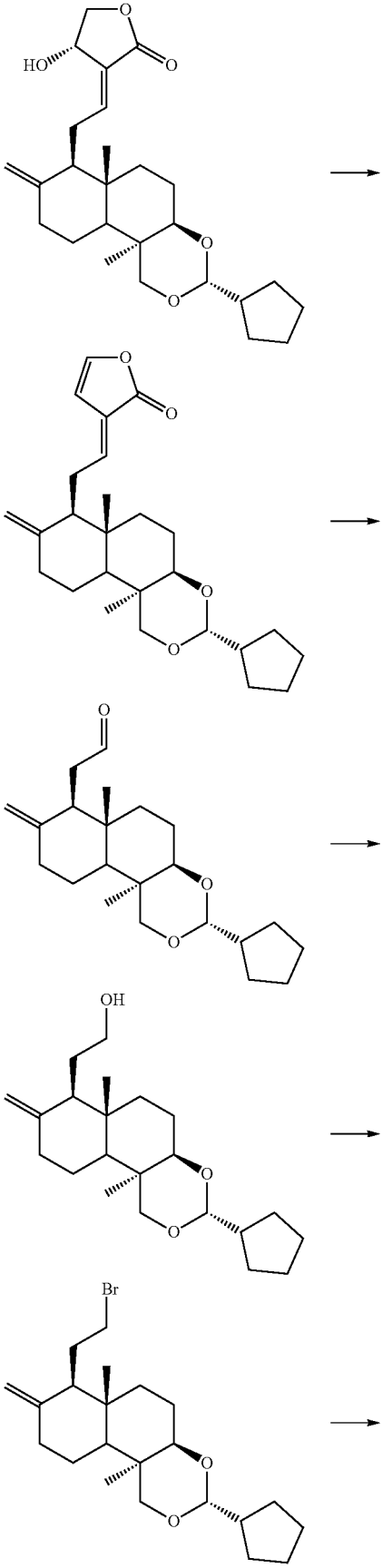

-continued

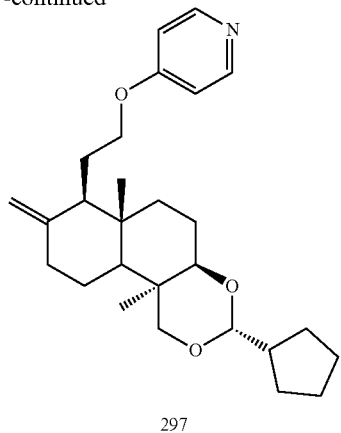

297

Step 1

4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethylidene)-4-hydroxydihydrofuran-2(3H)-one (4S,E)-4-hydroxy-3-(2-((1R,5R,6R,8aS)-6-hydroxy-5-(hydroxymethyl)-5,8a-dimethyl-2-methylenedecahydronaphthalenemethanol-1-yl) ethylene)dihydrofuran-2 (3H)-one (300.00 g, 856.04 mmol) was dissolved in dichloromethane (3.00 L), and cyclopentylcarbaldehyde (84.85 g, 864.60 mmol) and amberlyst-15 (300.00 g) were added in sequence, then stirred at 20° C. for 12 hours. The system was filtered and concentrated to give 300 g (4S,E)-3-(2-((3R,4aR,6aS,7R,10bR)-3-cyclopentyl-6a,10b-dimethyl-8-amethylene-decahydro-1H-naphtho[2,1-d][1,3]dioxin-7-yl)ethylene)-4-hydroxydihydrofuran-2(3H)-one as a white solid, yield: 81.39%.

$^1$H NMR (400 MHz, CDCl3) 6.97 (d, J=6.4 Hz, 1H), 5.05 (s, 1H), 4.92 (s, 1H), 4.62 (s, 2H), 4.46 (d, J=6 Hz, 1H), 4.29-4.26 (m, 1H), 4.03 (d, J=10.8 Hz, 1H), 3.49-3.44 (m, 2H), 2.59-2.46 (m, 4H), 2.21 (s, 1H), 2.08-1.87 (m, 2H), 1.85-1.71 (m, 3H), 1.69-1.56 (m, 9H), 1.54 (s, 3H), 1.52-1.26 (m, 3H), 0.83 (s, 3H).

Step 2

(E)-3-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethylidene)-furan-2 (3H)-one (4S,E)-3-(2-((3R,4aR,6aS,7R,10bR)-3-cyclopentyl-6a,10b-dimethyl-8-dihydromethylene-1H-naphtho[2,1-d][1,3]dioxin-7-yl)ethylidene)-4-hydroxydihydrofuran-2(3H)-one (200.00 g, 464.49 mmol) was dissolved in 2000 mL dichloromethane and added with acetic anhydride (490.50 g, 4.80 mol) and pyridine (392.00 g, 4.96 mol) at 0° C., then stirred at 20° C. for 17 hours. The reaction solution was concentrated under reduced pressure at 35° C., added with 6000 mL water to precipitate a precipitate, and filtered. The resulting residue was pulped with petroleum ether (500 mL*2) to give 200 g crude product of (E)-3-(2-((3R, 4aR,6aS,7R,10bR)-3-cyclopentyl-6a,10b-dimethyl-8-dihydromethylene decahydro-1H-naphtho[2,1-d][1,3]dioxin-7-yl)ethylidene)furan-2(3H)-one.

$^1$H NMR (400 MHz, CDCl$_3$) 7.02 (br. s., 1H), 6.71 (t, J=6.9 Hz, 1H), 6.19 (d, J=3.0 Hz, 1H), 4.88 (s, 1H), 4.62 (d, J=5.5 Hz, 1H), 4.45 (s, 1H), 4.04 (d, J=11.3 Hz, 1H), 3.55-3.36 (m, 2H), 2.63-2.52 (m, 1H), 2.48-2.38 (m, 2H), 2.35-2.23 (m, 1H), 2.15-1.99 (m, 2H), 1.94-1.82 (m, 3H), 1.72 (br. s., 3H), 1.64-1.45 (m, 6H), 1.39 (s, 3H), 1.27 (br. s., 3H), 0.83 (s, 3H).

Step 3

2-((3R,4aR,6aS,7R,10bR)-3-cyclopentyl-6a,10b-dimethyl-8-dihydromethylene decahydro-1H-naphtho[2,1-d][1,3]dioxin-7-yl) acetaldehyde (E)-3-(2-((3R,4aR,6aS,7R,10bR)-3-cyclopentyl-6a,10b-dimethyl-8-dihydromethylene-1H-naphtho[2,1-d][1,3]dioxin-7-yl)ethylidene)furan-2(3H)-one (200.00 g, 484.78 mmol) was dissolved in 2000 mL tetrahydrofuran, a solution of potassium permanganate (229.83 g, 1.45 mol) dissolved in 2000 mL water was added at 0° C., followed by being stirred at 20° C. for 6 hours. 1000 mL brine was added and the layers were separated. The organic phase was concentrated under reduced pressure and the residue was dissolved in 1000 mL ethyl acetate. 9000 mL petroleum ether was added and the mixture was filtered. The filtrate was concentrated under reduced pressure to give 78 g crude product of 2-((3R,4aR,6aS,7R,10bR)-3-cyclopentyl-6a,10b-dimethyl-8-dihydromethylenedecahydro-1H-naphtho[2,1-d][1,3]dioxin-7-yl)acetaldehyde.

$^1$H NMR (400 MHz, CDCl$_3$) 9.65 (d, J=2.0 Hz, 1H), 4.85 (s, 1H), 4.60 (d, J=6.0 Hz, 1H), 4.43 (s, 1H), 4.03 (d, J=11.0 Hz, 1H), 3.53-3.42 (m, 2H), 2.55-2.21 (m, 5H), 2.14-2.06 (m, 2H), 1.86-1.80 (m, 1H), 1.72-1.67 (m, 3H), 1.61-1.43 (m, 7H), 1.38 (s, 3H), 1.26-1.09 (m, 3H), 0.83-0.66 (m, 3H).

Step 4

2-((3R,4aR,6aS,7R,10bR)-3-cyclopentyl-6a,10b-dimethyl-8-dihydromethylene decahydro-1H-naphtho[2,1-d][1,3]dioxin-7-yl)ethanol 2-((3R,4aR,6aS,7R,10bR)-3-cyclopentyl-6a,10b-dimethyl-8-dihydromethylene decahydro-1H-naphtho[2,1-d][1,3]dioxin-7-yl) acetaldehyde (70.00 g, 202.02 mmol) was dissolved in 1000 mL tetrahydrofuran, and sodium borohydride (22.93 g, 606.06 mmol) was added at 0° C., followed by stirring at 25° C. for 4 hours. The reaction was quenched by adding 500 mL water, and extracted with ethyl acetate (200 mL*5). The combined organic phases were washed with saturated sodium chloride solution (200 mL*1), dried over anhydrous sodium sulfate, filtered, and the filtrate was concentrated under reduced pressure. After that, the resulting residue was purified by silica gel column chromatography with the eluent system PE:EA=10:1 to 2:1 to give 2-((3R,4aR,6aS,7R,10bR)-3-cyclopentyl-6a,10b-dimethyl-8-dihydromethylene decahydro-1H-naphtho[2,1-d][1,3]dioxin-7-yl)ethanol, (40 g, yield: 56.8%).

$^1$H NMR (400 MHz, CDCl$_3$) 4.87 (s, 1H), 4.61 (d, J=6 Hz, 2H), 4.03 (d, J=11.2 Hz, 1H), 3.75 (s, 1H), 3.52-3.43 (m,

3H), 2.44-2.41 (m, 2H), 2.08-1.75 (m, 3H), 1.74-1.66 (m, 7H), 1.57-1.54 (m, 6H), 1.37 (s, 4H), 1.26-1.25 (m, 3H), 0.77 (s, 3H).

Step 5

(3R,4aR,6aS,7R,10bR)-7-(2-bromoethyl)-3-cyclopentyl-6a,10b-dimethyl-8-dihydromethylene decahydro-1H-naphtho[2,1-d][1,3]dioxin 2-((3R,4aR,6aS,7R,10bR)-3-cyclopentyl-6a,10b-dimethyl-8-dihydromethylene-1H-naphtho[2,1-d][1,3]dioxin-7-yl)ethanol (35.00 g, 100.42 mmol) was dissolved in 500 mL dichloromethane, and carbon tetrabromide (36.63 g, 110.46 mmol) and triphenylphosphine (28.97 g, 110.46 mmol) was added at 25° C., then stirred at 25° C. for 4 hours. The reaction was quenched with 200 mL water, extracted with dichloromethane (200 mL*3), and the organic phases were combined, washed with saturated sodium chloride solution (200 mL*1), dried over anhydrous sodium sulfate, filtered, and the filtrate was concentrated under reduced pressure. After that, the resulting residue was purified by silica gel column chromatography with the eluent system PE:EtOAc=10:1 to 5:1 to give (3R,4aR,6aS,7R,10bR)-7-(2-bromoethyl)-3-cyclopentyl-6a,10b-dimethyl-8-dihydromethylene decahydro-1H-naphtho[2,1-d][1,3] dioxin (40 g, yield: 96.82%).

$^1$H NMR (400 MHz, CDCl$_3$) 4.89 (s, 1H), 4.61 (d, J=6 Hz, 1H), 4.53 (s, 1H), 4.02 (d, J=11.2 Hz, 1H), 3.55-3.52 (m, 3H), 3.46-3.29 (m, 1H), 2.42 (s, 1H), 2.08 (s, 1H), 2.04-1.84 (m, 4H), 1.84-1.81 (m, 3H), 1.72-1.70 (m, 3H), 1.59-1.54 (m, 6H), 1.38 (s, 3H), 1.26-1.22 (m, 3H), 0.78 (s, 3H).

Step 6

4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)pyridine (3R,4aR,6aS,7R,10bR)-7-(2-bromoethyl)-3-cyclopentyl-6a,10b-dimeth yl-8-dihydromethylene decahydro-1H-naphtho[2,1-d][1,3] dioxin (10.00 g, 24.31 mmol) was dissolved in 150 mL N,N-dimethylformamide, and potassium carbonate (6.72 g, 48.62 mmol) and 4-hydroxypyridine (2.31 g, 24.31 mmol) were added at 20° C., then stirred at 80° C. for 10 hours. The reaction solution was concentrated under reduced pressure, diluted with 500 mL water, and extracted with ethyl acetate (250 mL*3). The organic phases were combined, washed with saturated sodium chloride solution (200 mL*1), dried over anhydrous sodium sulfate and filtered, and the filtrate was concentrated under reduced pressure. After that, the resulting residue was purified by silica gel column chromatography with an eluent system of PE:EtOAc=5:1 to 1:1 to give 5.3 g 4-(2-((3R,4aR,6aS,7R,10bR)-3-cyclopentyl-6a,10b-dimethyl-8-dihydromethylene decahydro-1H-naphtho[2,1-d][1,3]dioxin-7-yl) ethoxy) pyridine 297.

MS m/z (ESI): 426.6 [M+1]

$^1$H NMR (400 MHz, CDCl$_3$) 8.42 (d, J=5.0 Hz, 2H), 6.78 (d, J=5.3 Hz, 2H), 4.91 (s, 1H), 4.74-4.44 (m, 2H), 4.14-4.07 (m, 1H), 4.04 (d, J=11.3 Hz, 1H), 3.94-3.84 (m, 1H), 3.56-3.40 (m, 2H), 2.44 (d, J=12.8 Hz, 1H), 2.29 (dq, J=3.3, 13.2 Hz, 1H), 2.14-1.97 (m, 3H), 1.93-1.79 (m, 4H), 1.71 (dd, J=4.4, 8.7 Hz, 3H), 1.61-1.41 (m, 6H), 1.38 (s, 3H), 1.30-1.16 (m, 3H), 0.80 (s, 3H).

Compound 420

4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-2-methoxypyridine

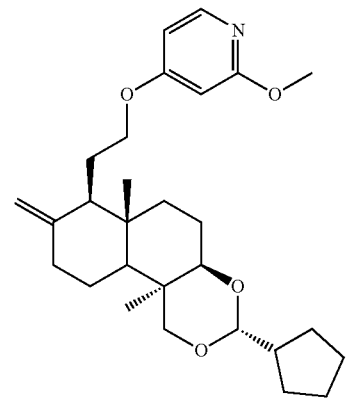

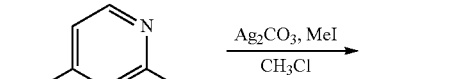

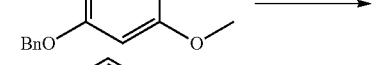

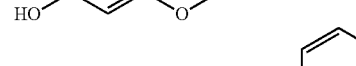

420

Step 1

4-benzyloxy-2-methoxypyridine

4-Benzyloxypyridin-2-ol (40.00 g, 198.79 mmol) was dissolved in chloroform (500.00 mL), and silver carbonate (109.63 g, 397.58 mmol, 18.03 mL) and methyl iodide (282.16 g, 1.99 mol, 123.75 mL) were added successively, and then stirred at 40° C. for 12 hours. The reaction was filtered, the filtrate was concentrated, and the residue was purified by column chromatography (silica, petroleum ether/ethyl acetate=30/1 to 10/1) to give 4-benzyloxy-2-methoxypyridine (a white solid, 18 g, yield: 42.06%).

$^1$H NMR (400 MHz, CDCl3) 8.00 (d, J=6 Hz, 1H), 7.43-7.36 (m, 5H), 6.58-6.56 (m, 1H), 6.29 (d, J=1.6 Hz, 1H), 5.09 (s, 2H), 3.94 (s, 3H).

Step 2

2-methoxypyridin-4-ol

4-Benzyloxy-2-methoxypyridine (1.00 g, 4.65 mmol) was dissolved in ethanol (20.00 mL), and palladium on carbon (100.00 mg, 10% purity) was added, and then stirred at 30° C. in 30 PSI hydrogen atmosphere for 3 hours. The reaction was filtered and the filtrate was concentrated to give 2-methoxypyridin-4-ol (a white solid, 450 mg, yield: 70.38%).

$^1$H NMR (400 MHz, CDCl3) 7.67 (d, J=6.4 Hz, 1H), 6.35-6.32 (m, 1H), 6.05 (d, J=2H, 1H), 3.88 (s, 3H).

Step 3

4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-2-methoxypyridine (3R,4aR,6aS,7R,10bR)-7-(2-bromoethyl)-3-cyclopentyl-6a,10b-dimethyl-8-dihydromethylene decahydro-1H-naphtho[2,1-d][1,3]dioxin (200.00 mg, 486.13 umol) was dissolved in N,N-dimethylformamide (10.00 mL), and cesium carbonate (316.78 mg, 972.26 umol) and 2-methoxypyridin-4-ol (66.91 mg, 534.74 umol) were added successively, then stirred at 70° C. for 4 hours. The reaction was quenched with 10 mL water and extracted with ethyl acetate (10 mL*3). The organic phases were combined and washed with saturated brine (10 mL*1), dried over anhydrous sodium sulfate, filtered, and the filtrate was concentrated. The residue was separated by preparative liquid chromatography (HCOOH) to give 4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-2-methoxypyridine 420 (50 mg, yield: 14.75%).

MS m/z (ESI):456.7 [M+1]

$^1$H NMR (400 MHz, CDCl3) 7.96 (d, J=6 Hz, 1H), 6.47-6.45 (m, 1H), 6.16 (d, J=2 Hz, 1H), 4.90 (s, 1H), 4.63-4.59 (m, 2H), 4.07-4.03 (m, 2H), 3.93 (s, 3H), 3.86-3.84 9 m, 1H), 3.53-3.44 (m, 2H), 2.45-2.42 (m, 1H), 2.08-2.02 (m, 1H), 1.83-1.71 (m, 3H), 1.71-1.70 (m, 4H), 1.69-1.54 (m, 10H), 1.38 (s, 3H), 1.27-1.25 (m, 3H), 0.80 (s, 3H).

Compound 321

4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-pyridin-2-amine

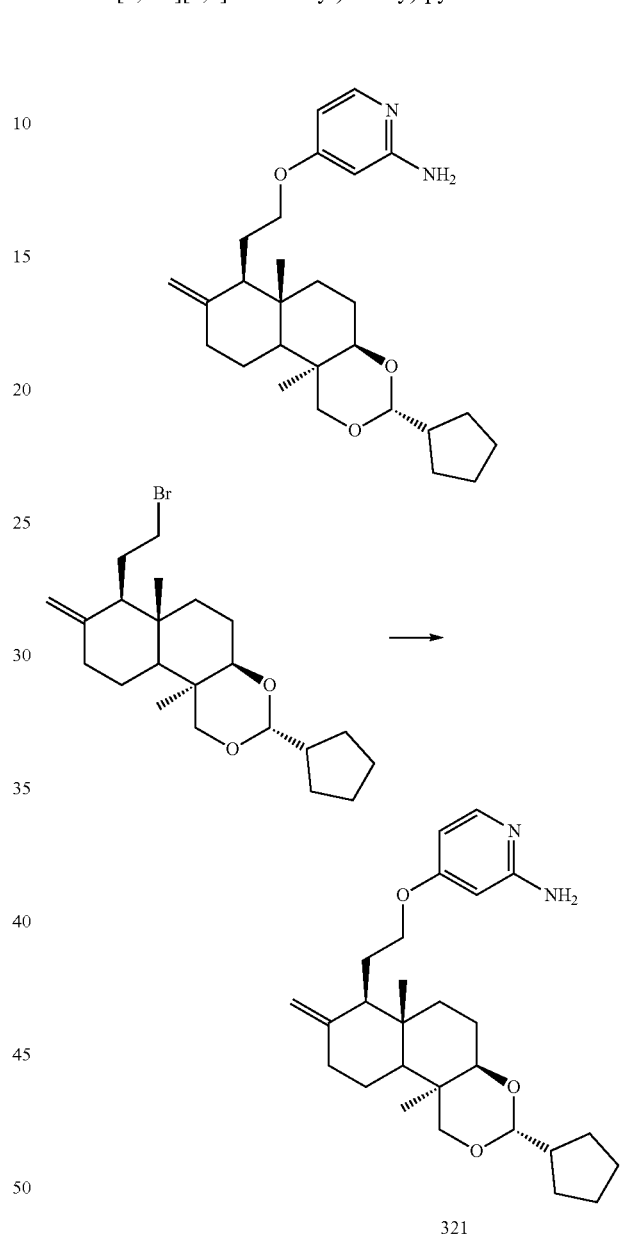

321

Step 1

4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-pyridin-2-amine (3R,4aR,6aS,7R,10bR)-7-(2-bromoethyl)-3-cyclopentyl-6a,10b-dimeth yl-8-methylenedecahydro-1H-naphtho[2,1-d][1,3]dioxin (500 mg, 1.14 mmol) was dissolved in 10 mL of N,N-dimethylformamide, followed by the sequential addition of 2-amino-4-hydroxypyridine (250 mg, 2.28 mmol) and potassium carbonate (314 mg, 2.28 mmol), then stirred at 60° C. for 12 hours. After the reaction was completed, the reaction solution was concentrated and separated by a column (Eluents by MeOH:DCM from 1:100 to 1:30) to give 4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-pyridin-2-amine 321 (100 mg, yield: 20%).

MS m/z (ESI): 441.6[M+1]

$^1$H NMR (400 MHz, CDCl3) 7.68 (br. s., 1H), 6.29 (s., 1H), 6.06 (br. s., 1H), 5.88 (brs, 2H), 4.89 (s, 1H), 4.59-4.55 (m, 2H), 4.09-3.89 (m, 3H), 3.48-3.43 (m, 2H), 2.52-2.13 (m, 2H), 2.11-1.27 (m, 17H), 1.36 (s, 3H), 1.25-0.87 (m, 2H), 0.79 (s, 3H).

Compound 319

4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-2-methylpyridine

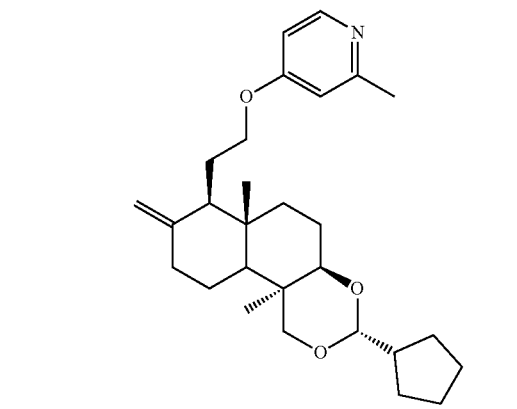

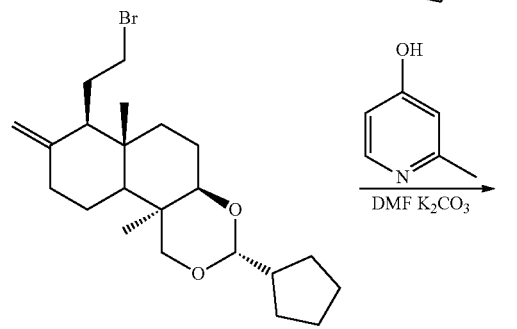

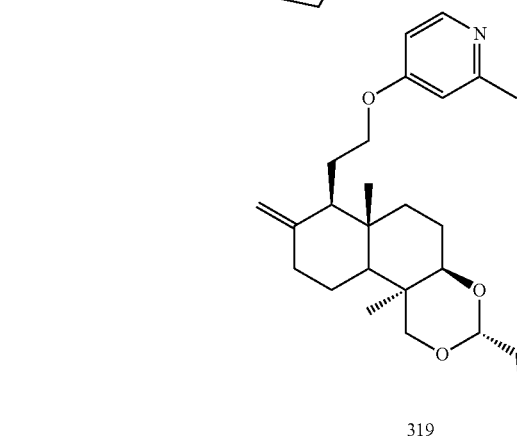

319

Step 1

4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-2-methylpyridine 2-Methylpyridin-4-ol (60 mg, 0.55 mmol) was dissolved in anhydrous N,N-dimethylformamide (10 mL), and potassium carbonate (75.5 mg, 0.55 mmol) and (3R,4aR,6aS,7R,10bR)-7-(2-bromoethyl)-3-cyclopentyl-6a,10b-dimethyl-8-methylenedecahydro-1H-naphtho[2,1-d][1,3]dioxin (150 mg, 0.37 mmol) were successively added to the reaction solution and stirred overnight at 60° C. The reaction solution was cooled and extracted with dichloromethane (30 mL). The organic layer was washed with water (10 mL×3), dried over anhydrous sodium sulfate, filtered, and the filtrate was concentrated under reduced pressure and then separated by column chromatography to give 4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-2-methylpyridine 319 (80 mg, yield: 50%).

MS m/z (ESI): 440.8 [M+1]

$^1$H NMR (400 MHz, CDCl$_3$) 8.31 (d, J=6.0 Hz, 1H), 6.67-6.64 (m, 1H), 4.91 (s, 1H), 4.63-4.60 (m, 2H), 4.10-3.88 (m, 3H), 3.53-3.45 (m, 2H), 2.54 (s, 3H), 2.46-1.56 (m, 18H), 1.55 (s, 3H), 1.39-1.27 (m, 3H), 0.81 (s, 3H).

Compound 430

4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)pyridin-2(1H)-one

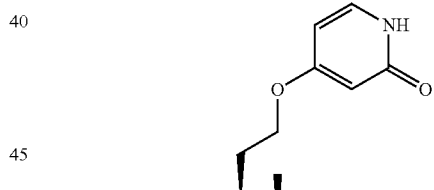

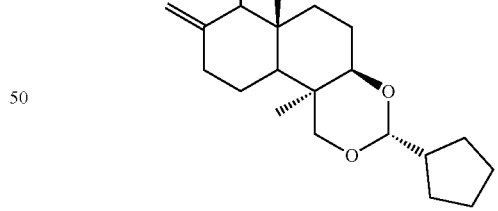

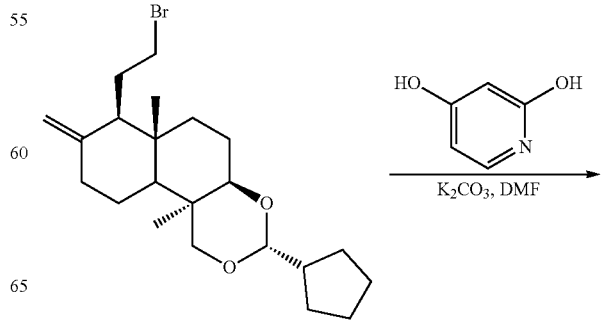

Step 1

4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)pyridin-2(1H)-one

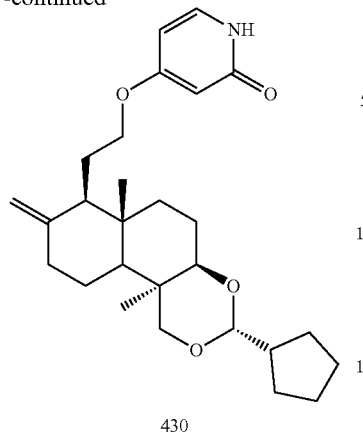

430

(3R,4aR,6aS,7R,10bR)-7-(2-bromoethyl)-3-cyclopentyl-6a,10b-dimethyl-8-methylenedecahydro-1H-naphtho[2,1-d][1,3]dioxin (400.00 mg, 972.27 umol) was dissolved in anhydrous N,N-dimethylformamide (10.00 mL), and potassium carbonate (268.75 mg, 1.94 mmol) and pyridine-2,4-diol (108.02 mg, 972.27 umol) were successively added and stirred at 70° C. under nitrogen atmosphere for 12 hours. The reaction was quenched by adding 30 mL water and extracted with ethyl acetate (30.00 mL). The organic phase was washed with water (30 mL) and saturated brine (30 mL) in sequence, dried over anhydrous sodium sulfate, filtered, and the filtrate was concentrated under reduced pressure. The residue was separated by column chromatography (silica, ethyl acetate/methanol=10/1) to give 4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)pyridin-2(1H)-one 430 (100 mg, yield: 23.29%).

MS m/z (ESI):442.2 [M+1]

$^1$H NMR (400 MHz, CDCl3) 12.46 (br. s., 1H), 7.20 (d, J=7.3 Hz, 1H), 5.95 (dd, J=1.9, 7.2 Hz, 1H), 5.80 (s, 1H), 4.88 (s, 1H), 4.60 (d, J=5.8 Hz, 1H), 4.55 (s, 1H), 4.02 (d, J=11.0 Hz, 2H), 3.86-3.75 (m, 1H), 3.58-3.36 (m, 2H), 2.42 (d, J=13.1 Hz, 1H), 2.32-2.19 (m, 1H), 2.13-2.03 (m, 1H), 2.02-1.93 (m, 2H), 1.90-1.81 (m, 2H), 1.78-1.63 (m, 5H), 1.61-1.49 (m, 4H), 1.48-1.39 (m, 2H), 1.36 (s, 3H), 1.29-1.16 (m, 3H), 0.77 (s, 3H).

Compound 357

4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-1-methylpyridin-2(1H)-one

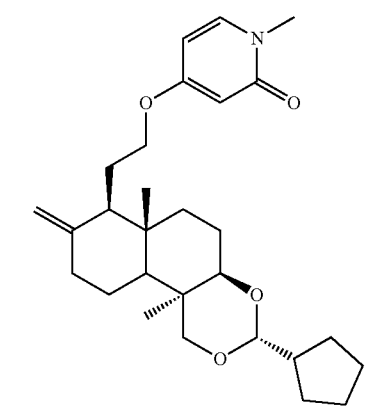

$\xrightarrow{\text{MeI}}{\text{NaH, DMF}}$

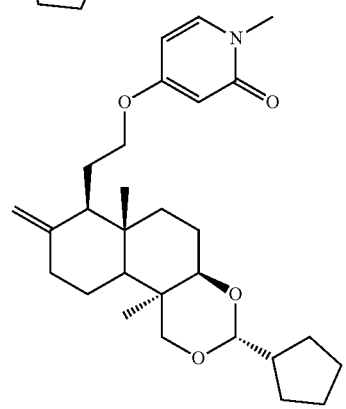

357

Step 1

4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-1-methylpyridin-2(1H)-one 4-(2-((3R,4aR,6aS,7R,10bR)-3-cyclopentyl-6a,10b-dimethyl-8-methylenedecahydro-1H-naphtho[2,1-d][1,3]dioxin-7-yl)ethoxy)pyridin-2(1H)-one (50 mg, 0.11 mmol) was dissolved in anhydrous N,N-dimethylformamide (10 mL), sodium hydrogen (4.1 mg, 0.17 mmol) was added at 0° C. and stirred for 15 minutes under nitrogen atmosphere at 0° C. Methyl iodide (190 mg, 1.34 mmol) was added to the reaction solution and stirred at 30° C. for 12 hours. The reaction solution was quenched with water and extracted with dichloromethane (30 mL). The organic layer was washed with water (10 mL×3), dried over anhydrous magnesium sulfate, filtered, and the filtrate was concentrated under reduced pressure and separated by thin layer chromatography to give 4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-1-methylpyridin-2(1H)-one 357 (20 mg, yield: 39%).

MS m/z (ESI): 478.3 [M+23]

$^1$H NMR (400 MHz, CDCl$_3$) 7.11 (d, J=7.2 Hz, 1H), 5.88-5.84 (m, 2H), 4.87 (s, 1H), 4.61-4.54 (m, 2H), 4.04-3.42 (m, 8H), 2.43-1.54 (m, 18H), 1.52 (s, 3H), 1.37-1.24 (m, 3H), 0.77 (s, 3H).

Compound 339

4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy) piperidin-3-amine

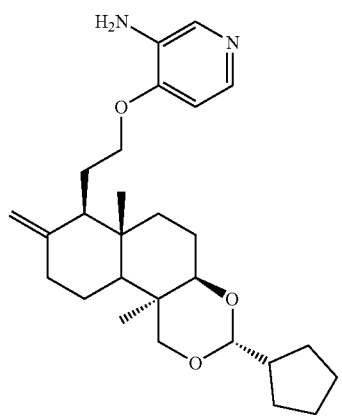

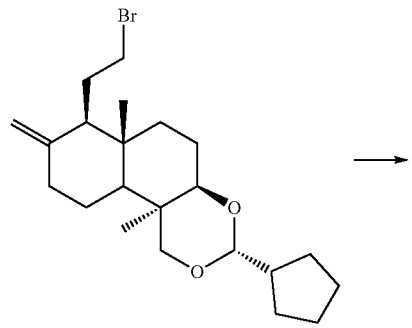

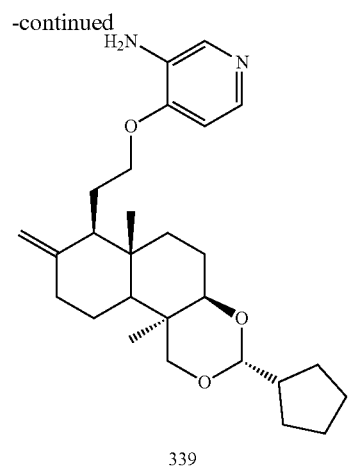

339

Step 1

4-(2-((3R,4aR,6aS,7R,10bR)-3-cyclopentyl-6a, 10b-dimethyl-8-dihydromethylene decahydro-1H-naphtho[2,1-d][1,3]dioxin-7-yl)ethoxy) piperidin-3-amine (3R,4aR,6aS,7R,10bR)-7-(2-bromoethyl)-3-cyclopentyl-6a,10b-dimethyl-8-methylenedecahydro-1H-naphtho[2,1-d][1,3]dioxin (100 mg, 0.24 mmol) was dissolved in 10 mL of N,N-dimethylformamide, followed by the addition of 3-amino-4-hydroxypyridine (32.12 mg, 0.29 mmol) and potassium carbonate (67.19 mg, 0.49 mmol), then stirred at 60° C. overnight. After the reaction was completed, the reaction solution was diluted with water and then extracted with dichloromethane. The resulting organic layer was washed with saturated brine, dried over anhydrous magnesium sulfate, concentrated, and separated by a preparative plate (Develop: EtOAc:MeOH=10:1) to give 4-(2-((3R,4aR,6aS,7R,10bR)-3-cyclopentyl-6a,10b-dimethyl-8-dihydromethylene decahydro-1H-naphtho[2,1-d][1,3]dioxin-7-yl) ethoxy) piperidin-3-amine 339 (30 mg, yield: 28.01%).

MS m/z (ESI): 441.2 [M+1]

$^1$H NMR (400 MHz, CDCl3) 8.16 (s, 1H), 8.00 (s, 1H), 6.76 (s, 1H), 4.91 (s, 1H), 4.61-4.59 (m, 2H), 4.18 (s, 1H), 4.04-4.01 (m, 2H), 3.55-3.48 (m, 2H), 2.44 (d, J=12.0 Hz, 1H), 2.33-2.23 (m, 1H), 2.08-1.43 (m, 16H), 1.37 (s, 3H), 1.25-1.15 (m, 3H), 0.79 (s, 3H).

Compound 344

4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-3-fluoropyridine

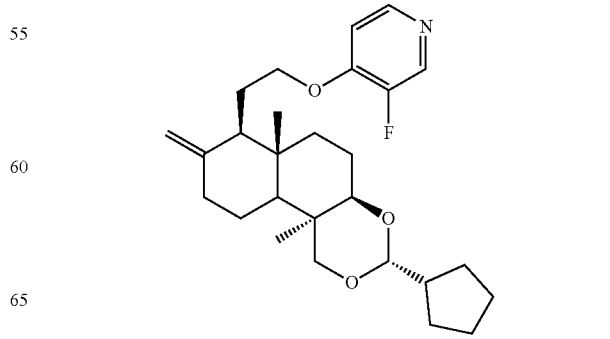

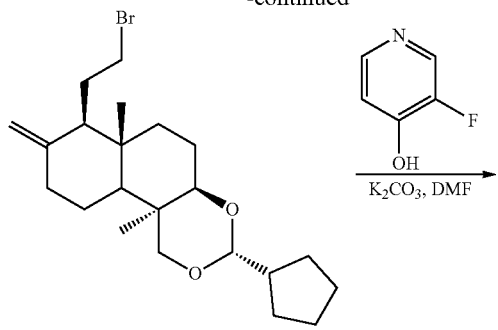

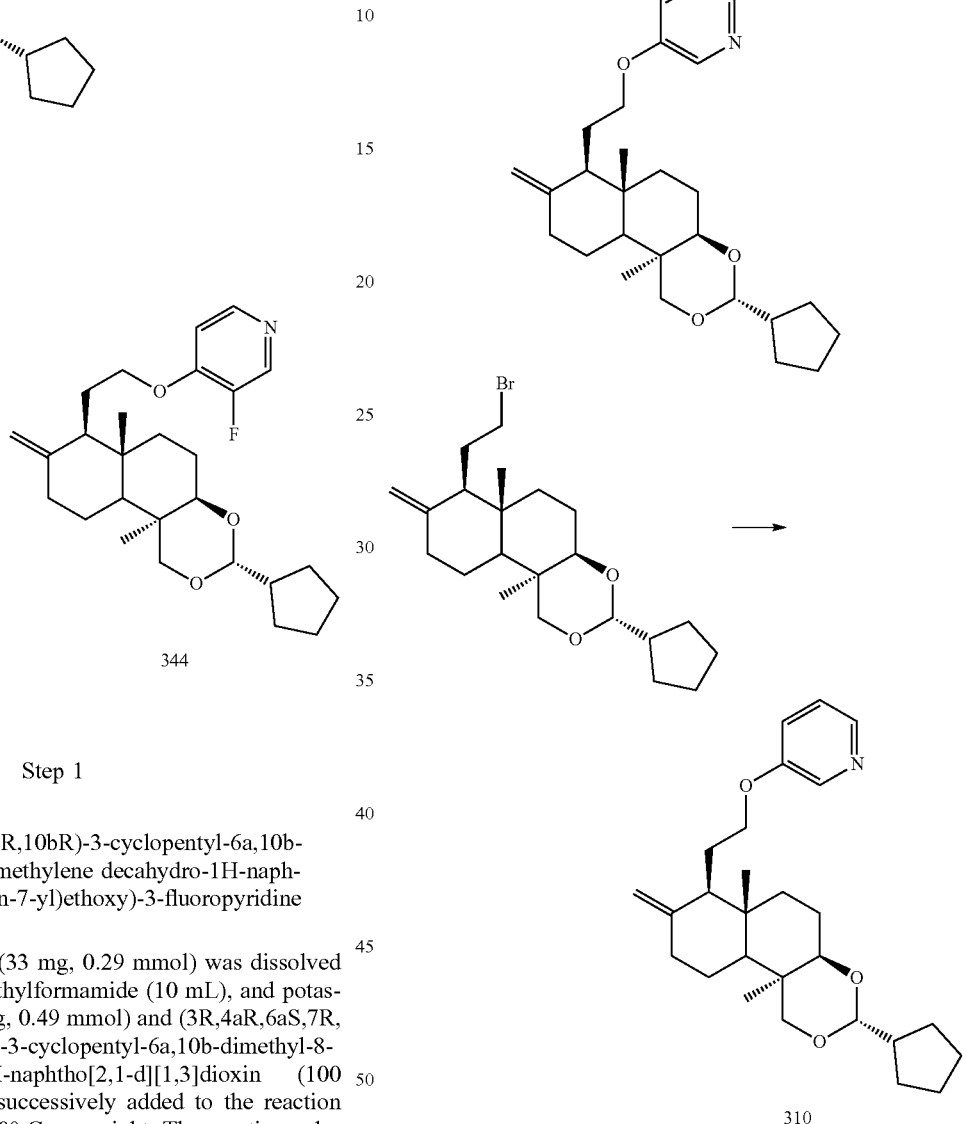

Step 1

4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-3-fluoropyridine 3-Fluoropyridin-4-ol (33 mg, 0.29 mmol) was dissolved in anhydrous N,N-dimethylformamide (10 mL), and potassium carbonate (67.2 mg, 0.49 mmol) and (3R,4aR,6aS,7R,10bR)-7-(2-bromoethyl)-3-cyclopentyl-6a,10b-dimethyl-8-methylenedecahydro-1H-naphtho[2,1-d][1,3]dioxin (100 mg, 0.24 mmol) were successively added to the reaction mixture and stirred at 60° C. overnight. The reaction solution was cooled and extracted with dichloromethane (30 mL). The organic layer was washed with water (10 mL×3), dried over anhydrous magnesium sulfate, filtered, and the filtrate was concentrated under reduced pressure and separated on a thin layer chromatography plate to give 4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-3-fluoropyridine 344 (55 mg, yield: 51.0%).

MS m/z (ESI): 460.3 [M+1]

$^1$H NMR (400 MHz, CDCl$_3$) 8.37 (s, 3H), 8.29 (s, 3H), 6.86 (s, 3H), 4.90 (s, 1H), 4.61-3.95 (m, 5H), 3.51-3.43 (m, 2H), 2.45-1.53 (m, 18H), 1.51 (s, 3H), 1.37-1.25 (m, 3H), 0.879 (s, 3H).

Compound 310

3-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-pyridine Step 1

3-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-pyridine (3R,4aR,6aS,7R,10bR)-7-(2-bromoethyl)-3-cyclopentyl-6a,10b-dimethyl-8-methylenedecahydro-1H-naphtho[2,1-d][1,3]dioxin (150 mg, 0.365 mmol) was dissolved in 10 mL anhydrous dimethyl sulfoxide, and 3-hydroxypyridine (52 mg, 0.547 mmol) and potassium hydroxide (30.6 mg, 0.547 mmol) were added successively and stirred at room temperature for 18 hours. After the reaction was completed, the reaction solution was diluted with water and then extracted with dichloromethane. The resulting organic phase was washed with anhydrous sodium sulfate, concentrated, and separated by a column (Eluents:PE:EtOAc=2:1) to give 3-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-pyridine 310 (50 mg, yield: 32.26%).

MS m/z (ESI): 426.7 [M+1]

¹H NMR (400 MHz, CDCl3) 8.29 (s, 1H), 8.21 (s, 1H), 7.25-7.20 (m, 2H), 4.89 (s, 1H), 4.60-4.59 (m, 2H), 4.10-4.09 (m, 1H), 4.03 (d, J=11.2 Hz, 1H), 3.89-3.83 (m, 1H), 3.51-3.43 (m, 2H), 2.43 (d, J=12.8 Hz, 1H), 2.33-2.25 (m, 1H), 2.09-1.53 (m, 19H), 1.37 (s, 3H), 1.26-1.18 (m, 3H), 0.77 (s, 3H).

Compound 443

5-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-pyridin-3-ol

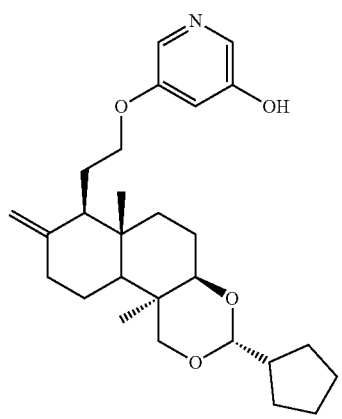

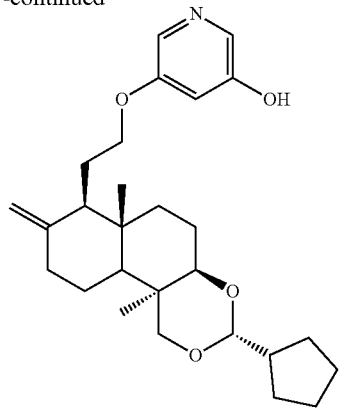

443

Step 1

5-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-pyridin-3-ol (3R,4aR,6aS,7R,10bR)-7-(2-bromoethyl)-3-cyclopentyl-6a,10b-dimethyl-8-dihydromethylene-1H-naphtho[2,1-d][1,3]dioxin (500.00 mg, 1.22 mmol) was dissolved in N,N-dimethylformamide (10.00 mL), followed by the successive addition of potassium carbonate (337.23 mg, 2.44 mmol) and pyridine-3,5-diol (149.10 mg, 1.34 mmol), then stirred at 80° C. for 12 hours. The reaction was quenched by adding 10 mL water and then extracted with ethyl acetate (20.00 mL*3). The organic phase was washed with saturated brine (20 mL), dried over anhydrous sodium sulfate, filtered, and the filtrate was concentrated under reduced pressure. The residue was separated by preparative liquid chromatography to give 5-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-pyridin-3-ol 443 (28 mg, yield: 5.15%).

MS m/z (ESI): 442.2[M+1]

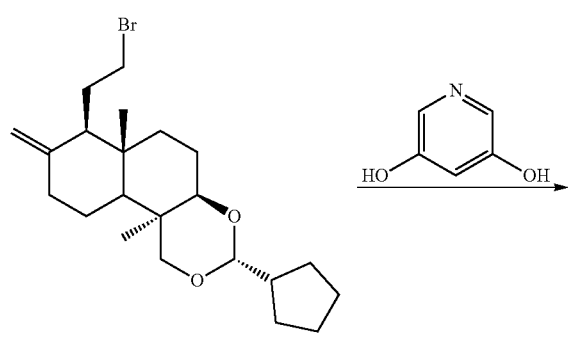

¹H NMR (400 MHz, CDCl3) 7.95 (s, 1H), 7.75 (s, 1H), 6.88 (s, 1H), 4.89 (s, 1H), 4.62-4.56 (m, 2H), 4.08-4.02 (m, 4H), 3.86 (d, J=6 Hz, 1H), 3.51-3.43 (m, 2H), 2.41 (s, 1H), 2.07 (s, 1H), 2.01-1.83 (m, 3H), 1.83-1.71 (m, 4H), 1.57-1.50 (m, 4H) 1.69-1.67 (m, 3H), 1.57-1.52 (m, 5H), 1.37-1.25 (m, 3H), 0.79 (s, 3H).

Compound 442

3-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-5-methoxypyridine

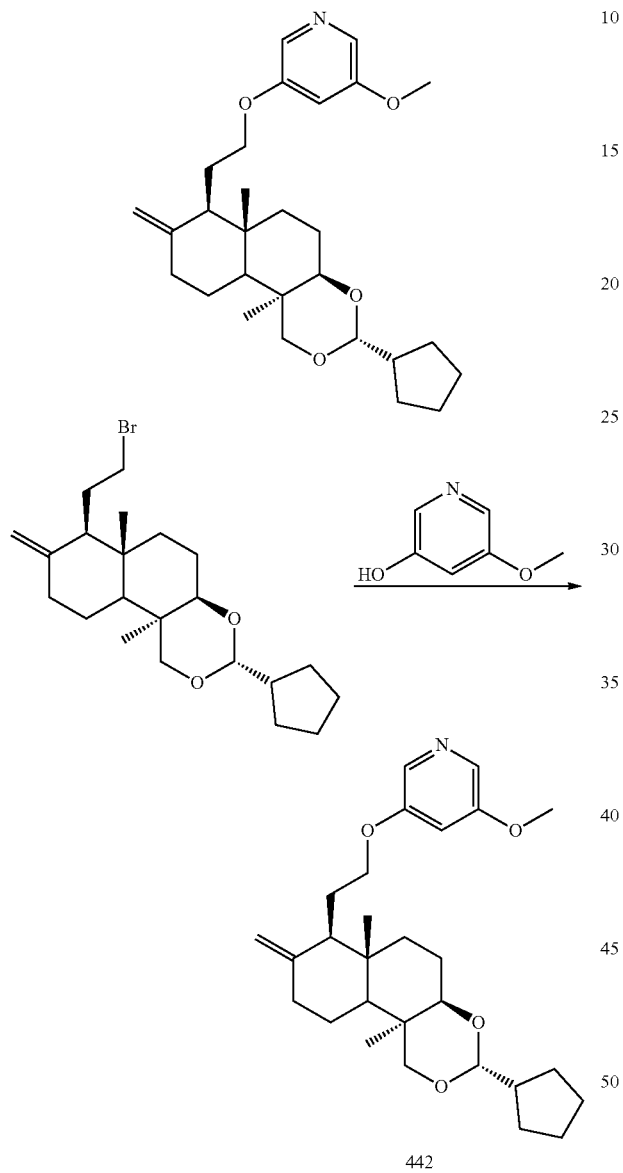

442

Step 1

3-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-5-methoxypyridine (3R,4aR,6aS,7R,10bR)-7-(2-bromoethyl)-3-cyclopentyl-6a,10b-dimethyl-8-dihydromethylene decahydro-1H-naphtho[2,1-d][1,3]dioxin (1.00 g, 2.43 mmol) was dissolved in N,N-dimethylformamide (10.00 mL), followed by successive addition of potassium carbonate (671.70 mg, 4.86 mmol) and 5-methoxypyridin-3-ol (334.47 mg, 2.67 mmol), then stirred at 80° C. for 12 hours. The reaction was quenched by adding 10 mL water and then extracted with ethyl acetate (20.00 mL*3). The organic phase was washed with saturated brine (20 mL), dried over anhydrous sodium sulfate, filtered, and the filtrate was concentrated under reduced pressure. The residue was separated by column chromatography (silica, petroleum ether/ethyl acetate=10/1 to 2/1) to give 3-(2-((3R,4aR,6aS,7R,10 bR)-3-cyclopentyl-6a,10b-dimethyl-8-dihydromethylene decahydro-1H-naphtho[2,1-d][1,3]dioxin-7-yl)ethoxy)-5-methoxypyridine 442 (700 mg, yield: 63.37%).

MS m/z (ESI): 456.6[M+1]

$^1$H NMR (400 MHz, CDCl3) 7.91 (d, J=8 Hz, 2H), 6.69 (t, J=4.4 Hz, 1H), 4.89 (s, 1H), 4.59 (t, J=6 Hz, 2H), 4.08-4.02 (m, 2H), 3.84 (s, 4H), 3.51-3.43 (m, 2H), 2.44-2.40 (m, 2H), 2.05-2.01 (m, 3H), 1.88-1.83 (m, 4H), 1.60 (s, 3H), 1.55-1.35 (m, 6H), 1.45-1.27 (m, 3H) 1.26-1.21 (m, 3H), 0.79 (s, 3H).

Compound 317

2-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy) pyridine

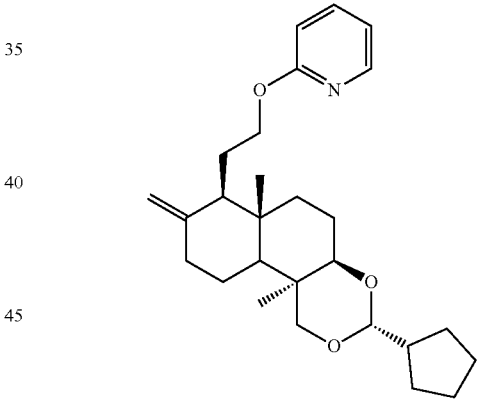

317

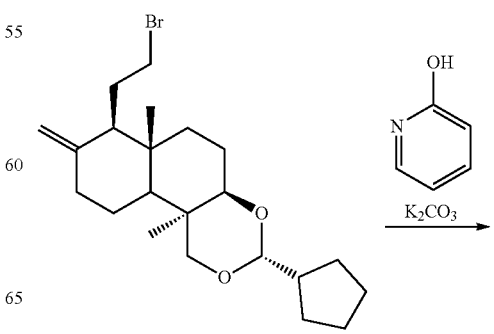

75
-continued

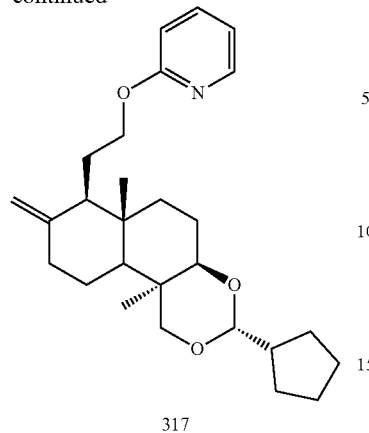

317

Step 1

2-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy) pyridine Pyridin-2-ol (45.1 mg, 0.47 mmol) was dissolved in anhydrous N,N dimethylformamide (5 mL), followed by successive addition of potassium carbonate (75.6 mg, 0.54 mmol) and (3R,4aR,6aS,7R,10bR)-7-(2-bromoethyl)-3-cyclopentyl-6a,10b-dimethyl-8-dihydromethylene decahydro-1H-naphtho[2,1-d][1,3]dioxin (150 mg, 0.37 mmol), then stirred at 80° C. overnight. The reaction solution was cooled and extracted with dichloromethane (30 mL). The organic layer was washed with water (10 mL×3), dried over anhydrous magnesium sulfate, filtered, and the filtrate was concentrated under reduced pressure and purified by column chromatography to give 40 mg 2-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy) pyridine 317.

MS m/z (ESI): 426.1 [M+1]

$^1$H NMR (400 MHz, CDCl$_3$) 8.14 (d, J=2.4 Hz, 1H), 7.58-7.54 (m, 1H), 6.86-6.83 (m, 1H), 6.72 (d, J=8.4 Hz, 1H), 4.88 (s, 1H), 4.69 (s, 1H), 4.61 (d, J=6.0 Hz, 1H), 4.40-4.02 (m, 3H), 3.52-3.42 (m, 2H), 2.43-1.51 (m, 18H), 1.37 (s, 3H), 1.25-1.21 (m, 3H), 0.78 (s, 3H).

Compound 351

4-((2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)methyl)pyridine

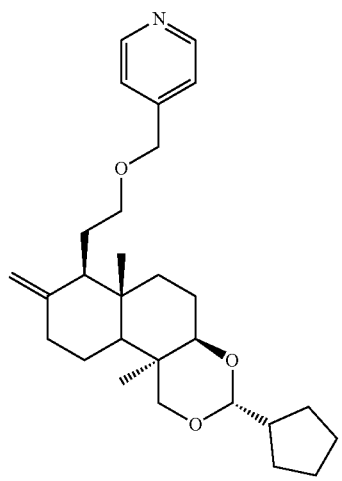

76
-continued

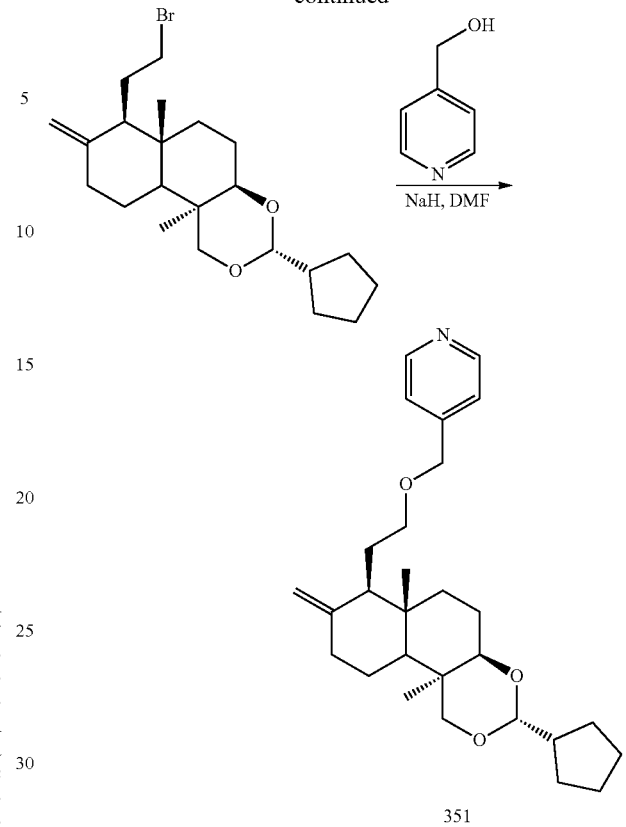

351

Step 1

4-((2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)methyl)pyridine Sodium hydrogen (14.6 mg, 0.36 mmol) was dissolved in anhydrous N,N-dimethylformamide (10 mL), added with pyridine-4-benzyl alcohol (26.5 mg, 0.24 mmol) at 0° C., and stirred under nitrogen atmosphere at 0° C. for 15 minutes. (3R,4aR,6aS,7R,10bR)-7-(2-bromoethyl)-3-cyclopentyl-6a,10b-dimethyl-8-methylenedecahydro-1H-naphtho[2,1-d][1,3]dioxin (100 mg, 0.24 mmol) was added to the reaction mixture and stirred at 25° C. for 2 hours. The reaction solution was cooled and extracted with dichloromethane (30 mL). The organic layer was washed with water (10 mL×3), dried over anhydrous magnesium sulfate, filtered, and the filtrate was concentrated under reduced pressure and then separated on a thin layer chromatography plate to give 4-((2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)methyl)pyridine 351 (60 mg, yield: 56%).

MS m/z (ESI): 440.2 [M+1]

$^1$H NMR (400 MHz, CDCl$_3$) 8.60 (d, J=4.0 Hz, 1H), 7.27 (d, J=5.6 Hz, 1H), 4.83 (s, 1H), 4.61-4.49 (m, 4H), 4.02 (d, J=11.2 Hz, 1H), 3.57-3.37 (m, 4H), 2.42-1.54 (m, 18H), 1.52 (s, 3H), 1.36-1.23 (m, 3H), 0.79 (s, 3H).

Compound 289

4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-2-methyl-1H-pyrazole

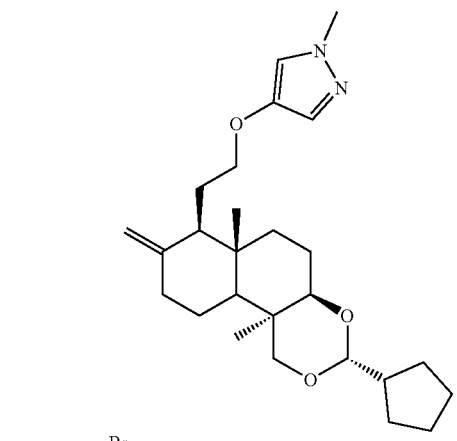

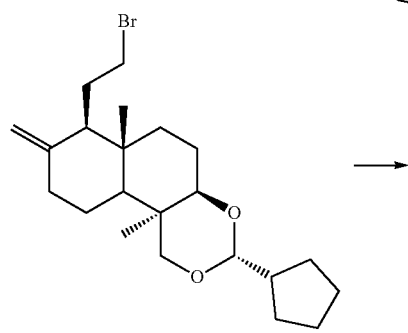

289

Step 1

4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-2-methyl-1H-pyrazole 1-Methyl-1H-imidazol-4-ol (28.61 mg, 0.292 mmol) was dissolved in 5 mL N,N-dimethylformamide, and added with sodium hydride (11.67 mg, 0.486 mmol) at 0° C., then stirred at 0° C. for 15 minutes. (3R,4aR,6aS,7R,10bR)-7-(2-bromoethyl)-3-cyclopentyl-6a,10b-dimethyl-8-methylenedecahydro-1H-naphtho[2,1-d][1,3]dioxin (100 mg, 0.243 mmol) was added at 0° C., then stirred at 0° C. for 12 hours. The reaction was quenched with 10 mL water and extracted with dichloromethane (25 mL*3), the organic phases were combined, washed with saturated sodium chloride solution (25 mL*2), dried over anhydrous sodium sulfate, filtered, and the filtrate was concentrated under reduced pressure. After that, the resulting residue was purified by thin layer chromatography to give 4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-2-methyl-1H-pyrazole 289 (20 mg, yield: 19.2%).

MS m/z (ESI): 429.5[M+1]

$^1$H NMR (400 MHz, CDCl$_3$) (s, 1H), 7.00 (s, 1H), 4.86 (s, 1H), 4.61-4.56 (m, 2H), 4.02 (d, J=11.6 Hz, 1H), 3.93-3.80 (m, 1H), 3.72 (s, 3H), 3.71-3.70 (m, 1H), 3.50-3.42 (m, 2H), 2.43-2.20 (m, 2H), 2.15-1.50 (m, 16H), 1.36 (s, 3H), 1.24-1.20 (m, 3H), 0.77 (s, 3H).

Compound 422

4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)benzoic acid

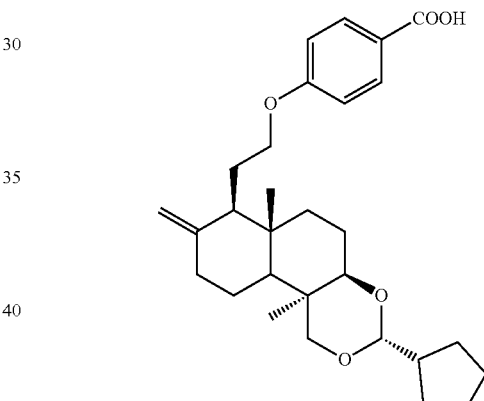

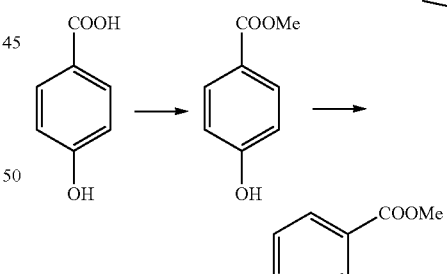

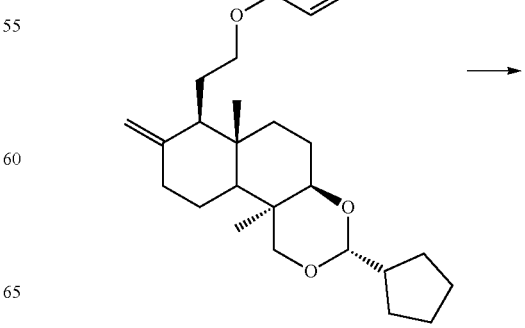

12.5 Hz, 1H), 3.42 (d, J=11.3 Hz, 1H), 2.41 (d, J=13.1 Hz, 1H), 2.26 (dq, J=3.3, 13.2 Hz, 1H), 2.05-1.42 (m, 16H), 1.35 (s, 3H), 1.27-1.15 (m, 3H), 0.78 (s, 3H).

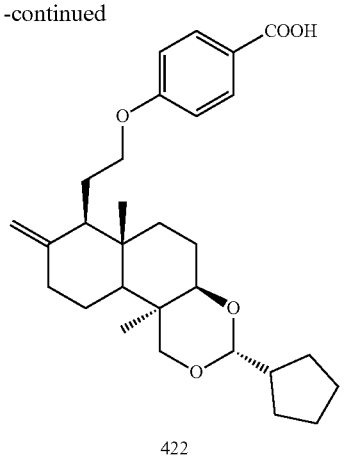

422

Step 1

Methyl 4-hydroxybenzoate

4-Hydroxybenzoic acid (2.00 g, 14.48 mmol) was dissolved in 20 mL methanol, and sulfuric acid (184.00 mg, 1.88 mmol) was added at room temperature, and then stirred at 70° C. for 48 hours. The reaction solution was added with 200 mL aqueous sodium bicarbonate solution (4M) and extracted with ethyl acetate (50 mL*3). The organic phases were combined, washed with saturated sodium chloride solution (50 mL*2), dried over anhydrous sodium sulfate, and filtered. The filtrate was concentrated under reduced pressure to give methyl 4-hydroxybenzoate (a white solid, 1.6 g, crude product).

$^1$H NMR (400 MHz, CDCl$_3$) 7.97 (d, J=8.5 Hz, 2H), 6.92 (d, J=8.5 Hz, 2H), 6.73 (br. s., 1H), 3.93 (s, 3H).

Step 2

Methyl 4-(2-((3R,4aR,6aS,7R,10bR)-3-cyclopentyl-6a, 10b-dimethyl-8-dihydromethylene decahydro-1H-naphtho[2,1-d][1,3]dioxin-7-yl)ethoxy)benzoate (3R,4aR,6aS,7R,10bR)-7-(2-bromoethyl)-3-cyclopentyl-6a,10b-dimeth yl-8-methylenedecahydro-1H-naphtho[2,1-d][1,3]dioxin (300.00 mg, 729.20 umol) was dissolved in 5 mL N,N-dimethylformamide, and cesium carbonate (700.88 mg, 2.15 mmol) and methyl 4-hydroxybenzoate (122.00 mg, 802.12 umol) were successively added at room temperature, and then stirred at 80° C. for 8 hours. 50 mL water was added and the mixture was extracted with ethyl acetate (50 mL*3). The organic phases were combined, washed with saturated sodium chloride solution (50 mL*2), dried over anhydrous sodium sulfate, and filtered. The filtrate was concentrated under reduced pressure to give methyl 4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)benzoate (a bright yellow oil, 250 mg, crude product).

$^1$H NMR (400 MHz, CDCl$_3$) 7.95 (d, J=9.0 Hz, 2H), 6.86 (d, J=8.8 Hz, 2H), 4.87 (s, 1H), 4.63-4.50 (m, 2H), 4.15-4.00 (m, 2H), 3.86 (s, 3H), 3.86-3.82 (m, 1H), 3.48 (dd, J=4.8,

Step 3

4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)benzoic acid Methyl 4-(2-((3R,4aR,6aS,7R,10bR)-3-cyclopentyl-6a, 10b-dimethyl-8-dihydromethylene decahydro-1H-naphtho [2,1-d][1,3]dioxin-7-yl)ethoxy)benzoate (250.00 mg, 517.97 umol) was dissolved in 5 mL methanol, 5 mL water and potassium hydroxide (290.63 mg, 5.18 mmol) were successively added at room temperature, and then stirred at 80° C. for 8 hours. 100 mL water was added and the mixture was extracted with ethyl acetate (50 mL*3). The organic phases were combined, washed with saturated sodium chloride solution (50 mL*2), dried over anhydrous sodium sulfate, and filtered. The filtrate was concentrated under reduced pressure to give 4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)benzoic acid 422 (210 mg, yield: 84.61%).

MS m/z (ESI): 467.3 [M-1]

$^1$H NMR (400 MHz, CDCl$_3$) 7.66 (br. s., 2H), 6.43 (br. s., 2H), 4.89 (br. s., 1H), 4.60 (d, J=9.3 Hz, 2H), 4.03 (d, J=10.8 Hz, 1H), 3.91 (d, J=19.1 Hz, 1H), 3.67 (br. s., 1H), 3.46 (d, J=9.8 Hz, 2H), 2.43-1.56 (m, 18H), 1.38 (br. s., 3H), 1.30-1.10 (m, 3H), 0.93-0.72 (m, 3H).

Compound 423

3-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)benzoic acid

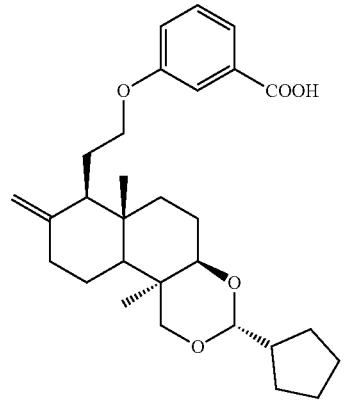

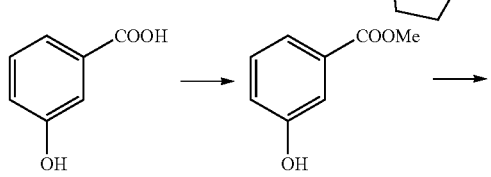

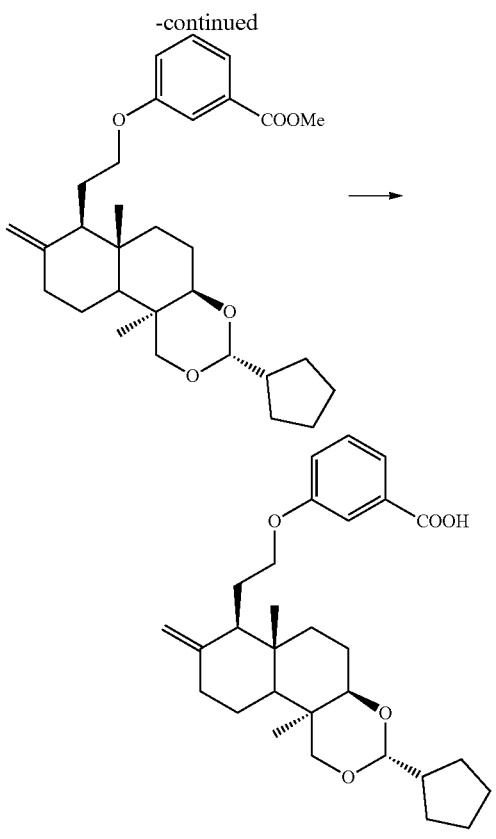

423

Step 1

Methyl 3-hydroxybenzoate

3-Hydroxybenzoic acid (2.00 g, 14.48 mmol) was dissolved in 20 mL of methanol, and sulfuric acid (184.63 mg, 1.88 mmol) was added at room temperature, and then stirred at 70° C. for 48 hours. 200 mL of aqueous sodium bicarbonate solution (4M) was added, and extracted with ethyl acetate (50 mL*3). The organic phases were combined, washed with saturated sodium chloride solution (50 mL*2), dried over anhydrous sodium sulfate, and filtered. The filtrate was concentrated under reduced pressure to give methyl 3-hydroxybenzoate as a white solid (2 g, crude product).

$^1$H NMR (400 MHz, CDCl$_3$) 7.65-7.52 (m, 2H), 7.30 (t, J=7.9 Hz, 1H), 7.11 (dd, J=1.9, 8.2 Hz, 1H), 6.04 (br. s., 1H), 3.92 (s, 3H).

Step 2

Methyl 3-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)benzoate (3R,4aR,6aS,7R,10bR)-7-(2-bromoethyl)-3-cyclopentyl-6a,10b-dimeth yl-8-methylenedecahydro-1H-naphtho[2,1-d][1,3]dioxin (300.00 mg, 729.20 umol) was dissolved in 5 mL N,N-dimethylformamide, and cesium carbonate (700.88 mg, 2.15 mmol) and methyl 3-hydroxybenzoate (122.00 mg, 802.12 umol) were successively added at room temperature, and then stirred at 80° C. for 8 hours. 50 mL water was added and the mixture was extracted with ethyl acetate (50 mL*3). The organic phases were combined, washed with saturated sodium chloride solution (50 mL*2), dried over anhydrous sodium sulfate, and filtered. The filtrate was concentrated under reduced pressure to give methyl 3-(2-((3R,4aR,6aS,7R,10 bR)-3-cyclopentyl-6a,10b-dimethyl-8-dihydromethylene decahydro-1H-naphtho[2,1-d][1,3]dioxin-7-yl)ethoxy)benzoate (a bright yellow oil, 250 mg, crude product).

$^1$H NMR (400 MHz, CDCl$_3$) 7.70-7.58 (m, 1H), 7.57-7.47 (m, 1H), 7.38-7.29 (m, 1H), 7.07 (dd, J=2.0, 8.0 Hz, 1H), 4.89 (s, 1H), 4.66-4.45 (m, 2H), 4.15-4.00 (m, 2H), 3.95-3.89 (m, 3H), 3.89-3.82 (m, 1H), 3.51 (dd, J=4.9, 12.7 Hz, 1H), 3.45 (d, J=11.3 Hz, 1H), 2.43 (d, J=13.3 Hz, 1H), 2.35-2.23 (m, 1H), 2.10-1.42 (m, 16H), 1.40-1.35 (m, 3H), 1.32-1.18 (m, 3H), 0.80 (s, 3H).

Step 3

3-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)benzoic acid Methyl 3-(2-((3R,4aR,6aS,7R,10 bR)-3-cyclopentyl-6a,10b-dimethyl-8-dihydromethylene decahydro-1H-naphtho[2,1-d][1,3]dioxin-7-yl)ethoxy)benzoate (250.00 mg, 517.97 umol) was dissolved in 5 mL methanol, 5 mL water and potassium hydroxide (290.64 mg, 5.18 mmol) were successively added at room temperature, and then stirred at 80° C. for 8 hours. 100 mL water was added and the mixture was extracted with ethyl acetate (50 mL*3). The organic phases were combined, washed with saturated sodium chloride solution (50 mL*2), dried over anhydrous sodium sulfate, and filtered. The filtrate was concentrated under reduced pressure to give 3-(2-((3R,4aR,6aS,7R,10bR)-3-cyclopentyl-6a, 10b-dimethyl-8-dihydromethylene decahydro-1H-naphtho[2,1-d][1,3]dioxin-7-yl)ethoxy)benzoic acid 423 (196 mg, yield: 80.75%).

MS m/z (ESI): 469.3 [M+1]

$^1$H NMR (400 MHz, CDCl$_3$) 7.29 (s, 2H), 6.89 (br. s., 1H), 6.73 (br. s., 1H), 4.77 (br. s., 1H), 4.60 (d, J=5.3 Hz, 1H), 4.48 (br. s., 1H), 4.00 (d, J=11.0 Hz, 1H), 3.81 (br. s., 1H), 3.62 (br. s., 1H), 3.42 (d, J=9.5 Hz, 2H), 2.24-1.48 (m, 18H), 1.34 (br. s., 3H), 1.26-1.01 (m, 3H), 0.72 (br. s., 3H).

Compound 407

2-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)benzoic acid

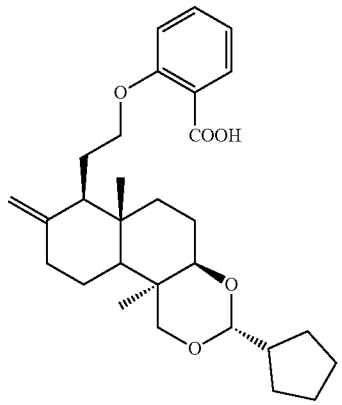

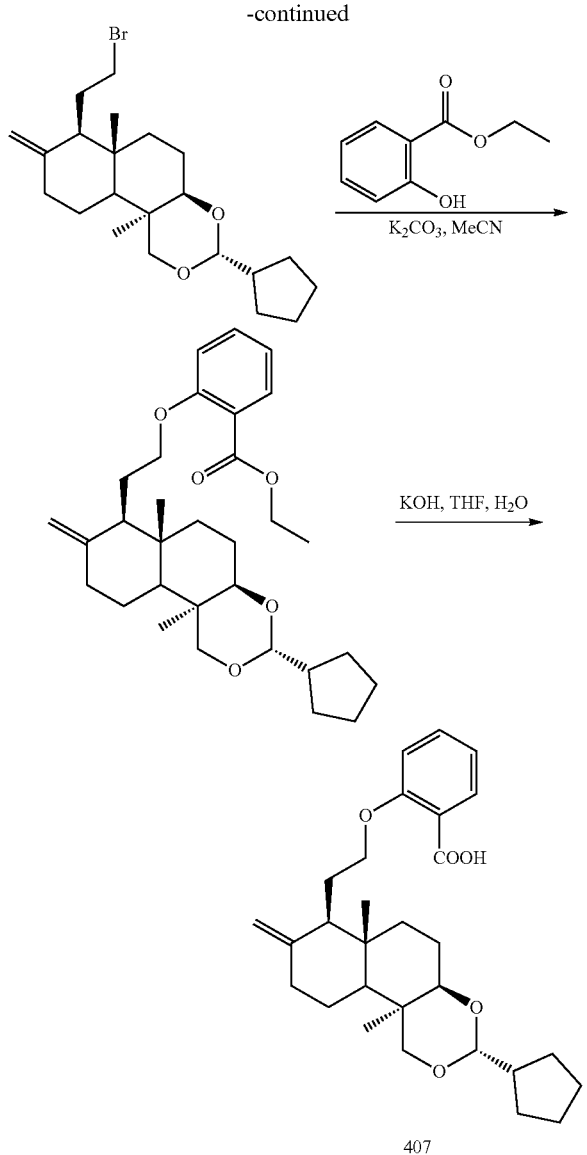

Step 1

Ethyl 2-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)benzoate (3R,4aR,6aS,7R,10bR)-7-(2-bromoethyl)-3-cyclopentyl-6a,10b-dimeth yl-8-methylenedecahydro-1H-naphtho[2,1-d][1,3]dioxin (400.00 mg, 972.27 umol) was dissolved in acetonitrile (10.00 mL), and potassium carbonate (134.38 mg, 972.27 umol) and ethyl 2-hydroxybenzoate (193.87 mg, 1.17 mmol) were successively added, and then stirred under nitrogen atmosphere at 75° C. for 12 hours. The reaction was quenched with 30 mL water and then extracted with ethyl acetate (30 mL). The organic phase was washed successively with water and saturated brine, dried over anhydrous sodium sulfate, filtered, and the filtrate was concentrated under reduced pressure. The residue was separated by column chromatography (silica, petroleum ether/ethyl acetate=8/1) to give ethyl 2-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)benzoate (a yellow oil, 200 mg, yield: 41.42%).

$^1$H NMR (400 MHz, CDCl3) 7.74 (dd, J=1.5, 7.8 Hz, 1H), 7.44-7.36 (m, 1H), 6.95 (t, J=7.5 Hz, 1H), 6.89 (d, J=8.3 Hz, 1H), 4.86 (s, 1H), 4.67-4.56 (m, 2H), 4.36 (q, J=7.0 Hz, 2H), 4.19-4.09 (m, 1H), 4.03 (d, J=11.3 Hz, 1H), 3.92-3.79 (m, 1H), 3.55-3.37 (m, 2H), 2.41 (d, J=13.3 Hz, 1H), 2.27 (dq, J=3.1, 13.2 Hz, 1H), 2.14-2.02 (m, 2H), 2.01-1.84 (m, 4H), 1.83-1.75 (m, 1H), 1.73-1.63 (m, 3H), 1.62-1.57 (m, 1H), 1.55-1.43 (m, 4H), 1.42-1.32 (m, 7H), 1.28-1.19 (m, 3H), 0.78 (s, 3H).

Step 2

2-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)benzoic acid Ethyl 2-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)benzoate (200.00 mg, 402.67 umol) was dissolved in tetrahydrofuran (2.00 mL), and potassium hydroxide (45.19 mg, 805.35 umol) and water (1.00 mL) were added successively, and then stirred at 75° C. under nitrogen atmosphere for 12 hours. The system was adjusted to neutrality with hydrochloric acid solution (1M). The organic phase was removed by rotary evaporation under reduced pressure, and the aqueous phase was separated by preparative liquid chromatography (HCOOH) to give 2-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)benzoic acid 407 (29 mg, yield: 15.37%).

MS m/z (ESI): 491.3 [M+23]

$^1$H NMR (400 MHz, CDCl3) 8.24-8.13 (m, 1H), 7.60-7.48 (m, 1H), 7.13 (t, J=7.5 Hz, 1H), 6.99 (d, J=8.3 Hz, 1H), 4.92 (s, 1H), 4.65-4.51 (m, 2H), 4.41-4.26 (m, 1H), 4.20-4.10 (m, 1H), 4.02 (d, J=11.3 Hz, 1H), 3.56-3.35 (m, 2H), 2.44 (d, J=12.0 Hz, 1H), 2.34-2.20 (m, 1H), 2.18-2.04 (m, 2H), 2.04-1.93 (m, 2H), 1.91-1.78 (m, 3H), 1.77-1.61 (m, 3H), 1.60-1.39 (m, 6H), 1.36 (s, 3H), 1.28-1.12 (m, 3H), 0.80 (s, 3H).

Compound 409

2-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-5-fluorobenzoic acid

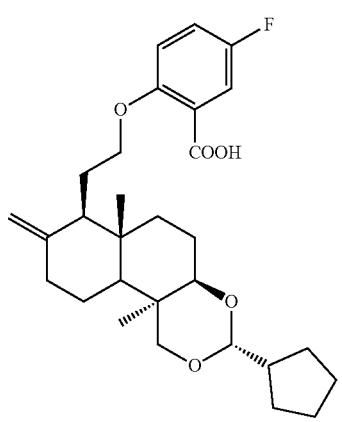

-continued

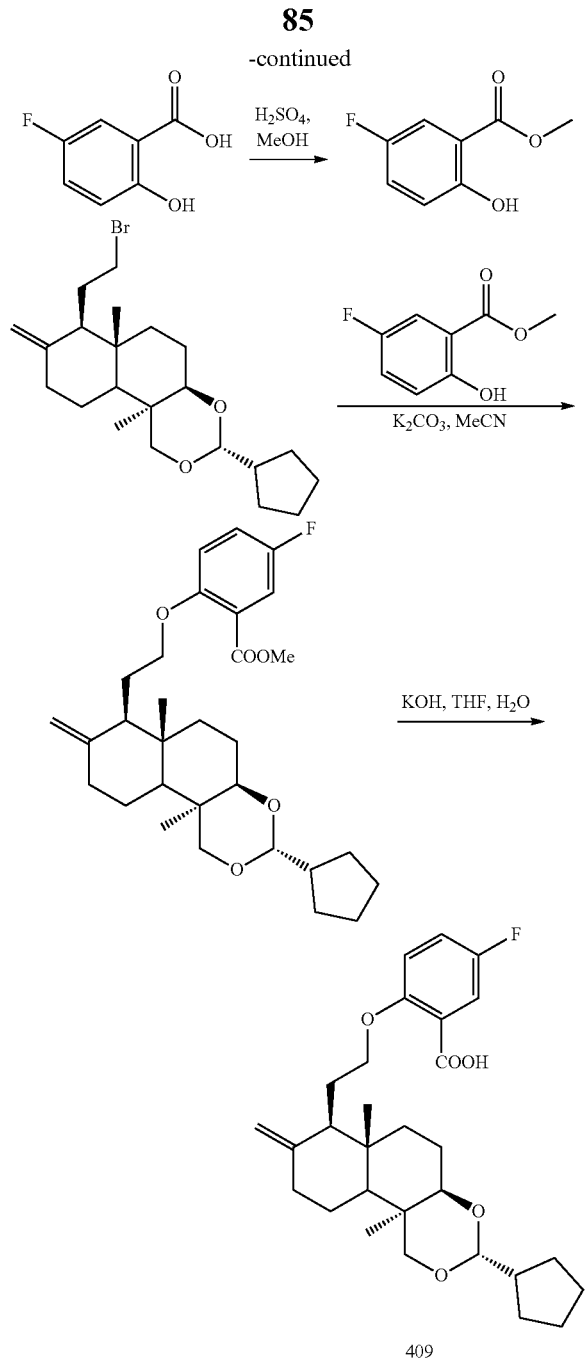

409

Step 1

Methyl 5-fluoro-2-hydroxybenzoate

5-Fluoro-2-hydroxybenzoic acid (2.50 g, 16.01 mmol) was dissolved in methanol (25.00 mL), added with sulfuric acid (78.51 mg, 800.50 umol), and then stirred at 70° C. for 12 hours under nitrogen atmosphere. After the reaction mixture was concentrated, the residue was dissolved in ethyl acetate (20.00 mL). The organic phase was washed sequentially with water and saturated brine, dried over anhydrous sodium sulfate, filtered, and the filtrate was concentrated under reduced pressure to give methyl 5-fluoro-2-hydroxybenzoate (a yellow oil, 2.0 g, crude product).

$^1$H NMR (400 MHz, CDCl3) 10.51 (s, 1H), 7.49 (dd, J=3.1, 8.7 Hz, 1H), 7.24-7.10 (m, 1H), 6.94 (dd, J=4.5, 9.0 Hz, 1H), 3.95 (s, 3H).

Step 2

Methyl 2-(2-((3R,4aR,6aS,7R,10 bR)-3-cyclopentyl-6a,10b-dimethyl-8-dihydromethylene decahydro-1H-naphtho[2,1-d][1,3]dioxin-7-yl)ethoxy)-5-fluorobenzoate (3R,4aR,6aS,7R,10bR)-7-(2-bromoethyl)-3-cyclopentyl-6a,10b-dimeth yl-8-methylenedecahydro-1H-naphtho[2,1-d][1,3]dioxin (400.00 mg, 972.27 umol) was dissolved in acetonitrile (10.00 mL), and potassium carbonate (268.75 mg, 1.94 mmol) and ethyl 5-fluoro-2-hydroxybenzoate (330.84 mg, 1.94 mmol) were successively added, and then stirred under nitrogen atmosphere at 75° C. for 12 hours. The reaction was quenched with 30 mL water and then extracted with ethyl acetate (30 mL). The organic phase was washed successively with water and saturated brine, dried over anhydrous sodium sulfate, filtered, and the filtrate was concentrated under reduced pressure. The residue was separated by column chromatography (silica, petroleum ether/ethyl acetate=8/1) to give methyl 2-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-5-fluorobenzoate (a yellow oil, 300 mg, yield: 61.63%).

$^1$H NMR (400 MHz, CDCl3) 7.50 (dd, J=3.1, 8.7 Hz, 1H), 7.14 (ddd, J=3.1, 7.7, 9.0 Hz, 1H), 6.87 (dd, J=4.3, 9.3 Hz, 1H), 4.88 (s, 1H), 4.68-4.55 (m, 2H), 4.20-4.00 (m, 2H), 3.96-3.79 (m, 4H), 3.57-3.38 (m, 2H), 2.44 (d, J=12.8 Hz, 1H), 2.29 (dq, J=3.0, 13.2 Hz, 1H), 2.14-2.05 (m, 2H), 2.01 (t, J=12.7 Hz, 1H), 1.97-1.86 (m, 3H), 1.86-1.79 (m, 1H), 1.71 (td, J=4.4, 8.8 Hz, 3H), 1.61-1.50 (m, 4H), 1.49-1.42 (m, 2H), 1.39 (s, 3H), 1.31-1.24 (m, 3H), 0.81 (s, 3H).

Step 3

2-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-5-fluorobenzoic acid Methyl 2-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-5-fluorobenzoate (300.00 mg, 599.23 umol) was dissolved in methanol (2.00 mL), and potassium hydroxide (67.25 mg, 1.20 mmol) and water (1.00 mL) were added successively, and then stirred at 75° C. under nitrogen atmosphere for 12 hours. The system was adjusted to neutrality with hydrochloric acid solution (1M). The organic phase was removed by rotary evaporation under reduced pressure, and the aqueous phase was separated by preparative liquid chromatography to give 2-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-5-fluorobenzoic acid 409 (205 mg, yield: 70.30%).

MS m/z (ESI): 509.3 [M+23]

$^1$H NMR (400 MHz, CDCl3) 7.84 (dd, J=3.3, 8.8 Hz, 1H), 7.26-7.17 (m, 1H), 6.95 (dd, J=3.8, 9.3 Hz, 1H), 4.92 (s, 1H), 4.65-4.49 (m, 2H), 4.37-4.25 (m, 1H), 4.16-4.06 (m, 1H), 4.01 (d, J=11.0 Hz, 1H), 3.54-3.37 (m, 2H), 2.44 (d, J=12.0 Hz, 1H), 2.26 (dq, J=2.8, 13.1 Hz, 1H), 2.16-2.02 (m, 2H), 2.02-1.91 (m, 2H), 1.90-1.77 (m, 3H), 1.74-1.63 (m, 3H), 1.59-1.40 (m, 6H), 1.35 (s, 3H), 1.28-1.12 (m, 3H), 0.79 (s, 3H).

87

Compound 441

2-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-4-fluorobenzoic acid

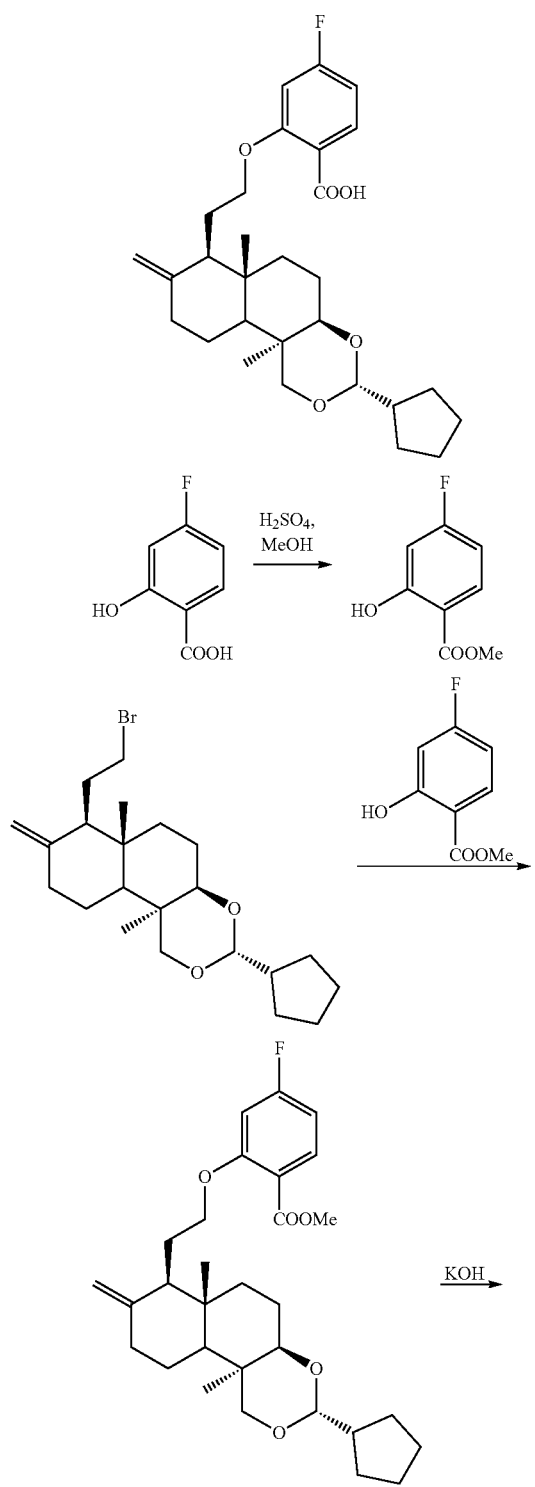

88

-continued

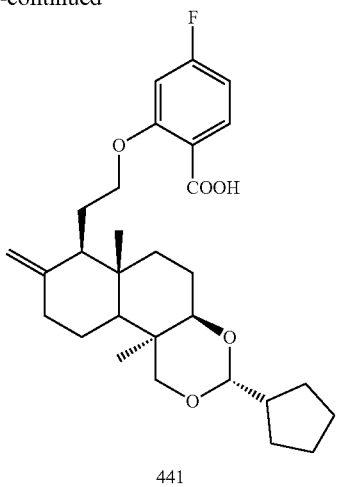

441

Step 1

Methyl 4-fluoro-2-hydroxybenzoate

4-Fluoro-2-hydroxybenzoic acid (5.00 g, 32.03 mmol) was dissolved in methanol (50.00 mL), added with sulfuric acid (920.00 mg, 9.38 mmol, 500.00 uL), and then stirred at 70° C. for 15 hours. The reaction mixture was concentrated and diluted with water (50.00 mL), and the system was adjusted to pH=9 with saturated sodium bicarbonate solution. The system was extracted with ethyl acetate (30.00 mL*3). The organic phase was washed with saturated brine (30.00 mL*2), dried over anhydrous sodium sulfate, filtered, and the filtrate was concentrated under reduced pressure to give methyl 4-fluoro-2-hydroxybenzoate (a white solid, 2.2 g, yield: 40.37%).

$^1$H NMR (400 MHz, CDCl3) 10.81 (d, J=1.0 Hz, 1H), 7.85 (dd, J=6.9, 8.9 Hz, 1H), 6.92-6.74 (m, 2H), 3.88 (s, 3H).

Step 2

Methyl 2-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-4-fluorobenzoate (3R,4aR,6aS,7R,10bR)-7-(2-bromoethyl)-3-cyclopentyl-6a,10b-dimeth yl-8-methylenedecahydro-1H-naphtho[2,1-d][1,3]dioxin (200.00 mg, 486.13 umol) was dissolved in N,N-dimethylformamide (3.00 mL), and potassium carbonate (134.38 mg, 972.26 umol) and methyl 4-fluoro-2-hydroxybenzoate (90.98 mg, 534.74 umol) were successively added, and then stirred at 70° C. for 15 hours. The reaction was quenched with 20 mL water and then extracted with ethyl acetate (20.00 mL*3). The organic phase was washed with saturated brine (25 mL*2), dried over anhydrous sodium sulfate, filtered, and the filtrate was concentrated under reduced pressure. The residue was separated by column chromatography (silica, petroleum ether/ethyl acetate=100/0 to 10/1) to give methyl 2-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-4-fluorobenzoate (a colorless oil, 240 mg, yield: 65.74%).

$^1$H NMR (400 MHz, CDCl3) 7.84 (dd, J=7.0, 8.5 Hz, 1H), 6.71-6.55 (m, 2H), 4.88 (s, 1H), 4.65-4.56 (m, 2H), 4.14-4.00 (m, 2H), 3.92-3.80 (m, 4H), 3.54-3.40 (m, 2H), 2.43 (d, J=12.8 Hz, 1H), 2.28 (dq, J=3.1, 13.3 Hz, 1H), 2.15-1.88 (m, 6H), 1.84-1.77 (m, 1H), 1.74-1.66 (m, 3H), 1.58-1.42 (m, 6H), 1.37 (s, 3H), 1.29-1.23 (m, 3H), 0.80 (s, 3H).

Step 3

2-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-4-fluorobenzoic acid Methyl 2-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-4-fluorobenzoate (240.00 mg, 179.39 umol) was dissolved in methanol (3.00 mL), and potassium hydroxide (161.39 mg, 2.88 mmol) and water (3.00 mL) were added successively, and then stirred at 70° C. for 24 hours. The reaction solution was diluted with 20 mL water, washed with 20 mL tert-butyl methyl ether, and the aqueous phase was adjusted to pH=4 with hydrochloric acid solution (1M). The system was extracted with ethyl acetate (30 mL*2), the organic phase was dried over anhydrous sodium sulfate, filtered, and the filtrate was concentrated under reduced pressure to give 2-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-4-fluorobenzoic acid 441 (73.6 mg, yield: 31.36%).

$^1$H NMR (400 MHz, DMSO-d$_6$) 7.70 (t, J=7.8 Hz, 1H), 6.92 (d, J=10.3 Hz, 1H), 6.84-6.68 (m, 1H), 4.84 (br. s., 1H), 4.65 (d, J=5.5 Hz, 1H), 4.58 (br. s., 1H), 4.11 (br. s., 1H), 3.94 (d, J=11.3 Hz, 1H), 3.83 (d, J=5.3 Hz, 1H), 3.61-3.45 (m, 2H), 2.43-2.11 (m, 3H), 2.10-1.84 (m, 4H), 1.76 (d, J=14.6 Hz, 3H), 1.63-1.32 (m, 8H), 1.29-1.11 (m, 6H), 0.71 (s, 3H).

Compound 448

4-chloro-2-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)benzoic acid

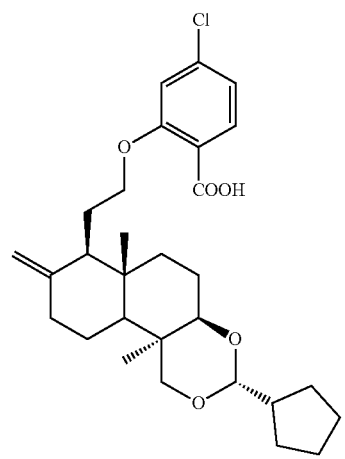

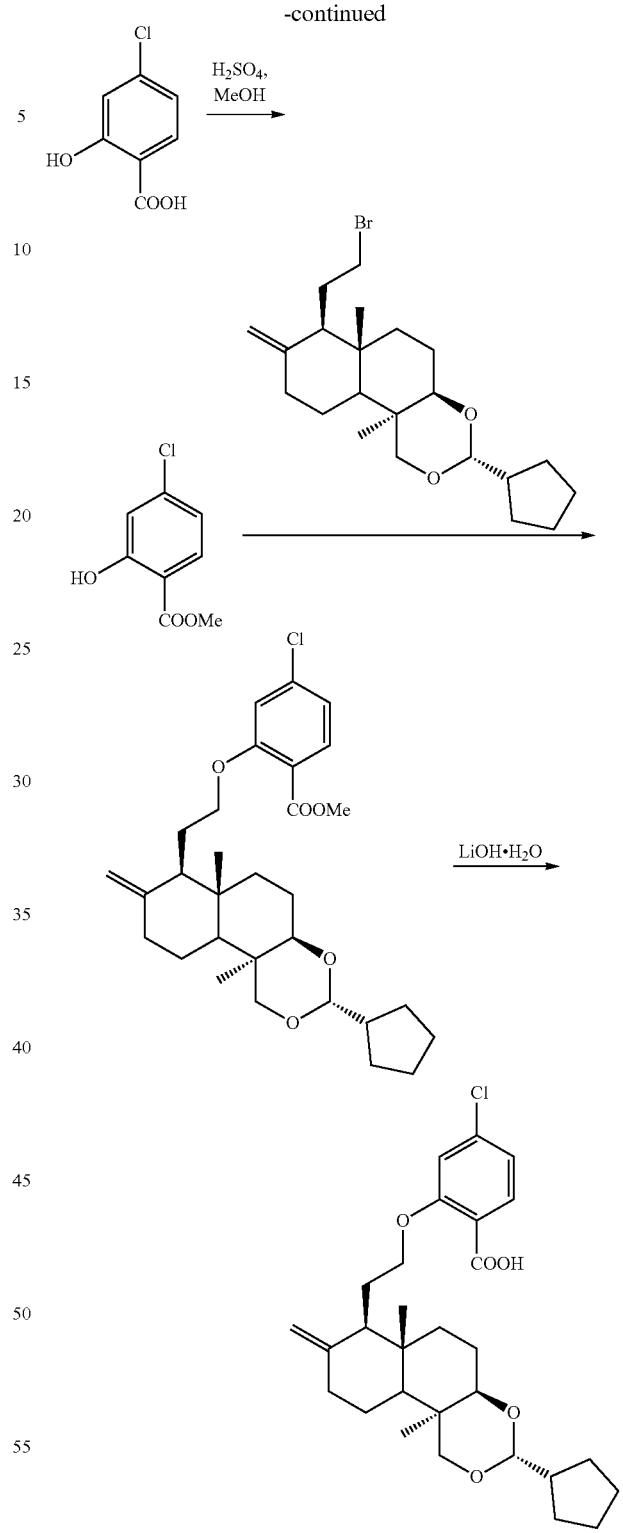

Step 1

Methyl 4-chloro-2-hydroxybenzoate

4-Chloro-2-hydroxybenzoic acid (5.00 g, 28.97 mmol) was dissolved in methanol (50.00 mL), sulfuric acid (4.26 g, 43.46 mmol, 2.32 mL) was added, and then stirred at 80° C. for 12 hours. The reaction was quenched with 30 mL of saturated sodium bicarbonate solution and extracted with dichloromethane (50 mL*3). The organic phases were combined and washed with saturated brine (20 mL), dried over anhydrous sodium sulfate, filtered and concentrated to give methyl 4-chloro-2-hydroxybenzoate (a white solid, 4.0 g, yield: 74.00%).

$^1$H NMR (400 MHz, CDCl3) 10.86 (s, 1H), 7.76 (d, J=8.4 Hz, 1H), 7.00 (s, 1H), 6.88-6.85 (m, 1H), 3.95 (s, 3H).

Step 2

Methyl 4-chloro-2-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)benzoate (3R,4aR,6aS,7R,10bR)-7-(2-bromoethyl)-3-cyclopentyl-6a,10b-dimeth yl-8-dihydromethylene decahydro-1H-naphtho[2,1-d][1,3]dioxin (200.00 mg, 486.13 umol) was dissolved in N,N-dimethylformamide (10.00 mL), and potassium carbonate (134.38 mg, 972.26 umol) and methyl 4-chloro-2-hydroxybenzoate (117.92 mg, 631.97 umol) were added successively, then stirred at 80° C. for 12 hours. The reaction solution was filtered and concentrated, and the residue was separated by column chromatography (silica, petroleum ether/ethyl acetate=10/1 to 1/1) to give methyl 4-chloro-2-(2-((3R,4aR,6aS,7R,10bR)-3-cyclopentyl-6a, 10b-dimethyl-8-dihydrometh ylene decahydro-1H-naphtho[2,1-d][1,3]dioxin-7-yl)ethoxy)benzoate (a white solid, 350 mg, yield: 69.62%).

$^1$H NMR (400 MHz, CDCl3) 7.73 (d, J=8.4 Hz, 1H), 6.95-6.89 (m, 2H), 4.88 (s, 1H), 4.61 (t, J=6 Hz, 2H), 4.11-3.88 (m, 2H), 3.85 (s, 3H), 3.52-3.42 (m, 3H), 2.44-2.40 (m, 2H), 2.08-1.69 (m, 9H), 1.52-1.37 (m, 7H), 1.25-1.21 (m, 3H), 0.76 (s, 3H).

Step 3

4-chloro-2-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)benzoic acid Methyl 4-chloro-2-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)benzoate (150.00 mg, 290.08 umol) was dissolved in tetrahydrofuran (12.00 mL), and lithium hydroxide monohydrate (60.86 mg, 1.45 mmol) and water (4.00 mL) were added successively, followed by stirring at 35° C. for 12 hours. The tetrahydrofuran was removed by rotary evaporation under reduced pressure, and the system was adjusted to pH=3 with a hydrochloric acid solution (1 M) and then extracted with ethyl acetate (30 mL*3). The organic phases were combined, washed with saturated brine and dried over anhydrous sodium sulfate, filtered and concentrated. The residue was separated by preparative liquid chromatography (HCOOH) to give 4-chloro-2-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)benzoic acid 448 (20 mg, yield: 13.29%).

$^1$H NMR (400 MHz, CDCl3) 8.11 (d, J=8.4 Hz, 1H), 7.13-7.10 (m, 1H), 6.99 (d, J=3.2 Hz, 1H), 4.94 (s, 1H), 4.59 (t, J=6 Hz, 2H), 4.14-4.01 (m, 3H), 3.51-3.42 (m, 2H), 2.45 (d, J=11.6 Hz, 1H), 2.12-1.69 (m, 11H), 1.57-1.52 (m, 6H), 1.51 (s, 3H), 1.37-1.25 (m, 3H), 0.81 (s, 3H).

Compound 447

2-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-4-methylbenzoic acid

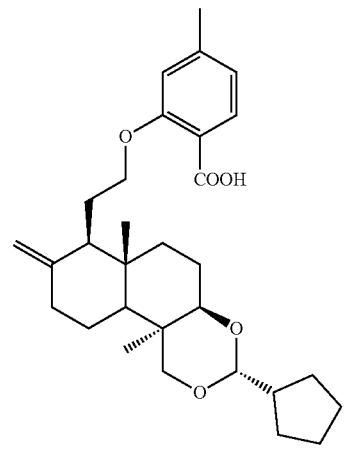

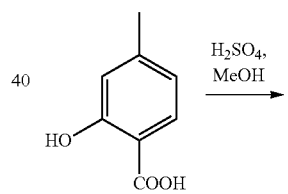

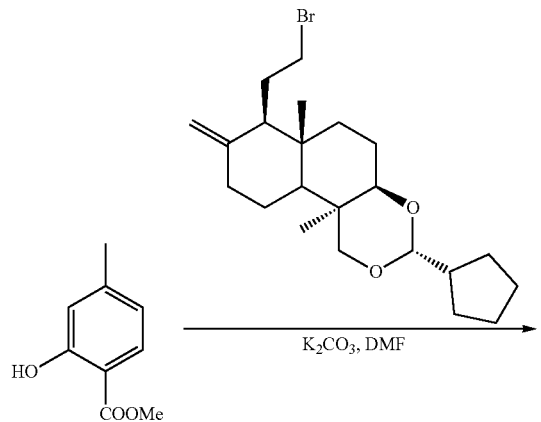

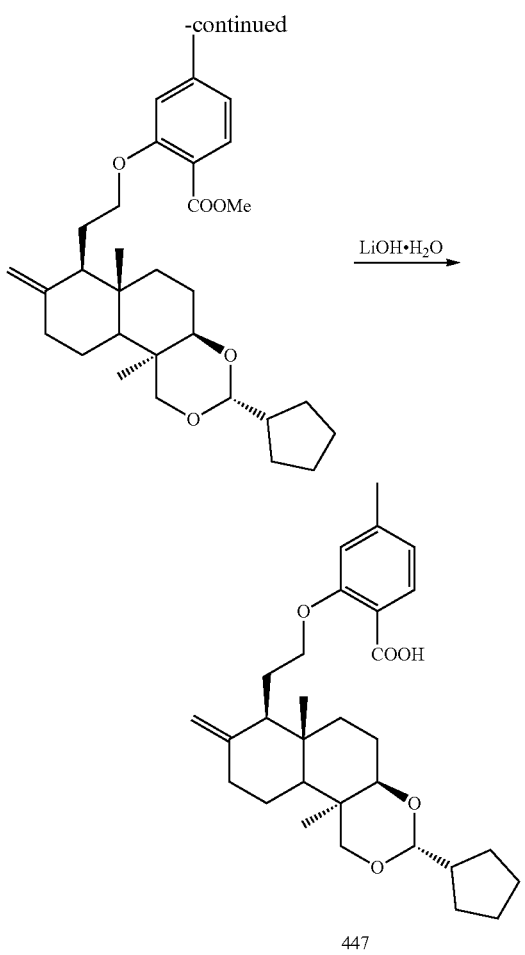

447

Step 1

Methyl 2-hydroxy-4-methylbenzoate 2-hydroxy-4-methylbenzoic acid (5.00 g, 32.86 mmol) was dissolved in methanol (50.00 mL), added with sulfuric acid (4.83 g, 49.29 mmol, 2.63 mL), and then stirred at 80° C. for 12 hours. The reaction was quenched with 50 mL saturated sodium bicarbonate solution and extracted with dichloromethane (50 mL*3). The organic phases were combined, washed with saturated brine (30 mL), dried over anhydrous sodium sulfate, filtered and concentrated to give methyl 2-hydroxy-4-methylbenzoate (a white solid, 4.5 g, yield: 82.41%).

$^1$H NMR (400 MHz, CDCl3) 10.78 (s, 1H), 7.71 (d, J=8.4 Hz, 1H), 6.79 (s, 1H), 6.69 (d, J=8.4 Hz, 1H), 3.93 (s, 3H), 2.35 (s, 3H).

Step 2

Methyl 2-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-4-methylbenzoate (3R,4aR,6aS,7R,10bR)-7-(2-bromoethyl)-3-cyclopentyl-6a,10b-dimethyl-8-dihydromethylene decahydro-1H-naphtho[2,1-d][1,3]dioxin (200.00 mg, 486.13 umol) was dissolved in N,N-dimethylformamide (10.00 mL), and potassium carbonate (134.38 mg, 972.26 umol) and methyl 2-hydroxy-4-methylbenzoate (105.01 mg, 631.97 umol) were added successively, then stirred at 80° C. for 12 hours. The reaction solution was filtered and concentrated, and the residue was separated by column chromatography (silica, petroleum ether/ethyl acetate=10/1 to 1/1) to give methyl 2-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-4-methylbenzoate (a white solid, 300 mg, yield: 62.12%).

$^1$H NMR (400 MHz, CDCl3) 7.69 (d, J=8 Hz, 1H), 6.76 (d, J=8 Hz, 1H), 6.70 (s, 1H), 4.87 (s, 1H), 4.61 (d, J=4.8 Hz, 2H), 4.12-4.02 (m, 2H), 3.85 (s, 4H), 3.52-3.42 (m, 2H), 2.43-2.08 (m, 5H), 1.95-1.68 (m, 9H), 1.56-1.52 (m, 4H), 1.43 (s, 3H), 1.37-1.25 (3H), 0.79 (s, 3H).

Step 3

2-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-4-methylbenzoic acid Methyl 2-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-4-methylbenzoate (150.00 mg, 302.01 umol) was dissolved in tetrahydrofuran (12.00 mL), and lithium hydroxide monohydrate (63.36 mg, 1.51 mmol) and water (4.00 mL) were added successively, followed by stirring at 35° C. for 12 hours. The tetrahydrofuran was removed by rotary evaporation under reduced pressure, and the system was adjusted to pH=3 with a hydrochloric acid solution (1 M) and then extracted with ethyl acetate (30 mL*3). The organic phases were combined, washed with saturated brine and dried over anhydrous sodium sulfate, filtered and concentrated to give 2-(2-((3R,4aR,6aS,7R,10bR)-3-cyclopentyl-6a, 10b-dimethyl-8-dihydromethylene decahydro-1H-naphtho[2,1-d][1,3]dioxin-7-yl)ethoxy)-4-methylbenzoic acid 447 (50 mg, yield: 32.93%).

MS m/z (ESI):483.4[M+1]

$^1$H NMR (400 MHz, CDCl3) 8.07 (d, J=8 Hz, 1H), 6.95 (d, J=8 Hz, 1H), 6.80 (s, 1H), 4.95 (s, 1H), 4.61 (d, J=6 Hz, 2H), 4.32 (s, 1H), 4.13-4.03 (m, 2H), 3.53-3.44 (m, 2H), 2.48-2.00 (m, 5H), 1.86-1.70 (m, 11H), 1.59-1.54 (m, 5H), 1.38 (s, 3H), 1.26-1.22 (m, 3H), 0.83 (s, 3H).

Compound 397

4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)nicotinic acid

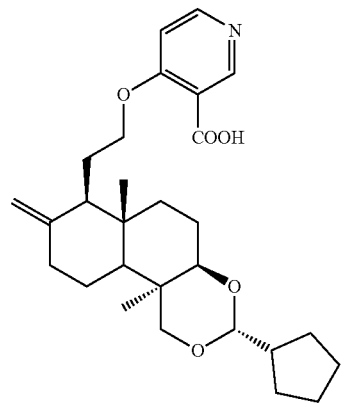

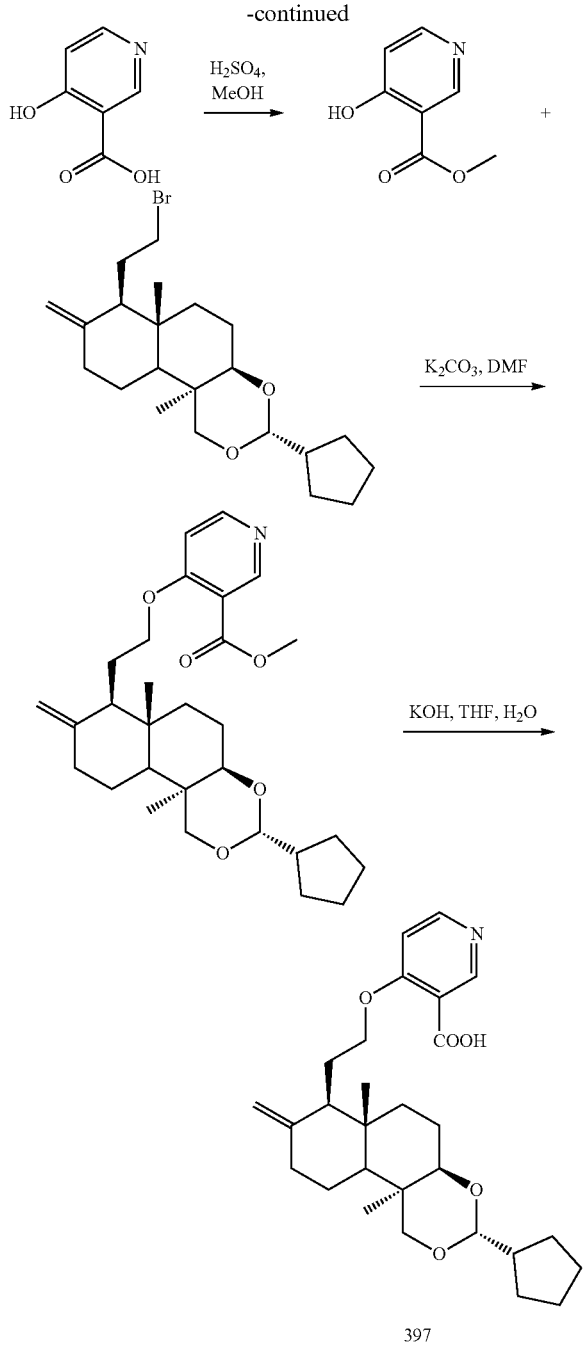

397

Step 1

Methyl 4-hydroxynicotinate

4-Hydroxynicotinic acid (5.00 g, 35.94 mmol) was dissolved in methanol (50.00 mL), added with sulfuric acid (18M, 100.00 uL), and then stirred at 70° C. under nitrogen atmosphere for 12 hours. After the reaction mixture was concentrated, the residue was dissolved in dichloromethane (50.00 mL) and the system was adjusted to pH=8 with saturated sodium bicarbonate solution. A white solid was slowly precipitated and filtered to give methyl 4-hydroxynicotinate (a white solid, 3.0 g, crude product).

$^1$H NMR (400 MHz, CDCl3) 8.27 (s, 1H), 7.67 (d, J=6.8 Hz, 1H), 6.21 (d, J=7.0 Hz, 1H), 3.69 (s, 3H).

Step 2

Methyl 4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy) nicotinate (3R,4aR,6aS,7R,10bR)-7-(2-bromoethyl)-3-cyclopentyl-6a,10b-dimethyl-8-dihydromethylene-1H-naphtho[2,1-d][1,3]dioxin (300.00 mg, 729.20 umol) was dissolved in N,N-dimethylformamide (5.00 mL), and potassium carbonate (201.57 mg, 1.46 mmol) and methyl 4-hydroxynicotate (223.34 mg, 1.46 mmol) were added successively and then stirred at 70° C. for 12 hours under nitrogen atmosphere. The reaction was quenched by adding 30 mL water and then extracted with ethyl acetate (30.00 mL). The organic phase was successively washed with water (30 mL) and saturated brine (30 mL), dried over anhydrous sodium sulfate, filtered, and the filtrate was concentrated under reduced pressure. The residue was separated by column chromatography (silica, petroleum ether/ethyl acetate=1/1) to give methyl 4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy) nicotinate (a yellow oil, 200 mg, yield: 56.71%).

$^1$H NMR (400 MHz, CDCl3) 8.89 (s, 1H), 8.51 (d, J=6.0 Hz, 1H), 6.80 (d, J=5.8 Hz, 1H), 4.88 (s, 1H), 4.66-4.50 (m, 2H), 4.24-4.14 (m, 1H), 4.03 (d, J=11.3 Hz, 1H), 3.98-3.85 (m, 4H), 3.54-3.39 (m, 2H), 2.42 (d, J=12.3 Hz, 1H), 2.27 (dq, J=3.0, 13.2 Hz, 1H), 2.16-2.04 (m, 2H), 1.95-1.87 (m, 3H), 1.83-1.76 (m, 1H), 1.72-1.67 (m, 3H), 1.54 (td, J=7.4, 19.3 Hz, 4H), 1.49-1.38 (m, 3H), 1.36 (s, 3H), 1.30-1.24 (m, 3H), 0.79 (s, 3H).

Step 3

4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)nicotinic acid Methyl 4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy) nicotinate (200.00 mg, 413.53 umol) was dissolved in tetrahydrofuran (2.00 mL), and potassium hydroxide (46.41 mg, 827.06 umol) and water (1.00 mL) were added successively, and then stirred at room temperature under nitrogen atmosphere for 12 hours. The system was adjusted to neutrality with hydrochloric acid solution (1M). The organic phase was removed by rotary evaporation under reduced pressure, and the aqueous phase was separated by preparative liquid chromatography (HCOOH) to give 4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)nicotinic acid 397 (54 mg, yield: 26.75%).

MS m/z (ESI):470.2 [M+1]

$^1$H NMR (400 MHz, CDCl3) 9.15 (s, 1H), 8.64 (d, J=5.8 Hz, 1H), 6.91 (d, J=6.0 Hz, 1H), 4.92 (s, 1H), 4.65-4.53 (m, 2H), 4.33 (dt, J=4.5, 7.9 Hz, 1H), 4.18-4.06 (m, 1H), 4.02 (d, J=11.3 Hz, 1H), 3.52-3.38 (m, 2H), 2.44 (d, J=12.0 Hz, 1H), 2.34-2.21 (m, 1H), 2.20-2.10 (m, 1H), 2.10-2.03 (m, 1H), 2.02-1.92 (m, 2H), 1.92-1.76 (m, 3H), 1.75-1.62 (m, 3H), 1.60-1.47 (m, 4H), 1.43 (dd, J=6.8, 12.3 Hz, 2H), 1.35 (s, 3H), 1.28-1.15 (m, 3H), 0.80 (s, 3H).

Compound 410

4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)picolinic acid

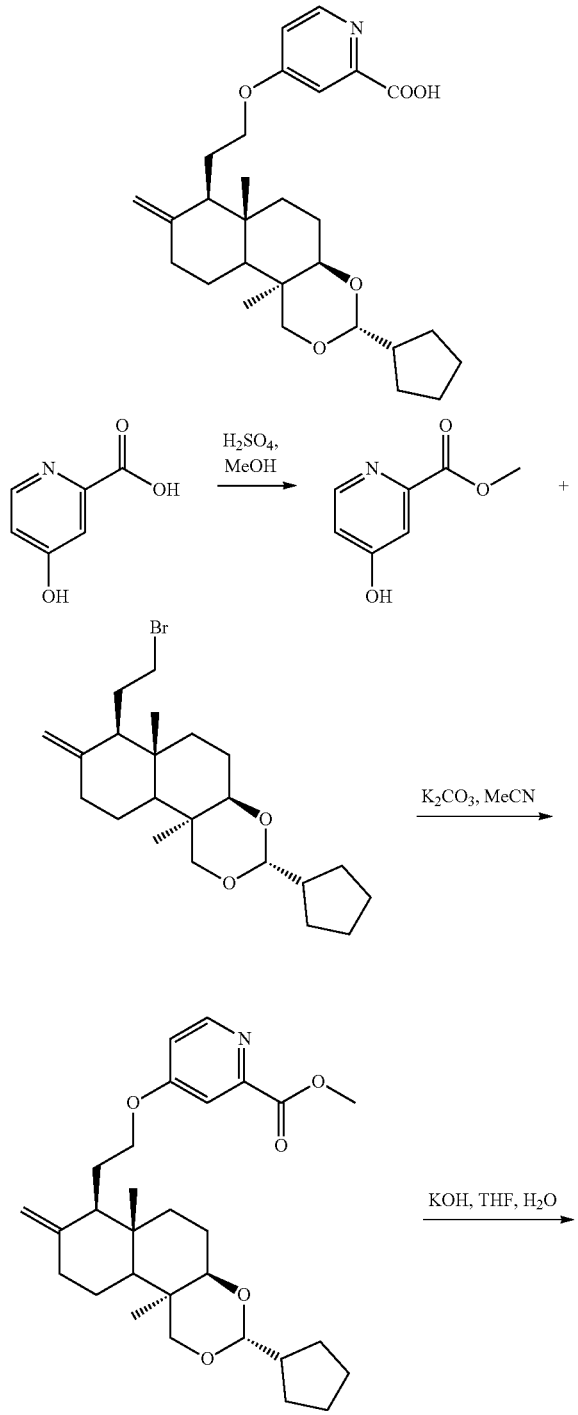

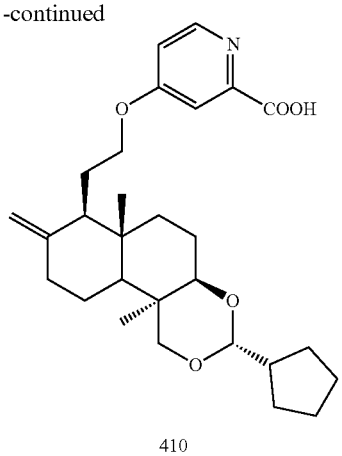

410

Step 1

Methyl 4-hydroxypicolinate

4-Hydroxypicolinic acid (2.50 g, 17.97 mmol) was dissolved in methanol (25.00 mL), added with sulfuric acid (88.13 mg, 898.50 umol), and then stirred at 70° C. under nitrogen atmosphere for 12 hours. After the reaction mixture was concentrated, the residue was dissolved in dichloromethane (50.00 mL) and the system was adjusted to pH=8 with saturated sodium bicarbonate solution. A white solid was slowly precipitated and filtered to give methyl 4-hydroxypicolinate (a white solid, 1.5 g, crude product).

$^1$H NMR (400 MHz, CDCl3) 7.72 (d, J=6.8 Hz, 1H), 6.80 (br. s., 1H), 6.35 (d, J=5.0 Hz, 1H), 3.38 (s, 3H).

Step 2

Methyl 4-(2-((3R,4aR,6aS,7R,10bR)-3-cyclopentyl-6a, 10b-dimethyl-8-dihydromethylene decahydro-1H-naphtho[2,1-d][1,3]dioxin-7-yl)ethoxy) picolinate (3R,4aR,6aS,7R,10bR)-7-(2-bromoethyl)-3-cyclopentyl-6a,10b-dimeth yl-8-dihydromethylene-1H-naphtho[2,1-d][1,3]dioxin (400.00 mg, 972.27 umol) was dissolved in acetonitrile (10.00 mL), and potassium carbonate (268.75 mg, 1.94 mmol) and methyl 4-hydroxypicolinate (297.79 mg, 1.94 mmol) were added successively and then stirred at 70° C. for 12 hours under nitrogen atmosphere. The reaction was quenched by adding 30 mL water and then extracted with ethyl acetate (30.00 mL). The organic phase was successively washed with water and saturated brine (30 mL), dried over anhydrous sodium sulfate, filtered, and the filtrate was concentrated under reduced pressure. The residue was separated by column chromatography (silica, petroleum ether/ethyl acetate=4/1) to give methyl 4-(2-((3R,4aR,6aS, 7R,10bR)-3-cyclopentyl-6a,10b-dimethyl-8-dihydromethylene decahydro-1H-naphtho[2,1-d][1,3]dioxin-7-yl) ethoxy) picolinate (a yellow oil, 200 mg, yield: 42.53%).

$^1$H NMR (400 MHz, CDCl3) 8.51 (d, J=5.5 Hz, 1H), 7.62 (d, J=2.3 Hz, 1H), 6.92 (dd, J=2.5, 5.8 Hz, 1H), 4.89 (s, 1H), 4.67-4.53 (m, 2H), 4.22-4.13 (m, 1H), 4.06-3.98 (m, 4H), 3.97-3.88 (m, 1H), 3.56-3.39 (m, 2H), 2.43 (d, J=12.8 Hz, 1H), 2.27 (dq, J=3.1, 13.3 Hz, 1H), 2.07 (d, J=3.0 Hz, 1H), 2.02-1.94 (m, 1H), 1.92-1.77 (m, 4H), 1.73-1.65 (m, 3H), 1.63 (s, 1H), 1.54 (dd, J=7.2, 11.7 Hz, 3H), 1.50-1.40 (m, 3H), 1.37 (s, 3H), 1.28-1.22 (m, 3H), 0.79 (s, 3H).

Step 3

4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)picolinic acid Methyl 4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy) picolinate (200.00 mg, 413.53 umol) was dissolved in methanol (2.00 mL), and potassium hydroxide (46.41 mg, 827.06 umol) and water (1.00 mL) were added successively, and then stirred at room temperature under nitrogen atmosphere for 12 hours. The system was adjusted to neutrality with hydrochloric acid solution (1M). The organic phase was removed by rotary evaporation under reduced pressure, and the aqueous phase was separated by preparative liquid chromatography (HCOOH) to give 4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)picolinic acid 410 (75 mg, yield: 38.62%).

MS m/z (ESI):470.3 [M+1]

$^1$H NMR (400 MHz, CDCl3) 8.87 (d, J=6.0 Hz, 1H), 7.85 (d, J=2.0 Hz, 1H), 7.14 (d, J=4.0 Hz, 1H), 4.91 (s, 1H), 4.66-4.50 (m, 2H), 4.31 (br. s., 1H), 4.18-4.06 (m, 1H), 4.02 (d, J=11.0 Hz, 1H), 3.57-3.38 (m, 2H), 2.43 (d, J=13.1 Hz, 1H), 2.34-2.20 (m, 1H), 2.15-2.02 (m, 2H), 2.01-1.90 (m, 2H), 1.90-1.77 (m, 3H), 1.75-1.63 (m, 3H), 1.61-1.40 (m, 6H), 1.37 (s, 3H), 1.30-1.11 (m, 3H), 0.79 (s, 3H).

Compound 415

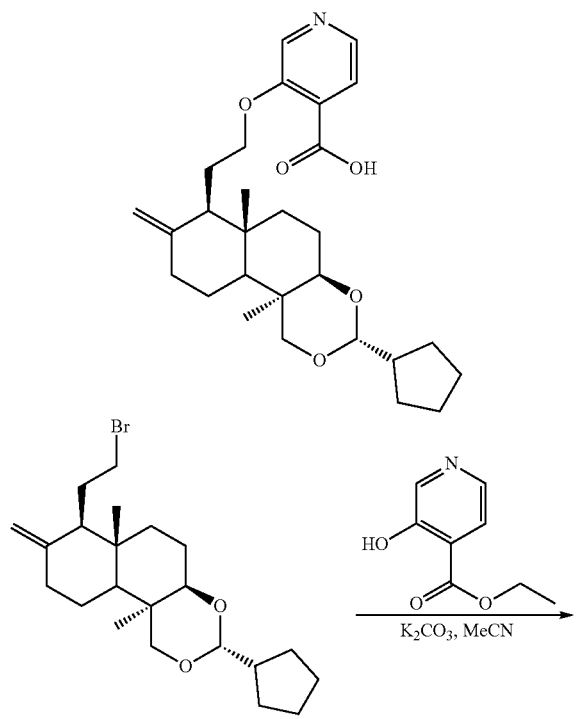

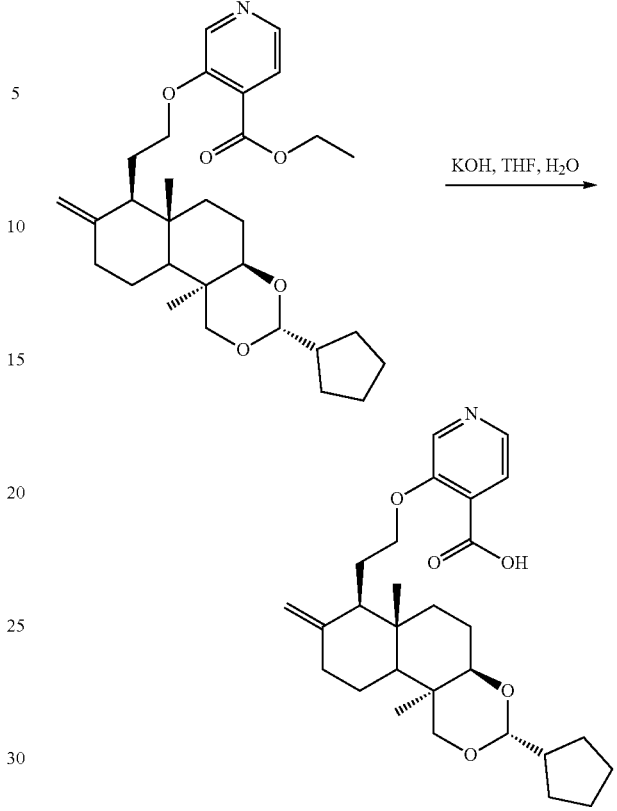

415

3-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)isonicotinic acid Step 1

Ethyl 3-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)isonicotinate (3R,4aR,6aS,7R,10bR)-7-(2-bromoethyl)-3-cyclopentyl-6a,10b-dimethyl-8-dihydromethylene-1H-naphtho[2,1-d][1,3]dioxin (400.00 mg, 972.27 umol) was dissolved in acetonitrile (10.00 mL), and potassium carbonate (268.75 mg, 1.94 mmol) and ethyl 3-hydroxyisopicolinate (243.79 mg, 1.94 mmol) were added successively and then stirred at 70° C. for 12 hours under nitrogen atmosphere. The reaction was quenched by adding 30 mL water and then extracted with ethyl acetate (30.00 mL). The organic phase was successively washed with water and saturated brine (30 mL), dried over anhydrous sodium sulfate, filtered, and the filtrate was concentrated under reduced pressure. The residue was separated by column chromatography (silica, petroleum ether/ethyl acetate=4/1) to give ethyl 3-(2-((3R,4aR,6aS,7R,10 bR)-3-cyclopentyl-6a,10b-dimethyl-8-dihydromethylene decahydro-1H-naphtho[2,1-d][1,3]dioxin-7-yl)ethoxy) isonicotinate (a yellow oil, 200 mg, yield: 41.33%).

$^1$H NMR (400 MHz, CDCl3) 8.36 (s, 1H), 8.29 (d, J=4.8 Hz, 1H), 7.53 (d, J=4.8 Hz, 1H), 4.88 (s, 1H), 4.64-4.55 (m, 2H), 4.39 (q, J=7.0 Hz, 2H), 4.28-4.20 (m, 1H), 4.06-3.94

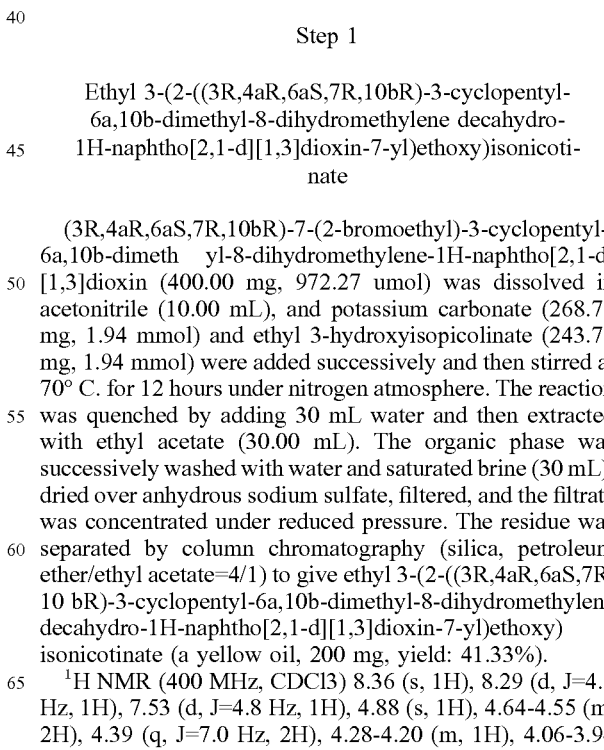

(m, 2H), 3.55-3.39 (m, 2H), 2.42 (d, J=12.8 Hz, 1H), 2.27 (dq, J=3.1, 13.3 Hz, 1H), 2.15-2.05 (m, 2H), 2.01-1.94 (m, 1H), 1.93-1.85 (m, 3H), 1.83-1.76 (m, 1H), 1.74-1.64 (m, 3H), 1.61-1.49 (m, 4H), 1.47-1.39 (m, 5H), 1.36 (s, 3H), 1.25-1.16 (m, 3H), 0.79 (s, 3H).

Step 2

3-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)isonicotinic acid Ethyl 3-(2-((3R,4aR,6aS,7R,10 bR)-3-cyclopentyl-6a,10b-dimethyl-8-dihydromethylene decahydro-1H-naphtho[2,1-d][1,3]dioxin-7-yl)ethoxy)isonicotinate (200.00 mg, 401.88 umol) was dissolved in methanol (2.00 mL), and potassium hydroxide (45.10 mg, 803.76 umol) and water (1.00 mL) were added successively, and then stirred at room temperature under nitrogen atmosphere for 12 hours. The system was adjusted to neutrality with hydrochloric acid solution (1M). The organic phase was removed by rotary evaporation under reduced pressure, and the aqueous phase was separated by preparative liquid chromatography (HCOOH) to give 3-(2-((3R,4aR,6aS,7R,10 bR)-3-cyclopentyl-6a,10b-dimethyl-8-dihydromethylene decahydro-1H-naphtho[2,1-d][1,3]dioxin-7-yl)ethoxy)isonicotinic acid 415 (75 mg, yield: 37.99%).

MS m/z (ESI): 470.2 [M+1]

$^1$H NMR (400 MHz, CDCl3) 8.60-8.33 (m, 2H), 7.86 (br. s., 1H), 4.91 (br. s., 1H), 4.58 (br. s., 2H), 4.42 (br. s., 1H), 4.21 (br. s., 1H), 4.00 (d, J=10.0 Hz, 1H), 3.49-3.36 (m, 2H), 2.43 (d, J=11.8 Hz, 1H), 2.30-2.16 (m, 1H), 2.06 (d, J=6.3 Hz, 1H), 1.97 (br. s., 2H), 1.83 (br. s., 3H), 1.68 (br. s., 4H), 1.53 (d, J=12.5 Hz, 4H), 1.44-1.38 (m, 2H), 1.35 (br. s., 3H), 1.22 (br. s., 3H), 0.78 (br. s., 3H).

Compound 406

5-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)nicotinic acid

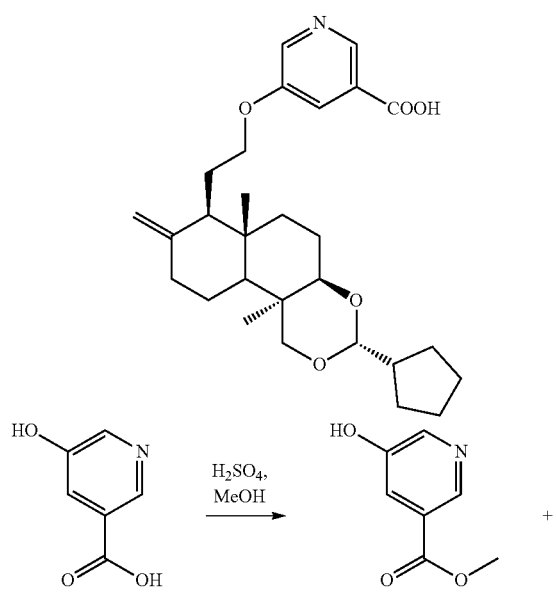

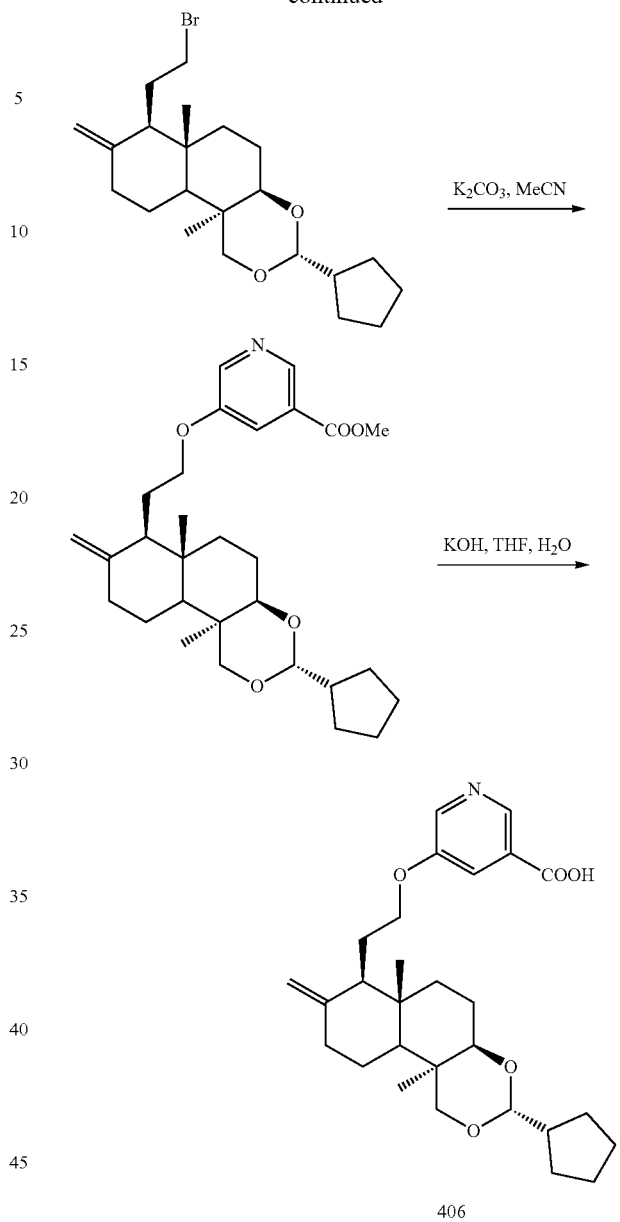

406

Step 1

Methyl 5-hydroxynicotinate

5-Hydroxynicotinic acid (2.50 g, 17.97 mmol) was dissolved in methanol (20.00 mL), added with sulfuric acid (18M, 47.90 uL), and then stirred at 70° C. under nitrogen atmosphere for 12 hours. After the reaction mixture was concentrated, the residue was dissolved in dichloromethane (50.00 mL) and the system was adjusted to pH=8 with saturated sodium bicarbonate solution. A white solid was slowly precipitated and filtered to give methyl 5-hydroxynicotinate (a white solid, 1.5 g, crude product).

$^1$H NMR (400 MHz, CDCl3) 8.25 (s, 1H), 8.13 (d, J=1.8 Hz, 1H), 7.38 (br. s., 1H), 3.17 (s, 3H).

Step 2

Methyl 5-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy) nicotinate (3R,4aR,6aS,7R,10bR)-7-(2-bromoethyl)-3-cyclopentyl-6a,10b-dimeth yl-8-dihydromethylene-1H-naphtho[2,1-d][1,3]dioxin (300.00 mg, 972.27 umol) was dissolved in acetonitrile (10.00 mL), and potassium carbonate (268.75 mg, 1.94 mmol) and methyl 5-hydroxynicotate (297.79 mg, 1.94 mmol) were added successively and then stirred at 70° C. for 12 hours under nitrogen atmosphere. The reaction was quenched by adding 30 mL water and then extracted with ethyl acetate (30.00 mL). The organic phase was successively washed with water (30 mL) and saturated brine (30 mL), dried over anhydrous sodium sulfate, filtered, and the filtrate was concentrated under reduced pressure. The residue was separated by column chromatography (silica, petroleum ether/ethyl acetate=4/1) to give methyl 5-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy) nicotinate (a yellow oil, 200 mg, yield: 21.27%).

$^1$H NMR (400 MHz, CDCl3) 8.79 (s, 1H), 8.43 (d, J=2.5 Hz, 1H), 7.71 (br. s., 1H), 4.89 (s, 1H), 4.67-4.52 (m, 2H), 4.12 (s, 1H), 4.03 (d, J=11.0 Hz, 1H), 3.98-3.86 (m, 4H), 3.58-3.34 (m, 2H), 2.43 (d, J=13.1 Hz, 1H), 2.27 (q, J=13.1 Hz, 1H), 2.13-2.07 (m, 1H), 2.04-1.94 (m, 2H), 1.93-1.78 (m, 4H), 1.71 (br. s., 3H), 1.61-1.40 (m, 6H), 1.37 (s, 3H), 1.26-1.16 (m, 3H), 0.79 (s, 3H).

Step 3

5-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)nicotinic acid Methyl 5-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy) nicotinate (200.00 mg, 413.53 umol) was dissolved in tetrahydrofuran (2.00 mL), and potassium hydroxide (46.41 mg, 827.06 umol) and water (1.00 mL) were added successively, and then stirred at room temperature under nitrogen atmosphere for 12 hours. The system was adjusted to neutrality with hydrochloric acid solution (1M). The organic phase was removed by rotary evaporation under reduced pressure, and the aqueous phase was separated by preparative liquid chromatography (HCOOH) to give 5-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)nicotinic acid 406 (38 mg, yield: 19.57%).

MS m/z (ESI):470.3 [M+1]

$^1$H NMR (400 MHz, CDCl3) 8.92 (s, 1H), 8.53 (d, J=2.5 Hz, 1H), 7.88 (br. s., 1H), 4.90 (s, 1H), 4.67-4.53 (m, 2H), 4.17 (br. s., 1H), 4.04 (d, J=11.3 Hz, 1H), 4.00-3.88 (m, 1H), 3.61-3.39 (m, 2H), 2.43 (d, J=13.3 Hz, 1H), 2.35-2.20 (m, 1H), 2.14-2.03 (m, 2H), 2.02-1.95 (m, 1H), 1.94-1.86 (m, 3H), 1.84-1.78 (m, 1H), 1.76-1.63 (m, 3H), 1.60-1.40 (m, 6H), 1.38 (s, 3H), 1.32-1.17 (m, 3H), 0.80 (s, 3H).

Compound 436

2-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)nicotinic acid

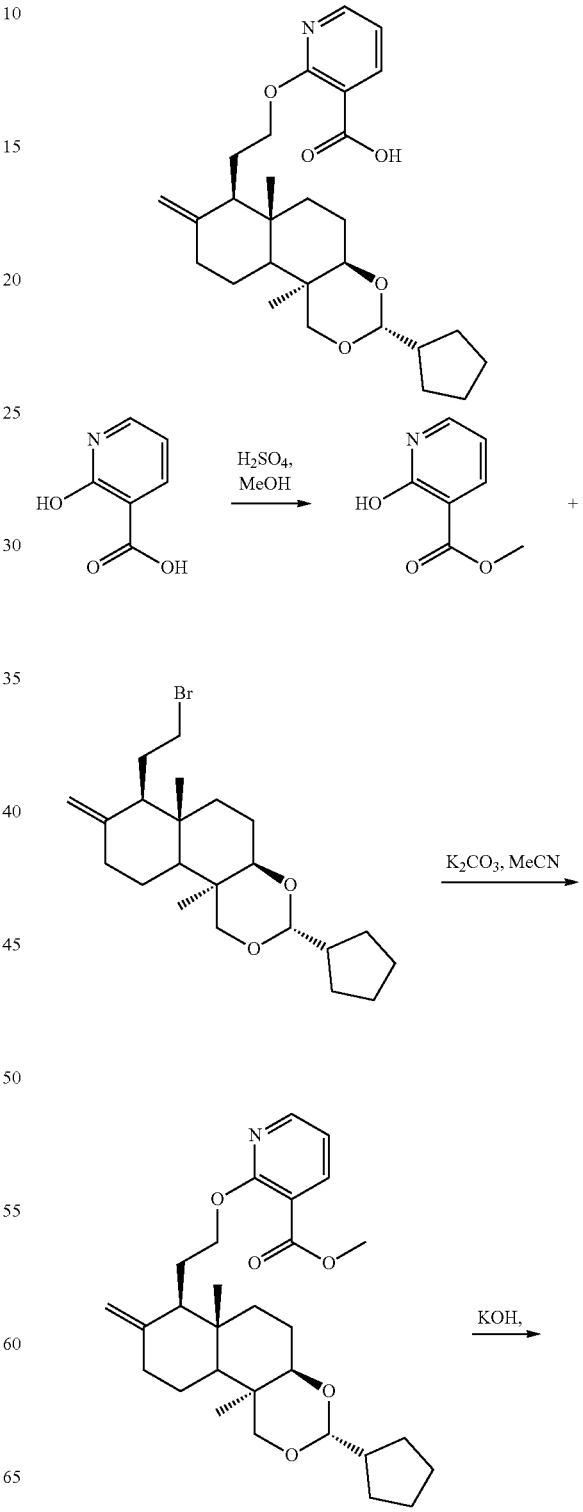

-continued

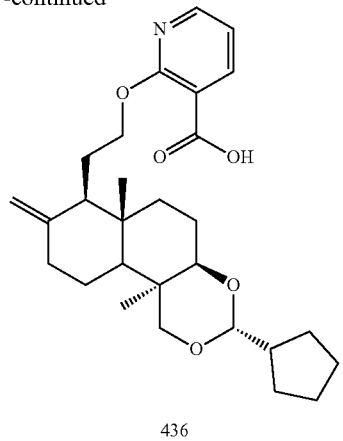

436

Step 1

Methyl 2-hydroxynicotinate

2-Hydroxynicotinic acid (2.50 g, 17.97 mmol) was dissolved in methanol (20.00 mL), added with sulfuric acid (18M, 47.90 uL), and then stirred at 70° C. under nitrogen atmosphere for 12 hours. After the reaction mixture was concentrated, the residue was dissolved in dichloromethane (50.00 mL) and the system was adjusted to pH=8 with saturated sodium bicarbonate solution. A white solid was slowly precipitated and filtered to give methyl 2-hydroxynicotinate (a white solid, 1.5 g, yield: 54.51%).

$^1$H NMR (400 MHz, CDCl3) 8.27 (dd, J=2.0, 7.0 Hz, 1H), 7.78 (dd, J=2.0, 6.0 Hz, 1H), 6.41 (t, J=6.8 Hz, 1H), 3.90 (s, 3H).

Step 2

Methyl 2-(2-((3R,4aR,6aS,7R,10 bR)-3-cyclopentyl-6a,10b-dimethyl-8-dihydromethylene decahydro-1H-naphtho[2,1-d][1,3]dioxin-7-yl)ethoxy) nicotinate (3R,4aR,6aS,7R,10bR)-7-(2-bromoethyl)-3-cyclopentyl-6a,10b-dimethyl-8-dihydromethylene-1H-naphtho[2,1-d][1,3]dioxin (400.00 mg, 972.27 umol) was dissolved in acetonitrile (10.00 mL), and potassium carbonate (268.75 mg, 1.94 mmol) and methyl 2-hydroxynicotate (148.89 mg, 972.27 umol) were added successively and then stirred at 70° C. for 2 hours under nitrogen atmosphere. The reaction was quenched by adding 30 mL water and then extracted with ethyl acetate (30.00 mL). The organic phase was successively washed with water (30 mL) and saturated brine (30 mL), dried over anhydrous sodium sulfate, filtered, and the filtrate was concentrated under reduced pressure. The residue was separated by column chromatography (silica, dichloromethane/ethyl acetate=4/1) to give methyl 2-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy) nicotinate (a yellow oil, 100 mg, yield: 21.27%).

$^1$H NMR (400 MHz, CDCl3) 8.27 (d, J=3.0 Hz, 1H), 8.14 (d, J=7.3 Hz, 1H), 6.91 (dd, J=5.0, 7.3 Hz, 1H), 4.88 (s, 1H), 4.72 (s, 1H), 4.61 (d, J=5.8 Hz, 1H), 4.58-4.46 (m, 1H), 4.28-4.16 (m, 1H), 4.04 (d, J=11.3 Hz, 1H), 3.90 (s, 3H), 3.59-3.33 (m, 2H), 2.42 (d, J=12.5 Hz, 1H), 2.34-2.18 (m, 1H), 2.08 (br. s., 1H), 2.01 (d, J=15.6 Hz, 2H), 1.95-1.84 (m, 3H), 1.82-1.76 (m, 1H), 1.70 (br. s., 3H), 1.56-1.41 (m, 6H), 1.37 (s, 3H), 1.25 (d, J=6.0 Hz, 3H), 0.78 (s, 3H).

Step 3

2-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)nicotinic acid Methyl 2-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy) nicotinate (100.00 mg, 206.77 umol) was dissolved in methane (2.00 mL), and potassium hydroxide (23.20 mg, 413.53 umol) and water (1.00 mL) were added successively, and then stirred at room temperature under nitrogen atmosphere for 12 hours. The system was adjusted to neutrality with hydrochloric acid solution (1M). The organic phase was removed by rotary evaporation under reduced pressure, and the aqueous phase was separated by preparative liquid chromatography (HCOOH) to give 2-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)nicotinic acid 436 (9.6 mg, yield: 9.89%).

MS m/z (ESI):470.3 [M+1]

$^1$H NMR (400 MHz, CDCl3) 8.47 (dd, J=1.8, 7.5 Hz, 1H), 8.36 (dd, J=1.9, 4.9 Hz, 1H), 7.12 (dd, J=5.0, 7.5 Hz, 1H), 4.93 (s, 1H), 4.79-4.66 (m, 2H), 4.60 (d, J=5.8 Hz, 1H), 4.51-4.38 (m, 1H), 4.02 (d, J=11.3 Hz, 1H), 3.54-3.39 (m, 2H), 2.44 (d, J=11.8 Hz, 1H), 2.32-2.18 (m, 1H), 2.13-2.04 (m, 2H), 2.03-1.93 (m, 2H), 1.88 (d, J=13.1 Hz, 1H), 1.84-1.76 (m, 2H), 1.69 (td, J=4.5, 8.8 Hz, 4H), 1.61-1.59 (m, 1H), 1.51 (d, J=6.8 Hz, 2H), 1.43 (dd, J=7.0, 12.0 Hz, 2H), 1.37 (s, 3H), 1.27-1.12 (m, 3H), 0.79 (s, 3H).

Compound 431

3-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-2-picolinic acid

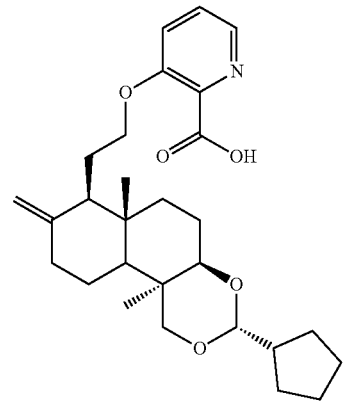

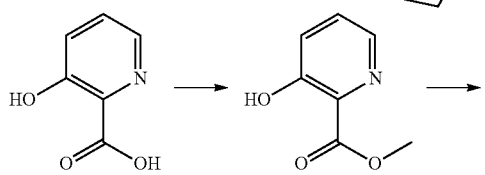

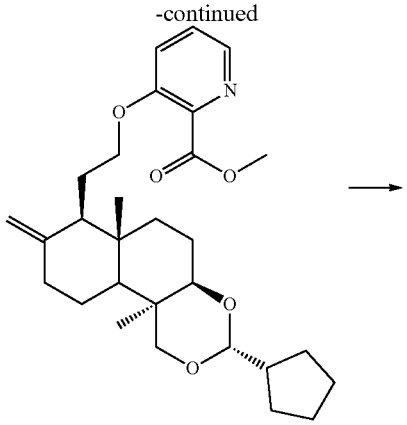

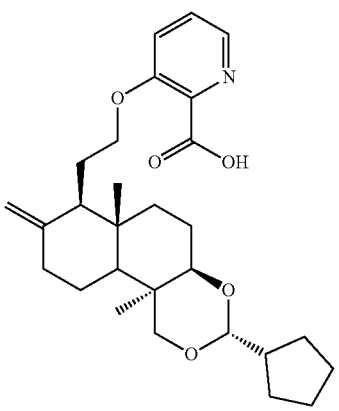

431

Step 1

Methyl 3-hydroxy-2-picolinate

3-Hydroxypyridin-2-carboxylic acid (2.50 g, 17.97 mmol) was dissolved in methanol (20.00 mL), added with sulfuric acid (18M, 47.90 uL) at room temperature, and then stirred at 70° C. for 12 hours. After the reaction mixture was concentrated, the residue was dissolved in dichloromethane (50.00 mL) and the system was adjusted to pH=8 with saturated sodium bicarbonate solution. A white solid was precipitated out, and the filter cake was dried to give methyl 3-hydroxy-2-picolinate (a white solid, 1.5 g, yield: 54.51%).

$^1$H NMR (400 MHz, CDCl$_3$) 10.63 (s, 1H), 8.27 (dd, J=1.3, 4.3 Hz, 1H), 7.49-7.40 (m, 1H), 7.40-7.31 (m, 1H), 4.05 (s, 3H).

Step 2

Methyl 3-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-2-picolinate (3R,4aR,6aS,7R,10bR)-7-(2-bromoethyl)-3-cyclopentyl-6a,10b-dimethyl-8-dihydromethylene-1H-naphtho[2,1-d][1,3]dioxin 432c (400.00 mg, 972.27 umol) was dissolved in acetonitrile (10.00 mL), and potassium carbonate (403.13 mg, 2.92 mmol) and methyl 3-hydroxy-2-picolinate (297.79 mg, 1.94 mmol) were added successively at room temperature and then stirred at 70° C. for 12 hours. The reaction was quenched by adding 30 mL water and then extracted with ethyl acetate (30.00 mL). The organic phases were combined and successively washed with water (30 mL) and saturated brine (30 mL), dried over anhydrous sodium sulfate, filtered, and the filtrate was concentrated under reduced pressure. The residue was purified by gel column chromatography (elution system: PE/EtOAc=1:2) to give methyl 3-(2-((3R, 4aR,6aS,7R,10 bR)-3-cyclopentyl-6a,10b-dimethyl-8-dihydromethylene decahydro-1H-naphtho[2,1-d][1,3]dioxin-7-yl)ethoxy)-2-picolinate (a yellow oil, 120 mg, yield: 25.52%).

$^1$H NMR (400 MHz, CDCl$_3$) 8.25 (d, J=3.8 Hz, 1H), 7.38-7.34 (m, 1H), 7.31-7.24 (m, 1H), 4.88 (s, 1H), 4.65-4.56 (m, 2H), 4.19-4.14 (m, 1H), 4.03 (d, J=11.3 Hz, 1H), 3.97 (s, 3H), 3.90 (dt, J=5.5, 8.4 Hz, 1H), 3.54-3.40 (m, 2H), 2.42 (d, J=13.1 Hz, 1H), 2.28 (dq, J=3.0, 13.2 Hz, 1H), 2.14-2.06 (m, 2H), 2.03-1.94 (m, 1H), 1.92 (d, J=2.8 Hz, 1H), 1.89-1.86 (m, 1H), 1.84-1.76 (m, 2H), 1.75-1.65 (m, 3H), 1.62-1.49 (m, 4H), 1.45 (dd, J=6.9, 12.2 Hz, 2H), 1.37 (s, 3H), 1.29-1.24 (m, 3H), 0.79 (s, 3H).

Step 3

3-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-2-picolinic acid Methyl 3-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-2-picolinate (100.00 mg, 206.77 umol) was dissolved in 1 mL tetrahydrofuran and 1 mL water, and potassium hydroxide (23.20 mg, 413.54 umol) was added, followed by stirring at room temperature for 12 hours. The system was adjusted to pH=7 with diluted hydrochloric acid solution (1M), and extracted with ethyl acetate (10 mL*2). The organic phases were combined, successively washed with water (10 mL) and saturated brine (10 mL), dried over anhydrous sodium sulfate, filtered, and the filtrate was concentrated under reduced pressure to give 3-(2-((3R,4aR,6aS,7R,10 bR)-3-cyclopentyl-6a,10b-dimethyl-8-dihydromethylene decahydro-1H-naphtho[2,1-d][1,3]dioxin-7-yl)ethoxy)-2-picolinic acid 431 (37 mg, yield: 36.20%).

MS m/z (ESI): 492.3 [M+23]

$^1$H NMR (400 MHz, CDCl$_3$) 8.11 (br. s., 1H), 7.46 (d, J=5.8 Hz, 1H), 7.38 (br. s., 1H), 4.83 (br. s., 1H), 4.65 (d, J=5.3 Hz, 1H), 4.58 (br. s., 1H), 4.11 (br. s., 1H), 3.93 (d, J=11.0 Hz, 1H), 3.84 (d, J=6.3 Hz, 1H), 3.30 (br. s., 2H), 2.39-2.17 (m, 2H), 2.01-1.84 (m, 4H), 1.74 (d, J=10.0 Hz, 3H), 1.55 (d, J=10.5 Hz, 2H), 1.51-1.36 (m, 7H), 1.24 (br. s., 3H), 1.21-1.11 (m, 3H), 0.70 (s, 3H).

Compound 432

5-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-2-picolinic acid

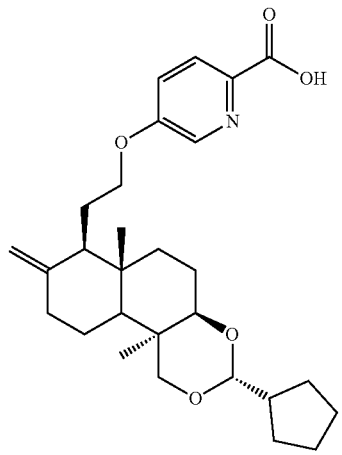

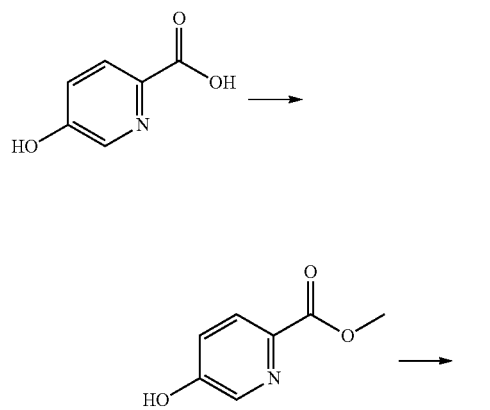

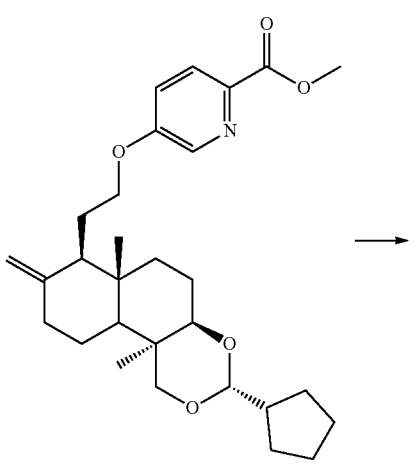

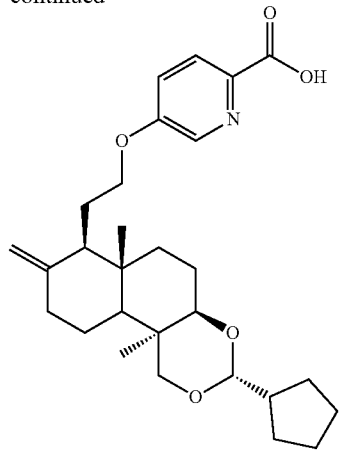

432

Step 1

Methyl 5-hydroxy-2-picolinate

5-Hydroxypyridin-2-carboxylic acid (2.50 g, 17.97 mmol) was dissolved in methanol (20.00 mL), added with sulfuric acid (18M, 47.90 uL) at room temperature, and then stirred at 70° C. for 12 hours. After the reaction mixture was concentrated, the residue was dissolved in dichloromethane (50.00 mL) and the system was adjusted to pH=8 with saturated sodium bicarbonate solution. A white solid was precipitated out, and the filter cake was dried to give methyl 5-hydroxy-2-picolinate (a white solid, 1.5 g, yield: 54.51%).
$^1$H NMR (400 MHz, CDCl$_3$) 10.82 (br. s., 1H), 8.20 (d, J=2.5 Hz, 1H), 7.92 (d, J=8.8 Hz, 1H), 7.25 (dd, J=2.8, 8.5 Hz, 1H), 3.80 (s, 3H).

Step 2

Methyl 5-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-2-picolinate (3R,4aR,6aS,7R,10bR)-7-(2-bromoethyl)-3-cyclopentyl-6a,10b-dimethyl-8-dihydromethylene-1H-naphtho[2,1-d][1,3]dioxin (400.00 mg, 972.27 umol) was dissolved in acetonitrile (10.00 mL), and potassium carbonate (268.75 mg, 1.94 mmol) and methyl 5-hydroxy-2-picolinate (148.89 mg, 972.27 umol) were added successively at room temperature and then stirred at 70° C. for 12 hours. The reaction was quenched by adding 30 mL water and then extracted with ethyl acetate (30.00 mL). The organic phases were combined and successively washed with water (30 mL) and saturated brine (30 mL), dried over anhydrous sodium sulfate, filtered, and the filtrate was concentrated under reduced pressure. The residue was purified by gel column chromatography (elution system: PE/EtOAc=1:3) to give methyl 5-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-2-picolinate (a yellow solid, 250 mg, yield: 53.17%).
$^1$H NMR (400 MHz, CDCl$_3$) 8.35 (d, J=2.8 Hz, 1H), 8.09 (d, J=8.8 Hz, 1H), 7.21 (dd, J=2.9, 8.7 Hz, 1H), 4.90 (s, 1H), 4.63-4.53 (m, 2H), 4.19-4.13 (m, 1H), 4.03 (d, J=11.3 Hz, 1H), 3.98 (s, 3H), 3.96-3.90 (m, 1H), 3.54-3.38 (m, 2H), 2.43 (d, J=13.1 Hz, 1H), 2.32-2.22 (m, 1H), 2.13-2.07 (m, 1H), 2.03-1.95 (m, 1H), 1.92-1.78 (m, 4H), 1.74-1.65 (m, 3H), 1.60-1.58 (m, 1H), 1.56-1.48 (m, 4H), 1.44 (dd, J=7.2, 12.2 Hz, 2H), 1.37 (s, 3H), 1.28-1.23 (m, 3H), 0.80 (s, 3H).

Step 3

5-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-2-picolinic acid Methyl 5-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-2-picolinate (100.00 mg, 206.77 umol) was dissolved in 1 mL tetrahydrofuran and 1 mL water, and potassium hydroxide 30.16 mg, 537.58 umol) was added, followed by stirring at room temperature for 12 hours. The system was adjusted to pH=7 with diluted hydrochloric acid solution (1M), and extracted with ethyl acetate (10 mL*2). The organic phases were combined, successively washed with water (10 mL) and saturated brine (10 mL), dried over anhydrous sodium sulfate, filtered, and the filtrate was concentrated under reduced pressure to give 5-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-2-picolinic acid 432 (73 mg, yield: 56.50%).

MS m/z (ESI): 470.7 [M+1]

$^1$H NMR (400 MHz, CDCl$_3$) 8.24 (br. s., 1H), 8.14 (br. s., 1H), 7.35-7.28 (m, 1H), 4.89 (br. s., 1H), 4.62-4.56 (m, 2H), 4.15 (br. s., 1H), 4.02 (d, J=11.0 Hz, 1H), 3.96 (br. s., 1H), 3.53-3.47 (m, 1H), 3.44 (d, J=11.3 Hz, 1H), 2.42 (d, J=12.0 Hz, 1H), 2.32-2.21 (m, 1H), 2.11-2.04 (m, 2H), 2.01-1.94 (m, 1H), 1.91-1.80 (m, 4H), 1.69-1.64 (m, 2H), 1.58-1.51 (m, 4H), 1.48-1.41 (m, 3H), 1.37 (s, 3H), 1.25 (br. s., 3H), 0.79 (br. s., 3H).

Compound 428

2-(4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-2-carbonylpyridin-1(2H)-yl)acetic acid

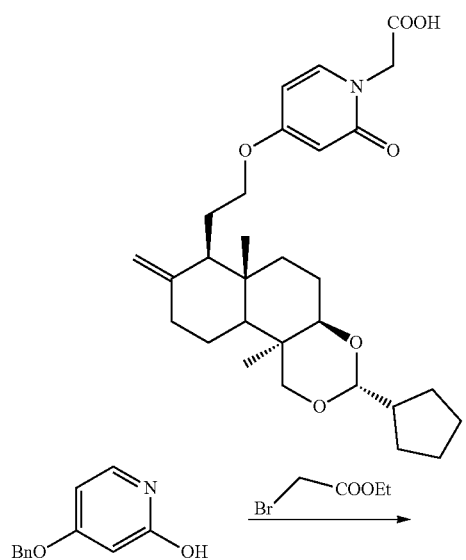

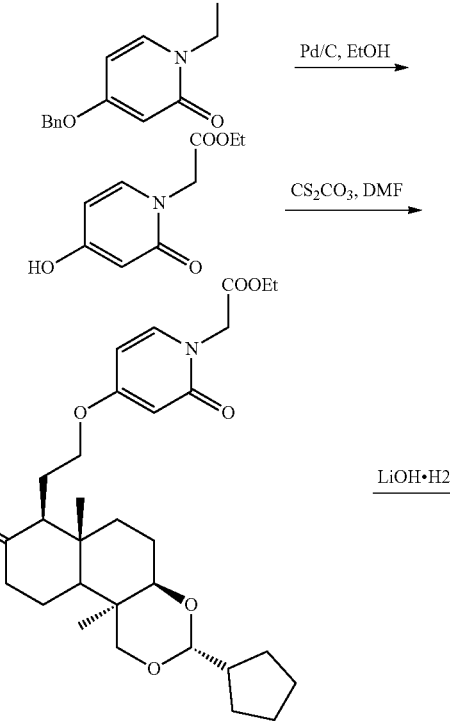

Step 1

Ethyl 2-(4-(benzyloxy)-2-carbonylpyridin-1 (2H)-yl)acetate

4-Benzyloxypyridin-2-ol (5.00 g, 24.85 mmol) in tetrahydrofuran (100.00 mL), and added with sodium hydrogen (1.99 g, 49.70 mmol, 60% purity) at 0° C., then stirred at 0° C. for 0.5 hours. Ethyl 2-bromoacetate (6.22 g, 37.28 mmol, 4.12 mL) was added to the reaction solution, followed by stirring at room temperature for 12 hours. The reaction was quenched with 20 mL water and extracted with ethyl acetate (30 mL*3). The combined organic phases were washed with saturated brine (20 mL*1), dried over anhydrous sodium sulfate, filtered, and the filtrate was concentrated to give 2-(4-(benzyloxy)-2-carbonylpyridin-1 (2H)yl) ethyl acetate (a white solid, 5 g, yield: 70.02%).

¹H NMR (400 MHz, CDCl3) 7.42-7.35 (m, 5H), 7.11 (d, J=8 Hz, 1H), 6.03-6.01 (m, 2H), 5.01 (s, 2H), 4.60 (s, 2H), 4.26-4.22 (m, 2H), 1.33-1.27 (m, 6H).

Step 2

Ethyl 2-(4-hydroxy-2-carbonylpyridin-1(2H)-yl) acetate

Ethyl 2-(4-(benzyloxy)-2-carbonylpyridin-1(2H)-yl) acetate (1.00 g, 3.48 mmol) was dissolved in ethanol (20.00 mL) and palladium on carbon (100.00 mg, 10% purity) was added, then stirred at 30° C. for 3 hours under 30 PSI of hydrogen atmosphere. The reaction was filtered and the filtrate was concentrated to give ethyl 2-(4-hydroxy-2-carbonylpyridin-1(2H))-yl)acetate (a white solid, 450 mg, yield: 65.58%).

¹H NMR (400 MHz, CDCl3) 7.47 (d, J=7.6 Hz, 1H), 6.09-6.06 (m, 1H), 5.83 (s, 1H), 4.66 (s, 2H), 4.21-4.19 (m, 2H), 1.30-1.26 (m, 5H).

Step 3

Ethyl 2-(4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-2-carbonylpyridin-1(2H)-yl) acetate (3R,4aR,6aS,7R,10bR)-7-(2-bromoethyl)-3-cyclopentyl-6a,10b-dimethyl-8-dihydromethylene decahydro-1H-naphtho[2,1-d][1,3]dioxin (500.00 mg, 1.22 mmol) was dissolved in N,N-dimethylformamide (20.00 mL), and cesium carbonate (791.96 mg, 2.43 mmol) and ethyl 2-(4-hydroxy-2-carbonylpyridin-1(2H)-yl)acetate (250.00 mg, 1.27 mmol) were successively added, and then stirred at 70° C. for 12 hours. The reaction was quenched with 10 mL water and extracted with dichloromethane (10 mL*3). The combined organic phases were washed with saturated brine (10 mL*1), dried over anhydrous sodium sulfate, filtered, and the filtrate was concentrated. The residue was purified by column chromatography (silica, petroleum ether/ethyl acetate=10/1 to 2/1) to give ethyl 2-(4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-2-carbonylpyridin-1(2H)-yl) acetate (a yellow solid, 280 mg, yield: 36.24%).

¹H NMR (400 MHz, CDCl3) 7.05 (d, J=7.6 Hz, 1H), 5.94-5.91 (m, 1H), 5.83 (d, J=2.4 Hz, 1H), 4.88 (s, 1H), 4.61-4.54 (m, 5H), 4.24-4.22 (m, 2H), 4.04-4.01 (m, 2H), 3.81-3.79 (m, 1H), 3.45-3.42 (m, 2H), 2.06-1.69 (m, 12H), 1.59-1.36 (m, 13H), 1.28-1.24 (m, 9H), 0.78 (s, 3H).

Step 4

2-(4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-2-carbonylpyridin-1(2H)-yl)acetic acid Ethyl 2-(4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-2-carbonylpyridin-1(2H)-yl) acetate (100.00 mg, 189.51 umol) was dissolved in tetrahydrofuran (6.00 mL), and lithium hydroxide monohydrate (39.76 mg, 947.55 umol) and water (2.00 mL) were successively added, followed by stirring at 40° C. for 12 hours. The tetrahydrofuran was removed by rotary evaporation under reduced pressure, the system was adjusted to pH=3 with a hydrochloric acid solution (1M), the reaction solution was extracted with ethyl acetate (30 mL*3), and the combined organic phases were washed with saturated brine, dried over anhydrous sodium sulfate and filtered, and the filtrate was concentrated to give 2-(4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-2-carbonylpyridin-1(2H)-yl)acetic acid 428 (46 mg, yield: 36.25%).

MS m/z (ESI): 500.3 [M+1]

¹H NMR (400 MHz, CDCl3) 7.15 (d, J=7.6 Hz, 1H), 8.06-8.03 (m, 1H), 5.93 (d, J=2 Hz, 1H), 4.88 (s, 1H), 4.61-4.53 (m, 4H), 4.03-3.82 (m, 3H), 3.51-3.42 (m, 2H), 2.27-2.25 (m, 2H), 1.98-1.67 (m, 18H), 1.53 (s, 3H), 1.52-1.25 (m, 4H), 0.78 (s, 3H).

Compound 417

4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)pyridine-3,5-dicarboxylic acid

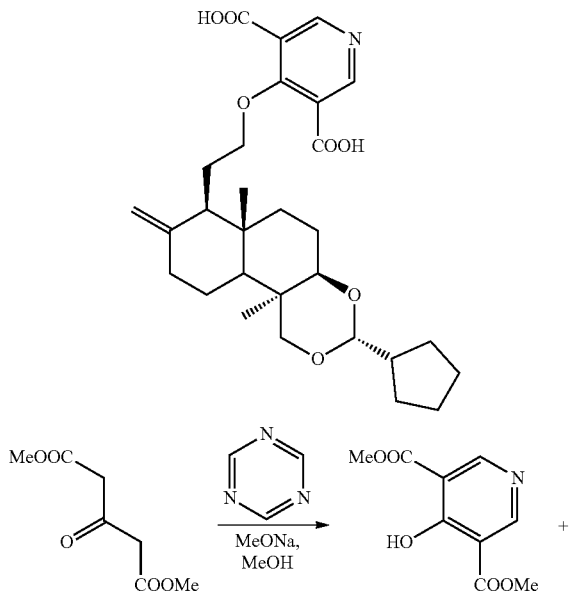

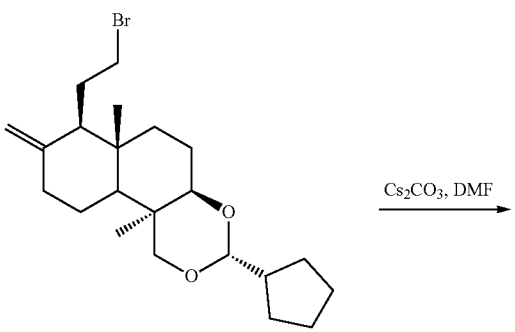

115

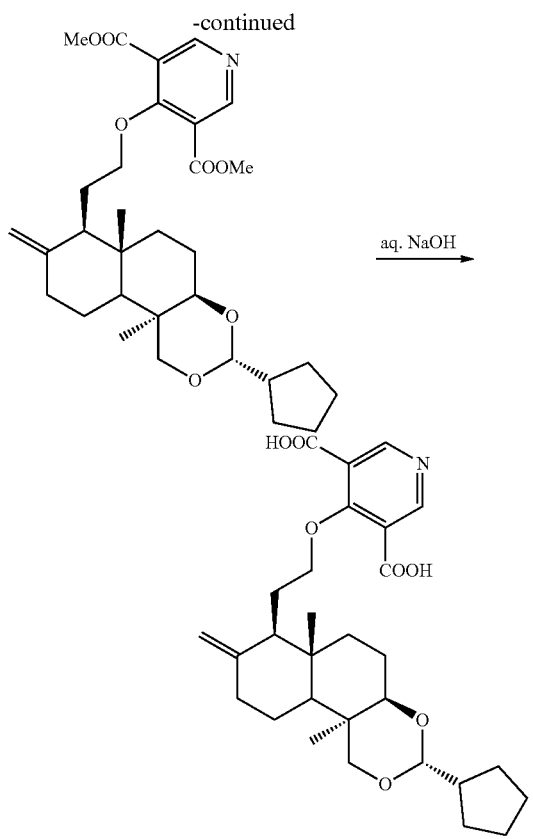

417

Step 1

Dimethyl 4-hydroxypyridine-3,5-dicarboxylate

Dimethyl 3-oxoglutarate (2.00 g, 11.48 mmol) was dissolved in methanol (20.00 mL) and sodium methoxide (639.00 mg, 11.82 mmol) and 1,3,5-triazine (903.22 mg, 11.14 mmol) were added successively, and then stirred for 10 minutes at room temperature and 30 minutes at 70° C. The system was adjusted to neutrality with concentrated hydrochloric acid, then allowed to stand for 2 hours, filtered, and the filter cake was washed successively with water (3*100 mL), methanol (3*50 mL) and petroleum ether (3*50 mL) to give dimethyl 4-hydroxypyridine-3,5-dicarboxylate (a light yellow solid, 1.45 g, crude product).

$^1$H NMR (400 MHz, DMSO-$d_6$) 12.05 (br. s., 1H), 8.20 (br. s., 2H), 3.70 (br. s., 6H).

Step 2

Dimethyl 4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)pyridine-3,5-dicarboxylate (3R,4aR,6aS,7R,10bR)-7-(2-bromoethyl)-3-cyclopentyl-6a,10b-dimeth yl-8-dihydromethylene decahydro-1H-naphtho[2,1-d][1,3]dioxin (200.00 mg, 486.13 umol) was dissolved in N,N-dimethylformamide (10.00 mL), and cesium carbonate (316.78 mg, 972.26 umol) and dimethyl 4-hydroxypyridine-3,5-dicarboxylate 417b (123.19 mg, 583.36

116 umol) were added successively, then stirred at 80° C. for 8 hours. The system was filtered and the filtrate was separated by preparative liquid chromatography to give dimethyl 4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)pyridine-3,5-dicarboxylate (a white solid, 40 mg, yield: 15.19%).

$^1$H NMR (400 MHz, CDCl3) 8.97 (s, 2H), 4.84 (s, 1H), 4.67-4.56 (m, 2H), 4.19-4.11 (m, 1H), 4.06-3.97 (m, 3H), 3.92 (s, 6H), 3.49-3.38 (m, 3H), 2.40 (d, J=13.3 Hz, 1H), 2.24 (t, J=13.1 Hz, 1H), 2.07-1.70 (m, 14H), 1.35 (br. s., 3H), 1.24 (br. s., 3H), 0.77 (s, 3H).

Step 3

4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)pyridine-3,5-dicarboxylic acid Dimethyl 4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)pyridine-3,5-dicarboxylate (35.00 mg, 64.61 umol) was dissolved in tetrahydrofuran (5.00 mL), and sodium hydroxide (2.58 mg, 64.61 umol) and water (5.00 mL) were successively added, followed by stirring at room temperature for 1 hour. Ethyl acetate (5.00 mL) was added to the system, and the organic phase was separated from the aqueous phase. The aqueous phase was separated by preparative liquid chromatography to give 4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)pyridine-3,5-dicarboxylic acid 417 (25 mg, yield: 71.49%).

MS m/z (ESI):514.2 [M+1]

$^1$H NMR (400 MHz, MeOD) 8.66 (s, 2H), 4.70 (d, J=5.5 Hz, 1H), 4.59 (s, 1H), 4.47 (d, J=6.8 Hz, 1H), 4.26-4.16 (m, 1H), 4.09 (d, J=11.0 Hz, 1H), 3.51 (dd, J=4.9, 12.4 Hz, 1H), 3.41 (d, J=11.3 Hz, 1H), 3.37 (br. s., 1H), 2.43-2.29 (m, 2H), 2.12-1.95 (m, 4H), 1.91-1.77 (m, 3H), 1.71-1.43 (m, 9H), 1.35 (s, 3H), 1.33-1.15 (m, 3H), 0.80 (s, 3H).

Compound 349

4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)cyanopyridine

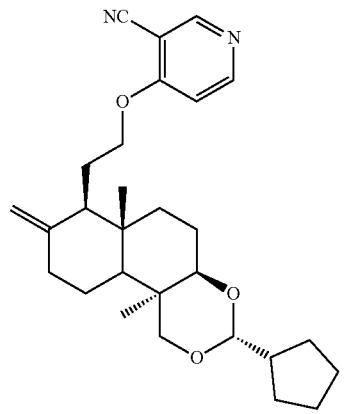

117

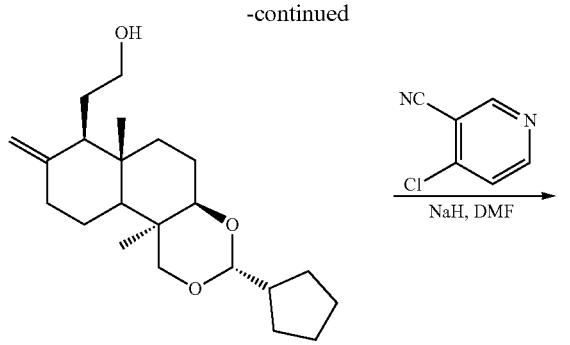

Step 2

4-(2-((3R,4aR,6aS,7R,10bR)-3-cyclopentyl-6a,10b-dimethyl-8-dihydromethylenedecahydro-1H-naphtho[2,1-d][1,3]dioxin-7-yl)ethoxy)cyanopyridine 2-((3R,4aR,6aS,7R,10bR)-3-cyclopentyl-6a,10b-dimethyl-8-methylene decahydro-1H-naphtho[2,1-d][1,3]dioxin-7-yl)ethanol (150 mg, 0.43 mmol) was dissolved in anhydrous N,N-dimethylformamide (15 mL), and sodium hydrogen (15.5 mg, 0.65 mmol) was added at 0° C. After stirring at 0° C. for 15 minutes, 4-chloro-3-cyanopyridine (71.6 mg, 0.52 mmol) was added to the reaction mixture and stirred at room temperature overnight. The reaction solution was quenched with water, extracted with dichloromethane, and the organic layer was washed with water and saturated brine and dried over anhydrous sodium sulfate, filtered, and the filtrate was concentrated under reduced pressure and then separated on a thin layer chromatography plate to give 4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)cyanopyridine 349 (75 mg, yield: 38.7%).

MS m/z (ESI): 451.2 [M+1]

$^1$H NMR (400 MHz, CDCl$_3$) 8.68 (s, 1H), 8.59 (d, J=5.6 HZ, 1H), 6.84 (d, J=6.0 HZ, 1H),4.91 (s, 1H), 4.61-4.00 (m, 5H), 3.53-3.43 (m, 2H), 2.45-1.52 (m, 18H), 1.51 (s, 3H), 1.37-1.25 (m, 3H), 0.80 (s, 3H).

118

Compound 312

4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)pyrimidine

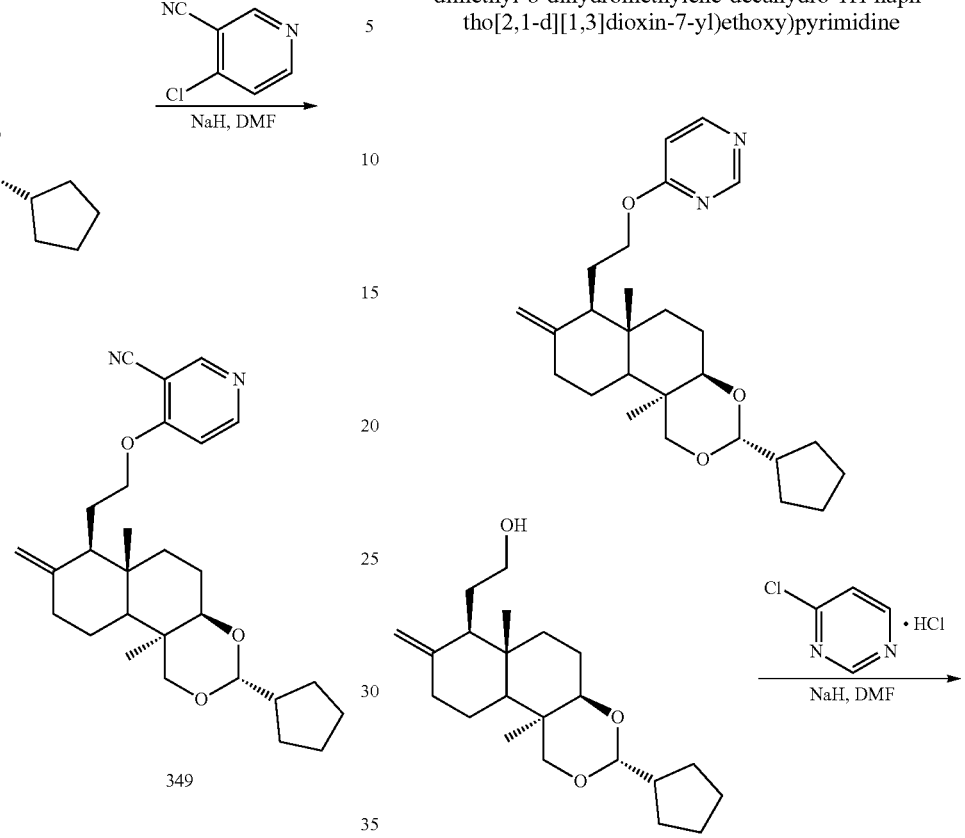

Step 1

4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)pyrimidine 2-((3R,4aR,6aS,7R,10bR)-3-cyclopentyl-6a,10b-dimethyl-8-methylene decahydro-1H-naphtho[2,1-d][1,3]dioxin-7-yl)ethanol (200 mg, 0.57 mmol) was dissolved in N,N-dimethylformamide (5 mL), and sodium hydrogen (48.2 mg, 2.01 mmol) was added at 0° C. and stirred for 15 minutes at 0° C. 2-chloropyrimidine hydrochloride 312b (173 mg, 1.15 mmol) was added to the reaction and stirred at room temperature overnight. The reaction solution was quenched with water (5 mL), extracted with dichloromethane (30 mL), the organic layer was washed with water (10 mL×3), dried over anhydrous magnesium sulfate and filtered. The filtrate was concentrated under reduced pressure, and separated through a thin layer chromatographic plate to give 4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)pyrimidine 312 (150 mg, yield: 61.3%).

MS m/z (ESI): 427.2 [M+1]

¹H NMR (400 MHz, CDCl₃) 8.75 (s, 1H), 8.41 (d, J=5.6 Hz, 1H), 6.71 (d, J=6.0 Hz, 1H), 4.90 (s, 1H), 4.67 (s, 1H), 4.60 (d, J=6.0 Hz, 1H), 4.50-4.01 (m, 4H), 3.50-3.43 (m, 2H), 2.44-1.52 (m, 18H), 1.37 (s, 3H), 1.25-1.19 (m, 3H), 0.78 (s, 3H).

Compound 453

4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)thiophene-3-carboxylic acid

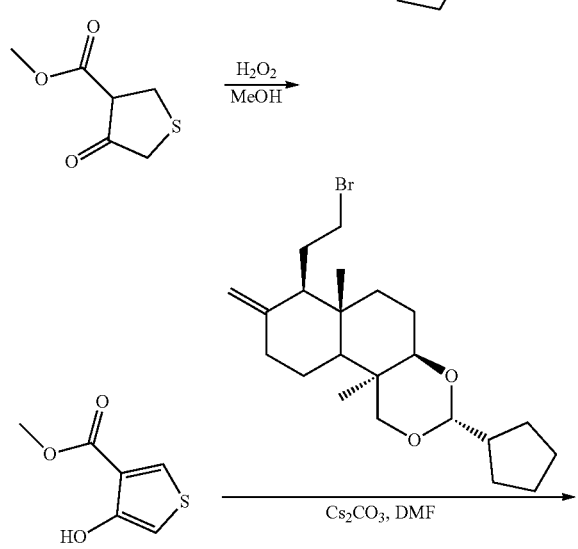

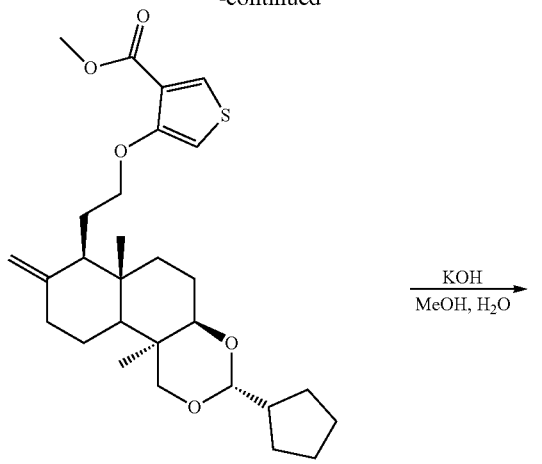

Step 1

Methyl 4-hydroxythiophene-3-carboxylate

Methyl 4-oxytetrahydrothiophene-3-carboxylate (1.00 g, 6.24 mmol) was dissolved in methanol (20.00 mL), and hydrogen peroxide (2.83 g, 24.96 mmol, 2.40 mL, 30% purity) was added dropwise under nitrogen atmosphere at 70° C., and then stirred at 70° C. for 2 hours. The reaction was quenched with 20 mL saturated sodium sulfite solution at 0° C. and the system was adjusted to pH=6-7 with hydrochloric acid solution (1M). The system was concentrated and the residue was dissolved in dichloromethane/methanol=5/1 (30 mL), filtered and concentrated to give methyl 4-hydroxythiophene-3-carboxylate (0.6 g, crude product).

¹H NMR (400 MHz, CDCl3) 8.73 (br. s., 1H), 7.90 (d, J=3.5 Hz, 1H), 6.40 (d, J=3.5 Hz, 1H), 3.93 (s, 3H).

Step 2

Methyl 4-(2-((3R,4aR,6aS,7R,10bR)-3-cyclopentyl-6a, 10b-dimethyl-8-dihydromethylene decahydro-1H-naphtho[2,1-d][1,3]dioxin-7-yl)ethoxy)thiophene-3-carboxylate (3R,4aR,6aS,7R,10bR)-7-(2-bromoethyl)-3-cyclopentyl-6a,10b-dimeth yl-8-dihydromethylene-1H-naphthop[2,1-d][1,3]dioxin (500.00 mg, 1.22 mmol) was dissolved in N,N-dimethylformamide (5.00 mL), and cesium carbonate (795.00 mg, 2.44 mmol) and methyl 4-hydroxythiophene-3-carboxylate (289.45 mg, 1.83 mmol) were added successively, and then stirred at 80° C. for 12 hours. The reaction solution was filtered and concentrated, and the residue was separated by column chromatography (silica, petroleum ether/ethyl acetate=5/1) to give methyl 4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)thiophene-3-carboxylate (a white solid, 100 mg, yield: 13.98%).

$^1$H NMR (400 MHz, CDCl3) 8.00 (d, J=3.5 Hz, 1H), 6.21 (d, J=3.8 Hz, 1H), 4.87 (s, 1H), 4.65-4.59 (m, 2H), 4.13-4.01 (m, 2H), 3.89-3.68 (m, 4H), 3.53-3.43 (m, 2H), 2.42 (d, J=13.1 Hz, 1H), 2.33-2.22 (m, 1H), 2.16-1.81 (m, 7H), 1.70 (dd, J=4.1, 8.7 Hz, 3H), 1.56-1.40 (m, 6H), 1.37 (s, 3H), 1.27-1.21 (m, 3H), 0.82-0.76 (m, 3H).

Step 3

4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)thiophene-3-carboxylic acid Methyl 4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)thiophene-3-carboxylate (100.00 mg, 204.63 umol) was dissolved in methanol (2.00 mL) and potassium hydroxide (68.89 mg, 1.23 mmol) and water (2.00 mL) were added successively, then stirred at 70° C. for 24 hours. The system was adjusted to pH=5-6 with hydrochloric acid solution (1M) and then extracted with ethyl acetate (30 mL*3). The combined organic phases were washed with saturated brine, dried over anhydrous sodium sulfate, filtered and concentrated to give 4-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)thiophene-3-carboxylic acid 453 (66.1 mg, yield: 64.84%).

MS m/z (ESI):475.3[M+1]

$^1$H NMR (400 MHz, DMSO-d$_6$) 7.97 (br. s., 1H), 6.54 (d, J=3.5 Hz, 1H), 4.84 (s, 1H), 4.65 (d, J=5.3 Hz, 1H), 4.60 (s, 1H), 4.01-3.90 (m, 2H), 3.79-3.69 (m, 1H), 3.61-3.49 (m, 2H), 2.38-2.21 (m, 3H), 1.98-1.84 (m, 4H), 1.81-1.70 (m, 3H), 1.57-1.40 (m, 8H), 1.25-1.17 (m, 6H), 0.75-0.68 (m, 3H).

Compound 445

4-cyano-2-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)benzoic acid

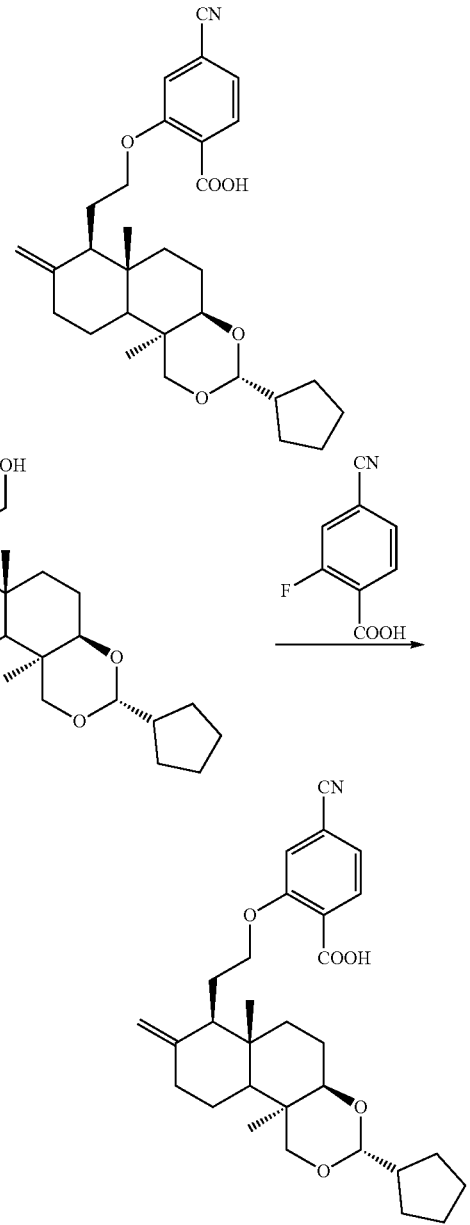

445

Step 1

4-cyano-2-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)benzoic acid 2-((3R,4aR,6aS,7R,10bR)-3-cyclopentyl-6a,10b-dimethyl-8-dihydromethylenepentahydro-1H-naphtho[2,1-d][1, 3]dioxin-7-yl)ethanol (500.00 mg, 1.43 mmol) was dissolved in N,N-dimethylformamide (20.00 mL) and sodium hydrogen (150.00 mg, 3.75 mmol, 60% purity) was added at 0° C., then stirred at 0° C. for 2 hours. 4-Cyano-2-fluorobenzoic acid (309.32 mg, 1.87 mmol) was then added at 0° C. and stirred at 95° C. for 10 hours. The reaction was quenched with 100 mL of saturated brine, diluted with 50 mL of dichloromethane, and extracted with 90 mL (30 mL*3) of dichloromethane. The organic phase was washed with saturated brine (50 mL*2), dried over anhydrous sodium sulfate, filtered, and the filtrate was concentrated under reduced pressure. The residue was separated by column chromatography (silica, dichloromethane/methanol=40/1) to give an initial product. The initial product was separated by preparative liquid chromatography to give 4-cyano-2-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)benzoic acid 445 (30 mg, yield: 4.25%).

MS m/z (ESI): 494.2[M+1]

$^1$H NMR (400 MHz, DMSO-d$_6$) 7.55 (d, J=7.5 Hz, 1H), 7.46 (br. s., 1H), 7.38 (d, J=7.5 Hz, 1H), 4.86 (s, 1H), 4.67 (d, J=5.5 Hz, 1H), 4.59 (br. s., 1H), 4.14 (br. s., 1H), 3.96 (d, J=11.0 Hz, 1H), 3.88 (d, J=6.5 Hz, 1H), 3.40 (d, J=12.5 Hz, 2H), 2.42-2.20 (m, 3H), 1.94 (d, J=10.0 Hz, 4H), 1.83-1.69 (m, 3H), 1.62-1.39 (m, 8H), 1.30-1.09 (m, 6H), 0.73 (s, 3H).

Compound 452

2-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-6-fluoro-benzoic acid

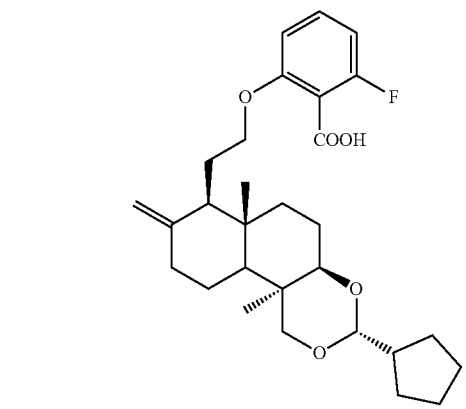

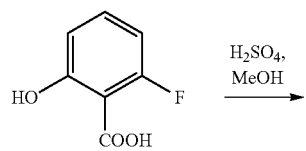

Step 1

Methyl 2-fluoro-6-hydroxybenzoate 2-fluoro-6-hydroxybenzoic acid (1.00 g, 6.41 mmol) was dissolved in methanol (10.00 mL), added with sulfuric acid (1.26 g, 12.82 mmol, 683.36 uL), and then stirred at 80° C. for 12 hours. The reaction was quenched with 20 mL saturated sodium bicarbonate solution and extracted with ethyl acetate (20 mL*3). The combined organic phases were washed with saturated brine (30 mL), dried over anhydrous sodium sulfate, filtered and concentrated to give 0.5 g methyl 2-fluoro-6-hydroxybenzoate. Yield: 45.85%.

$^1$H NMR (400 MHz, CDCl3) 11.24 (s, 1H), 7.42-7.36 (m, 1H), 6.81 (d, J=8.4 Hz, 1H), 6.65-6.6 (m, 1H).

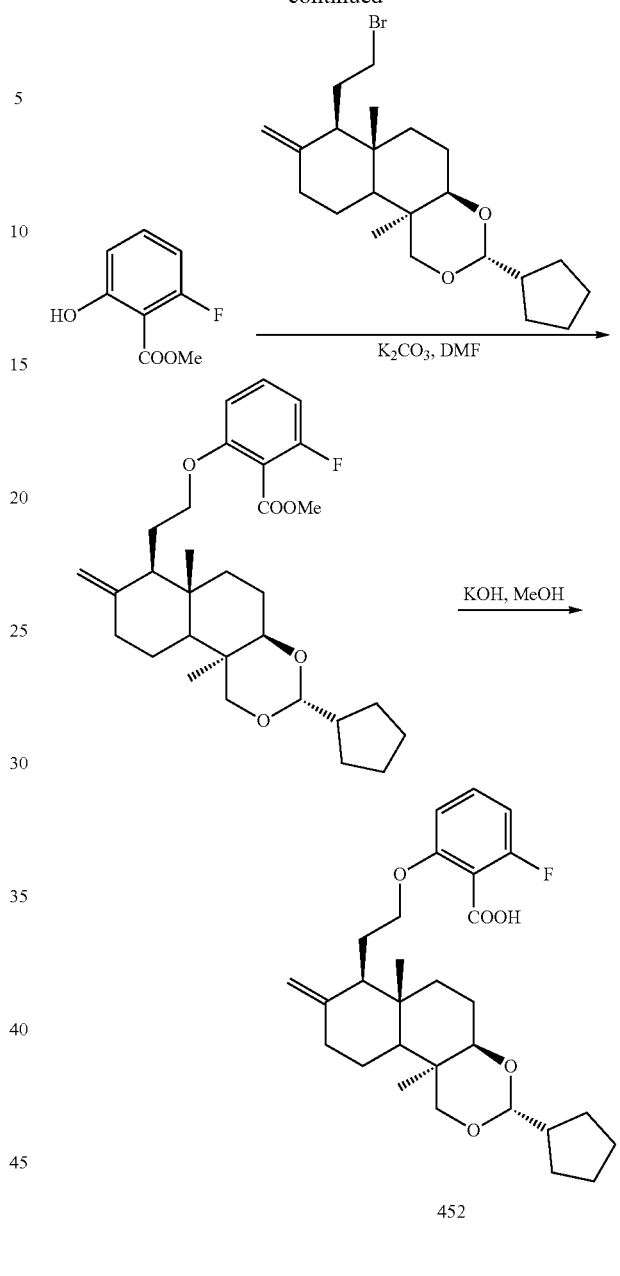

125
Step 2

Methyl 2-(2-((3R,4aR,6aS,7R,10bR)-3-cyclopentyl-6a, 10b-dimethyl-8-dihydromethylene decahydro-1H-naphtho[2,1-d][1,3]dioxin-7-yl)ethoxy)-6-fluoro-benzoate

(3R,4aR,6aS,7R,10bR)-7-(2-bromoethyl)-3-cyclopentyl-6a,10b-dimeth yl-8-dihydromethylene-1H-naphtho[2,1-d][1,3]dioxin (300.00 mg, 729.18 umol) was dissolved in N,N-dimethylformamide (10.00 mL) and potassium carbonate (201.56 mg, 1.46 mmol) and methyl 2-fluoro-6-hydroxybenzoate (148.88 mg, 875.02 umol) were added successively, then stirred at 80° C. for 12 hours. The reaction solution was filtered and concentrated, and the residue was separated by column chromatography (silica, petroleum ether/ethyl acetate=10/1 to 5/1) to give 120 mg methyl 2-(2-((3R,4aR,6aS, 7R, 10 bR)-3-cyclopentyl-6a,10b-dimethyl-8-dihydromethylene-1H-naphtho[2,1-d][1,3]dioxin7-yl)ethoxy)-6-fluoro-benzoate as a white solid. Yield: 32.87%.

$^1$H NMR (400 MHz, CDCl3) 7.27 (d, J=6.8 Hz, 1H), 6.72-6.63 (m, 2H), 4.86 (s, 1H), 4.61-4.57 (m, 2H), 4.10-4.01 (m, 2H), 3.92 (s, 3H), 3.84 (s, 1H), 3.50-3.42 (m, 2H), 2.42-2.39 (m, 2H), 1.99-1.70 (m, 10H), 1.56 (s, 3H), 1.42-1.36 (m, 5H), 1.37 (s, 3H), 1.24-1.20 (m, 4H), 0.88-0.84 (m, 3H), 0.77 (s, 3H).

Step 3

2-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)-6-fluoro-benzoic acid

Methyl 2-(2-((3R,4aR,6aS, 7R, 10 bR)-3-cyclopentyl-6a,10b-dimethyl-8-dihydromethylene-1H-naphtho[2,1-d][1,3] dioxin7-yl)ethoxy)-6-fluoro-benzoate (120 mg, 239.68 umol) was dissolved in methanol (6.00 mL), and potassium hydroxide (67.25 mg, 1.20 mmol) and water (3.00 mL) were added successively, then stirred at 40° C. for 12 hours. Methanol was removed by rotary evaporation under reduced pressure, and the system was adjusted to Ph=3 with a hydrochloric acid solution (1M) and then extracted with ethyl acetate (30 mL*3). The combined organic phases were washed with saturated brine, dried over anhydrous sodium sulfate, filtered and concentrated to give 60 mg 2-(2-((3R, 4aR,6aS,7R,10bR)-3-cyclopentyl-6a,10b-dimethyl-8-dihydromethylene decahydro-1H-naphtho[2,1-d][1,3]dioxin-7-yl)ethoxy)-6-fluoro-benzoic acid 452. Yield: 46.30%.

MS m/z (ESI):487.4[M+1]

$^1$H NMR (400 MHz, CDCl3) 7.41-7.35 (m, 1H), 6.81-6.71 (m, 2H), 4.89 (s, 1H), 4.59 (d, J=5.6 Hz, 2H), 4.23-4.21 (m, 1H), 4.02 (d, J=11.6 Hz, 2H), 3.50-3.41 (m, 2H), 2.44-2.09 (m, 2H), 2.07-1.54 (m, 16H), 1.50 (s, 3H), 1.42-1.24 (m, 3H), 0.79 (s, 3H).

126
Compound 454

5-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)pyrimidine-2-carboxylic acid

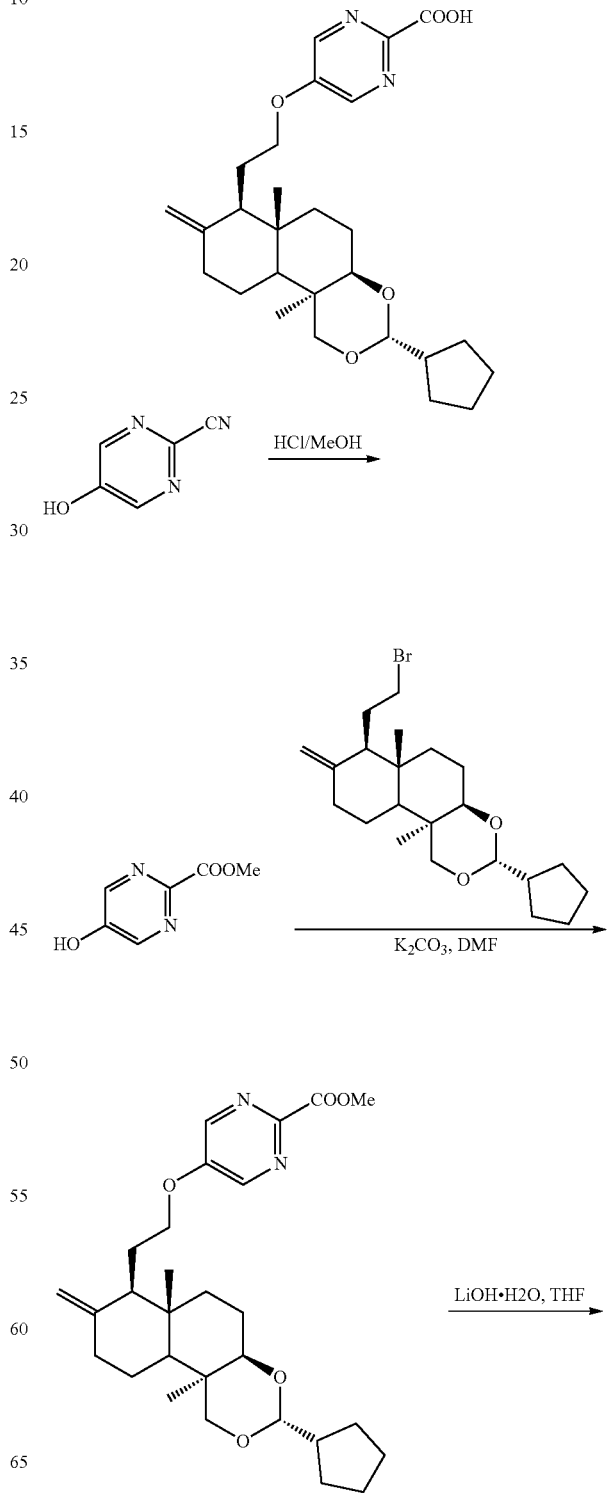

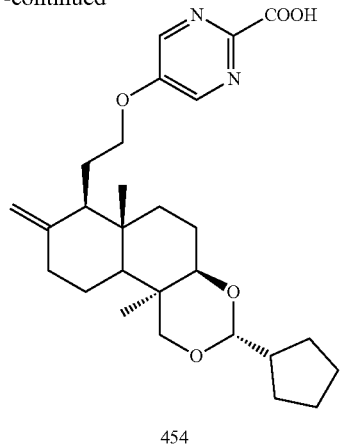

454

Step 1

Methyl 5-hydroxypyrimidine-2-carboxylate 5-hydroxypyrimidine-2-carbonitrile (200.00 mg, 1.65 mmol) was dissolved in methanol (5.00 mL), and methanolic hydrochloride (20.00 mmol, 3.00 mL, 4.0M) was added, and then stirred at 70° C. for 12 hours. The reaction was quenched with 20 mL saturated sodium bicarbonate solution and extracted with ethyl acetate (20 mL*3). The system was concentrated to give 0.18 g methyl 5-hydroxypyrimidine-2-carboxylate as a white solid. Yield: 70.78%.

$^1$H NMR (400 MHz, CDCl3) 8.50 (d, J=4.8 Hz, 2H), 3.84 (s, 3H).

Step 2

Methyl 5-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)pyrimidine-2-carboxylate (3R,4aR,6aS,7R,10bR)-7-(2-bromoethyl)-3-cyclopentyl-6a,10b-dimeth yl-8-dihydromethylene-1H-naphtho[2,1-d][1,3]dioxin (200.00 mg, 486.12 umol) was dissolved in N,N-dimethylformamide (5.00 mL), and potassium carbonate (134.37 mg, 972.24 umol) and methyl 5-hydroxypyrimidine-2-carboxylate (74.92 mg, 486.12 umol) were added successively, and then stirred at 80° C. for 4 hours. The reaction solution was filtered and concentrated, and the residue was separated by column chromatography (silica, petroleum ether/ethyl acetate=10/1 to 2/1) to give 120 mg methyl 5-(2-((3R,4aR,6aS,7R,10bR)-3-cyclopentyl-6a,10b-dimethyl-8-dihydromethylene-1H-naphtho[2,1-d][1,3]dioxin-7-yl)ethoxy) pyrimidine-2-carboxylate. Yield: 50.94%.

$^1$H NMR (400 MHz, CDCl3) 8.49 (s, 2H), 4.92 (s, 1H), 4.61-4.58 (m, 2H), 4.23 (s, 1H), 4.05-4.01 (m, 4H), 3.51-3.43 (m, 2H), 2.45-2.42 (m, 2H), 2.08-1.68 (m, 10H), 1.55-1.25 (m, 11H), 0.80 (s, 3H).

Step 3

5-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)pyrimidine-2-carboxylic acid Methyl 5-(2-((3R,4aR,6aS,7R,10bR)-3-cyclopentyl-6a,10b-dimethyl-8-dihydromethylene-1H-naphtho[2,1-d][1,3] dioxin-7-yl)ethoxy) pyrimidine-2-carboxylate (120.00 mg, 247.61 umol) was dissolved in tetrahydrofuran (6.00 mL), and lithium hydroxide monohydrate (51.95 mg, 1.24 mmol) and water (2.00 mL) were added successively, then stirred at 80° C. for 12 hours. The tetrahydrofuran was removed by rotary evaporation under reduced pressure, and the system was adjusted to Ph=3 with a hydrochloric acid solution (1M) and then extracted with ethyl acetate (50 mL*3). The combined organic phases were washed with saturated brine, dried over anhydrous sodium sulfate, filtered and concentrated to give 80 mg 5-(2-((3R,4aR,6aS,7R,10bR)-3-cyclopentyl-6a,10b-dimethyl-8-dihydromethylene decahydro-1H-naphtho[2,1-d][1,3]dioxin-7-yl)ethoxy)pyrimidine-2-carboxylic acid 454. Yield: 65.22%.

MS m/z (ESI):471.3[M+1]

$^1$H NMR (400 MHz, CDCl3) 8.51 (s, 2H), 4.92 (s, 1H), 4.61-4.58 (m, 2H), 4.23 (s, 1H), 4.05-4.01 (m, 2H), 3.51-3.43 (m, 2H), 2.45-2.42 (m, 2H), 2.08-1.68 (m, 10H), 1.55-1.25 (m, 11H), 0.80 (s, 3H).

Compound 385

(1R,2R,4aS,5R)-1-(hydroxymethyl)-1,4a-dimethyl-6-dihydromethylene-5-(2-(pyridin-4-oxy)ethyl) decahydronaphthalene-2-ol

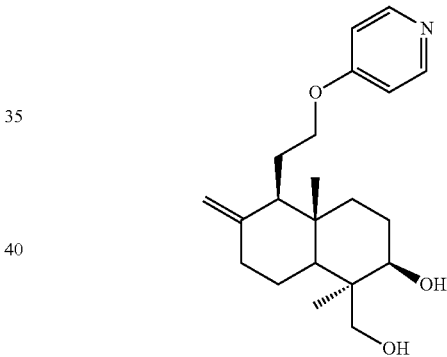

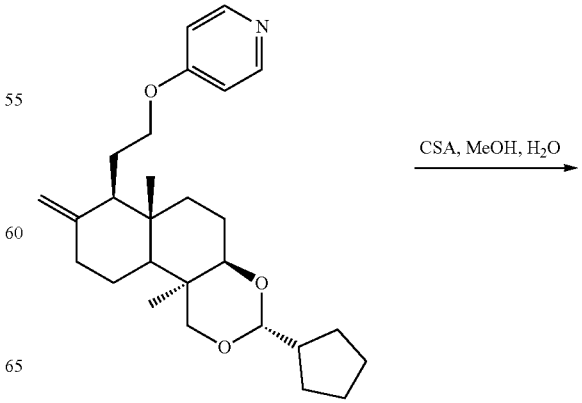

CSA, MeOH, H$_2$O

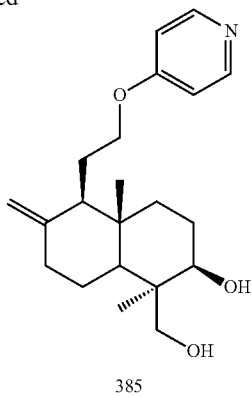

385

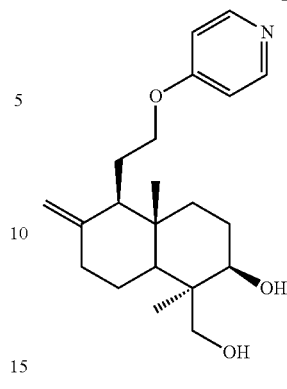

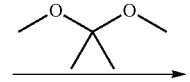

Step 1

(1R,2R,4aS,5R)-1-(hydroxymethyl)-1,4a-dimethyl-6-dihydromethylene-5-(2-(pyridin-4-oxy)ethyl)decahydronaphthalene-2-ol 4-(2-((3R,4aR,6aS,7R,10bR)-3-cyclopentyl-6a,10b-dimethyl-8-dihydromethylene-1H-naphtho[2,1-d][1,3]dioxin-7-yl)ethoxy)pyridine (150.00 mg, 352.44 umol) was dissolved in methanol (2.00 mL), followed by successive addition of L-camphorsulfonic acid (245.62 mg, 1.06 mmol)) and water (2.00 mL), then stirred at 70° C. for 12 hours. The system was adjusted to neutrality with saturated sodium bicarbonate solution and filtered. The filtrate was separated by preparative liquid chromatography (HCOOH) to give (1R,2R,4aS,5R)-1-(hydroxymethyl)-1,4a-dimethyl-6-dihydromethylene-5-(2-(pyridin-4-oxy)ethyl) decahydronaphthalene-2-ol 385 (2.5 mg, yield: 0.97%).

MS m/z (ESI): 345.9 [M+1]

$^1$H NMR (400 MHz, CDCl3) 8.41 (d, J=6.0 Hz, 2H), 6.78 (d, J=6.0 Hz, 2H), 4.89 (s, 1H), 4.56 (s, 1H), 4.19 (d, J=11.0 Hz, 1H), 4.13-4.03 (m, 1H), 3.93-3.81 (m, 1H), 3.51 (dd, J=4.8, 10.3 Hz, 1H), 3.33 (d, J=11.3 Hz, 1H), 2.43 (d, J=13.3 Hz, 1H), 2.07-1.91 (m, 2H), 1.89-1.79 (m, 6H), 1.31-1.20 (m, 6H), 0.67 (s, 3H).

Compound 402

4-(2-((4aR,6aS,7R,10bR)-3,3,6a, 10b-tetramethyl-8-dihydromethylenedecahydro-1H-naphtho[2,1-d][1,3]dioxin-7-yl)ethoxy)pyridine

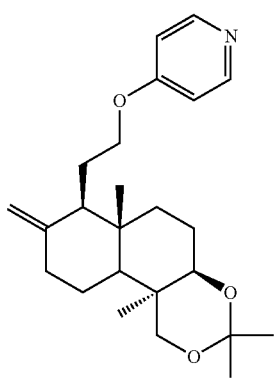

402

Step 1

4-(2-((4aR,6aS,7R,10bR)-3,3,6a, 10b-tetramethyl-8-dihydromethylenedecahydro-1H-naphtho[2,1-d][1,3]dioxin-7-yl)ethoxy)pyridine (1R,2R,4aS,5R)-1-(hydroxymethyl)-1,4a-dimethyl-6-dihydromethylene-5-(2-(pyridin-4-oxy)ethyl) decahydronaphthalene-2-ol (50.00 mg, 144.73 umol) was dissolved in dichloromethane (10.00 mL), and 2,2-dimethoxypropane (15.07 mg, 144.73 umol) and pyridinium 4-toluenesulfonate (254.59 mg, 1.01 mmol) were successively added, followed by stirring at room temperature for 2 hours. The reaction solution was concentrated. The residue was separated by preparative liquid chromatography to give 4-(2-((4aR,6aS,7R,10bR)-3,3,6a,10b-tetramethyl-8-dihydromethylenedecahydro-1H-naphtho[2,1-d][1,3]dioxin-7-yl)ethoxy)pyridine 402 (5 mg, yield: 7.44%).

MS m/z (ESI): 386.2 [M+1]

$^1$H NMR (400 MHz, CDCl3) 8.39 (d, J=5.6 Hz, 2H), 6.76 (d, J=5.6 Hz, 2H), 4.89 (s, 1H), 4.59 (s, 1H), 4.09-4.07 (m, 1H), 3.96 (d, J=11.6 Hz, 1H), 3.86 (s, 1H), 3.51 (t, J=4.8 Hz, 1H), 3.17 (d, J=11.6 Hz, 1H), 2.40 (s, 1H), 2.02-1.72 (m, 7H), 1.42 (s, 3H), 1.37-1.29 (m, 4H), 1.26 (s, 3H), 1.20 (s, 3H), 0.95 (s, 3H).

131

Compound 416

4-(2-((4a'R,6a'S,7'R, 10b'R)-6a', 10b'-dimethyl-8'-dihydromethylenedecahydro-1'H-spiro[cyclopentyl-1,3'-naphtho[2,1-d][1,3]dioxin-7-yl)ethoxy)pyridine

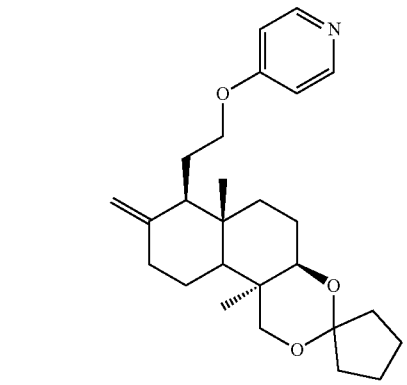

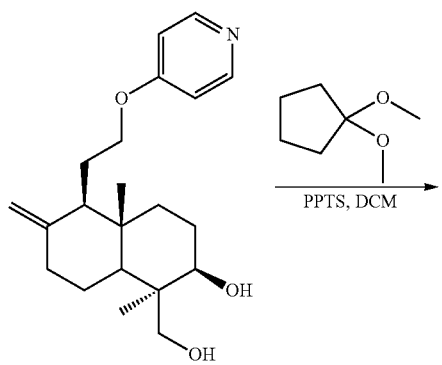

132

Step 1

4-(2-((4a'R,6a'S,7'R, 10b'R)-6a', 10b'-dimethyl-8'-dihydromethylenedecahydro-1'H-spiro[cyclopentyl-1,3'-naphtho[2,1-d][1,3]dioxin-7-yl)ethoxy)pyridine (1R,2R,4aS,5R)-1-(hydroxymethyl)-1,4a-dimethyl-6-dihydromethylene-5-(2-(pyridin-4-oxy)ethyl) decahydronaphthalene-2-ol (200.00 mg, 578.92 umol) was dissolved in dichloromethane (10.00 mL), and 1,1-dimethylcyclopentane (150.73 mg, 1.16 mmol) and pyridinium 4-toluenesulfonate (72.74 mg, 289.46 umol) were successively added, followed by stirring at 40° C. for 15 hours. The reaction was quenched with 50 mL saturated sodium bicarbonate solution, exacted with dichloromethane (50 mL*3), and the combined organic phases were washed with saturated brine, dried over anhydrous sodium sulfate, filtered and concentrated. The residue was separated by preparative liquid chromatography to give 4-(2-((4a'R, 6a'S, 7'R, 10b'R)-6a', 10b'-dimethyl-8'-dihydromethylenedecahydro-1'H-spiro[cyclopentyl-1,3'-naphtho[2,1-d][1,3]dioxin-7-yl)ethoxy)pyridine 416 (40.2 mg, yield: 16.07%).

MS m/z (ESI): 412.3 [M+1]

$^1$H NMR (400 MHz, CDCl3) 8.43 (br. s., 2H), 6.79 (d, J=5.3 Hz, 2H), 4.92 (s, 1H), 4.61 (s, 1H), 4.16-4.08 (m, 1H), 4.04 (d, J=11.5 Hz, 1H), 3.93-3.85 (m, 1H), 3.49 (dd, J=4.0, 11.0 Hz, 1H), 3.26 (d, J=11.3 Hz, 1H), 2.45 (d, J=12.0 Hz, 1H), 2.11-1.61 (m, 16H), 1.38-1.18 (m, 6H), 0.93-0.83 (m, 3H).

Compound 400

4-(2-((3R,4aR,6aS,7R,10bR)-3-cyclopropyl-6a,10b-dimethyl-8-dihydromethylenedecahydro-1H-naphtho[2,1-d][1,3]dioxin-7-yl)ethoxy)pyridine

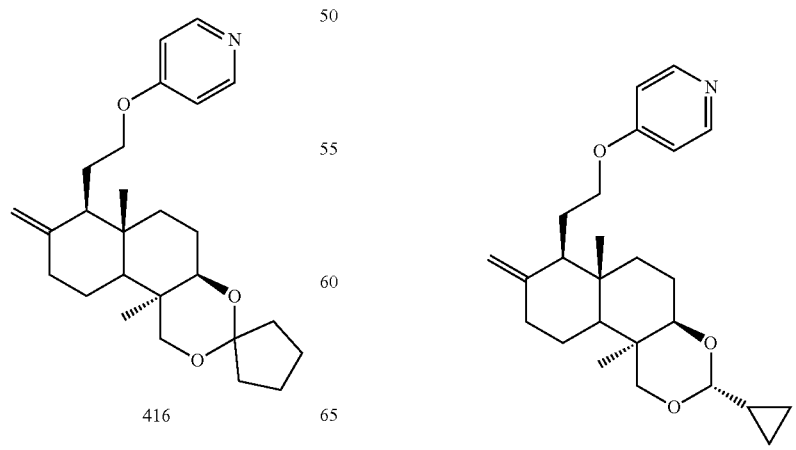

-continued

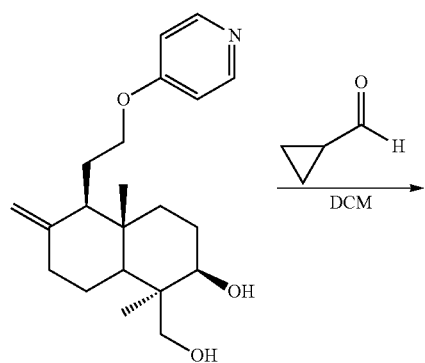

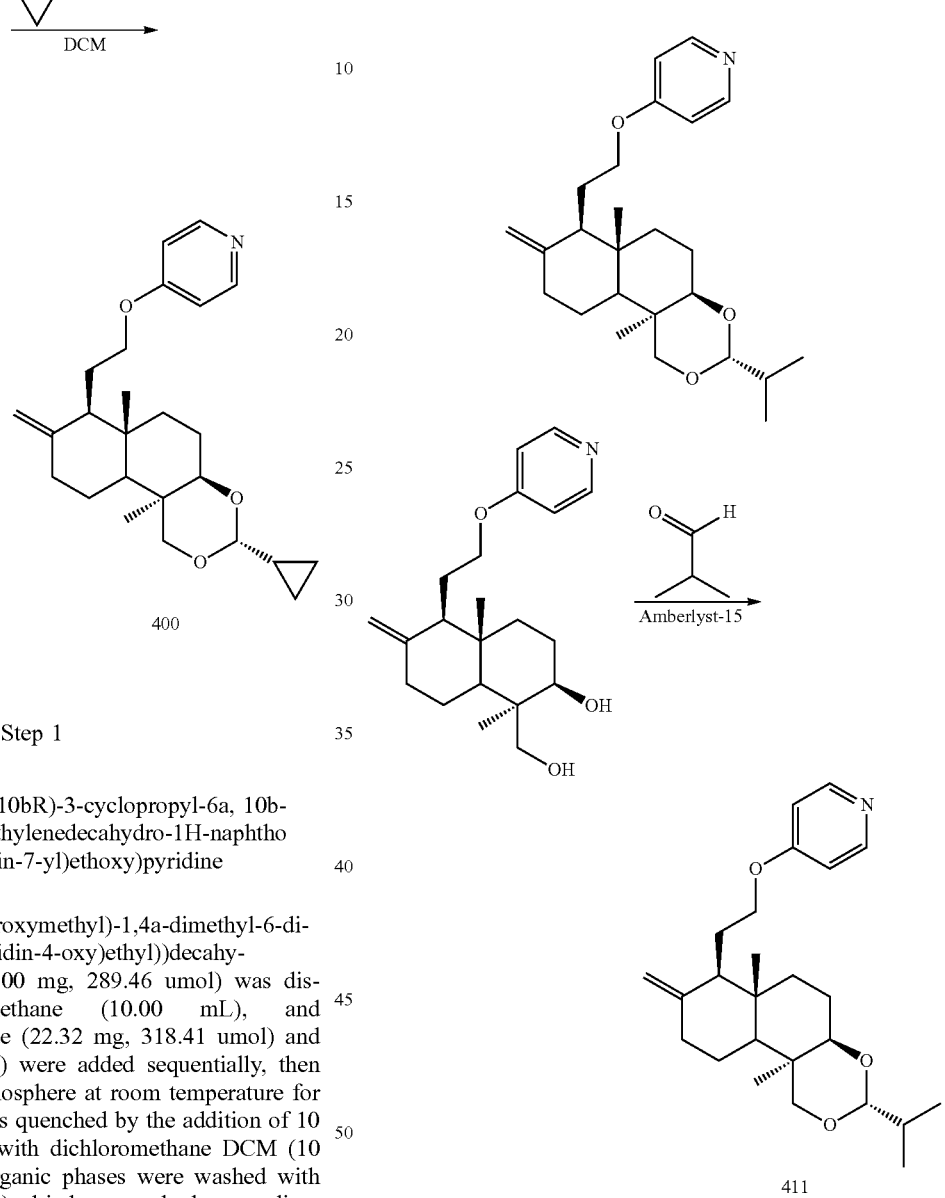

Step 1

4-(2-((3R,4aR,6aS,7R,10bR)-3-cyclopropyl-6a, 10b-dimethyl-8-dihydromethylenedecahydro-1H-naphtho[2,1-d][1,3]dioxin-7-yl)ethoxy)pyridine (1R,2R,4aS,5R)-1-(hydroxymethyl)-1,4a-dimethyl-6-dihydromethylene-5-(2-(pyridin-4-oxy)ethyl))decahydronaphthalene-2-ol (100.00 mg, 289.46 umol) was dissolved in dichloromethane (10.00 mL), and cyclopropylcarboxaldehyde (22.32 mg, 318.41 umol) and amberlyst-15 (100.00 mg) were added sequentially, then stirred under nitrogen atmosphere at room temperature for 12 hours. The reaction was quenched by the addition of 10 mL water and extracted with dichloromethane DCM (10 mL*3). The combined organic phases were washed with saturated brine (10 mL*1), dried over anhydrous sodium sulfate, filtered and concentrated. The residue was separated by preparative liquid chromatography to give 4-(2-((3R, 4aR,6aS,7R,10bR)-3-cyclopropyl-6a,10b-dimethyl-8-dihydromethylenedecahydro-1H-naphtho[2,1-d][1,3]dioxin-7-yl)ethoxy)pyridine 400 (5 mg, yield: 4.00%).

MS m/z (ESI): 398.2 [M+1]

$^1$H NMR (400 MHz, CDCl3) 8.42 (d, J=5.6 Hz, 2H), 6.78 (d, J=5.6 Hz, 2H), 4.91 (s, 1H), 4.60 (s, 1H), 4.38 (d, J=4.8 Hz, 1H), 4.11-4.03 (m, 2H), 3.89 (d, J=6 Hz, 1H), 3.56-3.45 (m, 2H), 2.47 (s, 1H), 2.43 (s, 1H), 2.04 (s, 1H), 1.92-1.87 (m, 4H), 1.73 (s, 2H), 1.40 (s, 3H), 1.27 (s, 3H), 1.13 (d, J=5.6 Hz, 1H), 0.79 (s, 3H), 0.54 (d, J=5.2 Hz, 2H), 0.53-0.43 (m, 2H).

Compound 411

4-(2-((3R,4aR,6aS,7R,10bR)-3-isopropyl-6a,10b-dimethyl-8-dihydromethylenedecahydro-1H-naphtho[2,1-d][1,3]dioxin-7-yl)ethoxy)pyridine Step 1

4-(2-((3R,4aR,6aS,7R,10bR)-3-isopropyl-6a,10b-dimethyl-8-dihydromethylenedecahydro-1H-naphtho[2,1-d][1,3]dioxin-7-yl)ethoxy)pyridine (1R,2R,4aS,5R)-1-(hydroxymethyl)-1,4a-dimethyl-6-dihydromethylene-5-(2-(pyridin-4-oxy)ethyl))decahydronaphthalene-2-ol (100.00 mg, 289.46 umol) was dissolved in 1,2-dichloroethane (2.00 mL), and isobutyraldehyde (208.73 mg, 2.89 mmol) and AMBERLYST® 15 HYDROGEN FORM (100.00 mg) were added successively, then stirred at 60° C. for 15 hours. The reaction solution was filtered, concentrated, and separated by a preparative liquid chromatography to give 4-(2-((3R,4aR,6aS,7R,10bR)-3-isopropyl-6a,10b-dimethyl-8-dihydromethylenedecahydro-1H-naphtho[2,1-d][1,3]dioxin-7-yl)ethoxy)pyridine 411 (8 mg, yield: 6.26%).

MS m/z (ESI): 400.3 [M+1]

¹H NMR (400 MHz, CDCl3) 8.47-8.35 (m, 2H), 6.82-6.72 (m, 2H), 4.90 (s, 1H), 4.63-4.50 (m, 2H), 4.17-3.82 (m, 3H), 3.57-3.38 (m, 2H), 2.44 (d, J=12.0 Hz, 1H), 2.35-2.20 (m, 1H), 2.02-1.71 (m, 8H), 1.38-1.33 (m, 3H), 1.29-1.11 (m, 3H), 0.99-0.89 (m, 6H), 0.88-0.77 (m, 3H).

Compound 412

4-(2-((3R,4aR,6aS,7R,10bR)-3-cyclobutyl-6a,10b-dimethyl-8-dihydro methylenedecahydro-1H-naphtho[2,1-d][1,3]dioxin-7-yl)ethoxy)pyridine

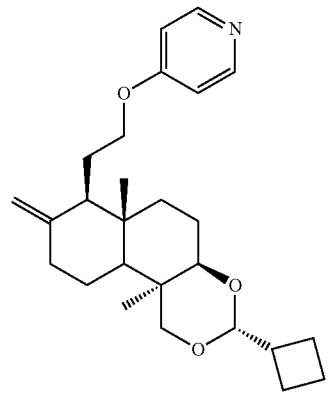

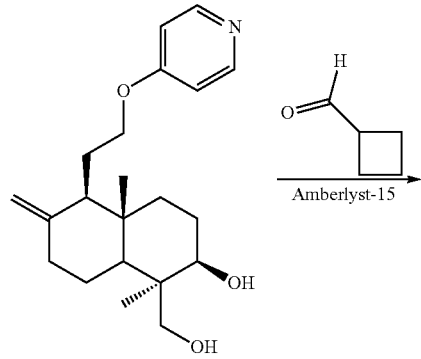

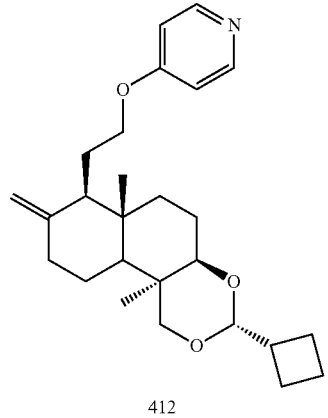

412

Step 1

4-(2-((3R,4aR,6aS,7R,10bR)-3-cyclobutyl-6a,10b-dimethyl-8-dihydro methylenedecahydro-1H-naphtho[2,1-d][1,3]dioxin-7-yl)ethoxy)pyridine (1R,2R,4aS,5R)-1-(hydroxymethyl)-1,4a-dimethyl-6-dihydromethylene-5-(2-(pyridin-4-oxy)ethyl))decahydronaphthalene-2-ol (100.00 mg, 289.46 umol) was dissolved in 1,2-dichloroethane (2.00 mL), and cyclobutylcarboxaldehyde (243.49 mg, 2.89 mmol) and AMBERLYST® 15 HYDROGEN FORM (100.00 mg) were added sequentially, then stirred at 60° C. for 15 hours. The reaction was filtered and concentrated and separated by preparative liquid chromatography to give 4-(2-((3R,4aR,6aS,7R,10bR)-3-cyclobutyl-6a,10b-dimethyl-8-dihydromethylenedecahydro-1H-naphtho[2,1-d][1,3]dioxin-7-yl)ethoxy)pyridine 412 (4 mg, yield: 3.23%).

MS m/z (ESI): 412.3[M+1]

¹H NMR (400 MHz, CDCl3) 8.41 (d, J=6.0 Hz, 2H), 6.77 (d, J=6.3 Hz, 2H), 4.90 (s, 1H), 4.76 (d, J=5.5 Hz, 1H), 4.60 (s, 1H), 4.15-4.00 (m, 2H), 3.93-3.83 (m, 1H), 3.56-3.41 (m, 2H), 2.57-2.39 (m, 2H), 2.37-2.22 (m, 1H), 2.05-1.81 (m, 12H), 1.72 (td, J=4.5, 8.7 Hz, 1H), 1.38-1.34 (m, 3H), 1.30-1.17 (m, 3H), 0.81 (s, 3H).

Compound 429

4-(2-((3R,4aR,6aS,7R,10bR)-3-cyclohexyl-6a,10b-dimethyl-8-dihydro methylenedecahydro-1H-naphtho[2,1-d][1,3]dioxin-7-yl)ethoxy)pyridine

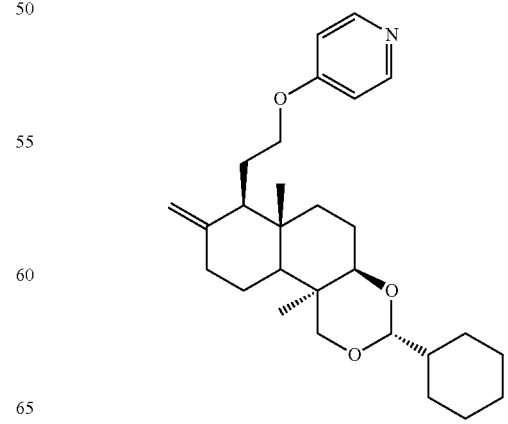

137

-continued

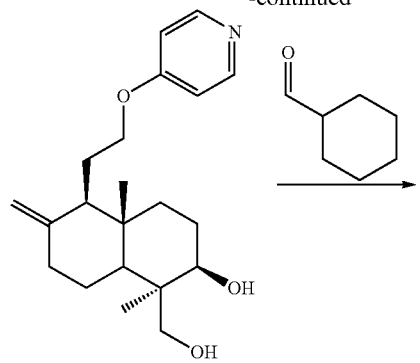

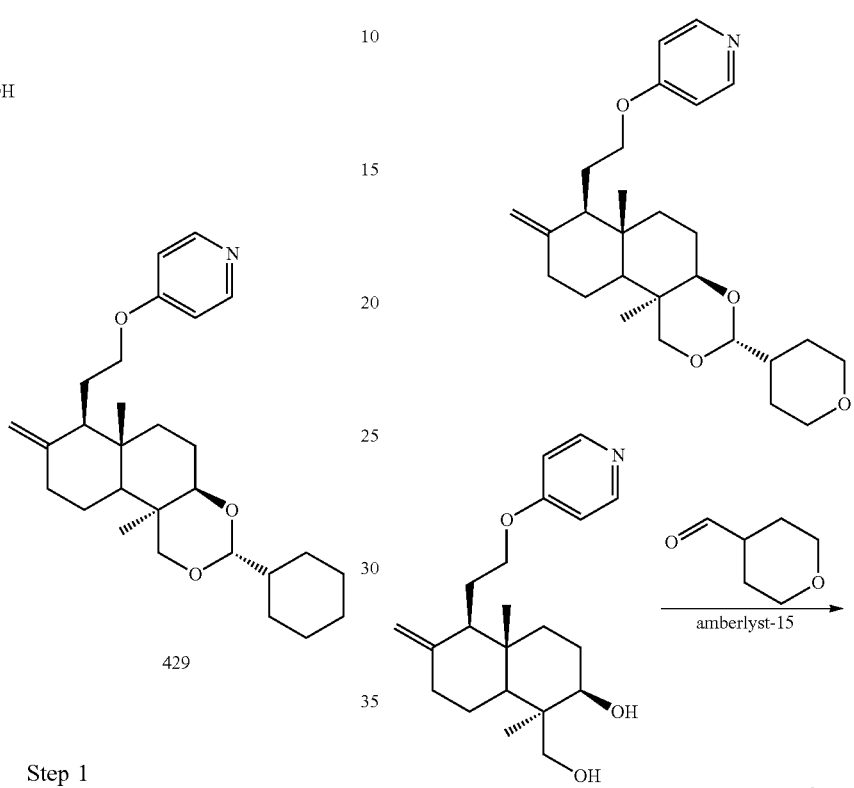

Step 1

4-(2-((3R,4aR,6aS,7R,10bR)-3-cyclohexyl-6a,10b-dimethyl-8-dihydro methylenedecahydro-1H-naphtho[2,1-d][1,3]dioxin-7-yl)ethoxy)pyridine (1R,2R,4aS,5R)-1-(hydroxymethyl)-1,4a-dimethyl-6-dihydromethylene-5-(2-(pyridin-4-oxy)ethyl))decahydronaphthalene-2-ol (200.00 mg, 578.92 umol) was dissolved in 1,2-dichloroethane (20.00 mL), and cyclohexylcarboxaldehyde (64.94 mg, 578.92 umol, 69.83 uL) and pyridinium 4-toluenesulfonate (72.74 mg, 289.46 umol) were added sequentially, then stirred at 80° C. for 12 hours. The reaction was quenched by the addition of 5 mL water and extracted with dichloromethane (10 mL*3). The combined organic phases were washed with saturated brine (10 mL*1), dried over anhydrous sodium sulfate, filtered and concentrated. The residue was separated by preparative liquid chromatography to give 4-(2-((3R,4aR,6aS,7R,10bR)-3-cyclohexyl-6a,10b-dimethyl-8-dihydromethylene-deca hydro-1H-naphtho[2,1-d][1,3]dioxin-7-yl)ethoxy)pyridine 429 (40 mg, yield: 7.86%).

MS m/z (ESI): 440.3 [M+1]

$^{1}$H NMR (400 MHz, CDCl3) 8.39 (d, J=6 Hz, 2H), 6.76 (d, J=6 Hz, 2H), 4.89 (s, 1H), 4.58-4.54 (m, 2H), 4.09-3.87 (m, 3H), 3.50-3.42 (m, 2H), 2.44-2.28 (m, 2H), 2.02-1.87 (m, 2H), 1.83-1.71 (m, 11H), 1.35 (s, 3H), 1.25-1.09 (m, 8H), 0.79 (s, 3H).

138

Compound 446

4-(2-((3R,4aR,6aS,7R,10bR)-6a,10b-dimethyl-8-dihydromethylene-3-(tetrahydro-2H-pyran-4-yl)decahydro-1H-naphtho[2,1-d][1,3]dioxin-7-yl)ethoxy)pyridine Step 1

4-(2-((3R,4aR,6aS,7R,10bR)-6a,10b-dimethyl-8-dihydromethylene-3-(tetrahydro-2H-pyran-4-yl)decahydro-1H-naphtho[2,1-d][1,3]dioxin-7-yl)ethoxy)pyridine (1R,2R,4aS,5R)-1-(hydroxymethyl)-1,4a-dimethyl-6-dihydromethylen e-5-(2-(pyridin-4-oxy)ethyl)decahydronaphthalene-2-ol (400.00 mg, 1.16 mmol) was dissolved in dichloromethane (20.00 mL), and tetrahydro-2H-pyran-4-carbaldehyde (1.32 g, 11.60 mmol) and amberlyst-15 (400.00 mg, 1.16 mmol) were added successively, and then stirred at 45° C. for 20 hours. The system was separated by preparative liquid chromatography to give 4-(2-((3R,4aR,6aS,7R,10bR)-6a,10b-dimethyl-8-dihydromethylene-3-(tetrahydro-2H-pyran-4-yl)decahydro-1H-naphtho[2,1-d][1,3]dioxin-7-yl)ethoxy)pyridine 446 (6.4 mg, yield: 1.24%).

MS m/z (ESI): 442.8 [M+1]

$^1$H NMR (400 MHz, CDCl3) 8.42 (d, J=3.5 Hz, 2H), 6.80 (d, J=5.0 Hz, 2H), 4.90 (br. s., 1H), 4.66-4.48 (m, 2H), 4.16-3.85 (m, 5H), 3.56-3.32 (m, 4H), 2.44 (d, J=12.0 Hz, 1H), 2.32-2.19 (m, 2H), 2.13-2.00 (m, 3H), 1.91-1.82 (m, 3H), 1.65 (d, J=11.5 Hz, 3H), 1.45 (dd, J=5.8, 11.8 Hz, 2H), 1.35 (s, 3H), 1.28-1.17 (m, 3H), 0.79 (s, 3H).

Compound 405

Methyl 3-((3R,4aR,6aS,7R,10bR)-6a,10b-dimethyl-8-dihydromethylenedecahydro-7-(2-pyridin-4-oxy)ethyl) 1H-naphtho[2,1-d][1,3]dioxin-3-yl)propanoate

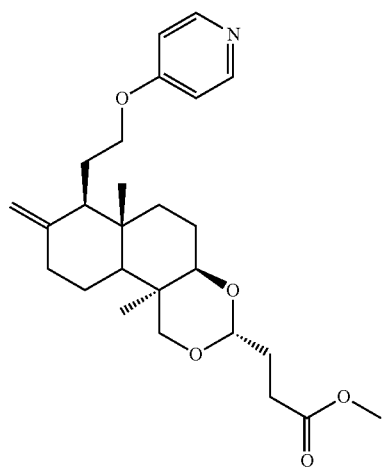

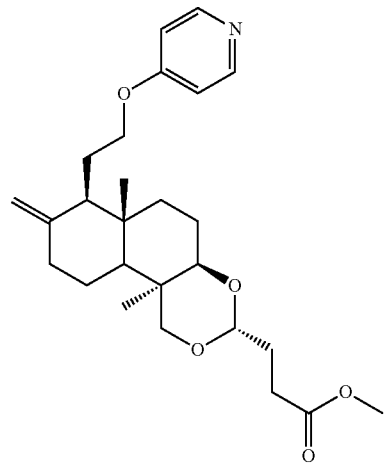

405

Step 1

Methyl 3-((3R,4aR,6aS,7R,10bR)-6a,10b-dimethyl-8-dihydromethylenedecahydro-7-(2-pyridin-4-oxy)ethyl) 1H-naphtho[2,1-d][1,3]dioxin-3-yl)propanoate (1R,2R,4aS,5R)-1-(hydroxymethyl)-1,4a-dimethyl-6-dihydromethylene-5-(2-(pyridin-4-oxy)ethyl))decahydronaphthalene-2-ol (80.00 mg, 231.57 umol) was dissolved in N,N-dimethylformamide (1.00 mL), and methyl 4,4-dimethoxybutyrate (160.00 mg, 986.49 umol) and 4-methylbenzenesulfonic acid (39.88 mg, 231.57 umol) were added successively, then stirred under microwave conditions at 80° C. for 2 hours. The reaction solution was concentrated and the residue was separated by preparative liquid chromatography to give methyl 3-((3R,4aR,6aS,7R,10bR)-6a,10b-dimethyl-8-dihydromethylenedecahydro-7-(2-pyridin-4-oxy)ethyl)1H-naphtho[2,1-d][1,3]dioxin-3-yl)propanoate 405 (29 mg, yield: 27.78%).

MS m/z (ESI): 445.2 [M+1]

$^1$H NMR (400 MHz, DMSO-d$_6$) 8.33 (d, J=6.0 Hz, 2H), 6.89 (d, J=6.0 Hz, 2H), 4.89-4.80 (m, 2H), 4.59 (s, 1H), 4.13-4.01 (m, 1H), 3.97-3.81 (m, 2H), 3.56 (s, 3H), 3.40 (dd, J=4.5, 12.3 Hz, 2H), 2.33 (t, J=7.5 Hz, 3H), 2.28-2.16 (m, 1H), 2.00-1.87 (m, 2H), 1.84-1.66 (m, 6H), 1.50 (dd, J=4.3, 9.0 Hz, 1H), 1.25 (br. s., 1H), 1.22 (s, 3H), 1.20-1.09 (m, 2H), 0.70 (s, 3H).

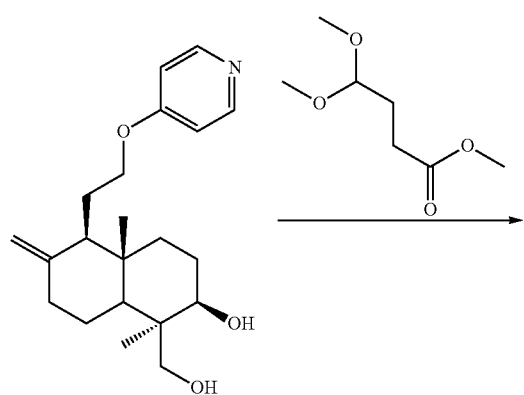

Compound 408

3-((3R,4aR,6aS,7R,10bR)-6a,10b-dimethyl-8-dihydromethylenedecahydro-7-(2-pyridin-4-oxy)ethyl) 1H-naphtho[2,1-d][1,3]dioxin-3-yl)propanoic acid

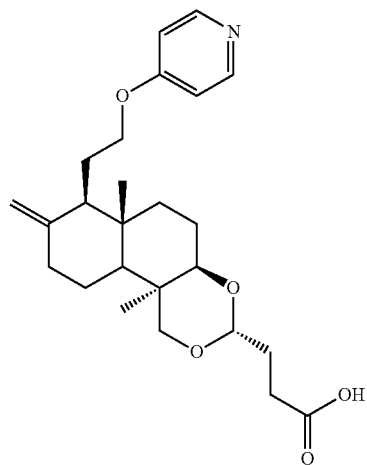

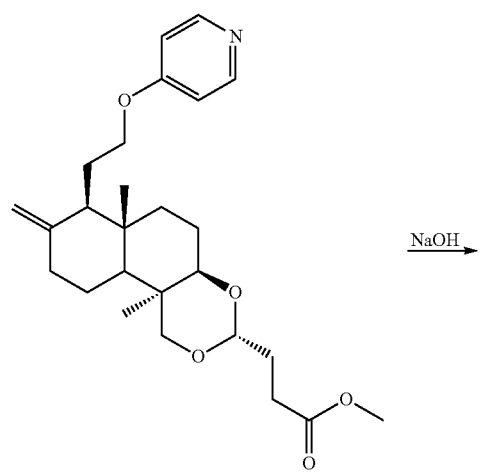

NaOH

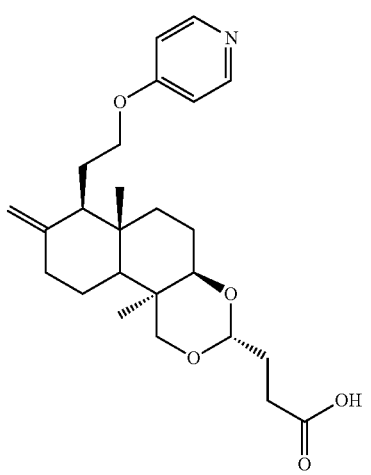

408

Step 1

3-((3R,4aR,6aS,7R,10bR)-6a,10b-dimethyl-8-dihydromethylenedecahydro-7-(2-pyridin-4-oxy)ethyl) 1H-naphtho[2,1-d][1,3]dioxin-3-yl)propanoic acid Methyl 3-((3R,4aR,6aS,7R,10bR)-6a,10b-dimethyl-8-dihydromethylenedecahydro-7-(2-pyridin-4-oxy)ethyl)-1H-naphtho[2,1-d][1,3]dioxin-3-yl)propanoate (25.00 mg, 56.36 umol) was dissolved in tetrahydrofuran (1.00 mL), and sodium hydroxide (6.76 mg, 169.08 umol) and water (1.00 mL) were added successively, then stirred at room temperature for 1 hour. Ethyl acetate (5.00 mL) was added to the system, and the organic phase and the aqueous phase were separated. The aqueous phase was separated by preparative liquid chromatography to give 3-((3R,4aR,6aS,7R,10bR)-6a,10b-dimethyl-8-dihydromethylenedecahydro-7-(2-pyridin-4-oxy)ethyl) 1H-naphtho[2,1-d][1,3]dioxin-3-yl) propanoic acid 408 (20 mg, yield: 82.36%).

MS m/z (ESI): 430.6 [M+1]

$^1$H NMR (400 MHz, DMSO-$d_6$) 8.33 (d, J=6.0 Hz, 2H), 6.88 (d, J=6.0 Hz, 2H), 4.85 (s, 2H), 4.59 (s, 1H), 4.07 (br. s., 1H), 3.95-3.82 (m, 2H), 3.46-3.38 (m, 2H), 2.37-2.07 (m, 4H), 2.01-1.85 (m, 2H), 1.84-1.63 (m, 6H), 1.49 (d, J=10.0 Hz, 1H), 1.27-1.23 (m, 1H), 1.22 (s, 3H), 1.15 (t, J=12.4 Hz, 2H), 0.70 (s, 3H).

Compound 399

2-((3R,4aR,6aS,7R,10bR)-3-cyclopentyl-6a,10b-dimethyl-8-dihydromethylenedecahydro-1H-naphtho[2,1-d][1,3]dioxin-7-yl)ethanol

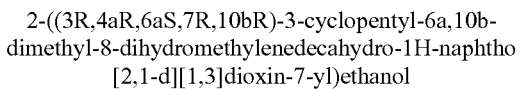

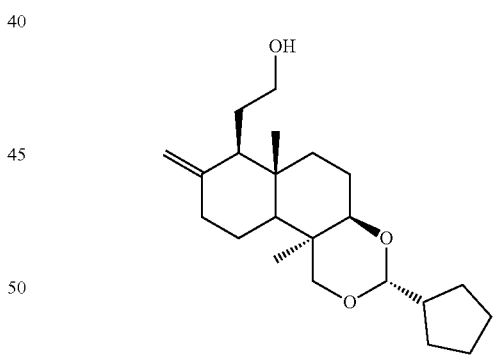

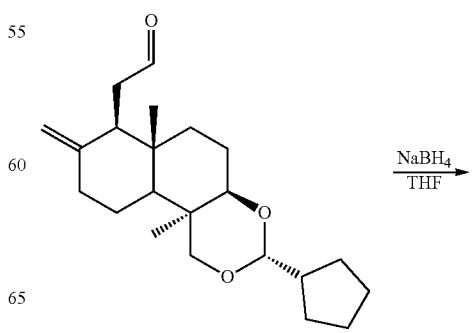

NaBH₄
THF

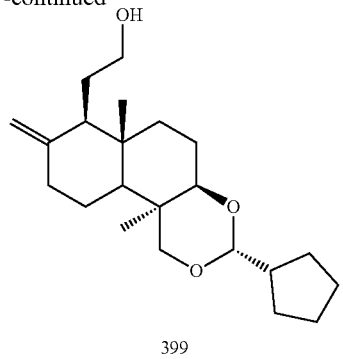

399

Step 1

2-((3R,4aR,6aS,7R,10bR)-3-cyclopentyl-6a,10b-dimethyl-8-dihydromethylenedecahydro-1H-naphtho[2,1-d][1,3]dioxin-7-yl)ethanol 2-((3R,4aR,6aS,7R,10bR)-3-cyclopentyl-6a,10b-dimethyl-8-dihydromethylenepentahydro-1H-naphtho[2,1-d][1,3]dioxin-7-yl)acetaldehyde (1.00 g, 2.89 mmol) was dissolved in tetrahydrofuran (20.00 mL), and sodium borohydride (327.99 mg, 8.67 mmol) was added to the system at 0° C. and stirred at room temperature for 18 hours. The reaction was quenched with 50 mL water and then extracted with ethyl acetate (25 mL*3). The combined organic phases were successively washed with water (25 mL*3) and saturated brine (25 mL*3), dried over anhydrous sodium sulfate, filtered and concentrated. The residue was separated by flash silica gel column (petroleum ether/ethyl acetate=100:0 to 50:50) to give 850 mg 2-((3R,4aR,6aS,7R,10bR)-3-cyclopentyl-6a, 10b-dimethyl-8-dihydromethylenedecahydro-1H-naphtho[2,1-d][1,3]dioxin-7-yl)ethanol 399. Yield: 84.39%.

MS m/z (ESI):349.2[M+1]

$^1$H NMR (400 MHz, CDCl3) 4.85 (s, 1H), 4.60 (d, J=6.02 Hz, 1H), 4.56 (s, 1H), 4.02 (d, J=11.04 Hz, 1H), 3.73 (br. s., 1H), 3.39-3.57 (m, 3H), 2.40 (d, J=13.05 Hz, 1H), 2.25 (dq, J=3.01, 13.22 Hz, 1H), 1.93-2.14 (m, 2H), 1.84-1.91 (m, 1H), 1.62-1.83 (m, 7H), 1.39-1.60 (m, 7H), 1.35 (s, 3H), 1.10-1.30 (m, 4H), 0.75 (s, 3H).

Compound 281

3-(2-((3R,4aR,6aS,7R,10bR)-3-cyclopentyl-6a,10b-dimethyl-8-dihydromethylenedecahydro-1H-naphtho[2,1-d][1,3]dioxin-7-yl)ethoxy)- N,N-dimethylpropan-1-amine

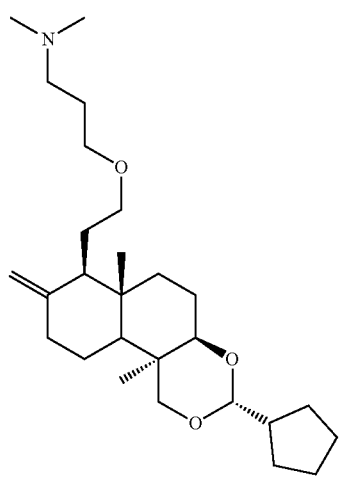

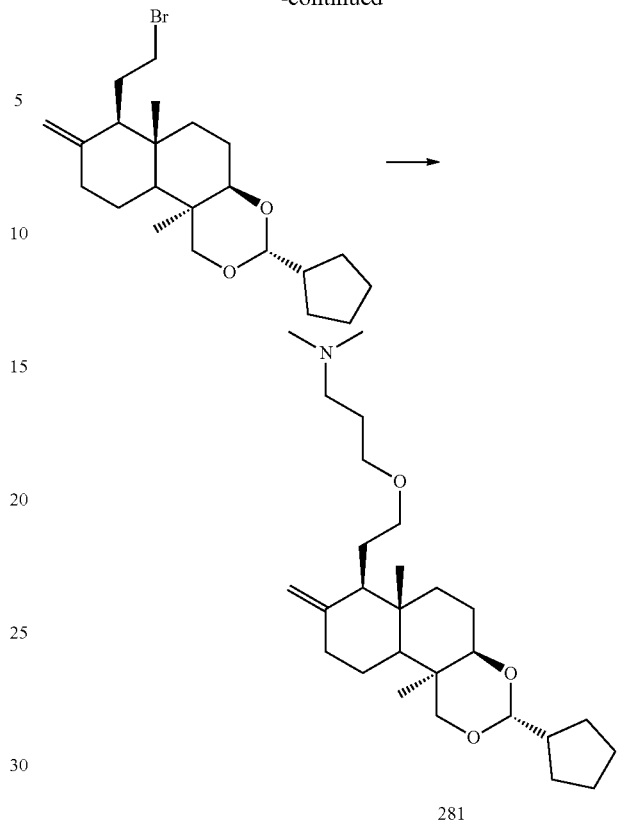

281

Step 1

3-(2-((3R,4aR,6aS,7R,10bR)-3-cyclopentyl-6a,10b-dimethyl-8-dihydromethylenedecahydro-1H-naphtho[2,1-d][1,3]dioxin-7-yl)ethoxy)- N,N-dimethylpropan-1-amine 3-(dimethylamino)propan-1-ol (55 mg, 0.537 mmol) was dissolved in 8 mL N,N-dimethylformamide, added with sodium hydride (18 mg, 0.732 mmol) at 0° C., then stirred at 0° C. for 15 minutes. (3R,4aR,6aS,7R,10bR)-7-(2-bromoethyl)-3-cyclopentyl-6a,10b-dimethyl-8-dihydromethylenedecahydro-1H-naphtho[2,1-d][1,3]dioxin (200 mg, 0.488 mmol) was added at 0° C. and then stirred at 50° C. for 2 hours. The reaction was quenched with 6 mL water and extracted with dichloromethane (15 mL*2). The organic phases were combined, washed with saturated sodium chloride solution (15 mL*2), dried over anhydrous sodium sulfate, filtered, and the filtrate was concentrated under reduced pressure, and separated by the preparative liquid chromatography to give 3-(2-((3R,4aR,6aS,7R,10bR)-3-cyclopentyl-6a,10b-dimethyl-8-dihydromethylenedecahydro-1H-naphtho[2,1-d][1,3]dioxin-7-yl)ethoxy)-N,N-dimethylpropan-1-amine 281 (70 mg, yield:33%).

MS m/z (ESI): 434.6[M+1]

$^1$H NMR (400 MHz, MeOD) 8.50 (s, 1H), 4.68 (d, J=5.77 Hz, 1H), 4.58 (s, 1H), 4.07 (d, J=11.29 Hz, 1H), 3.36-3.52 (m, 5H), 2.92-3.00 (m, 2H), 2.69 (s, 6H), 2.30-2.47 (m, 2H), 1.45-2.07 (m, 18H), 1.32 (s, 3H), 1.16-1.30 (m, 3H), 0.78 (s, 3H).

145

Compound 313

3-(2-((3R,4aR,6aS,7R,10bR)-3-cyclopentyl-6a,10b-dimethyl-8-dihydromethylenedecahydro-1H-naphtho[2,1-d][1,3]dioxin-7-yl)ethoxy)- 1-isopropyl azetidine

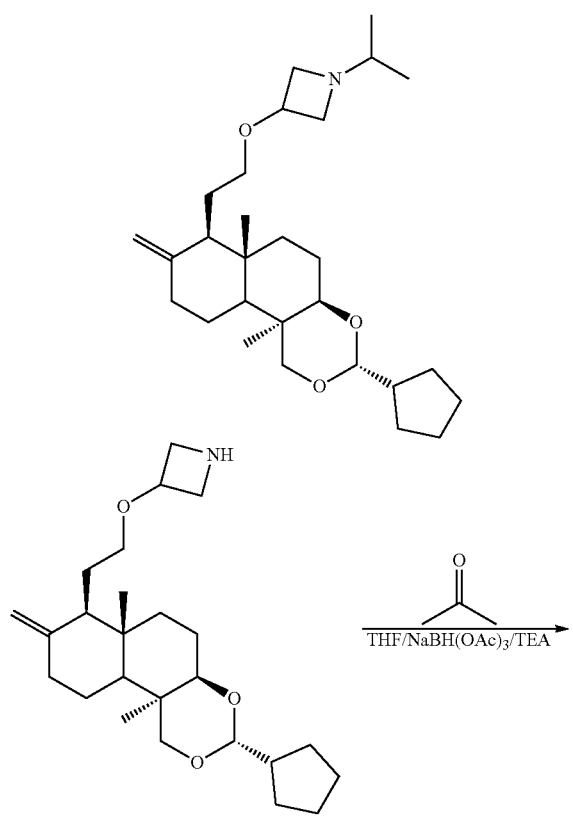

Step 1

3-(2-((3R,4aR,6aS,7R,10bR)-3-cyclopentyl-6a,10b-dimethyl-8-dihydromethylenedecahydro-1H-naphtho[2,1-d][1,3]dioxin-7-yl)ethoxy)- 1-isopropyl azetidine 3-(2-((3R,4aR,6aS,7R,10bR)-3-cyclopentyl-6a,10b-dimethyl-8-methylenedecahydro-1H-naphtho[2,1-d][1,3]dioxin-7-yl)ethoxy)azetidine (150 mg, 0.37 mmol) was dissolved in dichloromethane (10 mL), and acetone 313b (108 mg, 1.86 mmol) and triethylamine (75 mg, 0.74 mmol) were added successively and stirred at room temperature for 30 minutes. Sodium borohydride (236 mg, 1.11 mmol) was added to the reaction solution and stirred at room temperature for 12 hours. The reaction solution was concentrated under reduced pressure and separated by column chromatography to give 3-(2-((3R,4aR,6aS,7R,10 bR)-3-cyclopentyl-6a,10b-dimethyl-8-dihydromethylenedecahydro-1H-naphtho[2,1-d][1,3]dioxin-7-yl)ethoxy)-1-isopropyl azetidine 313 (15 mg, yield: 9%).

MS m/z (ESI): 446.3 [M+1]

$^1$H NMR (400 MHz, CDCl$_3$) 4.86 (br. s., 1H), 4.31-4.72 (m, 5H), 4.01 (d, J=11.2 Hz, 1H), 3.10-3.62 (m, 7H), 2.41 (d, J=12.4 Hz, 1H), 2.13-2.34 (m, 2H), 1.59-2.11 (m, 11H), 1.50-1.55 (m, 3H), 1.20-1.43 (m, 13H), 0.74 (s, 3H).

Compound 366

4-(2-((3R,4aR,6aS,7R,10bR)-3-cyclopentyl-6a,10b-dimethyl-8-dihydromethylenedecahydro-1H-naphtho[2,1-d][1,3]dioxin-7-yl)ethoxy)- 1-methylpiperidine

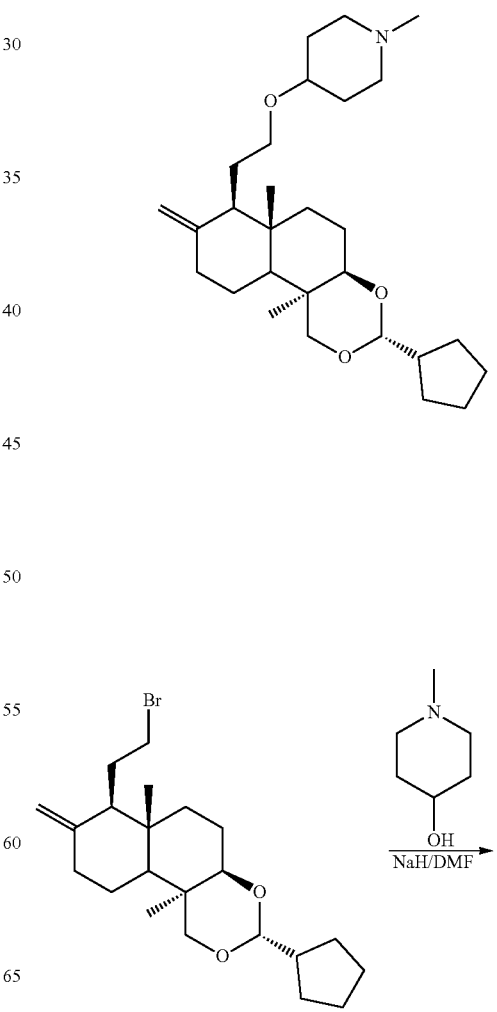

147

-continued

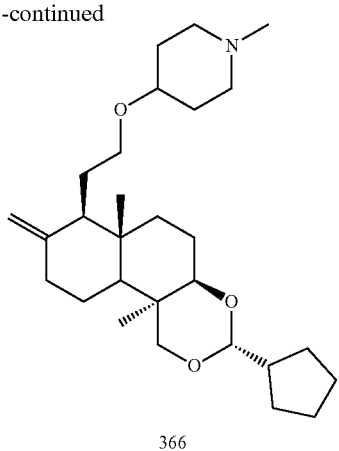

366

Step 1

4-(2-((3R,4aR,6aS,7R,10bR)-3-cyclopentyl-6a,10b-dimethyl-8-dihydromethylenedecahydro-1H-naphtho[2,1-d][1,3]dioxin-7-yl)ethoxy)-1-methylpiperidine 1-Methylpiperidin-4-ol (84 mg, 0.73 mmol) was dissolved in N,N-dimethylformamide (10 mL) and sodium hydrogen (32 mg, 1.01 mmol) was added at 0° C. and stirred at 0° C. for 15 minutes. (3R,4aR,6aS,7R,10bR)-7-(2-bromoethyl)-3-cyclopentyl-6a,10b-dimethyl-8-methylenedecahydro-1H-naphtho[2,1-d][1,3]dioxin (300 mg, 0.73 mmol) was added to the reaction mixture and stirred at room temperature for 12 hours. The reaction solution was added to water (5 mL) and extracted with ethyl acetate (30 mL). The organic layer was washed with water (10 mL×3), dried over anhydrous sodium sulfate, filtered, and the filtrate was concentrated under reduced pressure and separated by preparative liquid chromatography to give 4-(2-((3R,4aR,6aS,7R,10bR)-3-cyclopentyl-6a,10b-dimethyl-8-dihydromethylenedecahydro-1H-naphtho[2,1-d][1,3]dioxin-7-yl)ethoxy)-1-methylpiperidine 366 (20 mg, yield: 6.1%).

MS m/z (ESI): 446.6 [M+1]

$^1$H NMR (400 MHz, CDCl$_3$) 8.44-8.55 (m, 1H), 4.54-4.66 (m, 4H), 4.02-4.07 (m, 1H), 3.40-3.53 (m, 3H), 2.96-3.16 (m, 3H), 2.77-2.92 (m, 2H), 2.56-2.65 (m, 3H), 2.25-2.40 (m, 2H), 1.45-2.03 (m, 19H), 1.30 (s, 3H), 1.15-1.26 (m, 3H), 0.76 (s, 3H).

Compound 482

2-(4-(2-((3R,4aR,6aS,7R,10bR)-3-cyclopentyl-6a,10b-dimethyl-8-dihydromethylenedecahydro-1H-naphtho[2,1-d][1,3]dioxin-7-yl)ethoxy)piperidine-1-yl)ethanol

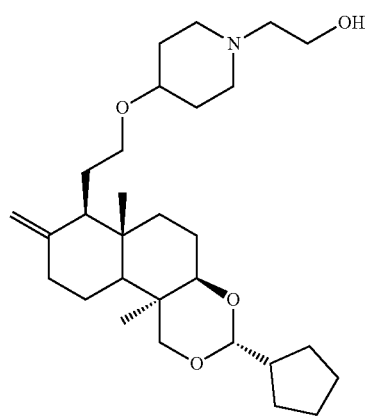

148

-continued

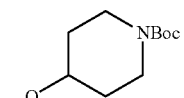

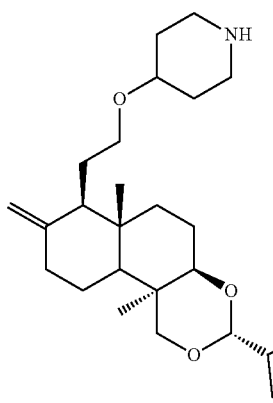

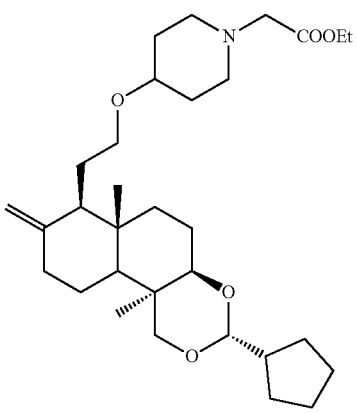

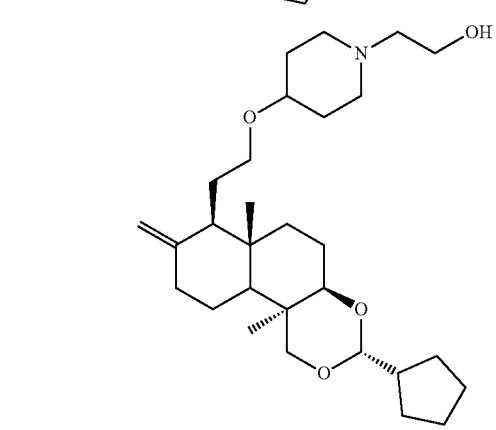

482

Step 1

4-(2-((3R,4aR,6aS,7R,10bR)-3-cyclopentyl-6a,10b-dimethyl-8-dihydromethylenedecahydro-1H-naphtho[2,1-d][1,3]dioxin-7-yl)ethoxy)piperidine Tert-butyl 4-(2-((3R,4aR,6aS,7R,10 bR)-3-cyclopentyl-6a,10b-dimethyl-8-dihydromethylene-1H-naphtho[2,1-d][1,3]dioxin-7-yl)ethoxy)piperidine-1-carboxylate (5.00 g, 9.40 mmol) was dissolved in 50 mL acetonitrile and added with ammonium nitrate (4.12 g, 7.52 mmol, 3.75 mL) at room temperature, then stirred at 80° C. for 12 hours. After the reaction solution was concentrated under reduced pressure, the resulting residue was purified by silica gel column chromatography using an eluent system of DCM:MeOH:NH$_3$—H$_2$O=100:1:0.5 to give 4-(2-((3R,4aR,6aS,7R,10bR)-3-cyclopentyl-6a,10b-dimethyl-8-dihydromethylenedecahydro-1H-naphtho[2,1-d][1,3]dioxin-7-yl)ethoxy)piperidine (3.1 g, yield: 92.7%).

MS m/z (ESI): 432.7[M+1]

$^1$H NMR (400 MHz, CDCl$_3$) 4.83 (s, 1H), 4.60 (d, J=6.0 Hz, 1H), 4.51 (s, 1H), 4.02 (d, J=10.8 Hz, 1H), 3.57-3.40 (m, 4H), 3.38-3.15 (m, 5H), 2.40 (d, J=11.5 Hz, 1H), 2.25 (q, J=3.1, 1H), 2.12-2.06 (m, 3H), 2.03-1.90 (m, 3H), 1.90-1.82 (m, 1H), 1.80-1.75 (m, 2H), 1.75-1.65 (m, 5H), 1.65-1.1.40 (m, 7H), 1.36 (s, 3H), 1.24-1.10 (m, 3H), 0.75 (s, 3H).

Step 2

Ethyl 2-(4-(2-((3R,4aR,6aS,7R,10bR)-3-cyclopentyl-6a,10b-dimethyl-8-dihydromethylenedecahydro-1H-naphtho[2,1-d][1,3]dioxin-7-yl)ethoxy)piperidin-1-yl)acetate 4-(2-((3R,4aR,6aS,7R,10bR)-3-cyclopentyl-6a,10b-dimethyl-8-dihydromethylenedecahydro-1H-naphtho[2,1-d][1,3]dioxin-7-yl)ethoxy)piperidine (1.00 g, 2.32 mmol) was dissolved in 20 mL tetrahydrofuran, and ethyl glyoxylate (2.12 g, 10.39 mmol) and triethylamine (744.19 mg, 7.35 mmol) were added successively at room temperature, and then stirred at room temperature for 20 minutes. Sodium borohydride (2.34 g, 11.04 mmol) was added at room temperature, followed by stirring at room temperature for 12 hours. The reaction was quenched with 100 mL water, extracted with ethyl acetate (100 mL*3), and the organic phases were combined, washed with saturated sodium chloride solution (100 mL*2), dried over anhydrous sodium sulfate, filtered, and the filtrate was concentrated under reduced pressure. After that, the resulting residue was purified by silica gel column chromatography with the eluent system PE:EA=4:1 to 2:1 to give ethyl 2-(4-(2-((3R,4aR,6aS,7R,10bR)-3-cyclopentyl-6a,10b-dimethyl-8-dihydromethylenedecahydro-1H-naphtho[2,1-d][1,3]dioxin-7-yl)ethoxy)piperidin-1-yl)acetate (630 mg, yield: 52.4%).

$^1$H NMR (400 MHz, CDCl$_3$) 4.84 (s, 1H), 4.63-4.53 (m, 2H), 4.19 (q, J=7.2 Hz, 2H), 4.03 (d, J=11.5 Hz, 1H), 3.55-3.40 (m, 3H), 3.31-3.24 (m, 2H), 3.22 (s, 2H), 2.81 (br. s., 2H), 2.44-2.17 (m, 4H), 2.01-1.41 (m, 20H), 1.36 (s, 3H), 1.31-1.22 (m, 6H), 0.75 (s, 3H).

Step 3

2-(4-(2-((3R,4aR,6aS,7R,10bR)-3-cyclopentyl-6a,10b-dimethyl-8-dihydromethylenedecahydro-1H-naphtho[2,1-d][1,3]dioxin-7-yl)ethoxy)piperidine-1-yl)ethanol Ethyl 2-(4-(2-((3R,4aR,6aS,7R,10bR)-3-cyclopentyl-6a,10b-dimethyl-8-dihydromethylenedecahydro-1H-naphtho[2,1-d][1,3]dioxin-7-yl)ethoxypiperidine-1-yl)acetate (430.00 mg, 830.53 umol) was dissolved in 5 mL tetrahydrofuran, added with lithium tetrahydroaluminum (47.91 mg, 1.26 mmol) at 0° C., and then stirred at 0° C. for 0.5 hours. The reaction was quenched by dropwise adding 0.5 mL aqueous sodium hydroxide solution (2.4N) at 0° C., diluted with 15 mL ethyl acetate, dried over anhydrous magnesium sulfate, filtered, and the filtrate was concentrated under reduced pressure. The resulting residue was purified by silica gel column chromatography with an eluent system DCM:MeOH=10:1 to give 2-(4-(2-((3R,4aR,6aS,7R,10bR)-3-cyclopentyl-6a,10b-dimethyl-8-dihydromethylenedecahydro-1H-naphtho[2,1-d][1,3]dioxin-7-yl)ethoxy)piperidin-1-yl)ethanol 482 (163.8 mg, yield: 41.46%).

MS m/z (ESI): 476.3[M+1]

$^1$H NMR (400 MHz, CDCl$_3$) 4.84 (s, 1H), 4.65-4.53 (m, 2H), 4.02 (d, J=11.3 Hz, 1H), 3.67 (t, J=5.1 Hz, 2H), 3.55-3.40 (m, 3H), 3.37-3.20 (m, 2H), 2.84 (br. s., 2H), 2.62 (t, J=5.0 Hz, 2H), 2.49-1.99 (m, 5H), 1.96-1.39 (m, 19H), 1.36 (s, 3H), 1.34-1.07 (m, 4H), 0.75 (s, 3H).

Compound 483

4-(2-((3R,4aR,6aS,7R,10bR)-3-cyclopentyl-6a,10b-dimethyl-8-dihydromethylenedecahydro-1H-naphtho[2,1-d][1,3]dioxin-7-yl)ethoxy)-1-(2,2,2,-trifluoroethyl)piperidine

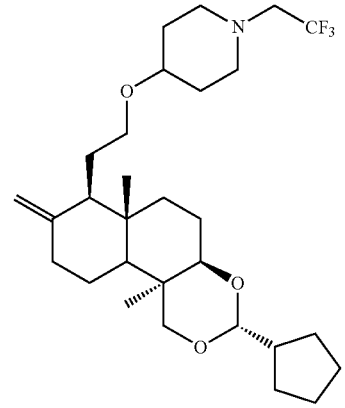

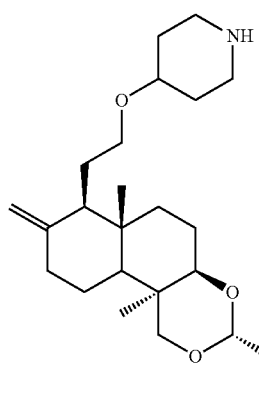

151

-continued

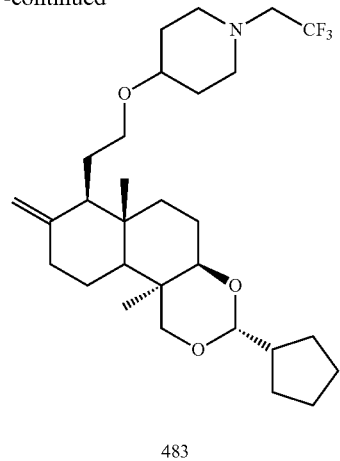

483

Step 1

4-(2-((3R,4aR,6aS,7R,10bR)-3-cyclopentyl-6a,10b-dimethyl-8-dihydromethylenedecahydro-1H-naphtho[2,1-d][1,3]dioxin-7-yl)ethoxy)- 1-(2,2,2,-trifluoro-ethyl)piperidine 4-(2-((3R,4aR,6aS,7R,10bR)-3-cyclopentyl-6a,10b-dimethyl-8-methylenedecahydro-1H-naphtho[2,1-d][1,3]dioxin-7-yl)ethoxy)piperidine (100 mg, 232 umol) dissolved in 8 mL acetonitrile, and triethylamine (70 mg, 696 umol) and 2,2,2-trifluoroethyl trifluoromethanesulfonate (161 mg, 696 umol) were added successively, then refluxed for 3 hours. The reaction solution was concentrated and separated through a column (eluent EA:PE from 1:20 to 1:10) to give 4-(2-((3R,4aR,6aS,7R,10bR)-3-cyclopentyl)-6a,10b-dimethyl-8-methylenedecahydro-1H-naphtho[2,1-d][1,3]dioxin-7-yl)ethoxy)-1-(2,2,2-trifluoroethyl)piperidine 483 (30 mg, yield: 25%).

MS m/z (ESI): 514.6 [M+1]

$^1$H NMR (400 MHz, CDCl$_3$) 4.83 (s, 1H), 4.60 (d, J=6.0 Hz, 1H), 4.56 (s, 1H), 4.02 (d, J=11.3 Hz, 1H), 3.55-3.38 (m, 3H), 3.30-3.19 (m, 2H), 2.96 (q, J=9.79 Hz, 2H), 2.85 (m., 2H), 2.52-2.33 (m, 3H), 2.25 (dd, J1=13.30 Hz, J2=3.01 Hz, 1H), 2.19-1.90 (m, 2H), 1.90-1.62 (m, 9H), 1.56-1.39 (m, 8H), 1.36 (s, 3H), 1.28-1.06 (m, 4H), 0.75 (s, 3H).

Compound 426

2-(4-(2-((3R,4aR,6aS,7R,10bR)-3-cyclopentyl-6a,10b-dimethyl-8-dihydromethylenedecahydro-1H-naphtho[2,1-d][1,3]dioxin-7-yl)ethoxy)piperidine-1-yl)acetic acid

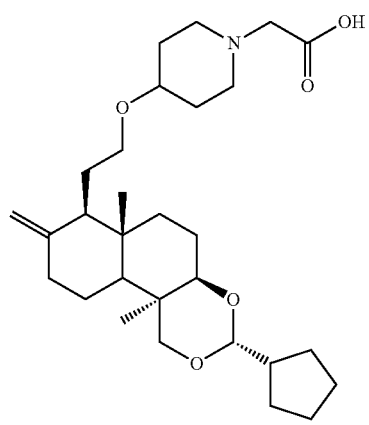

152

-continued

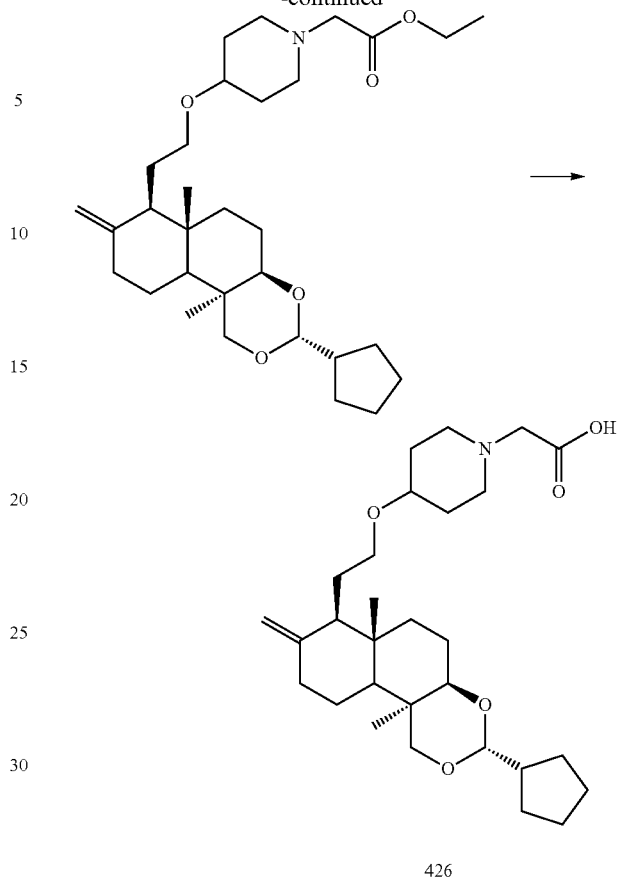

426

Step 1

2-(4-(2-((3R,4aR,6aS,7R,10bR)-3-cyclopentyl-6a,10b-dimethyl-8-dihydromethylenedecahydro-1H-naphtho[2,1-d][1,3]dioxin-7-yl)ethoxy)piperidine-1-yl)acetic acid Ethyl 2-(4-(2-((3R,4aR,6aS,7R,10bR)-3-cyclopentyl-6a,10b-dimethyl-8-dihydromethylenedecahydro-1H-naphtho[2,1-d][1,3]dioxin-1-piperidine-1-yl)acetate (500.00 mg, 965.74 umol) was dissolved in 5 mL tetrahydrofuran and 2.5 mL water, and sodium hydroxide (154.52 mg, 3.86 mmol) was added and stirred at room temperature for 2 hours. The reaction mixture was added with 100 mL water, adjusted to pH 6-7 with dilute hydrochloric acid and extracted with dichloromethane (150 mL*3). The organic phases were combined, dried over anhydrous sodium sulfate, filtered, and the filtrate was concentrated under reduced pressure to give 2-(4-(2-((3R,4aR,6aS,7R,10bR)-3-cyclopentyl-6a,10b-dimethyl-8-dihydromethylenedecahydro-1H-naphtho[2,1-d][1,3]dioxin-7-yl)ethoxy)piperidine-1-yl)acetic acid 426(420 mg, yield: 88.81%).

MS m/z (ESI): 491.1 [M+2]

$^1$H NMR (400 MHz, DMSO) 4.81 (s, 1H), 4.64 (d, J=5.3 Hz, 1H), 4.52 (s, 1H), 3.92 (d, J=11.3 Hz, 1H), 3.35-3.18 (m, 4H), 3.18-3.09 (m, 2H), 2.94 (br. s., 2H), 2.66 (d, J=9.3 Hz, 2H), 2.38-2.16 (m, 2H), 1.97-1.66 (m, 8H), 1.59-1.35 (m, 12H), 1.23 (s, 4H), 1.20-1.04 (m, 3H), 0.68 (s, 3H).

153

Compound 463

2-(4-(2-((3R,4aR,6aS,7R,10bR)-3-cyclopentyl-6a,10b-dimethyl-8-dihydromethylene-decahydro-1H-naphtho[2,1-d][1,3]dioxin-1-piperidine-1-yl)-2-methylpropanoic acid

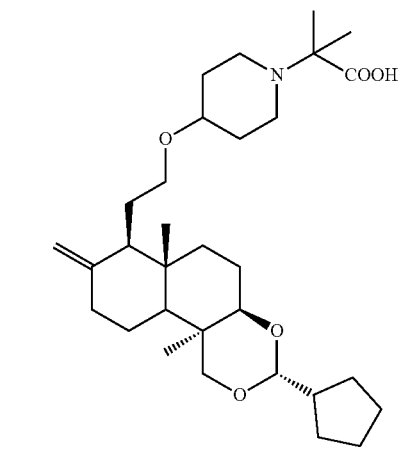

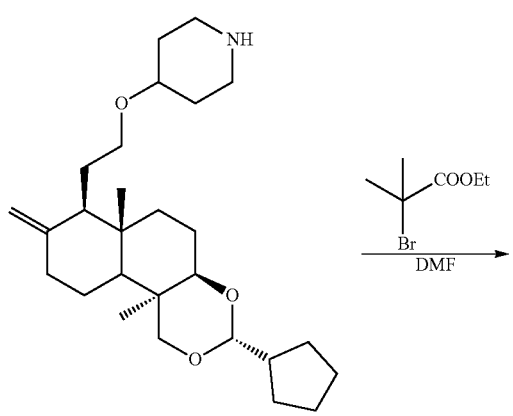

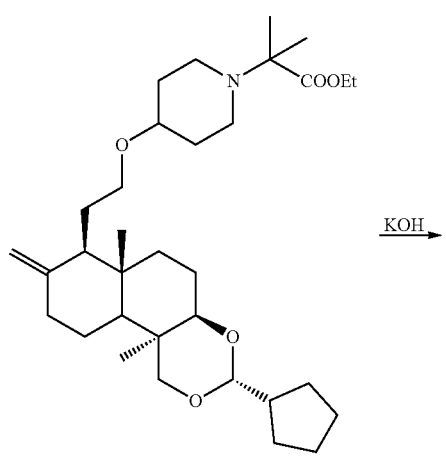

154

-continued

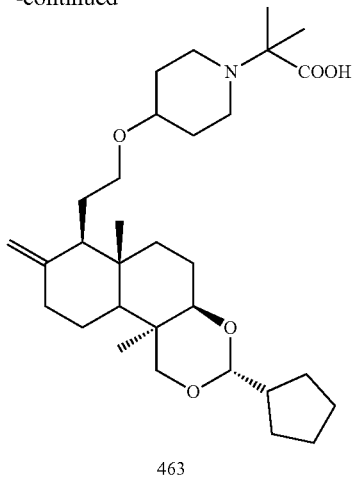

463

Step 1

Ethyl 2-(4-(2-((3R,4aR,6aS,7R,10bR)-3-cyclopentyl-6a,10b-dimethyl-8-dihydromethylene-decahydro-1H-naphtho [2,1-d][1,3]dioxin-7-yl)ethoxy)piperidine-1-yl)-2-methylpropanoate 4-(2-((3R,4aR,6aS,7R,10bR)-3-cyclopentyl-6a,10b-dimethyl-8-dihydromethylene-decahydro-1H-naphtho[2,1-d][1,3]dioxin-7-yl)ethoxy)piperidine (3.80 g, 8.80 mmol) was dissolved in N,N-dimethylformamide (160 mL), and ethyl 2-bromo-2-methylpropanoate (2.57 g, 13.20 mmol) and potassium carbonate (3.65 g, 26.40 mmol) were added successively, then stirred at 60° C. for 10 hours. The system was concentrated. The residue was purified by column chromatography (silica, petroleum ether/ethyl acetate=0/100 to 5/1 and dichloromethane/methanol/ammonia 10/1/0.1) to give ethyl 2-(4-(2-((3R,4aR,6aS,7R,10bR)-3-cyclopentyl-6a,10b-dimethyl-8-dihydromethylene-decahydro-1H-naphtho [2,1-d][1,3]dioxin-7-yl)ethoxy)piperidine-1-yl)-2-methylpropanoate (a colorless oil, 2.4 g, yield: 48.82%).

$^1$H NMR (400 MHz, CDCl3) 4.82 (s, 1H), 4.64-4.51 (m, 2H), 4.23-4.13 (m, 2H), 4.01 (d, J=11.0 Hz, 1H), 3.53-3.38 (m, 3H), 3.29-3.13 (m, 2H), 2.94-2.74 (m, 2H), 2.39 (d, J=11.5 Hz, 1H), 2.24 (d, J=10.0 Hz, 2H), 2.12-2.05 (m, 1H), 1.95-1.41 (m, 20H), 1.35 (s, 3H), 1.31-1.27 (m, 6H), 1.27-1.23 (m, 3H), 1.21-1.09 (m, 3H), 0.74 (s, 3H).

Step 2

2-(4-(2-((3R,4aR,6aS,7R,10bR)-3-cyclopentyl-6a,10b-dimethyl-8-dihydromethylene-decahydro-1H-naphtho[2,1-d][1,3]dioxin-7-yl)ethoxyl)piperidine-1-yl)-2-methylpropanoic acid Ethyl 2-(4-(2-((3R,4aR,6aS,7R,10bR)-3-cyclopentyl-6a,10b-dimethyl-8-dihydromethylene-decahydro-1H-naphtho [2,1-d][1,3]dioxin-7-yl)ethoxy)piperidine-1-yl)-2-methylpropanoate (2.40 g, 4.40 mmol) was dissolved in ethanol (50 mL), and water (50 mL) and potassium hydroxide (2.47 g, 44.00 mmol) were added successively, and then stirred at 70° C. for 10 hours. The ethanol was removed by rotary evaporation under reduced pressure, and the system was added with diluted hydrochloric acid (44 mL, 1M) and the reaction was extracted with ethyl acetate (200 mL*3). The organic phases were washed with saturated brine (100 mL*2), dried over anhydrous sodium sulfate, filtered and concentrated. The residue was separated by column chromatography (silica, dichloromethane/methanol/ammonia solution=50/1/0.1 to 20/1/0.1) to give 2-(4-(2-((3R,4aR,6aS,7R,10bR)-3-cyclopentyl-6a,10b-dimethyl-8-dihydromethylene-decahydro-1H-naphtho[2,1-d][1,3]dioxin-7-yl)ethoxyl)piperidine-1-yl)-2-methylpropanoic acid 463 (1.63 g, yield: 70.54%).

MS m/z (ESI):540.4 [M+23]

$^1$H NMR (400 MHz, DMSO-d$_6$) 4.83 (s, 1H), 4.66 (d, J=5.5 Hz, 1H), 4.54 (s, 1H), 3.94 (d, J=11.5 Hz, 1H), 3.45-3.38 (m, 3H), 3.32 (d, J=11.5 Hz, 1H), 3.26-3.19 (m, 1H), 2.97 (d, J=7.5 Hz, 2H), 2.79-2.74 (m., 2H), 2.39-2.23 (m, 2H), 1.99-1.82 (m, 4H), 1.81-1.64 (m, 6H), 1.60-1.39 (m, 10H), 1.24 (s, 9H), 1.19-1.02 (m, 3H), 0.69 (s, 3H).

Compound 484

4-(2-((3R,4aR,6aS,7R,10bR)-3-cyclopentyl-6a,10b-dimethyl-8-dihydromethylene-decahydro-1H-naphtho[2,1-d][1,3]dioxin-7-yl)ethoxyl)-1-(cyclopropylsulfonyl)piperidine

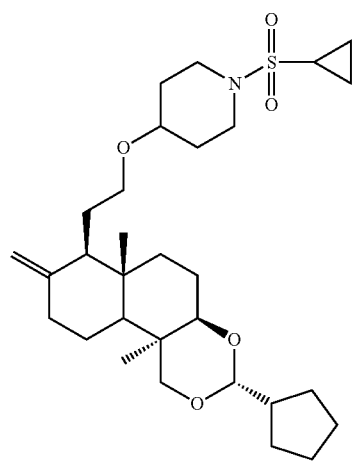

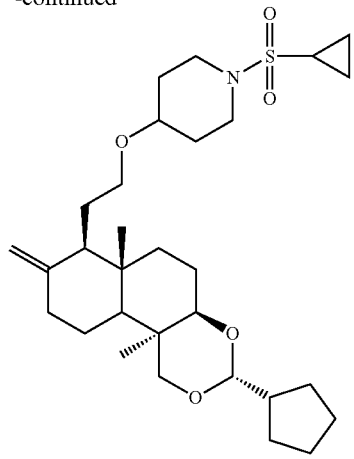

484

Step 1

4-(2-((3R,4aR,6aS,7R,10bR)-3-cyclopentyl-6a,10b-dimethyl-8-dihydromethylene-decahydro-1H-naphtho[2,1-d][1,3]dioxin-7-yl)ethoxyl)-1-(cyclopropylsulfonyl)piperidine 4-(2-((3R,4aR,6aS,7R,10bR)-3-cyclopentyl-6a,10b-dimethyl-8-methylenedecahydro-1H-naphtho[2,1-d][1,3]dioxin-7-yl)ethoxy)piperidine (150 mg, 0.349 mmol) was dissolved in 8 mL dichloromethane, and cyclopropylsulfonyl chloride (54 mg, 0.383 mmol) and triethylamine (39 mg, 0.383 mmol) were added successively, then stirred at room temperature for 12 hours. After the reaction was completed, the reaction solution was concentrated, and separated by preparative plate to give 4-(2-((3R,4aR,6aS,7R,10bR)-3-cyclopentyl-6a,10b-dimethyl-8-dihydromethylene-decahydro-1H-naphtho[2,1-d][1,3]dioxin-7-yl)ethoxyl)-1-(cyclopropylsulfonyl)piperidine 484 (20 mg, yield: 16.1%).

MS m/z (ESI): 558.1[M+23]

$^1$H NMR (CDCl3) ppm 4.84 (s, 1H), 4.59 (d, J=6.0 Hz, 1H), 4.55 (s, 1H), 4.02 (d, J=11.2 Hz, 1H), 3.53-3.39 (m, 6H), 3.31-3.13 (m, 3H), 2.41 (d, J=11.6 Hz, 1H), 2.32-2.18 (m, 2H), 2.14-1.57 (m, 17H), 1.35 (s, 3H), 1.21-1.16 (m, 7H), 0.98-0.85 (m, 3H), 0.75 (s, 3H).

Compound 373

2-Amino-1-(4-(2-((3R,4aR,6aS,7R,10bR)-3-cyclopentyl-6a,10b-dimethyl-8-methylenedecahydro-1H-naphtho[2,1-d][1,3]dioxin-7-yl)ethoxy)piperidine-1-yl)acetamide

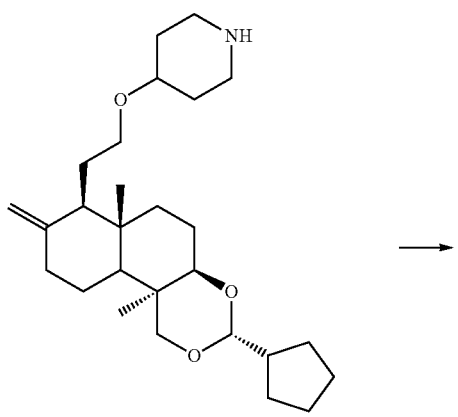 → 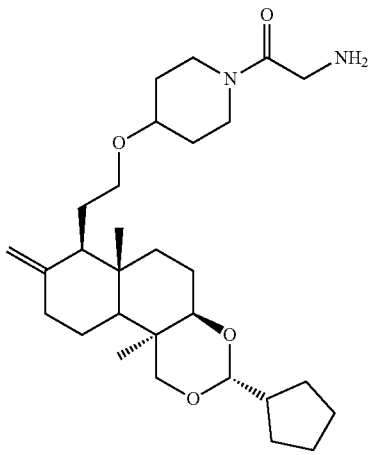

157
-continued

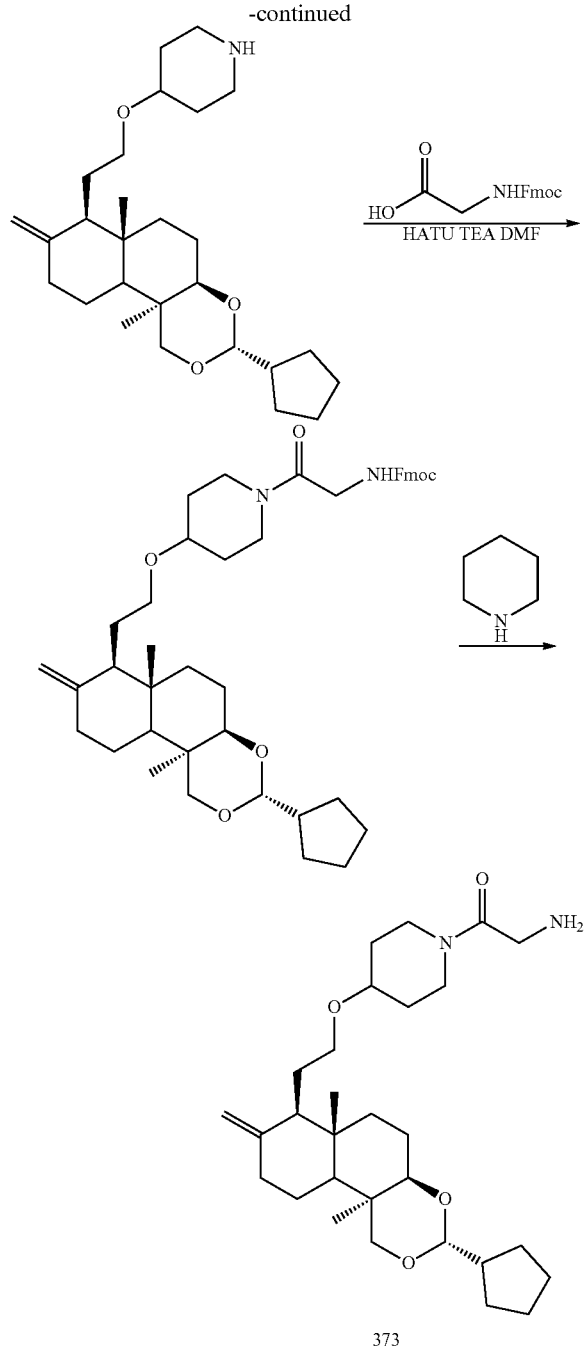

373

Step 1

(9H-fluoren-9-yl)methyl(2-(4-(2-((3R,4aR,6aS,7R,10bR)-3-cyclopentyl-6a,10b-dimethyl-8-methylene-decahydro-1H-naphtho[2,1-d][1,3]dioxin-7-yl) ethoxy) piperidine-1-yl)-2-oxoethyl)carbamate 2-((((9H-fluoren-9-yl)methoxy)carbonyl)amine)acetic acid (379 mg, 1.27 mmol) was dissolved in N,N-dimethylformamide (20 mL), and triethylamine (0.5 mL) and 2-(7-azobenzotriazole)-N,N,N',N'-tetramethyluronium hexafluorophosphate (660 mg, 1.74 mmol) were added successively, and stirred at room temperature for 0.5 hours. 4-(2-((3R,

158

4aR,6aS,7R,10bR)-3-cyclopentyl-6a,10b-dimethyl-8-methylenedecahydro-1H-naphtho[2,1-d][1,3]dioxin-7-yl)ethoxy) piperidine (500 mg, 1.16 mmol) was added to the reaction and stirred at room temperature for 18 hours. The reaction solution was quenched with water, extracted with dichloromethane, and the organic layer was washed with saturated brine and water. The organic layer was dried over anhydrous sodium sulfate and filtered. The filtrate was concentrated under reduced pressure and separated by column chromatography to give (9H-fluoren-9-yl)methyl(2-(4-(2-((3R,4aR,6aS,7R,10bR)-3-cyclopentyl-6a,10b-dimethyl-8-methylenedecahydro-1H-naphtho[2,1-d][1,3]dioxin-7-yl)ethoxy) piperidine-1-yl)-2-oxoethyl)carbamate (150 mg, yield: 18%).

Step 2

2-Amino-1-(4-(2-((3R,4aR,6aS,7R,10bR)-3-cyclopentyl-6a,10b-dimethyl-8-methylenedecahydro-1H-naphtho[2,1-d][1,3]dioxin-7-yl)ethoxy)piperidine-1-yl)acetamide (9H-fluoren-9-yl)methyl(2-(4-(2-((3R,4aR,6aS,7R,10bR)-3-cyclopenty 1-6a,10b-dimethyl-8-methylenedecahydro-1H-naphtho[2,1-d][1,3]dioxin-7-yl)ethoxy) piperidine-1-yl)-2-oxoethyl)carbamate (150 mg, 0.21 mmol) was dissolved in N,N-dimethylformamide (2.5 g, 34.2 mmol), and piperidine (500 mg, 5.87 mmol) was added at 25° C. under nitrogen atmosphere at room temperature, and stirred for 2 hours. The reaction solution was concentrated under reduced pressure and was separated by liquid chromatography to give 2-amino-1-(4-(2-((3R,4aR,6aS,7R,10 bR)-3-cyclopentyl-6a,10b-dimethyl-8-methylene decahydro-1H-naphtho[2,1-d][1,3]dioxin-7-yl)ethoxy)piperidine-1-yl) acetamide 373 (15 mg, yield: 15%).

MS m/z (ESI): 489.4 [M+1]

$^1$H NMR (400 MHz, CDCl$_3$) 4.86 (s, 1H), 4.62 (d, J=6.0 Hz, 1H), 4.56 (s, 1H), 4.04 (d, J=11.2 Hz, 1H), 3.79-3.43 (m, 11H), 2.44-1.52 (m, 22H), 1.50 (s, 3H), 1.38-1.24 (m, 3H), 0.77 (s, 3H).

Compound 386

(1R,2R,4aS,5R)-1-(hydroxymethyl)-1,4a-dimethyl-6-dihydromethylene-5-(2-((1-methylpiperidine-4-yl) oxy) ethyl) decahydronaphthalene-2-ol

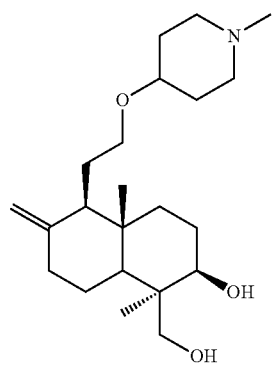

159

-continued

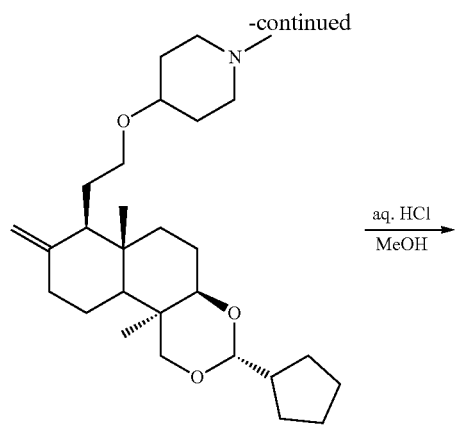

aq. HCl / MeOH →

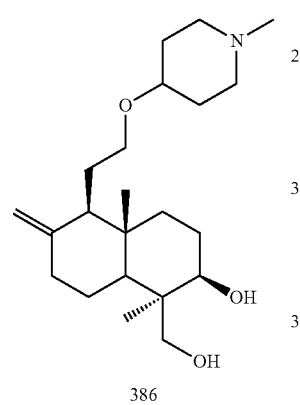

386

Step 1

(1R,2R,4aS,5R)-1-(hydroxymethyl)-1,4a-dimethyl-6-dihydromethylene-5-(2-((1-methylpiperidine-4-yl)oxy) ethyl) decahydronaphthalene-2-ol 4-(2-((3R,4aR,6aS,7R,10bR)-3-cyclopentyl-6a,10b-dimethyl-8-dihydromethylene-1H-naphtho[2,1-d][1,3]dioxin-7-yl)ethoxy)-1-methylpiperidine (300.00 mg, 673.13 umol) was dissolved in methanol (3.00 mL) and 3 mL hydrochloric acid (1M) was added to the system followed by stirring at 75° C. for 12 hours. The reaction solution was concentrated under reduced pressure, and the residue was purified by column chromatography (dichloromethane/methanol=100:0 to 85:15) to give a crude product. The crude product was separated by preparative liquid chromatography to give 23 mg (1R,2R,4aS,5R)-1-(hydroxymethyl)-1,4a-dimethyl-6-dihydromethylene-5-(2-((1-methylpiperidine-4-yl)oxy) ethyl) decahydronaphthalene-2-ol 386. Yield: 9.35%.

MS m/z (ESI): 366.1 [M+1]

¹H NMR (400 MHz, CDCl3) 4.24 (d, J=11.0 Hz, 1H), 3.52-3.26 (m, 5H), 2.96-2.60 (m, 4H), 2.50-2.33 (m, 2H), 2.31 (s, 3H), 2.24-1.61 (m, 15H), 1.45-1.15 (m, 6H), 0.92 (s, 3H).

160

Compound 403

2-((2-((3R,4aR,6aS,7R,10bR)-3-cyclopentyl-6a,10b-dimethyl-8-methylenedecahydro-1H-naphtho[2,1-d][1,3]dioxin-7-yl)ethyl)amino)acetic acid

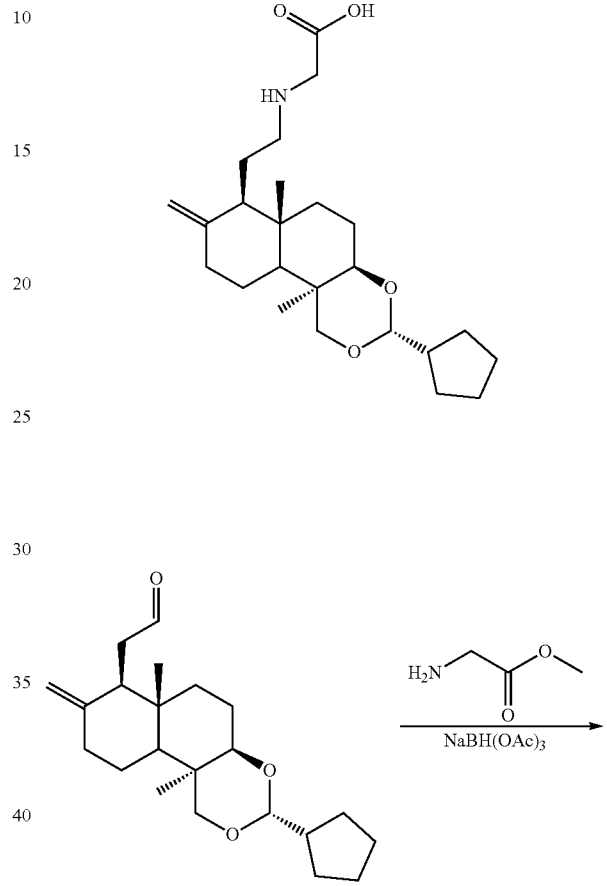

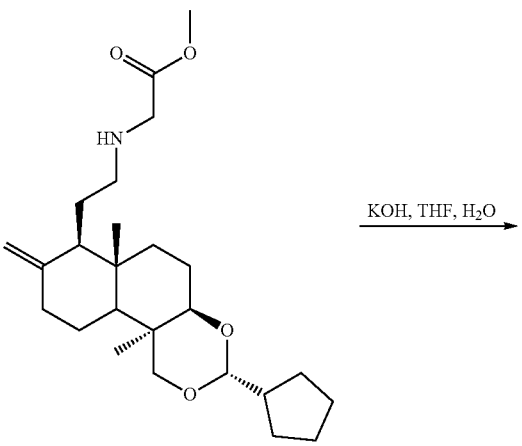

KOH, THF, H₂O →

-continued

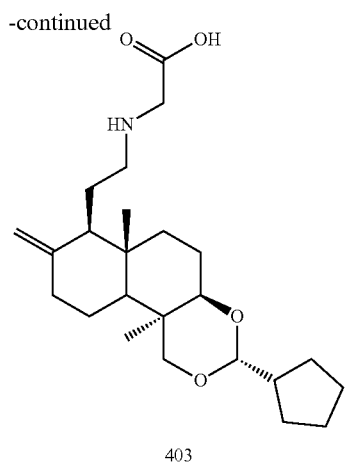

403

Step 1

Methyl 2-((2-((3R,4aR,6aS,7R,10bR)-3-cyclopentyl-6a,10b-dimethyl-8-methylenedecahydro-1H-naphtho[2,1-d][1,3]dioxin-7-yl)ethyl)amino)acetate 2-((3R,4aR,6aS,7R,10bR)-3-cyclopentyl-6a,10b-dimethyl-8-methylene-decahydro-1H-naphtho[2,1-d][1,3]dioxin-7-yl)acetaldehyde (2.00 g, 5.77 mmol) was dissolved in tetrahydrofuran (50 mL), and methyl 2-aminoacetate (1.09 g, 8.65 mmol, HCl) and triethylamine (2.34 g, 23.08 mmol) were added successively, then stirred at 25° C. for 4 hours. Sodium borohydride (6.11 g, 28.85 mmol) was added followed by stirring at 25° C. for 8 hours. The reaction solution was diluted with 100 mL water and extracted with ethyl acetate (100 mL*2). The organic phase was dried over anhydrous sodium sulfate, filtered and concentrated. The residue was separated by column chromatography (silica, petroleum ether/ethyl acetate/ammonia water=1:1:0.01) to give methyl 2-((2-((3R,4aR,6aS,7R,10bR)-3-cyclopentyl-6a,10b-dimethyl-8-methylenedecahydro-1H-naphtho[2,1-d][1,3]dioxin-7-yl)ethyl)amino)acetate (a yellow solid, 1.8 g, yield: 74.35%).

$^1$H NMR (400 MHz, CDCl3) 4.83 (s, 1H), 4.61-4.52 (m, 2H), 4.01 (d, J=11.3 Hz, 1H), 3.72 (s, 2H), 3.50-3.41 (m, 2H), 3.40 (s, 2H), 3.08 (br. s., 3H), 2.81-2.66 (m, 1H), 2.49-2.35 (m, 2H), 2.24 (dq, J=2.9, 13.2 Hz, 1H), 2.12-2.04 (m, 1H), 1.96 (t, J=11.8 Hz, 1H), 1.89-1.83 (m, 1H), 1.80-1.74 (m, 1H), 1.72-1.65 (m, 3H), 1.65-1.60 (m, 2H), 1.60-1.49 (m, 4H), 1.47-1.37 (m, 2H), 1.34 (s, 3H), 1.23-1.07 (m, 3H), 0.74 (s, 3H).

Step 2

2-((2-((3R,4aR,6aS,7R,10bR)-3-cyclopentyl-6a,10b-dimethyl-8-methylenedecahydro-1H-naphtho[2,1-d][1,3]dioxin-7-yl)ethyl)amino)acetic acid Methyl 2-((2-((3R,4aR,6aS,7R,10bR)-3-cyclopentyl-6a,10b-dimethyl-8-methylenedecahydro-1H-naphtho[2,1-d][1,3]dioxin-7-yl)ethyl)amino)acetate (200.00 mg, 476.64 umol) was dissolved in tetrahydrofuran (2.00 mL), and potassium hydroxide (53.49 mg, 953.29 umol) and water (1.00 mL) were added successively, then stirred at 25° C. for 12 hours. The system was separated by preparative liquid chromatography to give 80 mg 2-((2-((3R,4aR,6aS,7R,10bR)-3-cyclopentyl-6a, 10b-dimethyl-8-methylenedecahydro-1H-naphtho[2,1-d][1,3]dioxin-7-yl)ethyl)amino)acetic acid 403. Yield: 41.38%.

MS m/z (ESI):406.3 [M+1]

$^1$H NMR (400 MHz, MeOD) 4.92 (s, 1H), 4.69 (d, J=5.8 Hz, 1H), 4.64 (s, 1H), 4.07 (d, J=11.3 Hz, 1H), 3.52-3.37 (m, 4H), 3.13-3.01 (m, 1H), 2.85-2.71 (m, 1H), 2.49-2.28 (m, 2H), 2.11-1.95 (m, 2H), 1.93-1.76 (m, 4H), 1.74 (s, 1H), 1.72-1.55 (m, 5H), 1.55-1.41 (m, 4H), 1.34 (s, 3H), 1.32-1.20 (m, 3H), 0.81 (s, 3H).

Compound 404

2,2'-((2-((3R,4aR,6aS,7R,10bR)-3-cyclopentyl-6a,10b-dimethyl-8-methylene-decahydro-1H-naphtho[2,1-d][1,3]dioxin-7-yl)ethyl)azanediyl)diacetic acid

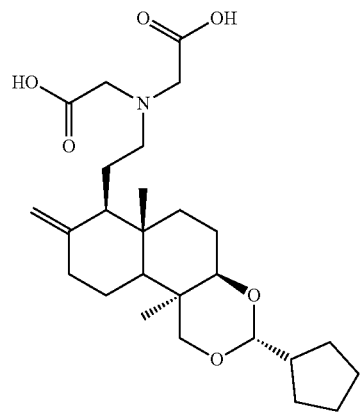

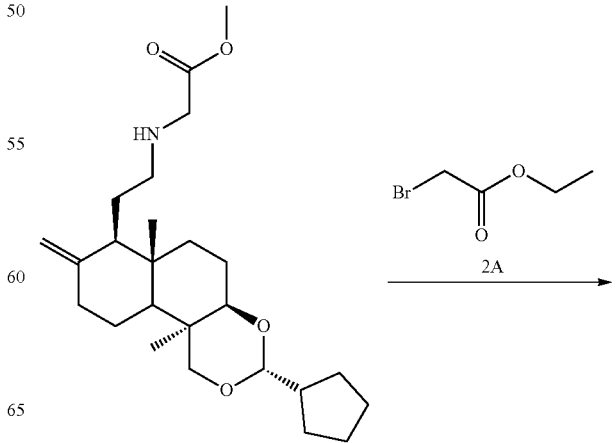

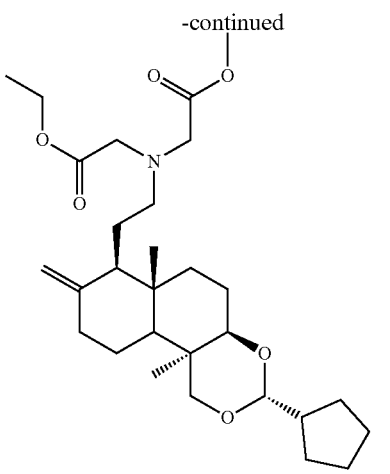

404

Step 1

Ethyl 2,2'-((2-((3R,4aR,6aS,7R,10bR)-3-cyclopentyl-6a,10b-dimethyl-8-methylene-decahydro-1H-naphtho[2,1-d][1,3]dioxin-7-yl)ethyl)(2-methoxy-2-oxoethyl)amino)acetate Methyl 2-((2-((3R,4aR,6aS,7R,10bR)-3-cyclopentyl-6a,10b-dimethyl-8-methylene-decahydro-1H-naphtho[2,1-d][1,3]dioxin-7-yl)ethyl)amino)acetate (200.00 mg, 476.64 umol) was dissolved in N,N-dimethylformamide (4 mL), and ethyl 2-bromoacetate (159.20 mg, 953.28 umol) and potassium carbonate (131.75 mg, 953.28 umol) were added successively, followed by stirring at 75° C. for 12 hours. The reaction solution was diluted with 10 mL water and extracted with ethyl acetate (10 mL*2). The organic phase was dried over anhydrous sodium sulfate, filtered and concentrated. The residue was separated by column chromatography (silica, petroleum ether/ethyl acetate=10/1) to give ethyl 2,2'-((2-((3R,4aR,6aS,7R,10bR)-3-cyclopentyl-6a,10b-dimethyl-8-methylene-decahydro-1H-naphtho[2,1-d][1,3]dioxin-7-yl)ethyl)(2-methoxy-2-oxoethyl)amino)acetate (a yellow oil, 100 mg, yield: 41.49%).

$^1$H NMR (400 MHz, CDCl3) 4.82 (s, 1H), 4.62-4.51 (m, 2H), 4.16 (q, J=7.3 Hz, 2H), 4.01 (d, J=11.0 Hz, 1H), 3.70 (s, 3H), 3.58-3.49 (m, 4H), 3.49-3.37 (m, 2H), 2.90-2.77 (m, 1H), 2.52-2.42 (m, 1H), 2.41-2.34 (m, 1H), 2.30-2.16 (m, 1H), 2.12-2.02 (m, 1H), 1.99-1.90 (m, 1H), 1.86 (d, J=13.1 Hz, 1H), 1.67 (dd, J=3.8, 8.0 Hz, 4H), 1.61 (d, J=5.8 Hz, 2H), 1.54 (dd, J=7.7, 12.4 Hz, 4H), 1.49-1.37 (m, 3H), 1.34 (s, 3H), 1.30-1.25 (m, 4H), 1.21-1.11 (m, 2H), 0.74 (s, 3H).

Step 2

2,2'-((2-((3R,4aR,6aS,7R,10bR)-3-cyclopentyl-6a,10b-dimethyl-8-methylene-decahydro-1H-naphtho[2,1-d][1,3]dioxin-7-yl)ethyl)azanediyl)diacetic acid Ethyl 2,2'-((2-((3R,4aR,6aS,7R,10bR)-3-cyclopentyl-6a,10b-dimethyl-8-methylene-decahydro-1H-naphtho[2,1-d][1,3]dioxin-7-yl)ethyl)(2-methoxy-2-oxoethyl)amino)acetate (100.00 mg, 197.75 umol) was dissolved in tetrahydrofuran (1.00 mL), and potassium hydroxide (22.19 mg, 395.50 umol) and water (1.00 mL) were successively added, and then stirred at 25° C. for 2 hours. The system was separated by preparative liquid chromatography to give 40 mg 2,2'-((2-((3R,4aR,6aS,7R,10bR)-3-cyclopentyl-6a,10b-dimethyl-8-methylene-decahydro-1H-naphtho[2,1-d][1,3]dioxin-7-yl)ethyl)azanediyl)diacetic acid 404. Yield: 43.63%.

MS m/z (ESI):464.2 [M+1]

$^1$H NMR (400 MHz, CDCl3) 4.86 (br. s., 1H), 4.66-4.52 (m, 2H), 3.97 (d, J=10.8 Hz, 1H), 3.72 (br. s., 3H), 3.43 (t, J=12.2 Hz, 2H), 3.31 (br. s., 1H), 2.95 (br. s., 1H), 2.63 (s, 1H), 2.38 (d, J=11.3 Hz, 1H), 2.23 (d, J=11.8 Hz, 1H), 2.12-2.00 (m, 1H), 1.96-1.77 (m, 4H), 1.69 (br. s., 4H), 1.58-1.38 (m, 7H), 1.35 (s, 3H), 1.19 (br. s., 3H), 0.75 (s, 3H).

Compound 284

2-((2-((3R,4aR,6aS,7R,10bR)-3-cyclopentyl-6a,10b-dimethyl-8-methylene-decahydro-1H-naphtho[2,1-d][1,3]dioxin-7-yl)ethyl)(3-(dimethylamino)propyl)amino)ethanol

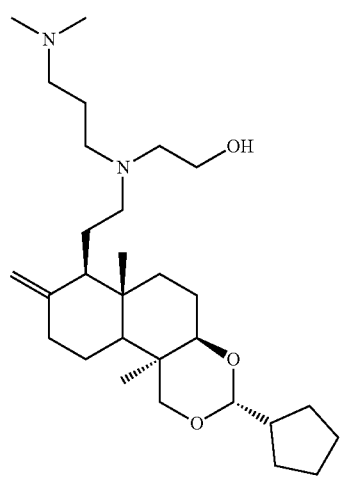

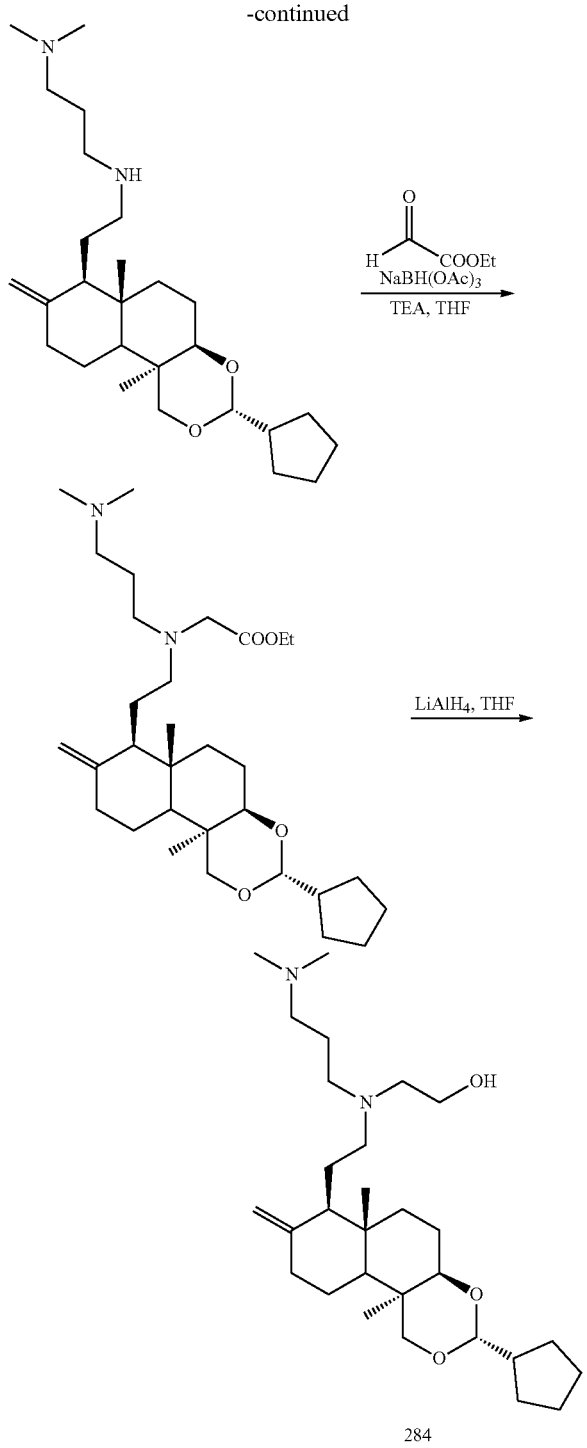

2.31 mmol) was dissolved in tetrahydrofuran (20 mL), and ethyl glyoxylate (354 mg, 3.47 mmol) and triethylamine (467 mg, 4.62 mmol) were successively added, followed by stirring at 15° C. for 0.5 hours. Sodium borohydride (1.47 g, 6.93 mmol) was added followed by stirring at 15° C. for 16 hours. The reaction solution was diluted with 100 mL water and extracted with dichloromethane (50 mL*5). The organic phase was dried over anhydrous sodium sulfate, filtered and concentrated. The residue was purified by column chromatography (silica, dichloromethane/ethanol=5:1) to give ethyl 2-((2-((3R,4aR,6aS,7R,10bR)-3-cyclopentyl-6a,10b-dimethyl-8-methylene-decahydro-1H-naphtho[2,1-d][1,3]dioxin-7-yl)ethyl)(3-(dimethylamino)propyl)amino)acetate (0.928 g, yield: 78%).

$^1$H NMR (400 MHz, CDCl3) 4.84 (s, 1H), 4.61 (d, J=5.6 Hz, 1H), 4.56 (s, 1H), 4.16 (q, J1=7.2 Hz, J2=14.0 Hz, 2H), 4.02 (d, J=11.2 Hz, 1H), 3.46-3.45 (m, 2H), 3.23 (s, 2H), 2.67-2.61 (m, 5H), 2.45 (s, 6H), 2.39-1.36 (m, 20H), 1.30 (s, 3H), 1.28-1.21 (m, 6H), 0.76 (s, 3H).

Step 2

2-((2-((3R,4aR,6aS,7R,10bR)-3-cyclopentyl-6a, 10b-dimethyl-8-methylene-decahydro-1H-naphtho [2,1-d][1,3]dioxin-7-yl)ethyl)(3-(dimethylamino) propyl)amino)ethanol Ethyl 2-((2-((3R,4aR,6aS,7R,10bR)-3-cyclopentyl-6a, 10b-dimethyl-8-methylene-decahydro-1H-naphtho[2,1-d] [1,3]dioxin-7-yl)ethyl)(3-(dimethylamino)propyl)amino)acetate (928 mg, 1.79 mmol) was dissolved in tetrahydrofuran (10.00 mL), and lithium aluminum tetrahydride (102 mg, 2.69 mmol) was added at 0° C., and then stirred at 15° C. for 0.5 h. The reaction was quenched by the addition of 1mL water, then dried over anhydrous sodium sulfate, filtered and concentrated to give 629 mg 2-((2-((3R,4aR,6aS,7R,10 bR)-3-cyclopentyl-6a,10b-dimethyl-8-methylene-decahydro-1H-naphtho[2,1-d][1,3]dioxin-7-yl)ethyl)(3-(dimethylamino)propyl)amino)ethanol 284. Yield: 73.7%.

$^1$H NMR (400 MHz, CDCl3) 4.87 (s, 1H), 4.62 (d, J=6.4 Hz, 1H), 4.57 (s, 1H), 4.03 (d, J=11.6 Hz, 1H), 3.59 (t, J1=4.8 Hz, J=9.6 Hz, 2H), 3.47-3.43 (m, 2H), 2.60-1.54 (m, 34H), 1.37 (s, 3H), 1.22-1.61 (m, 3H), 0.77 (s, 3H).

Compound 191

3-((2-((3R,4aR,6aS,7R,10bR)-3-cyclopentyl-6a,10b-dimethyl-8-methylene-decahydro-1H-naphtho[2,1-d] [1,3]dioxin-7-yl)ethyl)amino)N,N-diethanolamine

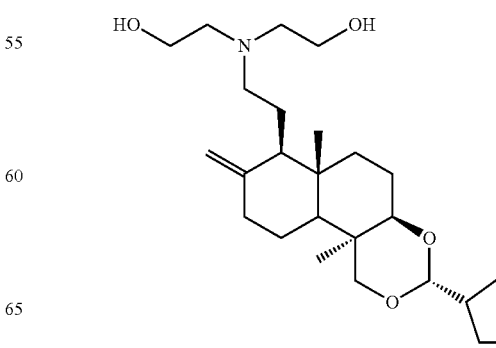

Step 1

Ethyl 2-((2-((3R,4aR,6aS,7R,10bR)-3-cyclopentyl-6a, 10b-dimethyl-8-methylene-decahydro-1H-naphtho[2,1-d][1,3]dioxin-7-yl)ethyl)(3-(dimethylamino) propyl)amino)acetate $N^1$-(2-((3R,4aR,6aS,7R,10bR)-3-cyclopentyl-6a,10b-dimethyl-8-methylene-decahydro-1H-naphtho[2,1-d][1,3]dioxin-7-yl)ethyl)-$N^3$,$N^3$-dimethylpropan-1,3-diamine (1.0 g,

167

-continued

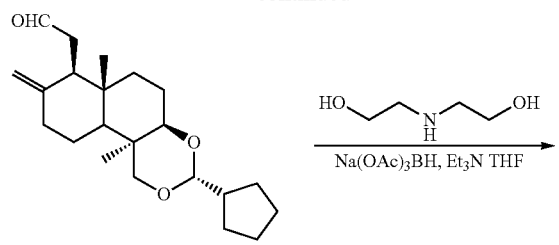

Step 1

3-((2-((3R,4aR,6aS,7R,10bR)-3-cyclopentyl-6a,10b-dimethyl-8-methylene-decahydro-1H-naphtho[2,1-d][1,3]dioxin-7-yl)ethyl)amino)N,N-diethanolamine 2-((3R,4aR,6aS,7R,10bR)-3-cyclopentyl-6a,10b-dimethyl-8-decahydro methylene-1H-naphtho[2,1-d][1,3]dioxin-7-yl)acetaldehyde 191a (100 mg, 0.29 mmol) was dissolved in tetrahydrofuran (20 mL), followed by successive addition of $N^1,N^1$-diethanolamine (61.2 mg, 0.58 mmol) and triethylamine (58.6 mg, 0.58 mmol), and stirred at room temperature for 0.5 h. Sodium borohydride-acetic acid (184.7 mg, 0.87 mmol) was slowly added to the reaction solution, followed by stirring at room temperature for 12 hours. The reaction solution was poured into a saturated ammonium chloride solution, the organic layer was extracted with ethyl acetate, and the organic layer was washed with water and saturated brine, dried over anhydrous sodium sulfate, filtered and concentrated under reduced pressure to give 3-((2-((3R,4aR,6aS,7R,10bR)-3-cyclopentyl-6a,10b-dimethyl-8-methylene-decahydro-1H-naphtho[2,1-d][1,3]dioxin-7-yl)ethyl)amino)N,N-diethanolamine 191 (40 mg, yield: 32%).

MS m/z (ESI): 436.9 [M+1]

$^1$H NMR (400 MHz, CDCl$_3$) 8.44 (s, 1H), 4.91 (s, 1H), 4.60-4.58 (m, 2H), 4.01-3.94 (m, 5H), 3.43-3.18 (m, 8H), 2.05-1.64 (m, 17H), 1.34 (s, 3H), 1.24-1.19 (m, 4H), 0.65 (s, 3H)

168

Compound 207

N-(2-((3R,4aR,6aS,7R,10bR)-3-cyclopentyl-6a,10b-dimethyl-8-decahydromethylene-1H-naphtho[2,1-d][1,3]dioxin-7-yl)ethyl)isoxazol-4-amine

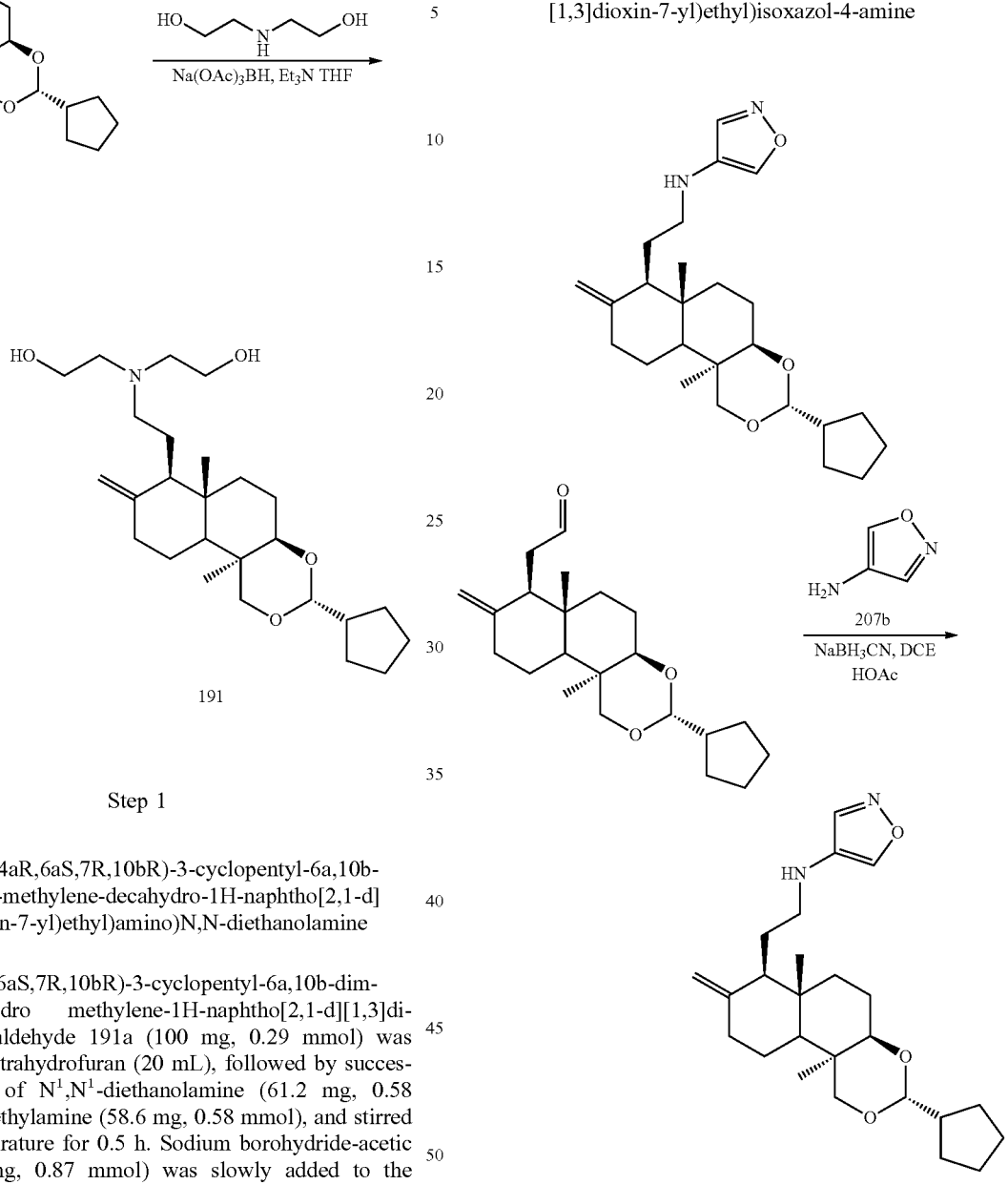

Step 1

N-(2-((3R,4aR,6aS,7R,10bR)-3-cyclopentyl-6a,10b-dimethyl-8-decahydromethylene-1H-naphtho[2,1-d][1,3]dioxin-7-yl)ethyl)isoxazol-4-amine 2-((3R,4aR,6aS,7R,10bR)-3-cyclopentyl-6a,10b-dimethyl-8-decahydro methylene-1H-naphtho[2,1-d][1,3]dioxin-7-yl)acetaldehyde (346.5 mg, 1.0 mmol) was dissolved in 1,2-dichloroethane (20 mL), followed by successively addition of isoxazole-4-amine (84 mg, 1.0 mmol) and acetic acid (0.2 mL), and stirred at 25° C. for 2 hours. Sodium cyanoborohydride (130 mg, 2.0 mmol) was added and stirred at 25° C. for 15 hours. The reaction solution was washed with water (10 mL), and the organic layer was dried over anhydrous sodium sulfate, filtered, and the filtrate was concentrated under reduced pressure and separated by preparative chromatography to give N-(2-((3R,4aR,6aS,7R,10bR)-3-cyclopentyl-6a,10b-dimethyl-8-decahydromethylene-1H-naphtho[2,1-d][1,3]dioxin-7-yl)ethyl)isoxazol-4-amine 201 (11 mg, yield: 5.3%).

MS m/z (ESI): 415.1 [M+1]

$^1$H NMR (400 MHz, CDCl$_3$) 8.01 (s, 1H), 7.88 (s, 1H), 4.88 (s, 1H), 4.60-4.58 (m, 2H), 4.01 (d, J=11.6 Hz, 1H), 3.50-3.42 (m, 2H), 3.06-1.54 (m, 20H), 1.52 (s, 3H), 1.36-1.11 (m, 3H), 0.76 (s, 3H).

Compound 345

N-(2-((3R,4aR,6aS,7R,10bR)-3-cyclopentyl-6a,10b-dimethyl-8-decahydromethylene-1H-naphtho[2,1-d][1,3]dioxin-7-yl)ethyl)-3-fluoropyridin-4-amine

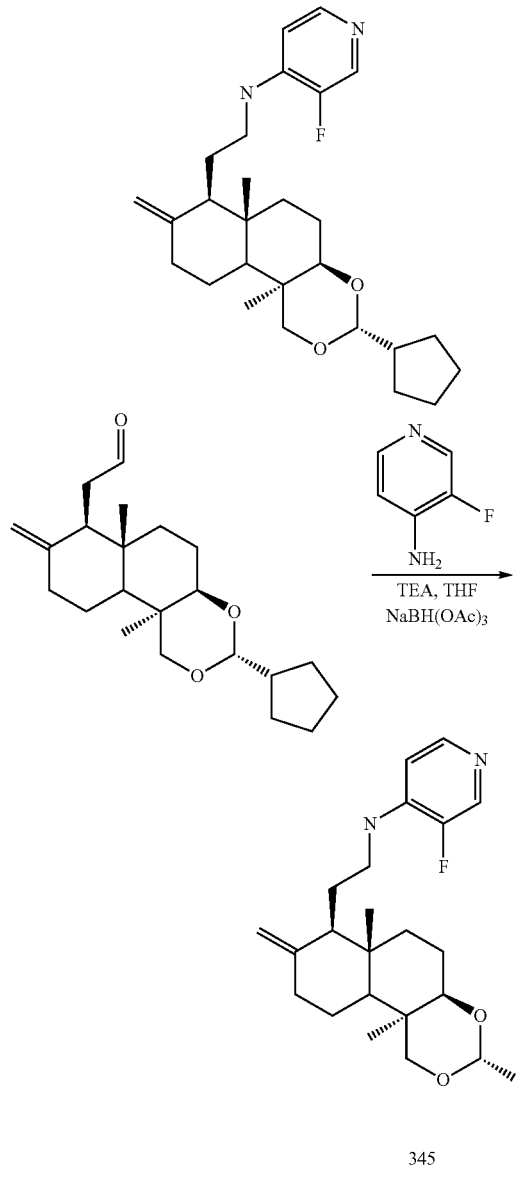

Step 1

N-(2-((3R,4aR,6aS,7R,10bR)-3-cyclopentyl-6a,10b-dimethyl-8-decahydromethylene-1H-naphtho[2,1-d][1,3]dioxin-7-yl)ethyl)-3-fluoropyridin-4-amine 2-((3R,4aR,6aS,7R,10bR)-3-cyclopentyl-6a,10b-dimethyl-8-methylene decahydro-1H-naphtho[2,1-d][1,3]dioxin-7-yl)acetaldehyde (150 mg, 0.43 mmol) was dissolved in anhydrous tetrahydrofuran (10 mL), and 3-fluoropyridin-4-amine (73 mg, 0.65 mmol) and triethylamine (87 mg, 0.86 mmol) were successively added to the reaction solution, followed by stirring at 60° C. for 0.5 hours. Sodium borohydride-acetic acid (273 mg, 1.29 mmol) was added to the reaction solution and stirred at 60° C. for 16 hours. The reaction solution was concentrated under reduced pressure and separated by column chromatography to give N-(2-((3R,4aR,6aS,7R,10bR)-3-cyclopentyl-6a,10b-dimethyl-8-decahydromethylene-1H-naphtho[2,1-d][1,3]dioxin-7-yl)ethyl)-3-fluoropyridin-4-amine 345 (38 mg, yield: 19.9%).

MS m/z (ESI): 443.7 [M+1]

$^1$H NMR (400 MHz, CDCl$_3$) 8.14 (d, J=4.8 HZ, 1H), 8.09 (d, J=5.6 HZ, 1H), 6.55-6.51 (m, 1H), 4.95 (s, 1H), 4.64-4.61 (m, 2H), 4.41 (s, 1H), 4.03 (d, J=11.2 HZ, 1H), 3.52-3.10 (m, 4H), 2.49-1.54 (m, 18H), 1.53 (s, 3H), 1.38-1.25 (m, 3H), 0.79 (s, 3H).

Compound 355

(1-(2-((3R,4aR,6aS,7R,10bR)-3-cyclopentyl-6a,10b-dimethyl-8-methylenedecahydro-1H-naphtho[2,1-d][1,3]dioxin-7-yl)ethyl)oxetane-3-yl)methanol

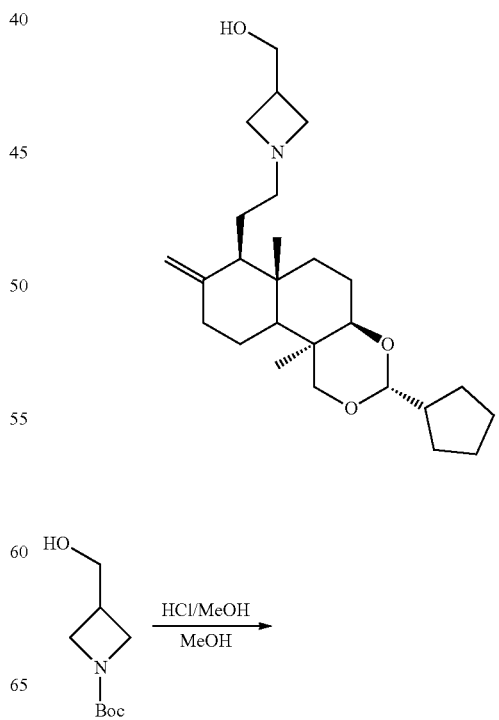

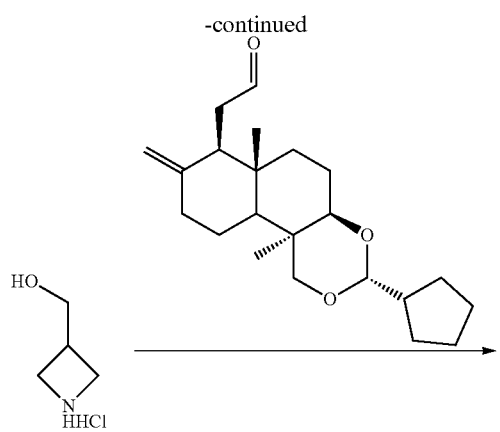

Step 1

Azetidin-3-ylmethanol hydrochloride

Tert-butyl 3-(hydroxymethyl)azetidin-1-carboxylate (200 mg, 1.07 mmol) was dissolved in anhydrous methanol (10 mL), added with 4M ethyl acetate-hydrochloric acid (2.2 mL) under nitrogen atmosphere at 0° C., and stirred at room temperature for 2 hours. The reaction was concentrated under reduced pressure to give azetidin-3-ylmethanol hydrochloride (100 mg, crude product).

$^1$H NMR (400 MHz, MeOD) 4.15-4.01 (m, 2H), 4.00-3.97 (m, 2H), 3.68 (d, J=4.4 Hz, 2H), 3.06-3.00 (m, 1H).

Step 2

(1-(2-((3R,4aR,6aS,7R,10bR)-3-cyclopentyl-6a,10b-dimethyl-8-methylenedecahydro-1H-naphtho[2,1-d][1,3]dioxin-7-yl)ethyl)oxetane-3-yl)methanol 2-((3R,4aR,6aS,7R,10bR)-3-cyclopentyl-6a, 10b-dimethyl-8-methylene decahydro-1H-naphtho[2,1-d][1,3]dioxin-7-yl)acetaldehyde (150 mg, 0.43 mmol) was dissolved in anhydrous tetrahydrofuran (10 mL), followed by successively addition of azetidin-3-ylmethanol hydrochloride (70 mg, 0.56 mmol) and triethylamine (0.18 mL, 1.29 mmol), and stirred at room temperature for 0.5 h. Sodium borohydride-acetic acid (276 mg, 1.3 mmol) was added to the reaction mixture, followed by stirring at room temperature for 18 hours. The reaction solution was cooled and extracted with dichloromethane (30 mL). The organic layer was washed with water (10 mL×3), dried over anhydrous magnesium sulfate, filtered, and the filtrate was concentrated under reduced pressure and separated by high performance liquid chromatography to give (1-(2-((3R,4aR,6aS,7R,10bR)-3-cyclopentyl-6a,10b-dimethyl-8-methylenedecahydro-1H-naphtho[2,1-d][1,3]dioxin-7-yl)ethyl)oxetane-3-yl)methanol 355 (25 mg, yield: 14%).

MS m/z (ESI): 418.7 [M+1]

$^1$H NMR (400 MHz, CDCl$_3$) 4.92 (s, 1H), 4.61 (d, J=5.6 Hz, 1H), 4.02-3.16 (m, 11H), 2.44-1.55 (m, 20H), 1.53 (s, 3H), 1.36-1.22 (m, 3H), 0.76 (s, 3H).

Compound 196

3-(2-((3R,4aR,6aS,7R,10bR)-3-cyclopentyl-6a,10b-dimethyl-8-decahydromethylene-1H-naphtho[2,1-d][1,3]dioxin-7-yl)ethyl)oxazolidin-2-one

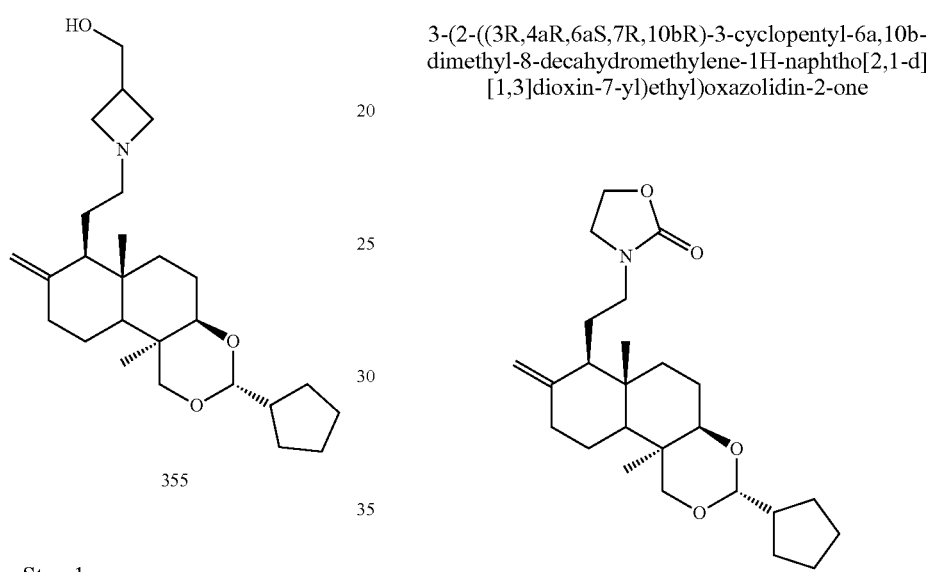

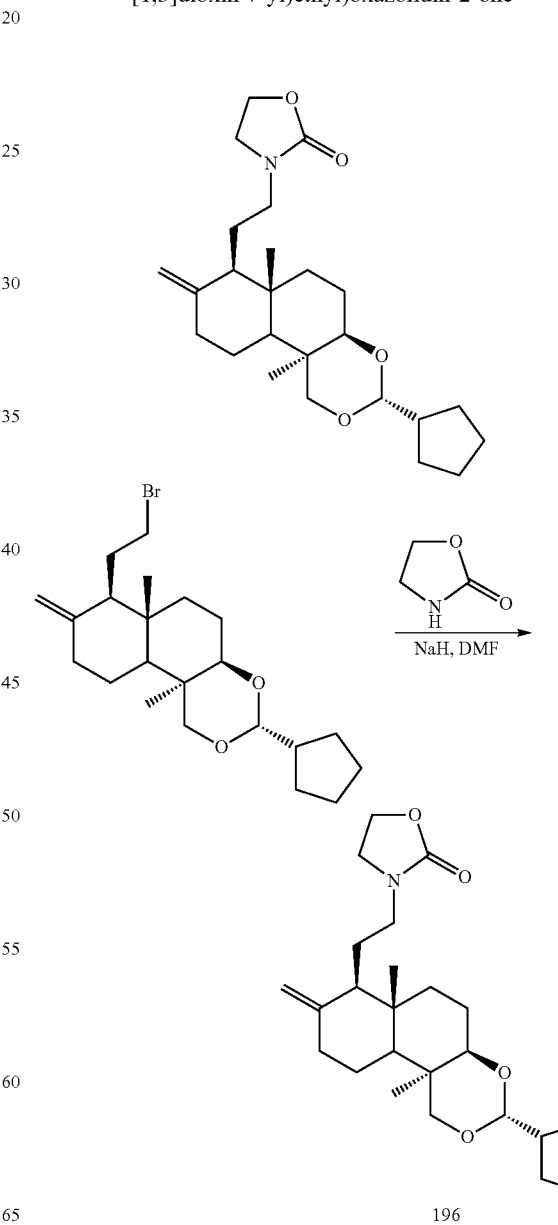

Step 1

3-(2-((3R,4aR,6aS,7R,10bR)-3-cyclopentyl-6a,10b-dimethyl-8-decahydromethylene-1H-naphtho[2,1-d][1,3]dioxin-7-yl)ethyl)oxazolidin-2-one Oxazolidin-2-one (105 mg, 1.2 mmol) was dissolved in N,N-dimethylformamide (3 mL), added with sodium hydrogen (56 mg, 1.4 mmol) at 0° C. and stirred at 0° C. for 0.5 hours and at 20° C. for 0.5 hours. (3R,4aR,6aS,7R,10bR)-7-(2-bromoethyl)-3-cyclopentyl-6a,10b-dimethyl-8-decahydromethylene-1H-naphtho[2,1-d][1,3]dioxin (400 mg, 0.97 mmol) was slowly added to the reaction solution at 0° C., followed by stirring at 20° C. for 20 hours. The reaction was quenched with water and extracted with dichloromethane (50 mL×3). The organic layer was dried over anhydrous sodium sulfate, filtered, and the filtrate was concentrated under reduced pressure and separated by preparative liquid chromatography to give 3-(2-((3R,4aR,6aS,7R,10 bR)-3-cyclopentyl-6a,10b-dimethyl-8-decahydromethylene-1H-naphtho[2,1-d][1,3]dioxin-7-yl)ethyl)oxazolidin-2-one 196 (102.5 mg, yield: 25.2%).

MS m/z (ESI): 418.1 [M+1]

$^1$H NMR (400 MHz, CDCl$_3$) 4.88 (s, 1H), 4.60-4.57 (m, 2H), 4.30 (t, J=8.0 Hz, 2H), 3.99 (d, J=11.2 Hz, 2H), 3.59-3.40 (m, 6H), 2.42-2.39 (m, 1H), 1.78-1.51 (m, 17H), 1.49 (s, 3H), 1.34-1.11 (m, 3H), 0.74 (s, 3H).

Compound 149

N-((3S)-1-(2-((3R,4aR,6aS,7R,10bR)-3-cyclopentyl-6a,10b-dimethyl-8-methylenedecahydro-1H-naphtho[2,1-d][1,3]dioxain-7-yl)ethyl)pyrrolidin-3-yl)acetamide

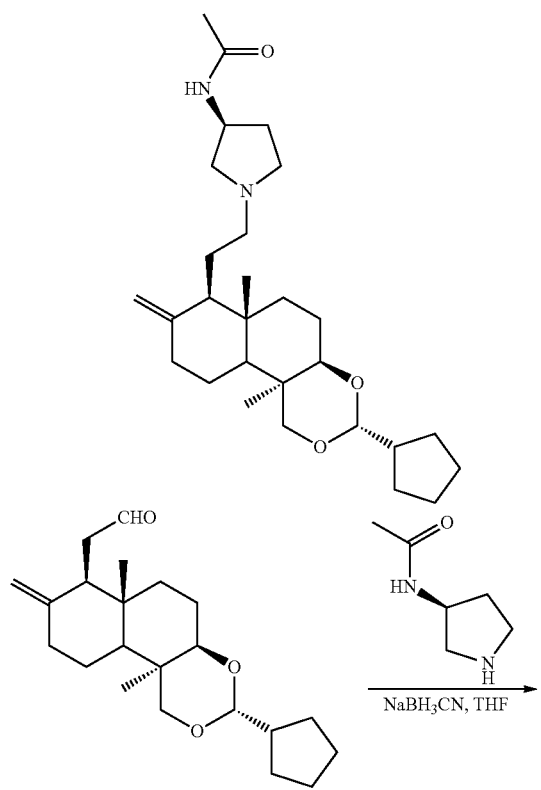

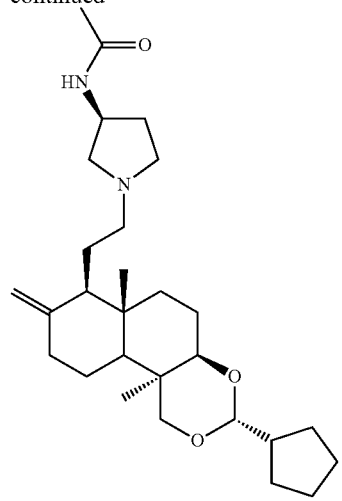

149

Step 1

N-((3S)-1-(2-((3R,4aR,6aS,7R,10bR)-3-cyclopentyl-6a,10b-dimethyl-8-methylenedecahydro-1H-naphtho[2,1-d][1,3]dioxain-7-yl)ethyl)pyrrolidin-3-yl)acetamide 2-((3R,4aR,6aS,7R,10bR)-3-cyclopentyl-6a,10b-dimethyl-8-methylene decahydro-1H-naphtho[2,1-d][1,3]dioxin-7-yl)acetaldehyde (200 mg, 0.58 mmol) was dissolved in tetrahydrofuran (10 mL) and added with (S)—N-(pyrrolidin-3-yl)acetamide (113 mg, 0.87 mmol), followed by stirring at room temperature for 10 hours. Sodium cyanoborohydride (54 mg, 0.87 mmol) was added to the reaction solution and stirred at room temperature for 2 hours. The solvent was distilled off under reduced pressure, and the residue was dissolved in ethyl acetate. The organic layer was washed with saturated brine and water, dried over anhydrous sodium sulfate, filtered, and the filtrate was concentrated under reduced pressure to give N-((3S)-1-(2-((3R,4aR,6aS,7R,10bR)-3-cyclopentyl-6a,10b-dimethyl-8-methylenedecahydro-1H-naphtho[2,1-d][1,3]dioxain-7-yl)ethyl)pyrrolidin-3-yl)acetamide 149 (106 mg, yield: 29.1%).

MS m/z (ESI): 459.2 [M+1]

$^1$H NMR (400 MHz, CDCl$_3$) 8.50 (s, 1H), 4.92 (s, 1H), 4.89 (s, 1H), 4.58 (s, 1H), 4.00-3.40 (m, 5H), 2.90-2.79 (m, 4H), 2.43-1.84 (m, 9H), 1.69-1.55 (m, 12H), 1.35 (s, 2H), 1.23-1.20 (m, 3H), 0.76 (s, 2H).

Compound 163

1-(2-((3R,4aR,6aS,7R,10bR)-3-cyclopentyl-6a,10b-dimethyl-8-methylenedecahydro-1H-naphtho[2,1-d][1,3]dioxin-7-yl)ethyl)pyrrolidine-2-carboxylic acid

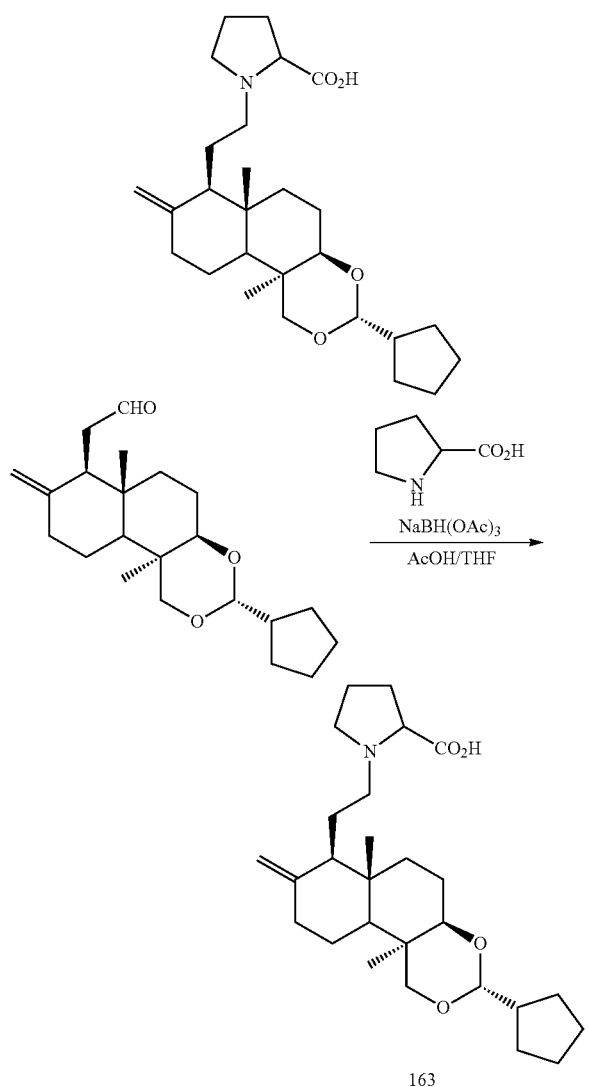

163

Step 1

1-(2-((3R,4aR,6aS,7R,10bR)-3-cyclopentyl-6a,10b-dimethyl-8-methylenedecahydro-1H-naphtho[2,1-d][1,3]dioxin-7-yl)ethyl)pyrrolidine-2-carboxylic acid 2-((3R,4aR,6aS,7R,10bR)-3-cyclopentyl-6a,10b-dimethyl-8-methylene decahydro-1H-naphtho[2,1-d][1,3]dioxin-7-yl)acetaldehyde (100 mg, 0.3 mmol) was dissolved in tetrahydrofuran (5 mL), and pyrrolidine-2-carboxylic acid (40 mg, 0.3 mmol) and sodium borohydride-acetic acid (245 mg, 1.1 mmol) and acetic acid (1 mL) were added successively to the reaction mixture, followed by stirring at room temperature for 12 hours. The reaction solution was poured into a saturated aqueous solution of ammonium chloride and extracted with ethyl acetate. The organic layer was washed with saturated brine and water, dried over anhydrous sodium sulfate, filtered, and the filtrate was concentrated under reduced pressure and then separated by liquid chromatography to give 1-(2-((3R,4aR,6aS,7R,10bR)-3-cyclopentyl-6a,10b-dimethyl-8-methylenedecahydro-1H-naphtho[2,1-d][1,3]dioxin-7-yl)ethyl)pyrrolidine-2-carboxylic acid 163 (20 mg, 15.5%).

MS m/z (ESI): 446.0 [M+1]

$^1$H NMR (400 MHz, CDCl$_3$) 4.94-4.82 (m, 1H), 4.57 (d, J=5.6 Hz, 2H), 3.97 (d, J=11.2 Hz, 1H), 3.94-3.85 (m, 1H), 3.76-3.58 (m, 1H), 3.51-3.35 (m, 2H), 3.32-3.19 (m, 1H), 3.18-3.03 (m, 1H), 3.01-2.88 (m, 1H), 2.78 (d, J=9.6 Hz, 2H), 2.46-2.14 (m, 4H), 2.02 (d, J=19.2 Hz, 5H), 1.87-1.36 (m, 12H), 1.34 (s, 2H), 1.19 (br. s., 2H), 0.74 (s, 3H).

Compound 435

(2S)-1-(2-((3R,4aR,6aS,7R,10bR)-3-cyclopentyl-6a,10b-dimethyl-8-m ethylene-decahydro-1H-naphtho)[2,1-d][1,3]dioxin-7-yl)ethyl)pyrrolidine-2-carboxylic acid

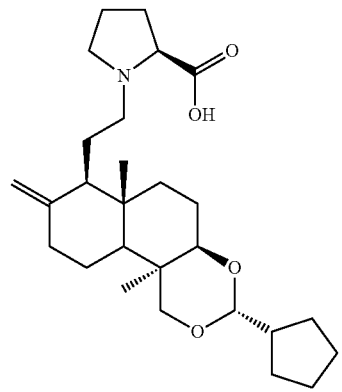

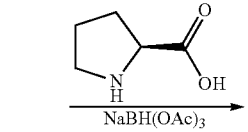

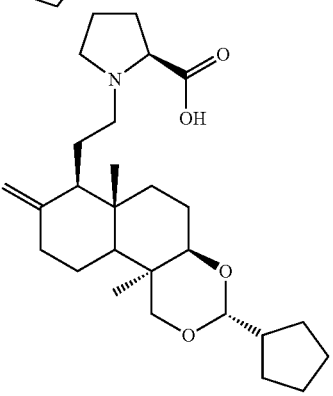

435

Step 1

(2S)-1-(2-((3R,4aR,6aS,7R,10bR)-3-cyclopentyl-6a,
10b-dimethyl-8-m ethylene-decahydro-1H-naphtho)
[2,1-d][1,3]dioxin-7-yl)ethyl)pyrrolidine-2-carbox-
ylic acid 2-((3R,4aR,6aS,7R,10bR)-3-cyclopentyl-6a,10b-dimethyl-8-methylene-decahydro-1H-naphtho[2,1-d][1,3]dioxin-7-yl)acetaldehyde (1.00 g, 2.89 mmol) was dissolved in tetrahydrofuran (30 mL), and (S)-pyrrolidine-2-carboxylic acid (431.95 mg, 3.75 mmol) and acetic acid (173.30 mg, 2.89 mmol, 165.05 uL) were added successively, and then stirred at 30° C. for 1 hour. Sodium borohydride-acetic acid (1.83 g, 8.66 mmol) was added followed by stirring at 30° C. for 11 hours. The system was filtered and concentrated. The residue was separated by column chromatography (silica, petroleum ether/ethyl acetate=10/1 to 1/1) to give (2S)-1-(2-((3R,4aR,6aS,7R,10bR)-3-cyclopentyl-6a,10b-dimethyl-8-methylene-decahydro-1H-naphtho)[2,1-d][1,3]dioxin-7-yl)ethyl)pyrrolidine-2-carboxylic acid 435 (240 mg, yield: 18.64%).

MS m/z (ESI):446.1 [M+1]

$^1$H NMR (400 MHz, CDCl3) 4.89 (s, 1H), 4.57 (d, J=5.6 Hz, 2H), 3.99-3.96 (m, 2H), 3.69 (d, J=2.8 Hz, 1H), 3.46-3.39 (m, 2H), 3.23 (s, 1H), 2.89-2.75 (m, 2H), 2.39-2.29 (m, 4H), 1.99-1.67 (m, 11H), 1.58-1.53 (m, 7H), 1.51 (s, 3H), 1.34-1.18 (m, 3H), 0.73 (s, 3H).

Compound 450

(2R)-1-(2-((3R,4aR,6aS,7R,10bR)-3-cyclopentyl-6a,
10b-dimethyl-8-m ethylene-decahydro-1H-naphtho)
[2,1-d][1,3]dioxin-7-yl)ethyl)pyrrolidine-2-carboxyli
c acid

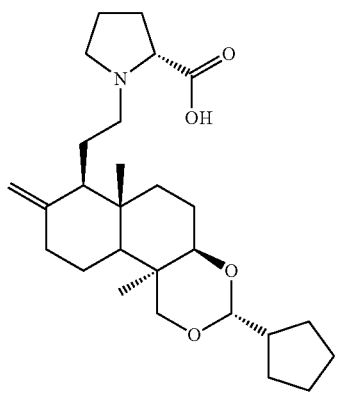

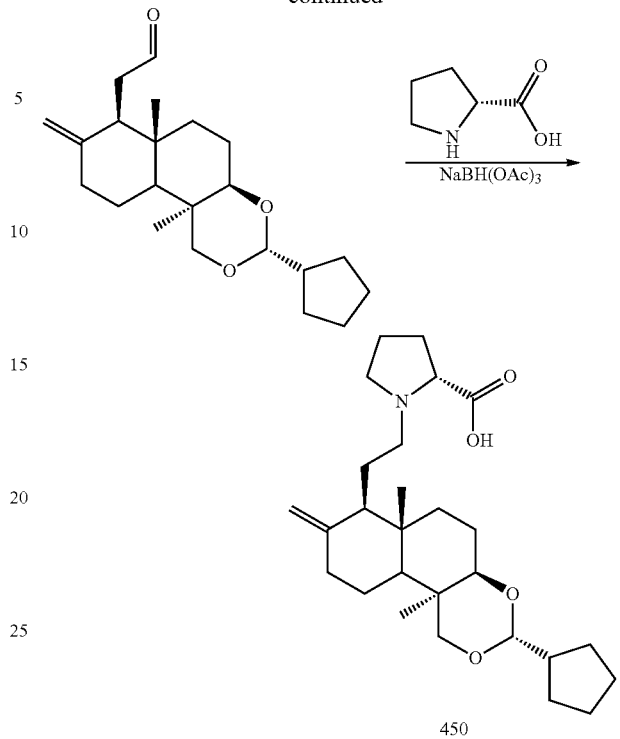

450

Step 1

(2R)-1-(2-((3R,4aR,6aS,7R,10bR)-3-cyclopentyl-6a,
10b-dimethyl-8-m ethylene-decahydro-1H-naphtho)
[2,1-d][1,3]dioxin-7-yl)ethyl)pyrrolidine-2-carboxyli
c acid 2-((3R,4aR,6aS,7R,10bR)-3-cyclopentyl-6a,10b-dimethyl-8-methylene-decahydro-1H-naphtho[2,1-d][1,3]dioxin-7-yl)acetaldehyde (1.50 g, 4.33 mmol) was dissolved in tetrahydrofuran (50 mL), and (R)-pyrrolidine-2-carboxylic acid (747.77 mg, 6.49 mmol) and acetic acid (260.03 mg, 4.33 mmol, 247.65 uL) were added successively, and then stirred at 40° C. for 1 hour. Sodium borohydride-acetic acid (2.75 g, 12.99 mmol) was added followed by stirring at 40° C. for 12 hours. The reaction was added with 20 mL saturated sodium bicarbonate and extracted with ethyl acetate (50 mL*5). The organic phase was dried over anhydrous sodium sulfate, filtered and concentrated. The residue was separated by column chromatography (silica, petroleum ether/ethyl acetate=10/1 to 1/1) to give (2R)-1-(2-((3R,4aR,6aS,7R,10bR)-3-cyclopentyl-6a,10b-dimethyl-8-methylene-decahydro-1H-naphtho)[2,1-d][1,3]dioxin-7-yl)ethyl)pyrrolidine-2-carboxylic acid 450 (650 mg, yield: 33.69%).

MS m/z (ESI):446.9 [M+1]

$^1$H NMR (400 MHz, CDCl3) 4.87 (s, 1H), 4.59-4.55 (m, 2H), 3.99-3.71 (m, 2H), 3.68 (d, J=2.8 Hz, 1H), 3.42-3.87 (m, 3H), 2.81-2.78 (m, 2H), 2.38-2.24 (m, 4H), 2.24-1.97 (m, 8H), 1.81-1.68 (m, 3H), 1.57-1.51 (m, 7H), 1.50 (s, 3H), 1.34-1.19 (m, 3H), 0.75 (s, 3H).

Compound 116

1-(2-((3R,4aR,6aS,7R,10bR)-3-cyclopentyl-6a,10b-dimethyl-8-methylene-decahydro-1H-naphtho)[2,1-d][1,3]dioxin-7-yl)ethyl)-3-methoxypyrrolidine

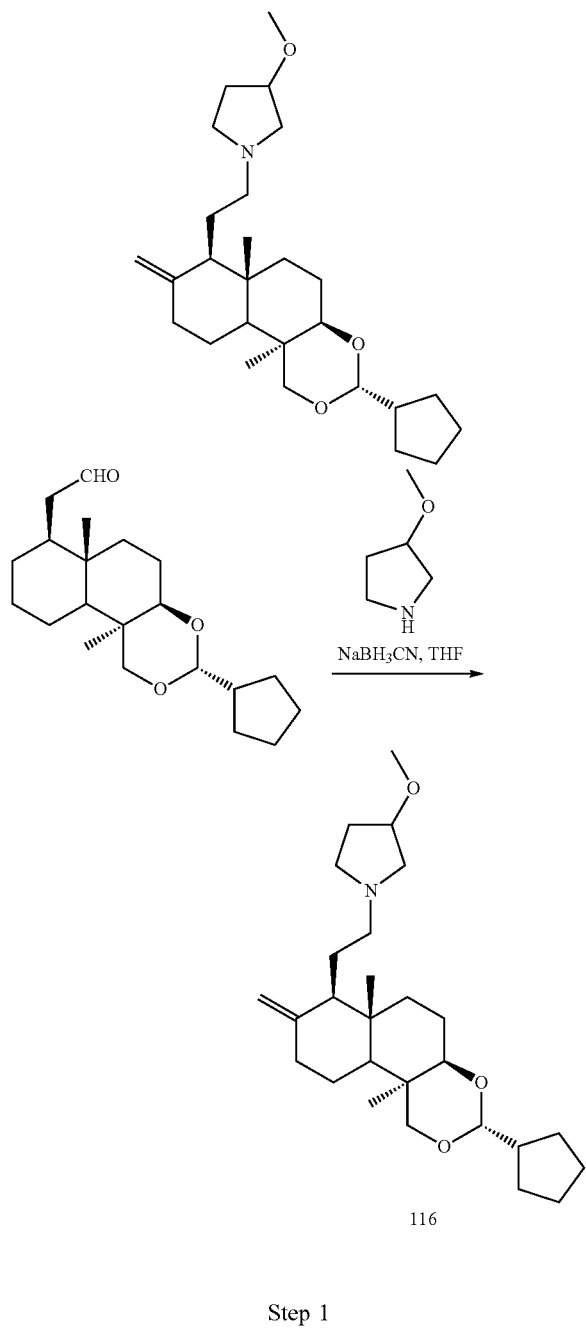

116

Step 1

1-(2-((3R,4aR,6aS,7R,10bR)-3-cyclopentyl-6a,10b-dimethyl-8-methylene-decahydro-1H-naphtho)[2,1-d][1,3]dioxin-7-yl)ethyl)-3-methoxypyrrolidine 2-((3R,4aR,6aS,7R,10bR)-3-cyclopentyl-6a,10b-dimethyl-8-methylene decahydro-1H-naphtho[2,1-d][1,3]dioxin-7-yl)acetaldehyde (200 mg, 0.58 mmol) was dissolved in tetrahydrofuran (10 mL), and 3-methoxypyrrolidine (88 mg, 0.87 mmol) was added, and stirred at room temperature for 10 hours. Sodium cyanoborohydride (54 mg, 0.87 mmol) was added to the reaction solution and stirred at room temperature for 2 hours. The solvent was evaporated under reduced pressure and the residue was dissolved in ethyl acetate. The organic layer was washed with saturated brine and water, dried over anhydrous sodium sulfate, filtered, and the filtrate was concentrated under reduced pressure and then separated by liquid chromatography to give 1-(2-((3R,4aR,6aS,7R,10bR)-3-cyclopentyl-6a,10b-dimethyl-8-methylene-decahydro-1H-naphtho)[2,1-d][1,3]dioxin-7-yl)ethyl)-3-methoxypyrrolidine 116 (89 mg, yield: 35.7%).

MS m/z (ESI): 432.3 [M+1]

$^1$H NMR (400 MHz, CDCl$_3$) 8.55 (s, 1H), 4.85 (s, 1H), 4.58 (d, J=4.8 Hz, 1H), 4.01-3.96 (m, 2H), 3.47-3.39 (m, 2H), 3.28 (s, 3H), 3.78-1.51 (m, 24H), 1.49 (s, 3H), 1.33-1.19 (m, 3H), 0.74 (s, 3H).

Compound 455

(3S)-1-(2-((3R,4aR,6aS,7R,10bR)-3-cyclopentyl-6a,10b-dimethyl-8-m ethylene-decahydro-1H-naphtho)[2,1-d][1,3]dioxin-7-yl)ethyl)pyrrolidine-2-carboxylic acid

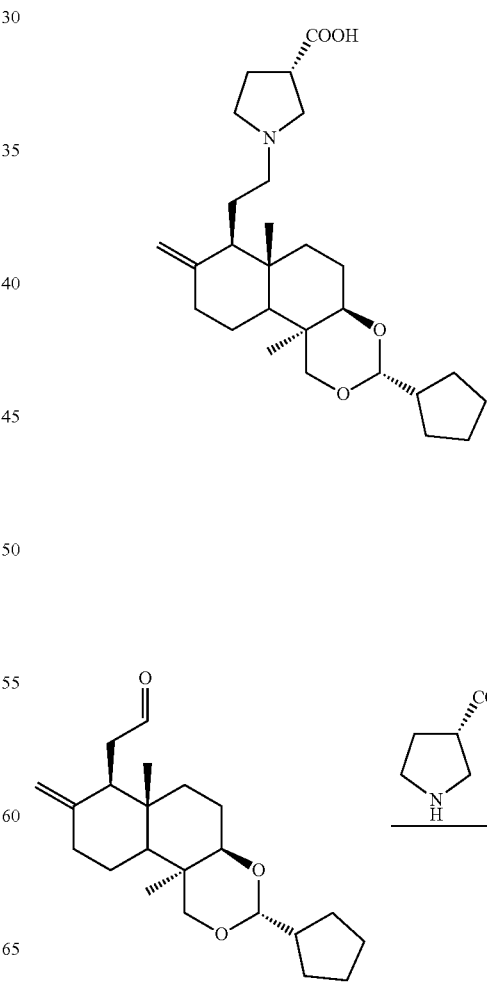

-continued

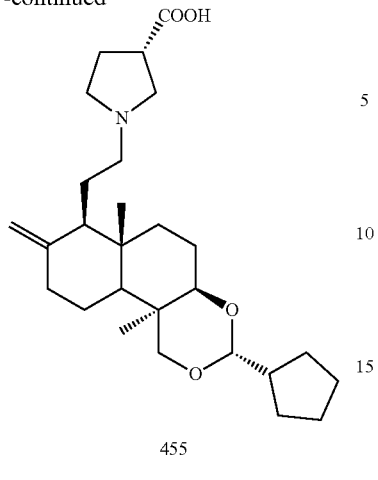

455

Step 1

(3S)-1-(2-((3R,4aR,6aS,7R,10bR)-3-cyclopentyl-6a,10b-dimethyl-8-m ethylene-decahydro-1H-naphtho)[2,1-d][1,3]dioxin-7-yl)ethyl)pyrrolidine-2-carboxylic acid 2-((3R,4aR,6aS,7R,10bR)-3-cyclopentyl-6a,10b-dimethyl-8-methylene-decahydro-1H-naphtho[2,1-d][1,3]dioxin-7-yl)acetaldehyde (500.00 mg, 1.44 mmol) was dissolved in tetrahydrofuran (30 mL), and (S)-pyrrolidine-3-carboxylic acid (200.00 mg, 1.74 mmol) and acetic acid (1.05 g, 17.48 mmol, 1.00 mL) were added successively, and then stirred at 45° C. for 1 hour. Sodium borohydride-acetic acid (1.00 g, 4.72 mmol) was added followed by stirring at 45° C. for 8 hours. The system was concentrated. The residue was separated by column chromatography (silica, dichloromethane/methanol=10/1 to 6/1) to give (3 S)-1-(2-((3R,4aR,6aS,7R,10bR)-3-cyclopentyl-6a,10b-dimethyl-8-methylene-decahydro-1H-naphtho)[2,1-d][1,3]dioxin-7-yl)ethyl)pyrrolidine-2-carboxylic acid 455 (257 mg, 39.97%).

MS m/z (ESI):446.0 [M+1]

$^1$H NMR (400 MHz, CDCl3) 4.86 (s, 1H), 4.69-4.51 (m, 2H), 3.97 (d, J=11.3 Hz, 1H), 3.67 (d, J=18.3 Hz, 1H), 3.53 (br. s., 1H), 3.47-3.31 (m, 3H), 3.06 (br. s., 3H), 2.71 (br. s., 1H), 2.35-1.50 (m, 20H), 1.33 (s, 3H), 1.23-1.10 (m, 3H), 0.73 (s, 3H).

Compound 147

(2S)-methyl-1-(2-((4aR,6aS,7R,10bR)-3-cyclopentyl-6a,10b-dimethyl-8-methylene-decahydro-1H-naphtho) [2,1-d][1,3]dioxin-7-yl)ethyl)pyrrolidine-2-carboxylate

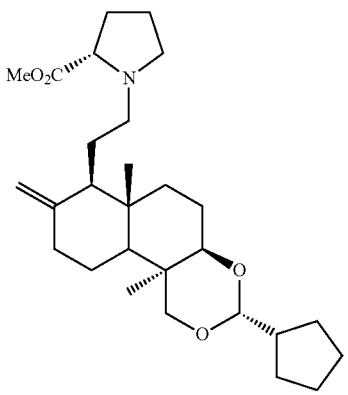

-continued

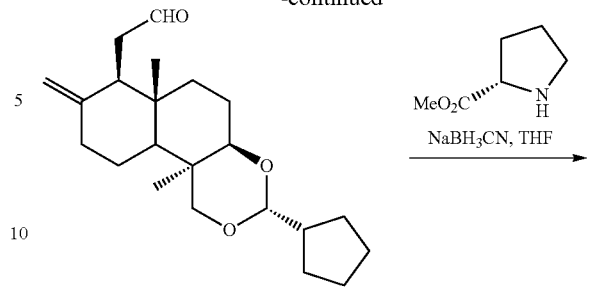

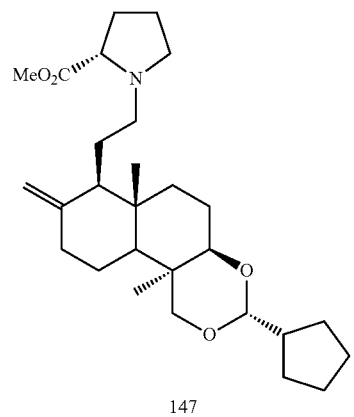

147

Step 1

(2S)-methyl-1-(2-((4aR,6aS,7R,10bR)-3-cyclopentyl-6a,10b-dimethyl-8-methylene-decahydro-1H-naphtho) [2,1-d][1,3]dioxin-7-yl)ethyl)pyrrolidine-2-carboxylate 2-((3R,4aR,6aS,7R,10bR)-3-cyclopentyl-6a,10b-dimethyl-8-methylene decahydro-1H-naphtho[2,1-d][1,3]dioxin-7-yl)acetaldehyde (200 mg, 0.58 mmol) was dissolved in tetrahydrofuran (10 mL), added with (S)-methylpyrrolidine-2-carboxylate (112 mg, 0.87 mmol) and stirred for 10 hours at room temperature. Sodium cyanoborohydride (54 mg, 0.87 mmol) was added to the reaction solution and stirred at room temperature for 2 hours. The solvent was evaporated under reduced pressure and the residue was dissolved in ethyl acetate. The organic layer was washed with saturated brine and water, dried over anhydrous sodium sulfate, filtered, and the filtrate was concentrated under reduced pressure and then separated by liquid chromatography to give (2 S)-methyl-1-(2-((4aR,6aS,7R,10 bR)-3-cyclopentyl-6a,10b-dimethyl-8-methylene-decahydro-1H-naphtho)[2,1-d][1,3]dioxin-7-yl)ethyl)pyrrolidine-2-carboxylate 147 (89 mg, yield: 33.6%).

MS m/z (ESI): 460.1 [M+1]

$^1$H NMR (400 MHz, CDCl$_3$) 8.20 (s, 1H), 4.82 (s, 1H), 4.59-4.54 (m, 2H), 4.00 (d, J=11.2 Hz, 1H), 3.48 (s, 3H), 3.48-3.26 (m, 4H), 2.58-1.53 (m, 27H), 1.51 (s, 3H), 1.42-1.20 (m, 3H), 0.73 (s, 3H).

Compound 181

2-(2-((3R,4aR,6aS,7R,10bR)-3-cyclopentyl-6a,10b-dimethyl-8-methyl ene-decahydro-1H-naphtho)[2,1-d][1,3]dioxin-7-yl)ethyl)-8-methyl-2,8-diazaspiro[4,5]decane

Step 1

2-(2-((3R,4aR,6aS,7R,10bR)-3-cyclopentyl-6a,10b-dimethyl-8-methyl ene-decahydro-1H-naphtho)[2,1-d][1,3]dioxin-7-yl)ethyl)-8-methyl-2,8-di azaspiro[4,5]decane 2-((3R,4aR,6aS,7R,10bR)-3-cyclopentyl-6a,10b-dimethyl-8-decahydro methylene-1H-naphtho[2,1-d][1,3]dioxin-7-yl)acetaldehyde (150 mg, 0.43 mmol) was dissolved in tetrahydrofuran (10 mL), and 8-methyl-2,8-diazaspiro [4.5]. decane (180.1 mg, 0.52 mmol) and sodium borohydride-acetic acid (183.8 mg, 0.88 mmol) were added successively, then stirred at room temperature for 12 hours. The reaction solution was poured into a saturated ammonium chloride solution, the organic layer was extracted with ethyl acetate, and the organic layer was washed with water and saturated brine and dried over anhydrous sodium sulfate. The mixture was filtered, concentrated under reduced pressure and separated by the preparative liquid chromatography to give 2-(2-((3R,4aR,6aS,7R,10bR)-3-cyclopentyl-6a,10b-dimethyl-8-methylene-decahydro-1H-naphtho)[2,1-d][1,3]dioxin-7-yl)ethyl)-8-methyl-2,8-diazaspiro[4,5]decane 181 (30 mg, yield: 14.3%).

MS m/z (ESI): 485.2 [M+1]

$^1$H NMR (400 MHz, CDCl$_3$) 8.41 (s, 1H), 4.89 (s, 1H), 4.60-4.58 (m, 2H), 4.04-4.01 (m, 2H), 3.47-2.76 (m, 11H), 2.61 (s, 3H), 2.04-1.67 (m, 22H), 1.34 (s, 2H), 1.33-1.20 (m, 3H), 0.75 (s, 3H).

Compound 361

(1-(2-((3R,4aR,6aS,7R,10bR)-3-cyclopentyl-6a,10b-dimethyl-8-methylenedecahydro-1H-naphtho[2,1-d][1,3]dioxin-7-yl)ethyl)pyrrolidin-3-yl)methanol

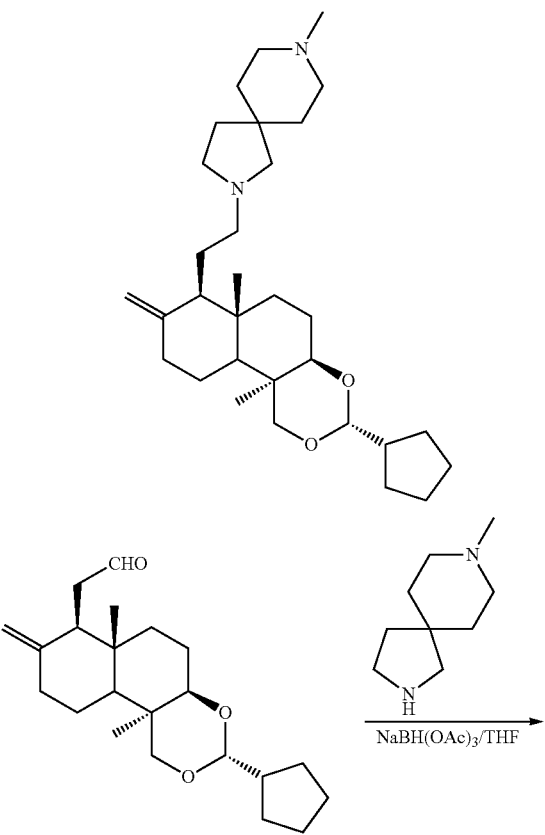

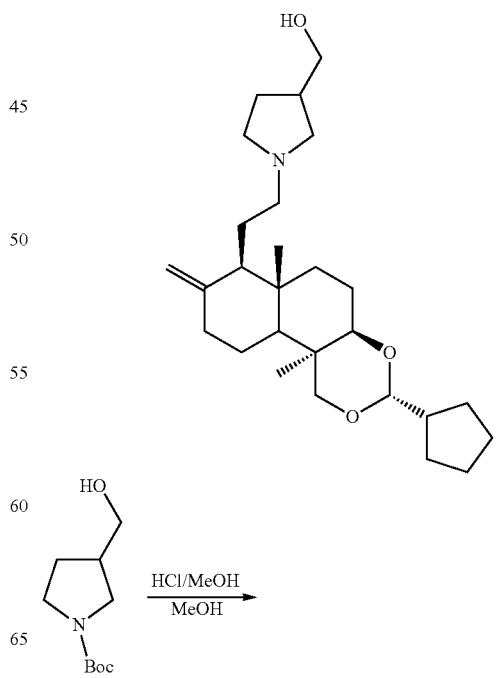

-continued

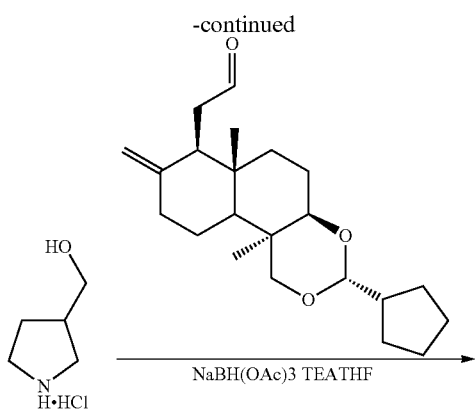

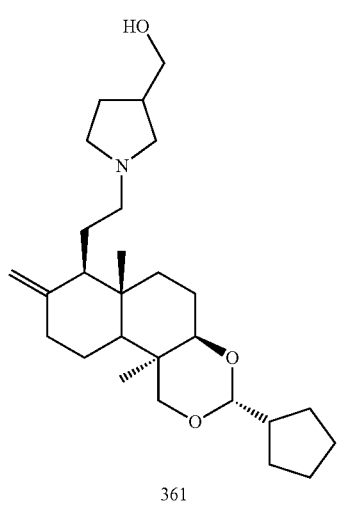

361

Step 1

Pyrrolidine-3-methanol hydrochloride

Tert-butyl 3-(hydroxymethyl)pyrrolidine-1-carboxylate (500 mg, 2.48 mmol) was dissolved in dry methanol (10 mL), added with 4M hydrochloric acid in methanol (4 mL) at 0° C. under nitrogen atmosphere, and stirred for 2 hours at room temperature. The reaction solution was concentrated under reduced pressure to give pyrrolidine-3-methanol hydrochloride (375 mg, crude product).

$^1$H NMR (400 MHz, MeOD) 3.66-3.57 (m, 2H), 3.41-3.13 (m, 4H), 2.59-2.57 (m, 1H), 2.18-2.14 (m, 1H), 1.88-1.84 (m, 1H).

Step 2

(1-(2-((3R,4aR,6aS,7R,10bR)-3-cyclopentyl-6a,10b-dimethyl-8-methylenedecahydro-1H-naphtho[2,1-d][1,3]dioxin-7-yl)ethyl)pyrrolidin-3-yl)methanol 2-((3R,4aR,6aS,7R,10bR)-3-cyclopentyl-6a,10b-dimethyl-8-methylene decahydro-1H-naphtho[2,1-d][1,3]dioxin-7-yl)acetaldehyde (150 mg, 0.43 mmol) was dissolved in anhydrous tetrahydrofuran (10 mL), and pyrrolidine-3-carbinol hydrochloride (77 mg, 0.56 mmol) and triethylamine (0.18 mL, 1.29 mmol) were added successively, then stirred at room temperature for 0.5 hours. Sodium borohydride-acetic acid (276 mg, 1.3 mmol) was added to the reaction mixture, followed by stirring at room temperature for 18 hours. The reaction solution was cooled and extracted with dichloromethane (30 mL). The organic layer was washed with water (10 mL×3), dried over anhydrous magnesium sulfate, filtered, and the filtrate was concentrated under reduced pressure and separated by column chromatography to give (1-(2-((3R,4aR,6aS,7R,10bR)-3-cyclopentyl-6a,10b-dimethyl-8-methylenedecahydro-1H-naphtho[2,1-d][1,3]dioxin-7-yl)ethyl)pyrrolidin-3-yl)methanol 361 (35 mg, yield: 19%).

MS m/z (ESI): 431.7 [M+1]

$^1$H NMR (400 MHz, CDCl$_3$) 4.90 (s, 1H), 4.64-4.58 (m, 2H), 4.00 (d, J=11.6 Hz, 1H), 3.72-3.67 (m, 4H), 3.44-3.40 (m, 4H), 2.67-1.51 (m, 23H), 1.50 (s, 3H), 1.34-1.20 (m, 4H), 0.76 (s, 3H).

Compound 123

4-(2-((3R,4aR,6aS,7R,10bR)-3-cyclopentyl-6a,10b-dimethyl-8-methylenedecahydro-1H-naphtho[2,1-d][1,3]dioxin-7-yl)ethyl)morpholine

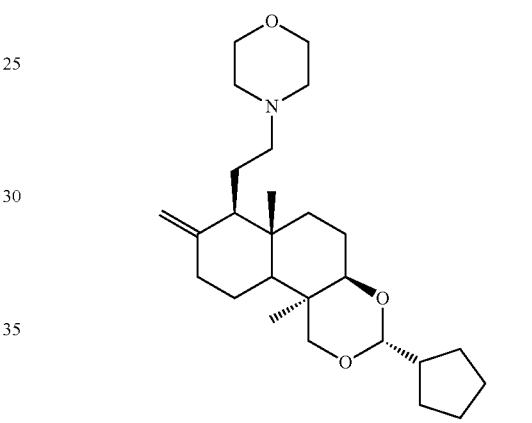

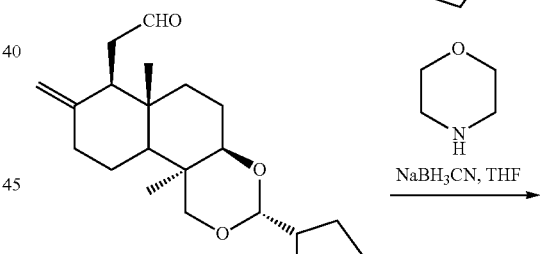

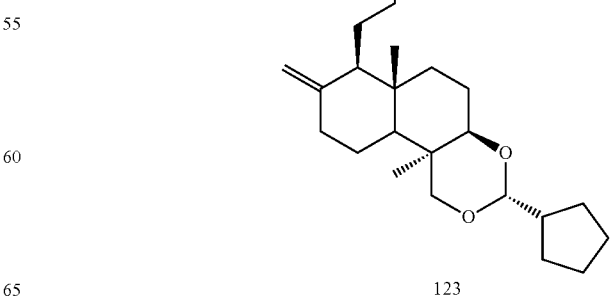

123

Step 1

4-(2-((3R,4aR,6aS,7R,10bR)-3-cyclopentyl-6a,10b-dimethyl-8-methylenedecahydro-1H-naphtho[2,1-d][1,3]dioxin-7-yl)ethyl)morpholine 2-((3R,4aR,6aS,7R,10bR)-3-cyclopentyl-6a,10b-dimethyl-8-methylene decahydro-1H-naphtho[2,1-d][1,3]dioxin-7-yl)acetaldehyde (200 mg, 0.58 mmol) was dissolved in tetrahydrofuran (10 mL), added with morpholine (76 mg, 0.87 mmol) and stirred at room temperature for 10 hours. Sodium cyanoborohydride (54 mg, 0.87 mmol) was added to the reaction solution and stirred at room temperature for 2 hours. The solvent was distilled off under reduced pressure, and the residue was dissolved in ethyl acetate. The organic layer was washed with saturated brine and water, dried over anhydrous sodium sulfate, filtered, and the filtrate was concentrated under reduced pressure to give 4-(2-((3R,4aR,6aS,7R,10bR)-3-cyclopentyl-6a,10b-dimethyl-8-methylenedecahydro-1H-naphtho[2,1-d][1,3]dioxin-7-yl)ethyl)morpholine 123 (86 mg, yield: 35.7%).

MS m/z (ESI): 418.2 [M+1]

$^1$H NMR (400 MHz, CDCl$_3$) 8.51 (s, 2H), 4.88 (s, 2H), 4.59-4.51 (m, 3H), 4.15 (d, J=11.2 Hz, 1H), 3.99 (d, J=11.2 Hz, 1H), 3.71-3.69 (m, 4H), 3.48-3.29 (m, 3H), 2.95-1.77 (m, 15H), 1.34 (s, 3H), 1.24-1.20 (m, 7H), 0.75 (s, 3H), 0.64 (s, 3H).

Compound 433

1-(2-((3R,4aR,6aS,7R,10bR)-3-cyclopentyl-6a,10b-dimethyl-8-methyl ene-decahydro-1H-naphtho[2,1-d][1,3]dioxin-7-yl)ethyl)-4-methylpiperazine

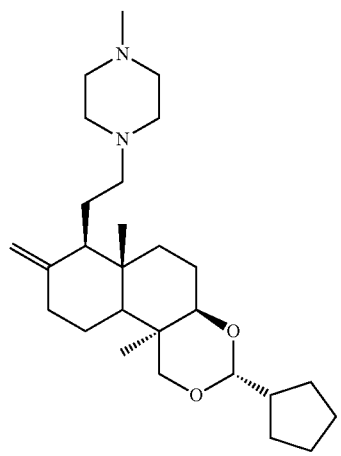

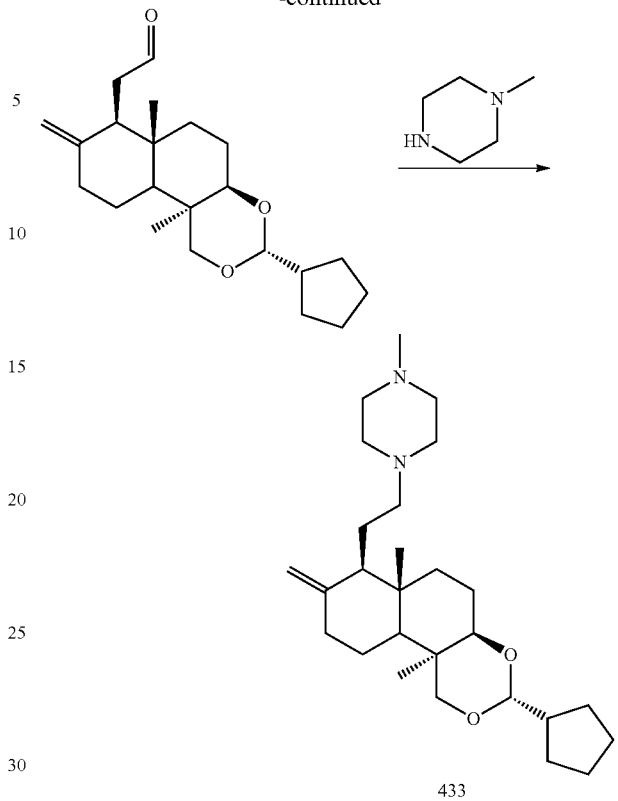

433

Step 1

1-(2-((3R,4aR,6aS,7R,10bR)-3-cyclopentyl-6a,10b-dimethyl-8-methyl ene-decahydro-1H-naphtho[2,1-d][1,3]dioxin-7-yl)ethyl)-4-methylpiperazine 2-((3R,4aR,6aS,7R,10bR)-3-cyclopentyl-6a,10b-dimethyl-8-methylene-decahydro-1H-naphtho[2,1-d][1,3]dioxin-7-yl)acetaldehyde (3.00 g, 8.66 mmol) was dissolved in tetrahydrofuran (20 mL), and 1-methylpiperazine (4.34 g, 43.30 mmol, 4.82 mL) and triethylamine (4.38 g, 43.29 mmol, 6.00 mL) were added successively, and then stirred at 25° C. for 4 hours. Sodium borohydride-acetic acid (5.50 g, 25.97 mmol) was added and stirred at 25° C. for 8 hours. The reaction solution was diluted with 20 mL water and extracted with ethyl acetate (20 mL*2). The organic phase was dried over anhydrous sodium sulfate, filtered and concentrated. The residue was separated by column chromatography (silica, dichloromethane/methanol=50/1 to 10/1) to give 1-(2-((3R,4aR,6aS,7R,10bR)-3-cyclopentyl-6a,10b-dimethyl-8-methylene-decahydro-1H-naphtho[2,1-d][1,3]dioxin-7-yl)ethyl)-4-methylpiperazine 433 (1 g, yield: 26.81%).

MS m/z (ESI):431.4 [M+1]

$^1$H NMR (400 MHz, CDCl3) 4.83 (s, 1H), 4.64-4.51 (m, 2H), 4.01 (d, J=11.3 Hz, 1H), 3.54-3.33 (m, 2H), 2.71-2.33 (m, 9H), 2.29 (s, 3H), 2.26-2.15 (m, 2H), 2.12-2.02 (m, 2H), 1.98-1.84 (m, 2H), 1.80-1.62 (m, 5H), 1.60-1.38 (m, 8H), 1.34 (s, 3H), 1.25-1.06 (m, 3H), 0.74 (s, 3H).

Compound 160

1-(2-((3R,4aR,6aS,7R,10bR)-3-cyclopentyl-6a,10b-dimethyl-8-methyl ene-decahydro-1H-naphtho[2,1-d][1,3]dioxin-7-yl)ethyl)-4-(pyrrolidin-1-yl)piperidine

Step 1

1-(2-((3R,4aR,6aS,7R,10bR)-3-cyclopentyl-6a,10b-dimethyl-8-methyl ene-decahydro-1H-naphtho[2,1-d][1,3]dioxin-7-yl)ethyl)-4-(pyrrolidin-1-yl)piperidine 2-((4aR,6aS,7R,10bR)-3-cyclopentyl-6a,10b-dimethyl-8-methylenedecahydro-1H-naphtho[2,1-d][1,3]dioxin-7-yl) acetaldehyde (300 mg, 0.87 mmol) was dissolved in tetrahydrofuran (10 mL), added with 4-(pyrrolidin-1-yl)piperidine (200 mg, 1.30 mmol) and stirred for 10 hours at room temperature. Sodium cyanoborohydride (426 mg, 1.74 mmol) was added to the reaction solution and stirred at room temperature for 2 hours. The solvent was distilled off under reduced pressure and the residue was dissolved in ethyl acetate. The organic layer was washed with saturated brine and water, dried over anhydrous sodium sulfate, filtered, and the filtrate was concentrated under reduced pressure to give 1-(2-((3R,4aR,6aS,7R,10bR)-3-cyclopentyl-6a,10b-dimethyl-8-methylene-decahydro-1H-naphtho[2,1-d][1,3]dioxin-7-yl)ethyl)-4-(pyrrolidin-1-yl)piperidine 160 (59 mg, yield: 12.2%).

MS m/z (ESI): 485.2 [M+1]

$^1$H NMR (400 MHz, CDCl$_3$) 8.40 (s, 1H), 4.86 (s, 1H), 4.59-4.56 (m, 1H), 4.15-3.98 (m, 1H), 3.48-3.10 (m, 10H), 2.48-1.55 (m, 29H), 1.34 (s, 3H), 1.23-1.15 (m, 4H), 0.75 (s, 3H).

Compound 150

1-(2-((4aR,6aS,7R,10bR)-3-cyclopentyl-6a,10b-dimethyl-8-methylene-decahydro-1H-naphtho[2,1-d][1,3]dioxin-7-yl)ethyl)-N,N-diethylpiperidin-4-amine

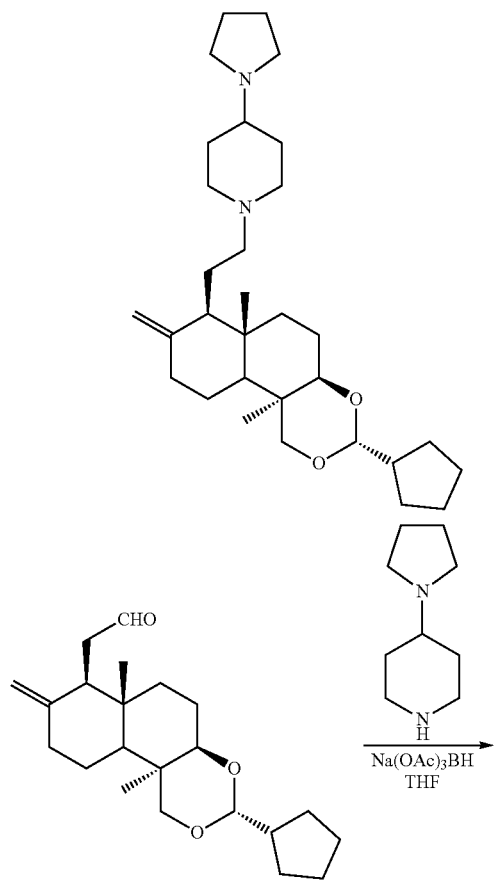

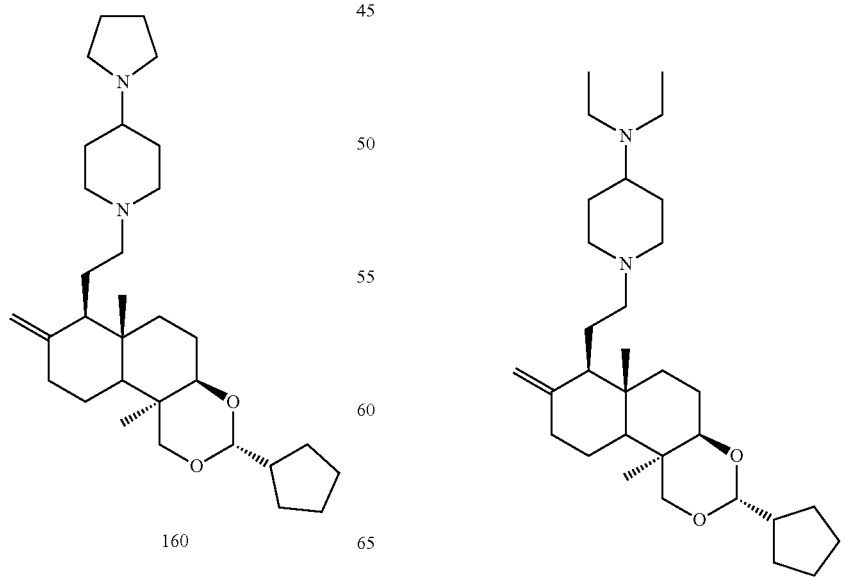

-continued

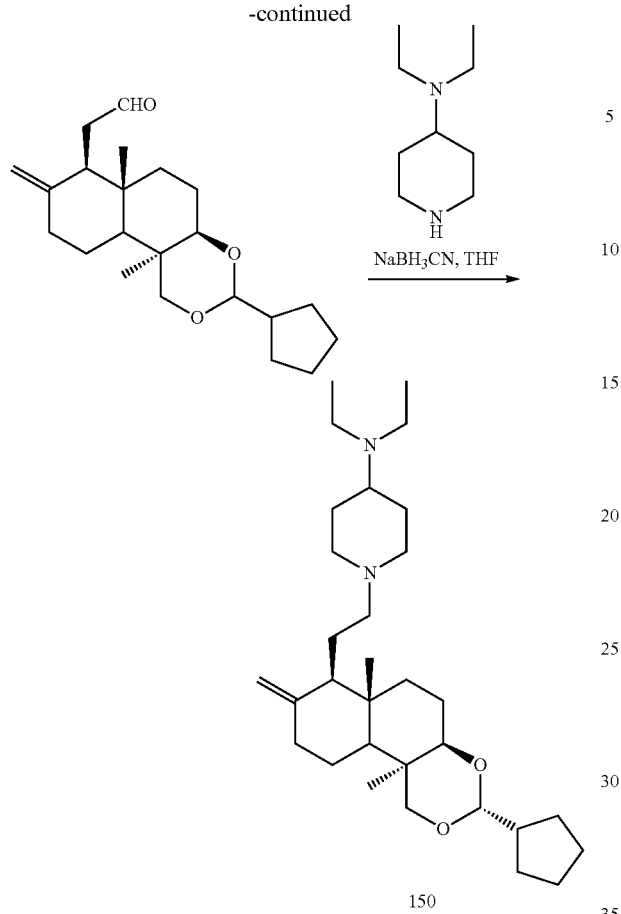

Step 1

1-(2-((4aR,6aS,7R,10bR)-3-cyclopentyl-6a,10b-dimethyl-8-methylene-decahydro-1H-naphtho[2,1-d][1,3]dioxin-7-yl)ethyl)-N,N-diethylpiperidin-4-amine 2-((4aR,6aS,7R,10bR)-3-cyclopentyl-6a,10b-dimethyl-8-methylenedecahydro-1H-naphtho[2,1-d][1,3]dioxin-7-yl)acetaldehyde (200 mg, 0.58 mmol) was dissolved in tetrahydrofuran (10 mL), added with N,N-diethylpiperidin-4-amine (136 mg, 0.87 mmol), and stirred at room temperature for 10 hours. Sodium cyanoborohydride (54 mg, 0.87 mmol) was added to the reaction solution and stirred at room temperature for 2 hours. The solvent was distilled off under reduced pressure, and the residue was dissolved in ethyl acetate. The organic layer was washed with saturated brine and water, dried over anhydrous sodium sulfate, filtered, and the filtrate was concentrated under reduced pressure to give 1-(2-((4aR,6aS,7R,10bR)-3-cyclopentyl-6a,10b-dimethyl-8-methylene-decahydro-1H-naphtho[2,1-d][1,3]dioxin-7-yl)ethyl)-N,N-diethylpiperidin-4-amine 150 (106 mg, yield: 37.8%).

MS m/z (ESI): 487.2 [M+1]

$^1$H NMR (400 MHz, CDCl$_3$) 8.44 (s, 1H), 4.86 (s, 1H), 4.59-4.56 (m, 2H), 4.00 (d, J=11.6 Hz, 1H), 3.45-2.96 (m, 9H), 2.40-1.51 (m, 27H), 1.37-1.20 (m, 14H), 0.75 (s, 3H).

Compound 451

(2R)-1-(2-((3R,4aR,6aS,7R,10bR)-3-cyclopentyl-6a,10b-dimethyl-8-m ethylene-decahydro-1H-naphtho[2,1-d][1,3]dioxin-7-yl)ethyl)piperidine-2-carboxylic acid

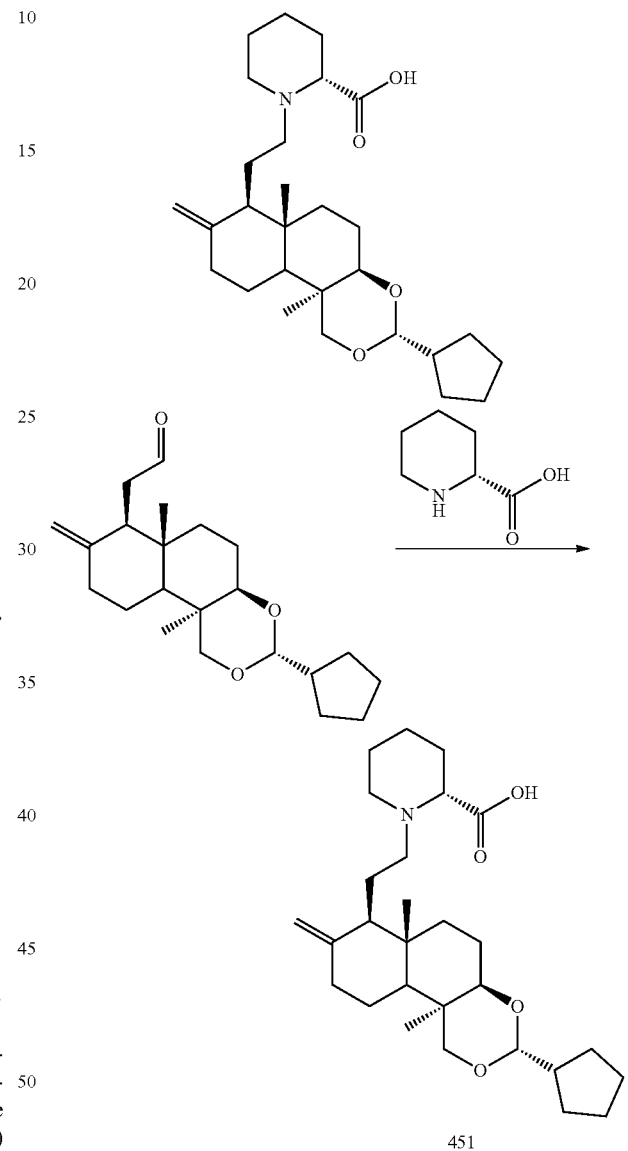

Step 1

(2R)-1-(2-((3R,4aR,6aS,7R,10bR)-3-cyclopentyl-6a,10b-dimethyl-8-m ethylene-decahydro-1H-naphtho[2,1-d][1,3]dioxin-7-yl)ethyl)piperidine-2-carb oxylic acid 2-((3R,4aR,6aS,7R,10bR)-3-cyclopentyl-6a,10b-dimethyl-8-methylene-decahydro-1H-naphtho[2,1-d][1,3]dioxin-7-yl)acetaldehyde (500.00 mg, 1.44 mmol) was dissolved in tetrahydrofuran (20 mL), and piperidine-2-carboxylic acid (280.00 mg, 2.17 mmol) and acetic acid (1.05 g, 17.48 mmol, 1.00 mL) were added successively and stirred at 45° C. for 1 hour. Sodium borohydride-acetic acid (915.58 mg, 4.32 mmol) was added followed by stirring at 45° C. for 8 hours. The reaction solution was diluted with 150 mL water and extracted with ethyl acetate (50 mL*3). The organic phase was dried over anhydrous sodium sulfate, filtered and concentrated. The residue was separated by column chromatography (silica, dichloromethane/methanol 20/1) to give (2R)-1-(2-((3R,4aR,6aS,7R,10 bR)-3-cyclopentyl-6a,10b-dimethyl-8-methylene-decahydro-1H-naphtho[2,1-d][1,3]dioxin-7-yl)ethyl)piperidine-2-carboxylic acid 451 (83 mg, yield: 12.54%).

MS m/z (ESI):460.4 [M+1]

$^1$H NMR (400 MHz, CDCl3) 4.84 (s, 1H), 4.59 (d, J=5.5 Hz, 1H), 4.53 (br. s., 1H), 3.98 (d, J=11.5 Hz, 1H), 3.63 (d, J=9.5 Hz, 1H), 3.49-3.32 (m, 4H), 2.94-2.68 (m, 2H), 2.42-2.17 (m, 3H), 2.14-1.39 (m, 21H), 1.34 (s, 3H), 1.27-1.11 (m, 3H), 0.74 (s, 3H).

Compound 002

(1-(2-((3R,4aR,6aS,7R,10bR)-3-cyclopentyl-6a,10b-dimethyl-8-methylene-decahydro-1H-naphtho[2,1-d][1,3]dioxin-7-yl)ethyl)piperidin-4-yl)methanol

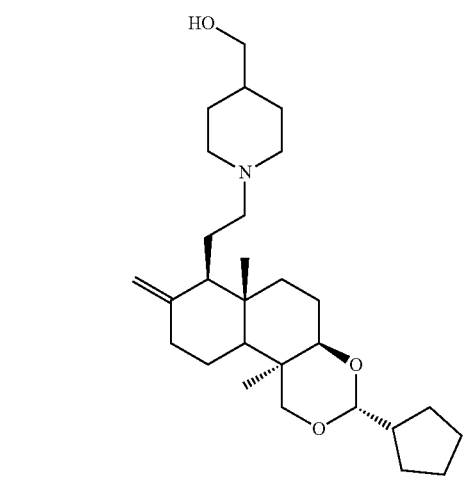

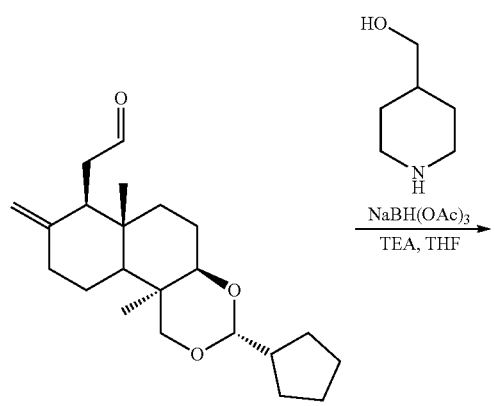

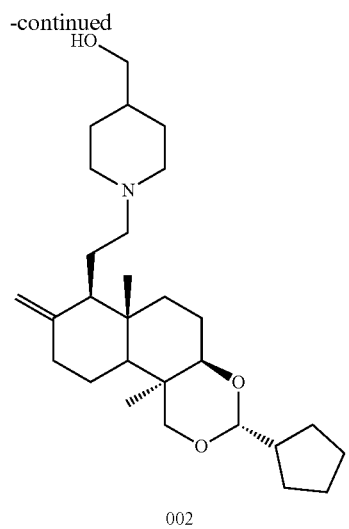

Step 1

(1-(2-((3R,4aR,6aS,7R,10bR)-3-cyclopentyl-6a,10b-dimethyl-8-methylene-decahydro-1H-naphtho[2,1-d][1,3]dioxin-7-yl)ethyl)piperidin-4-yl)methanol 2-((3R,4aR,6aS,7R,10bR)-3-cyclopentyl-6a,10b-dimethyl-8-methylene-decahydro-1H-naphtho[2,1-d][1,3]dioxin-7-yl)acetaldehyde (2.0 g, 5.8 mmol) was dissolved in tetrahydrofuran (30 mL), and piperidin-4-ylmethanol (1.0 g, 8.7 mmol) and triethylamine (1.17 g, 11.6 mmol) were added successively, then stirred at 20° C. for 2 hours. Sodium borohydride-acetic acid (3.69 g, 17.4 mmol) was added followed by stirring at 20° C. for 24 hours. The reaction solution was diluted with 20 mL water and extracted with dichloromethane (50 mL*5). The organic phase was dried over anhydrous sodium sulfate, filtered and concentrated. The residue was separated by column chromatography (silica, dichloromethane/methanol=10/1) to give (1-(2-((3R,4aR,6aS,7R,10bR)-3-cyclopentyl-6a,10b-dimethyl-8-methylene-decahydro-1H-naphtho[2,1-d][1,3]dioxin-7-yl)ethyl)piperidin-4-yl)methanol 002 (2 g, yield: 77.8%).

MS m/z (ESI):446.9 [M+1]

$^1$H NMR (400 MHz, CDCl3) 4.86 (s, 1H), 4.60-4.58 (m, 2H), 4.01 (d, J=10.8 Hz, 1H), 3.53-3.40 (m, 4H), 3.38-3.25 (m, 2H), 2.75-2.60 (m, 1H), 2.41-2.38 (m, 2H), 2.23-2.10 (m, 3H), 2.10-1.50 (m, 22H), 1.35 (s, 3H), 1.20-1.10 (m, 3H), 0.75 (s, 3H).

Compound 256

1-(2-((3R,4aR,6aS,7R,10bR)-3-cyclopentyl-6a,10b-dimethyl-8-methyl ene-decahydro-1H-naphtho[2,1-d][1,3]dioxin-7-yl)ethyl)piperidin-4-carboxylic acid

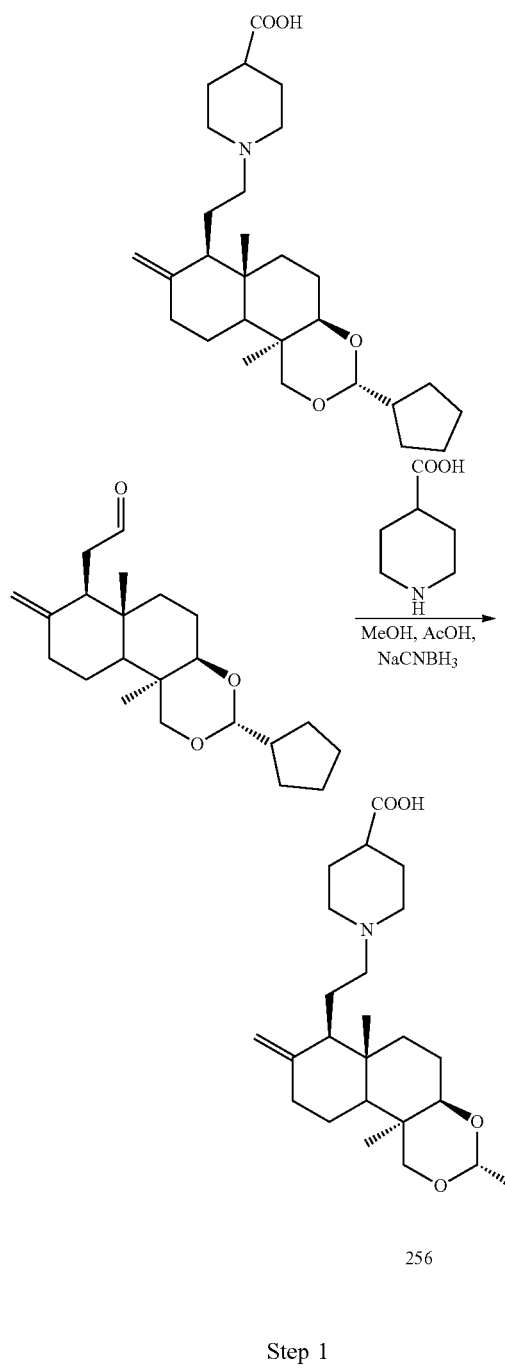

Step 1

1-(2-((3R,4aR,6aS,7R,10bR)-3-cyclopentyl-6a,10b-dimethyl-8-methyl ene-decahydro-1H-naphtho[2,1-d][1,3]dioxin-7-yl)ethyl)piperidin-4-carboxylic acid 2-((3R,4aR,6aS,7R,10bR)-3-cyclopentyl-6a,10b-dimethyl-8-methylene decahydro-1H-naphtho[2,1-d][1,3]dioxin-7-yl)acetaldehyde (150 mg, 0.43 mmol) was dissolved in methanol (10 mL), and piperidine-4-carboxylic acid (280 mg, 2.17 mmol) and three drops of acetic acid were added successively to the reaction solution and stirred at room temperature for 0.5 hours. Sodium cyanoborohydride (75 mg, 1.29 mmol) was added to the reaction solution and stirred at room temperature for 17 hours. The reaction solution was added to water (20 mL), extracted with dichloromethane (20 mL×8), and the organic layer was dried over anhydrous sodium sulfate, filtered, and the filtrate was concentrated under reduced pressure and separated by preparative liquid chromatography to give 1-(2-((3R,4aR,6aS,7R,10bR)-3-cyclopentyl-6a,10b-dimethyl-8-methylene-decahydro-1H-naphtho[2,1-d][1,3]dioxin-7-yl)ethyl)piperidin-4-carboxylic acid 256 911 mg, yield: 5.5%).

MS m/z (ESI): 460.1 [M+1]

$^1$H NMR (400 MHz, CDCl$_3$) 4.89 (s, 1H), 4.62-4.60 (m, 1H), 4.01 (d, J=11.2 Hz, 1H), 3.49-3.42 (m, 3H), 2.98-1.36 (m, 26H), 1.22 (m, 3H), 0.77 (s, 3H).

Compound 456

(3R)-4-(2-((3R,4aR,6aS,7R,10bR))-3-cyclopentyl-6a,10b-dimethyl-8-methylene-decahydro-1H-naphtho[2,1-d][1,3]dioxin-7-yl)ethyl)morpholine-3-carboxylic acid

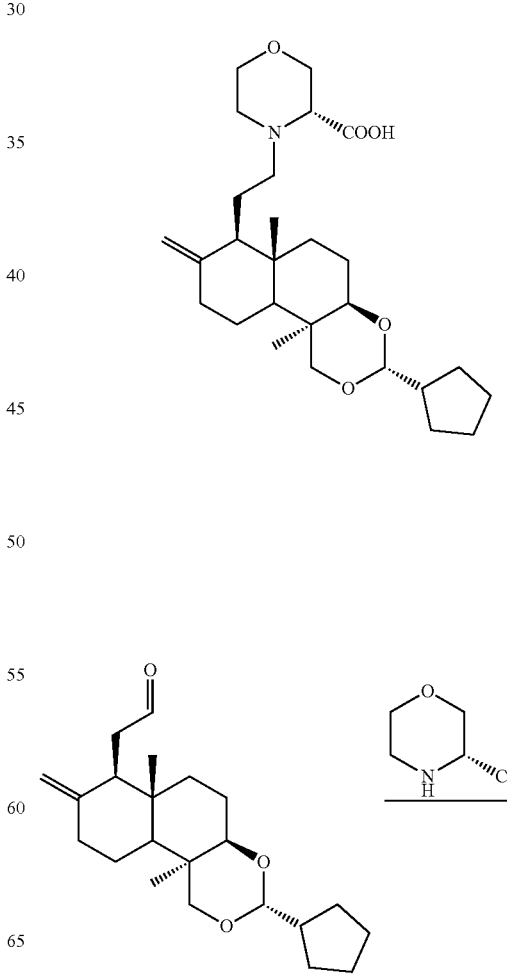

197

-continued

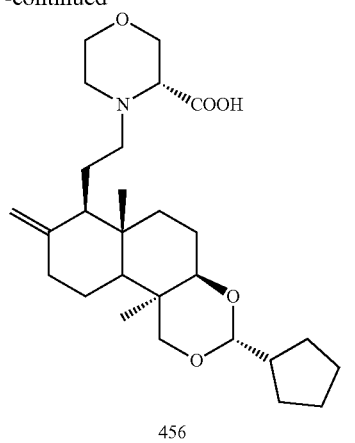

456

Step 1

(3R)-4-(2-((3R,4aR,6aS,7R,10bR))-3-cyclopentyl-6a,10b-dimethyl-8-methylene-decahydro-1H-naphtho[2,1-d][1,3]dioxin-7-yl)ethyl)morpholine-3-carboxylic acid 2-((3R,4aR,6aS,7R,10bR)-3-cyclopentyl-6a,10b-dimethyl-8-methylene-decahydro-1H-naphtho[2,1-d][1,3]dioxin-7-yl)acetaldehyde (250.00 mg, 721.50 umol) was dissolved in tetrahydrofuran (20 mL), and (3R)-morpholine-3-carboxylic acid (100.29 mg, 764.79 umol) and acetic acid (525.00 mg, 8.74 mmol, 500.00 uL) were added successively, then stirred at 45° C. for 1 hour. Sodium borohydride-acetic acid (500.00 mg, 2.36 mmol) was added and stirred at 45° C. for 8 hours. The system was concentrated. The residue was separated by column chromatography (silica, dichloromethane/methanol=20/1 to 10/1) to give (3R)-4-(2-((3R,4aR,6aS,7R,10bR))-3-cyclopentyl-6a,10b-dimethyl-8-methylene-deca hydro-1H-naphtho[2,1-d][1,3]dioxin-7-yl) ethyl)morpholine-3-carboxylic acid 456 (84 mg, yield: 25.22%).

MS m/z (ESI):462.1 [M+1]

$^1$H NMR (400 MHz, MeOD) 4.88-4.83 (m, 1H), 4.76 (s, 1H), 4.70 (d, J=5.5 Hz, 1H), 4.16 (d, J=10.5 Hz, 1H), 4.08 (d, J=11.3 Hz, 1H), 4.01 (d, J=12.3 Hz, 1H), 3.78 (t, J=11.4 Hz, 1H), 3.69 (t, J=10.9 Hz, 1H), 3.55-3.42 (m, 3H), 3.02 (t, J=9.8 Hz, 1H), 2.75 (br. s., 1H), 2.49-2.30 (m, 2H), 2.24-1.38 (m, 18H), 1.35 (s, 3H), 1.31-1.21 (m, 3H), 0.84 (s, 3H).

198

Compound 457

1-(2-((3R,4aR,6aS,7R,10bR)-3-cyclopentyl-6a,10b-dimethyl-8-dihydromethylene-1H-naphtho[2,1-d][1,3]dioxin-7-yl)ethyl)-6-oxo-1,6-dihydropyridine-3-carboxylic acid

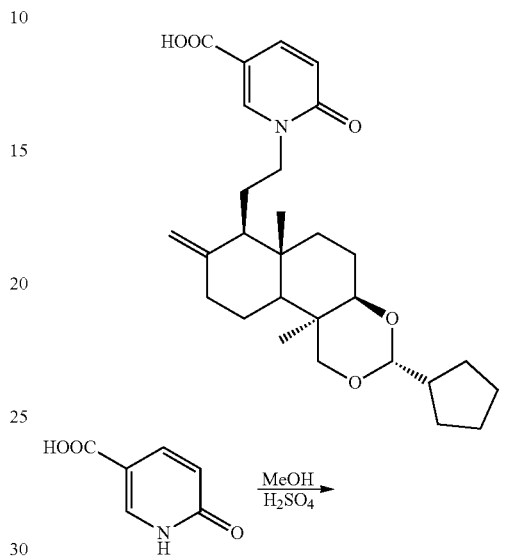

199

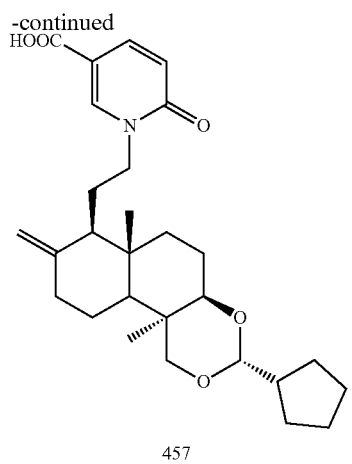

457

Step 1

Methyl 6-oxo-1,6-dihydropyridine-3-carboxylate

6-Oxo-1,6-dihydropyridine-3-carboxylic acid (1.00 g, 7.19 mmol) was dissolved in methanol (20.00 mL) and added with sulfuric acid (1.11 g, 11.29 mmol, 601.72 uL), then stirred at 70° C. for 10 hours. The reaction was quenched with 40 mL saturated sodium bicarbonate solution and extracted with ethyl acetate (50 mL*3). The combined organic phases were washed with saturated brine (40 mL), dried over anhydrous sodium sulfate, filtered and concentrated to give methyl 6-oxo-1,6-dihydropyridine-3-carboxylate (0.8 g, crude product).

$^1$H NMR (400 MHz, CDCl3) 13.17 (br. s., 1H), 8.21 (d, J=2.5 Hz, 1H), 8.01 (dd, J=2.5, 9.5 Hz, 1H), 6.58 (d, J=9.5 Hz, 1H), 3.87 (s, 3H).

Step 2

Methyl 1-(2-((3R,4aR,6aS,7R,10bR)-3-cyclopentyl-6a,10b-dimethyl-8-dihydromethylene-1H-naphtho[2,1-d][1,3]dioxin-7-yl)ethyl)-6-oxo-1,6-dihydropyridine-3-carboxylate (3R,4aR,6aS,7R,10bR)-7-(2-bromoethyl)-3-cyclopentyl-6a,10b-dimeth yl-8-dihydromethylene-1H-naphtho[2,1-d][1,3]dioxin (700.00 mg, 1.70 mmol) was dissolved in N,N-dimethylformamide (20.00 mL), cesium carbonate (1.66 g, 5.10 mmol) and methyl 6-oxo-1,6-dihydropyridine-3-carboxylate (299.39 mg, 1.95 mmol) were added successively, then stirred at 80° C. for 10 hours. The reaction solution was filtered and concentrated, and the residue was separated by column chromatography (silica, petroleum ether/ethyl acetate=100/0 to 2/1) to give methyl 1-(2-((3R,4aR,6aS,7R,10bR)-3-cyclopentyl-6a,10b-dimethyl-8-dihydromethylene-1H-naphtho[2,1-d][1,3]dioxin-7-yl)ethyl)-6-oxo-1,6-dihydropyridine-3-carboxylate (a colorless oil, 450 mg, crude product).

$^1$H NMR (400 MHz, CDCl3) 8.06 (d, J=2.5 Hz, 1H), 7.81 (dd, J=2.3, 9.3 Hz, 1H), 6.49 (d, J=9.5 Hz, 1H), 4.94 (s, 1H), 4.79 (s, 1H), 4.55 (d, J=6.0 Hz, 1H), 4.20-4.11 (m, 1H), 3.97 (d, J=11.0 Hz, 1H), 3.84 (s, 3H), 3.66 (ddd, J=6.8, 8.8, 12.5 Hz, 1H), 3.46-3.35 (m, 2H), 2.42 (d, J=13.6 Hz, 1H), 2.19 (dq, J=2.8, 13.1 Hz, 1H), 2.05-1.44 (m, 16H), 1.34-1.29 (m, 3H), 1.24-1.06 (m, 3H), 0.72 (s, 3H).

200

Step 3

1-(2-((3R,4aR,6aS,7R,10bR)-3-cyclopentyl-6a,10b-dimethyl-8-dihydromethylene-1H-naphtho[2,1-d][1,3]dioxin-7-yl)ethyl)-6-oxo-1,6-dihydropyridine-3-carboxylic acid Methyl 1-(2-((3R,4aR,6aS,7R,10bR)-3-cyclopentyl-6a,10b-dimethyl-8-dihydromethylene-1H-naphtho[2,1-d][1,3]dioxin-7-yl)ethyl)-6-oxo-1,6-dihydropyridine-3-carboxylate (450.00 mg, 930.44 umol) was dissolved in methanol (10.00 mL), and potassium hydroxide (300.00 mg, 5.35 mmol) and water (10.00 mL) were added successively, followed by stirring at 70° C. for 8 hours. The system was adjusted to pH=5-6 with hydrochloric acid solution (1M) and then extracted with ethyl acetate (30 mL*3). The combined organic phases were washed with saturated brine, dried over anhydrous sodium sulfate, filtered and concentrated to give 1-(2-((3R,4aR,6aS,7R,10bR)-3-cyclopentyl-6a,10b-dimethyl-8-dihydromethylene-1H-naphtho[2,1-d][1,3]dioxin-7-yl)ethyl)-6-oxo-1,6-dihydropyridine-3-carboxylic acid 457 (260 mg, yield: 55.1%).

MS m/z (ESI):470.3[M+1]

$^1$H NMR (400 MHz, DMSO-$d_6$) 8.08 (br. s., 1H), 7.82 (d, J=9.5 Hz, 1H), 6.23 (d, J=9.0 Hz, 1H), 4.91 (d, J=11.0 Hz, 2H), 4.62 (d, J=5.0 Hz, 1H), 4.13-4.00 (m, 1H), 3.91 (d, J=11.0 Hz, 1H), 3.56 (d, J=12.0 Hz, 1H), 3.31 (d, J=11.5 Hz, 2H), 2.40-2.18 (m, 2H), 1.98-1.39 (m, 16H), 1.23 (s, 3H), 1.17-1.02 (m, 3H), 0.66 (s, 3H).

Compound 458

1-(2-((3R,4aR,6aS,7R,10bR)-3-cyclopentyl-6a,10b-dimethyl-8-dihydromethylene-1H-naphtho[2,1-d][1,3]dioxin-7-yl)ethyl)-1H-pyrazole-4-carboxylic acid

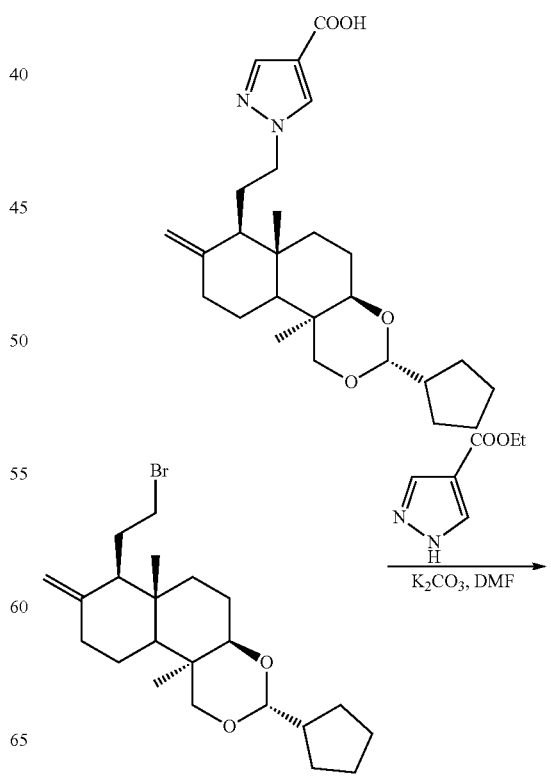

-continued

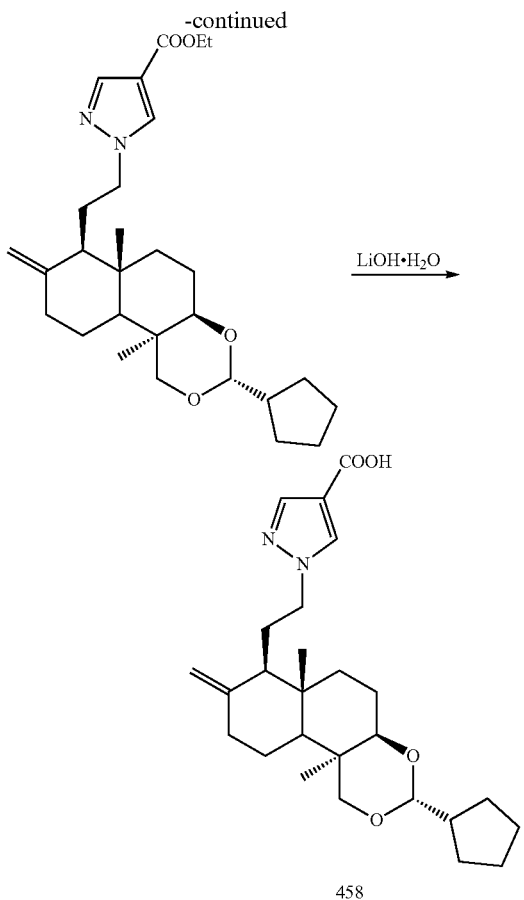

458

Step 1

Ethyl 1-(2-((3R,4aR,6aS,7R,10bR)-3-cyclopentyl-6a,10b-dimethyl-8-dihydromethylene-1H-naphtho[2,1-d][1,3]dioxin-7-yl)ethyl)-1H-pyrazole-4-carboxylate (3R,4aR,6aS,7R,10bR)-7-(2-bromoethyl)-3-cyclopentyl-6a,10b-dimeth yl-8-dihydromethylene-1H-naphtho[2,1-d][1,3]dioxin (500.00 mg, 1.22 mmol) was dissolved in N,N-dimethylformamide (10.00 mL), followed by successive addition of potassium carbonate (337.23 mg, 2.44 mmol) and ethyl 1H-pyrazole-4-carboxylate (222.26 mg, 1.59 mmol), then stirred at 80° C. for 4 hours. The reaction solution was filtered and concentrated, and the residue was separated by column chromatography (silica, petroleum ether/ethyl acetate=10/1 to 2/1) to give ethyl 1-(2-((3R,4aR,6aS,7R,10bR)-3-cyclopentyl-6a,10b-dimethyl-8-dihydromethylene-1H-naphtho[2,1-d][1,3]dioxin-7-yl)ethyl)-1H-pyrazole-4-carboxylate (a white solid, 300 mg, yield: 52.25%).

$^1$H NMR (400 MHz, CDCl3) 7.93 (s, 1H), 7.84 (s, 1H), 4.97 (s, 1H), 4.66 (s, 1H), 4.60 (d, J=6 Hz, 1H), 4.34-4.29 (m, 3H), 4.03-4.00 (m, 2H), 3.46-3.42 (m, 2H), 2.21 (s, 1H), 2.06-1.65 (m, 7H), 1.56-1.51 (m, 9H), 1.50-1.35 (m, 11H), 1.18-0.83 (m, 3H), 0.78 (s, 3H).

Step 2

1-(2-((3R,4aR,6aS,7R,10bR)-3-cyclopentyl-6a,10b-dimethyl-8-dihydromethylene-1H-naphtho[2,1-d][1,3]dioxin-7-yl)ethyl)-1H-pyrazole-4-carboxylic acid Ethyl 1-(2-((3R,4aR,6aS,7R,10bR)-3-cyclopentyl-6a,10b-dimethyl-8-dihydromethylene-1H-naphtho[2,1-d][1,3]dioxin-7-yl)ethyl)-1H-pyrazole-4-carboxylate (200.00 mg, 424.95 umol) was dissolved in tetrahydrofuran (9.00 mL), and lithium hydroxide monohydrate (89.15 mg, 2.12 mmol) and water (3.00 mL) were added, followed by stirring at 40° C. for 12 hours. The tetrahydrofuran was removed by rotary evaporation under reduced pressure, and the system was adjusted to pH=3 with a hydrochloric acid solution (1M) and then extracted with ethyl acetate (50 mL*3). The combined organic phases were washed with saturated brine, dried over anhydrous sodium sulfate, filtered and concentrated to give 1-(2-((3R,4aR,6aS,7R,10bR)-3-cyclopentyl-6a,10b-dimethyl-8-dihydromethylene-1H-naphtho[2,1-d][1,3]dioxin-7-yl)ethyl)-1H-pyrazole-4-carboxylic acid 458 (100 mg, yield: 52.11%).

MS m/z (ESI):443.2[M+1]

$^1$H NMR (400 MHz, CDCl3) 7.96 (s, 1H), 7.86 (s, 1H), 4.95 (s, 1H), 4.64 (s, 1H), 4.58 (d, J=5.6 Hz, 1H), 4.25 (s, 1H), 4.01-3.98 (m, 2H), 3.46-3.40 (m, 2H), 2.42 (s, 1H), 2.20-1.65 (m, 7H), 1.56-1.51 (m, 9H), 1.50-1.35 (m, 11H), 1.18-0.83 (m, 3H), 0.78 (s, 3H).

Compound 130

(1-(2-((3R,4aR,6aS,7R,10bR)-3-(3,4-difluorophenyl)-6a,10b-dimethyl-8-methylenedecahydro-1H-naphtho[2,1-d][1,3]dioxin-7-yl)ethyl)piperidin-4-yl)methanol

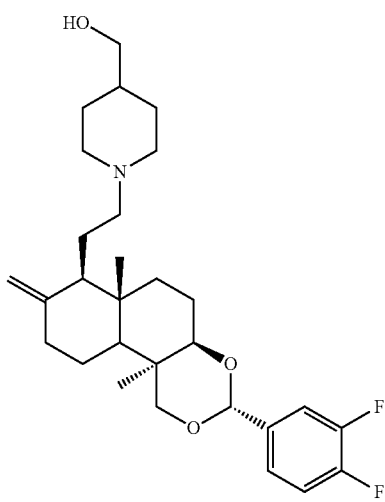

203

-continued

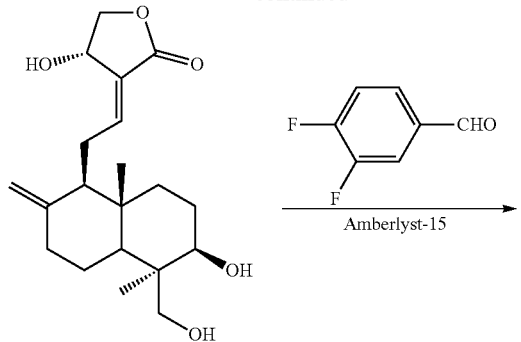

204

-continued

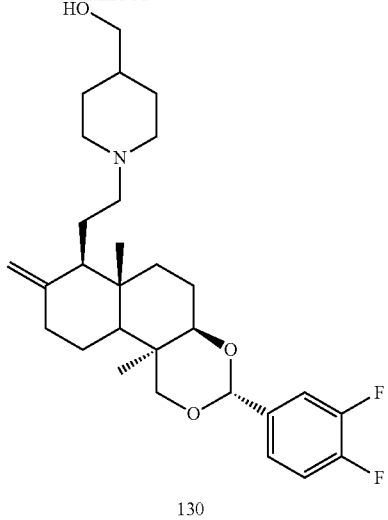

130

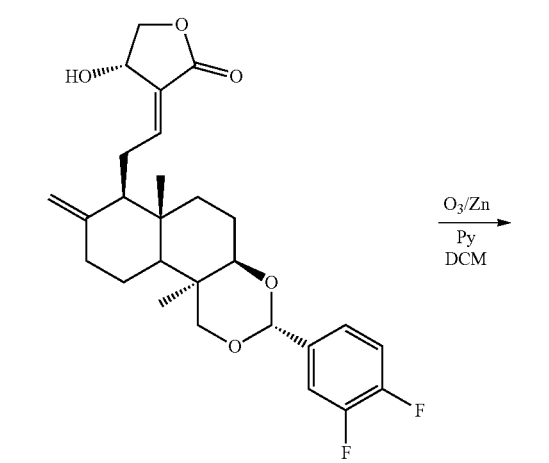

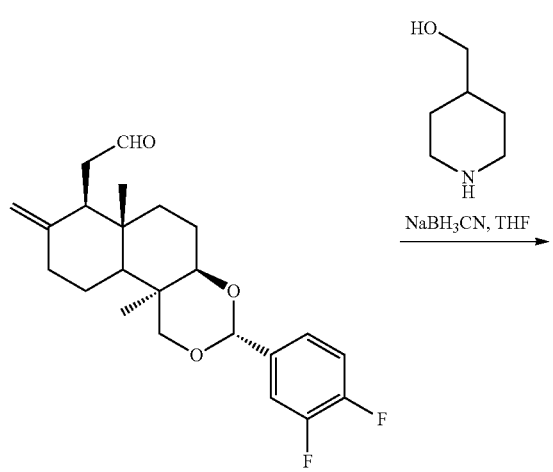

Step 1

(4S,E)-3-(2-((3R,4aR,6aS,7R,10bR)-3-(3,4-difluoro-phenyl)-6a,10b-dimethyl-8-methylenedecahydro-1H-naphtho[2,1-d][1,3]dioxin-7-yl)ethylene)-4-hydroxydihydrofuran-2(3H)-one (4S,E)-4-hydroxy-3-(2-((1R,5R,6R,8aS)-6-hydroxy-5-(hydroxymethyl)-5,8a-dimethyl-2-methylenedecahydronaphthalen-1-yl)ethylene)dihydrofuran-2(3H)-one (30 g, 85.7 mmol) was dissolved in dichloromethane (100 mL), and 3,4-difluoro benzaldehyde (12.5 g, 85.7 mol) and Macroporous resin-15 (30 g) were added successively. The mixture was stirred at room temperature until the reaction of the starting material was completed. The reaction solution was filtered, the filter cake was washed with dichloromethane, the filtrates were combined and concentrated under reduced pressure to give (4S,E)-3-(2-((3R,4aR,6aS,7R,10bR)-3-(3,4-difluorophenyl)-6a,10b-dimethyl-8-methylenedecahydro-1H-naphtho[2,1-d][1,3]dioxin-7-yl)ethylene)-4-hydroxydihydrofuran-2(3H)-one (28.3 g, crude product, yield: 69.7%).

Step 2

2-((3R,4aR,6aS,7R,10bR)-3-(3,4-difluorophenyl)-6a,10b-dimethyl-8-methylenedecahydro-1H-naphtho[2,1-d][1,3]dioxin-7-yl)acetaldehyde (4S,E)-3-(2-((3R,4aR,6aS,7R,10bR)-3-(3,4-difluorophenyl)-6a,10b-di methyl-8-methylenedecahydro-1H-naphtho[2,1-d][1,3]dioxin-7-yl)ethylene)-4-hydroxydihydrofuran-2(3H)-one (10 g, 21.1 mmol) was dissolved in dichloromethane (150 mL) and pyridine (5 mL), added with zinc dust (1.37 g, 21.1 mmol) at −78° C., and introduced with ozone at this temperature, followed by stirring for 5 minutes. The remaining ozone gas was discharged with nitrogen. After the temperature was gradually raised to room temperature, the zinc powder was removed by filtration. The filtrate was concentrated under reduced pressure and separated by column chromatography to give 2-((3R,4aR,6aS, 7R,10bR)-3-(3,4-difluorophenyl)-6a,10b-dimethyl-8-methylenedecahydro-1H-naphtho[2,1-d][1,3]dioxin-7-yl) acetaldehyde (1.2 g, yield: 14.5%).

Step 3

(1-(2-((3R,4aR,6aS,7R,10bR)-3-(3,4-difluorophenyl)-6a,10b-dimethyl-8-methylenedecahydro-1H-naphtho[2,1-d][1,3]dioxin-7-yl)ethyl)piperidin-4-yl)methanol 2-((3R,4aR,6aS,7R,10bR)-3-(3,4-difluorophenyl)-6a,10b-dimethyl-8-methylenedecahydro-1H-naphtho[2,1-d][1,3]dioxin-7-yl)acetaldehyde (200 mg, 0.51 mmol) was dissolved in tetrahydrofuran (10 mL), added with piperidine-4-methanol (88 mg, 0.77 mmol) and stirred at room temperature for 10 hours. Sodium cyanoborohydride (63 mg, 1.02 mmol) was added to the reaction mixture and stirred at room temperature for 2 hours. The solvent was distilled off under reduced pressure and the residue was dissolved in ethyl acetate. The organic layer was washed with saturated brine and water, dried over anhydrous sodium sulfate, filtered, and the filtrate was concentrated under reduced pressure and then separated by liquid chromatography to give (1-(2-((3R,4aR,6aS,7R,10bR)-3-(3,4-difluorophenyl)-6a,10b-dimethyl-8-methylenedecahydro-1H-naphtho[2,1-d][1,3]dioxin-7-yl)ethyl)piperidin-4-yl)methanol 130 (82 mg, yield: 32.8%).

MS m/z (ESI): 490.3 [M+1]

$^1$H NMR (400 MHz, CDCl$_3$) 7.25-7.09 (m, 3H), 5.70 (s, 1H), 4.85 (s, 1H), 4.61 (s, 1H), 4.23 (d, J=11.2 Hz, 1H), 3.67-3.49 (m, 4H), 2.99-2.94 (m, 2H), 2.47-1.60 (m, 19H), 1.43 (s, 3H), 1.31-1.18 (m, 5H), 0.80 (s, 3H).

Compound 214

1-(2-((3R,4aR,6aS,7R,10bR)-3-(3,4-difluorophenyl)-6a,10b-dimethyl-8-methylenedecahydro-1H-naphtho[2,1-d][1,3]dioxin-7-yl)ethyl)pyrrolidine-2,5-dione

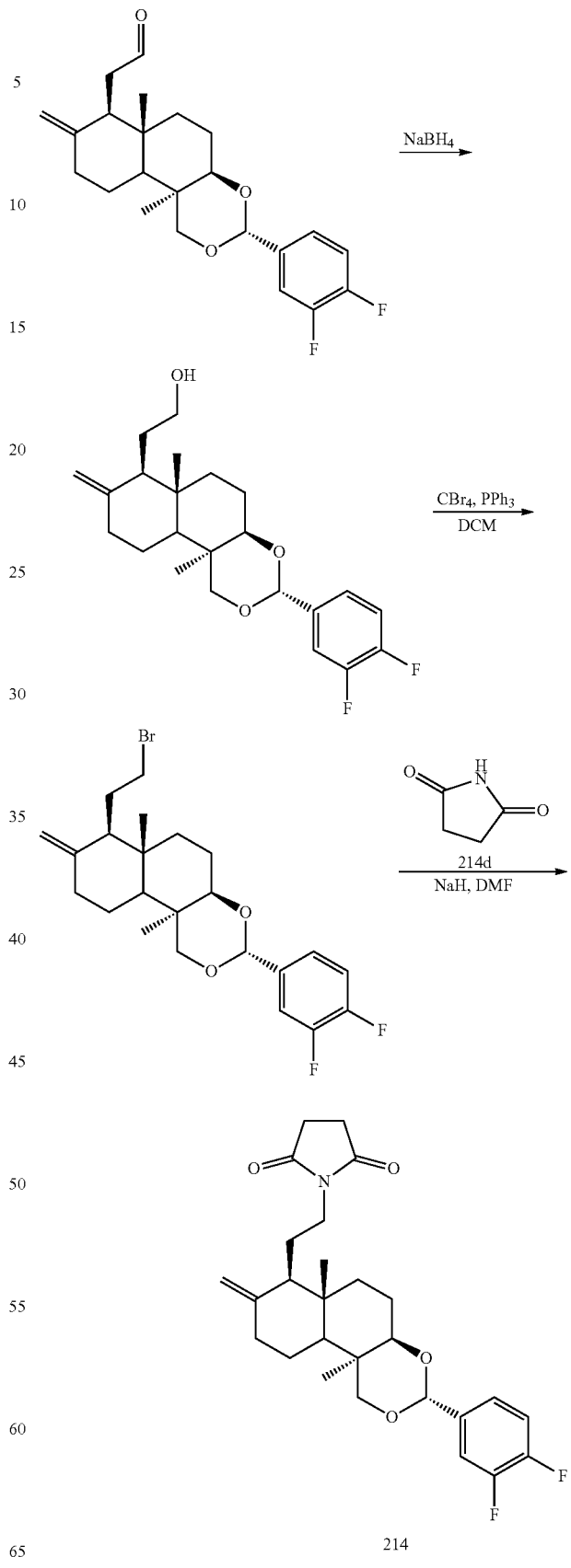

Step 1

2-((3R,4aR,6aS,7R,10bR)-3-(3,4-difluorophenyl)-6a, 10b-dimethyl-8-methylenedecahydro-1H-naphtho[2, 1-d][1,3]dioxin-7-yl)ethanol 2-((3R,4aR,6aS,7R,10bR)-3-(3,4-difluorophenyl)-6a, 10b-dimethyl-8-methylenedecahydro-1H-naphtho[2,1-d][1, 3]dioxin-7-yl)acetaldehyde (10.0 g, 25.6 mmol) was dissolved in 150 mL tetrahydrofuran, and added with sodium borohydride (2.91 g, 76.8 mmol) at 0° C. The reaction was stirred at 25° C. for 3 hours, quenched with 100 mL water, and the mixture solution was extracted with ethyl acetate (50 mL*3). The organic phases were combined, washed with saturated sodium chloride solution (30 mL*1), dried over anhydrous sodium sulfate and filtered, and the filtrate was concentrated under reduced pressure to give 2-((3R,4aR, 6aS,7R,10bR)-3-(3,4-difluorophenyl)-6a,10b-dimethyl-8-methylenedecahydro-1H-naphtho[2,1-d][1,3]dioxin-7-yl) ethanol (7 g, crude product).

Step 2

(3R,4aR,6aS,7R,10bR)-7-(2-bromoethyl)-3-(3,4-difluorophenyl)-6a, 10 b-dimethyl-8-methylenedecahydrogen-1H-naphtho[2,1-d][1,3]dioxin 2-((3R,4aR,6aS,7R,10bR)-3-(3,4-difluorophenyl)-6a, 10b-dimethyl-8-methylenedecahydro-1H-naphtho[2,1-d][1, 3]dioxin-7-yl)ethanol (1.0 g, 2.5 mmol) and carbon tetrabromide (1.7 g, 5.1 mmol) were dissolved in dichloromethane (15 mL), added with triphenylphosphine (1.3 g, 5.1 mmol) at 0° C. and stirred at room temperature for 18 hours. The reaction solution was added with water (30 mL) and extracted with dichloromethane (80 mL). The organic layer was washed with saturated brine and water, dried over anhydrous sodium sulfate, filtered, and the filtrate was concentrated under reduced pressure and separated by column chromatography to give (3R,4aR,6aS,7R,10bR)-7-(2-bromoethyl)-3-(3,4-difluorophenyl)-6a,10b-dimethyl-8-methylenedecahydrogen-1H-naphtho[2,1-d][1,3]dioxin (1.02 g, yield: 87.9%).

$^1$H NMR (400 MHz, CDCl$_3$) 7.35-7.20 (m, 1H), 7.20-7.13 (m, 2H), 5.72 (s, 1H), 4.90 (s, 1H), 4.54 (s, 1H), 4.24 (d, J=11.6 Hz, 1H), 3.67-3.55 (m, 3H), 3.31-3.29 (m, 1H), 2.43-1.82 (m, 9H), 1.45 (s, 3H), 1.32-1.27 (m, 3H), 0.82 (s, 3H).

Step 3

1-(2-((3R,4aR,6aS,7R,10bR)-3-(3,4-difluorophenyl)-6a,10b-dimethyl-8-methylenedecahydro-1H-naphtho [2, 1-d][1,3]dioxin-7-yl)ethyl)pyrrolidine-2,5-dione Sodium hydrogen (22 mg, 0.55 mmol) was dissolved in N,N-dimethylformamide (10 mL), and pyrrolidine-2,5-dione (36 mg, 0.37 mmol) was added at 0° C. and stirred at 0° C. for 10 minutes. (3R,4aR,6aS,7R,10bR)-7-(2-bromoethyl)-3-(3,4-difluorophenyl)-6a,10b-dimethyl-8-methylenedecahydro-1H-naphtho[2,1-d][1,3]dioxin (200 mg, 0.44 mmol) was added to the reaction mixture and stirred at room temperature for 18 hours. The reaction solution was quenched with water (10 mL) and extracted with ethyl acetate (30 mL). The organic layer was washed with saturated brine and water, dried over anhydrous sodium sulfate, filtered, and the filtrate was concentrated under reduced pressure and separated on a thin layer chromatography plate to give 1-(2-((3R,4aR,6aS,7R,10bR)-3-(3,4-difluorophenyl)-6a,10b-dimethyl-8-methylenedecahydro-1H-naphtho [2,1-d][1,3]dioxin-7-yl)ethyl)pyrrolidine-2,5-dione 214 (92 mg, yield: 53.1%).

$^1$H NMR (400 MHz, CDCl$_3$) 7.38-7.33 (m, 1H), 7.21-7.12 (m, 2H), 5.72 (s, 1H), 4.97 (s, 1H), 4.86 (s, 1H), 4.25 (d, J=11.6 Hz, 1H), 3.76-3.41 (m, 4H), 2.72 (s, 4H), 2.45-1.83 (m, 6H), 1.83 (s, 3H), 1.75 (s, 3H), 1.69-1.25 (m, 3H), 0.80 (s, 3H).

Compound 212

3-(2-((3R,4aR,6aS,7R,10bR)-3-(3,4-difluorophenyl)-6a,10b-dimethyl-8-decahydromethylene-1H-naphtho [2,1-d][1,3]dioxin-7-yl)ethyl)-1-methyltetrahydroimidazol-2-one

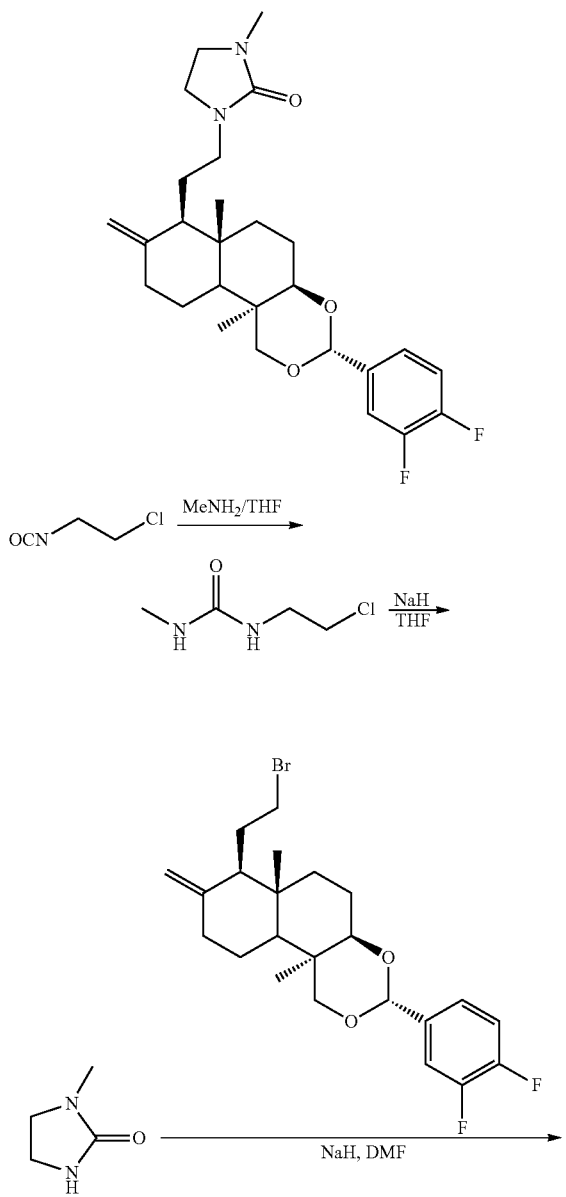

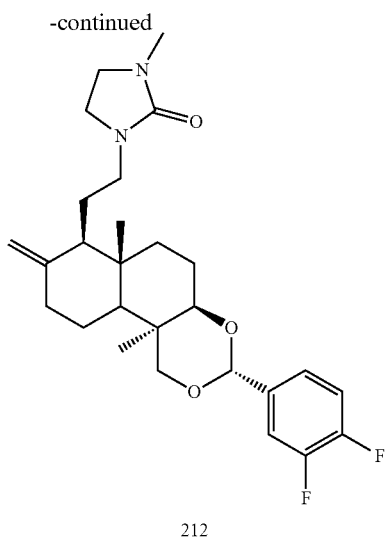

212

Step 1

1-(2-Chloroethyl)-3-methylurea

1-Chloro-2-isocyanatoethane (5.0 g, 47.4 mmol) was dissolved in dry tetrahydrofuran (200 mL), and slowly added with 2M methylamine tetrahydrofuran solution (23.7 mL) at 0° C., and stirred for 3 hours at room temperature. The reaction solution was concentrated under reduced pressure to give 1-(2-chloroethyl)-3-methylurea (6.2 g, yield: 95.8%).

$^1$H NMR (400 MHz, DMSO) 6.17 (brs, 1H), 5.91 (brs, 1H), 3.55 (t, J=6.0 Hz, 2H), 3.31 (s, 1H), 3.28 (t, J=6.0 Hz, 1H), 2.53 (d, J=4.8 Hz, 3H).

Step 2

1-methyltetrahydroimidazol-2-one 1-(2-Chloroethyl)-3-methylurea (2.0 g, 14.64 mmol) was dissolved in dry tetrahydrofuran (100 mL) and sodium hydrogen (1.4 g, 35.14 mmol) was added in portions at 0° C. Upon the completion of addition, the reaction was stirred at room temperature overnight. The reaction solution was quenched with water (1 mL), concentrated under reduced pressure and passed through column chromatography to give 1-methyltetrahydroimidazol-2-one (1.3 g, yield: 89%).

$^1$H NMR (400 MHz, CDCl$_3$) 4.83 (brs, 1H), 3.42 (t, J=2.4 Hz, 4H), 2.78 (s, 3H).

Step 3

3-(2-((3R,4aR,6aS,7R,10bR)-3-(3,4-difluorophenyl)-6a,10b-dimethyl-8-decahydromethylene-1H-naphtho[2,1-d][1,3]dioxin-7-yl)ethyl)-1-methyltetrahydroimidazol-2-one 1-methyltetrahydroimidazol-2-one (26 mg, 0.26 mmol) was dissolved in N,N-dimethylformamide (1 mL) and sodium hydrogen (13 mg, 0.33 mmol) was slowly added at 0° C., and stirred at 0° C. for 0.5 hours, then stirred at room temperature for 0.5 hours. (3R,4aR,6aS,7R,10bR)-7-(2-bromoethyl)-3-(3,4-difluorophenyl)-6a,10b-dimethyl-8-decahydromethylene-1H-naphtho[2,1-d][1,3]dioxin (100 mg, 0.22 mmol) was added to the reaction mixture at 0° C. and stirred at 20° C. for 20 hours. The reaction solution was extracted with ethyl acetate (50 mL×3), and the organic layer was washed with saturated brine and water, dried over anhydrous sodium sulfate, filtered, and the filtrate was concentrated under reduced pressure and separated on a thin layer chromatography plate to give 3-(2-((3R,4aR,6aS,7R,10bR)-3-(3,4-difluorophenyl)-6a,10b-dimethyl-8-decahydromethylene-1H-naphtho[2,1-d][1,3]dioxin-7-yl)ethyl)-1-methyltetrahydroimidazol-2-one 212 (19 mg, yield: 18.3%).

MS m/z (ESI): 475.2 [M+1]

$^1$H NMR (400 MHz, CDCl$_3$) 7.37-7.32 (m, 1H), 7.20-7.13 (m, 2H), 5.72 (s, 1H), 4.91 (s, 1H), 4.68 (s, 1H), 4.24 (d, J=11.6 Hz, 1H), 3.65-3.12 (m, 8H), 2.79 (s, 3H), 2.42-1.76 (m, 6H), 1.66 (s, 2H), 1.44 (s, 3H), 1.29-1.23 (m, 3H), 0.81 (s, 3H).

Compound 215

3-(2-((3R,4aR,6aS,7R,10bR)-3-(3,4-difluorophenyl)-6a,10b-dimethyl-8-methylenedecahydro-1H-naphtho[2,1-d][1,3]dioxin-7-yl)ethyl)oxazolidine-2,4-dione

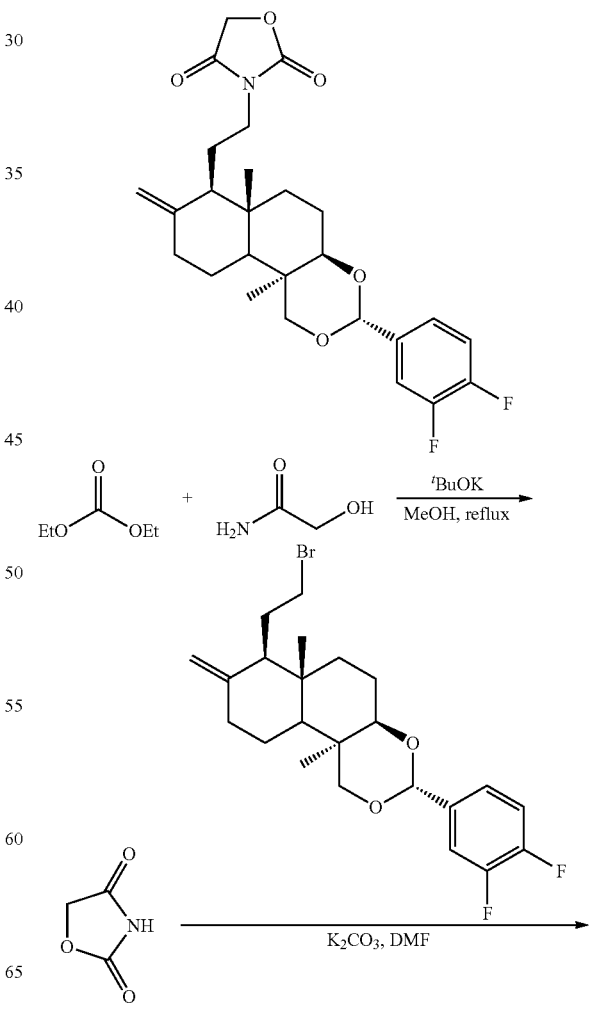

211

-continued

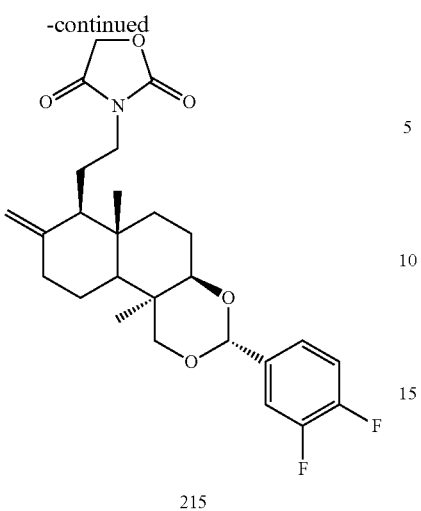

215

Step 1

Oxazolidine-2,4-dione

2-Hydroxyacetamide (2.0 g, 26.6 mmol) and potassium tert-butoxide (3.0 g, 26.6 mmol) were dissolved in dry methanol (50 mL), added with diethyl carbonate (3.8 g, 31.9 mmol) and stirred at reflux for 20 hours. The reaction solution was cooled, concentrated under reduced pressure, dissolved in water and acidified to pH=2 with 6M hydrochloric acid solution. The mixture was extracted with ethyl acetate (100 mL×3), and the organic layer was washed with saturated brine and water, dried over anhydrous sodium sulfate, filtered, and the filtrate was concentrated under reduced pressure to give oxazolidine-2,4-dione (1.2 g, crude product).

$^1$H NMR (400 MHz, DMSO) 4.75 (s, 2H), 3.91 (s, 1H).

Step 2

3-(2-((3R,4aR,6aS,7R,10bR)-3-(3,4-difluorophenyl)-6a,10b-dimethyl-8-methylenedecahydro-1H-naphtho[2,1-d][1,3]dioxin-7-yl)ethyl)oxazolidine-2,4-dione (4aR,6aS,7R,10bR)-7-(2-bromoethyl)-3-(3,4-difluorophenyl)-6a,10b-dimethyl-8-methylenedecahydro-1H-naphtho[2,1-d][1,3]dioxin (150 mg, 0.33 mmol) and potassium carbonate (91 mg, 0.66 mmol) were dissolved in N,N-dimethylformamide (2 mL), added with oxazolidine-2,4-dione (67 mg, 0.66 mmol) and stirred at 80° C. for 1.5 hours. The reaction solution was quenched with water and extracted with dichloromethane (50 mL×3). The organic layer was washed with saturated brine and water, dried over anhydrous sodium sulfate, filtered, and the filtrate was concentrated under reduced pressure and separated on a thin layer chromatography plate to give 3-(2-((3R,4aR,6aS,7R,10bR)-3-(3,4-difluorophenyl)-6a,10b-dimethyl-8-methylenedecahydro-1H-naphtho[2,1-d][1,3]dioxin-7-yl)ethyl)oxazolidine-2,4-dione 215 (70 mg, yield: 44.7%).

$^1$H NMR (400 MHz, CDCl$_3$) 7.36-7.31 (m, 1H), 7.19-7.12 (m, 2H), 5.70 (s, 1H), 4.96 (s, 1H), 4.78 (s, 1H), 4.68 (s, 1H), 4.22 (d, J=11.6 Hz, 1H), 3.68-3.45 (m, 4H), 2.48-1.78 (m, 6H), 1.69 (s, 3H), 1.28-1.25 (m, 3H), 0.79 (s, 3H).

212

Compound 230

3-(2-((3R,4aR,6aS,7R,10bR)-3-(3,4-difluorophenyl)-6a,10b-dimethyl-8-methylenedecahydro-1H-naphtho[2,1-d][1,3]dioxin-7-yl)ethyl)tetrahydroimidazole-2,4-dione

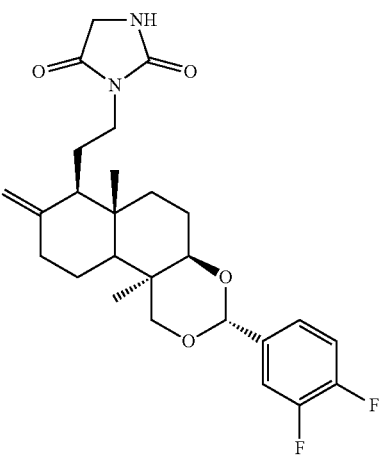

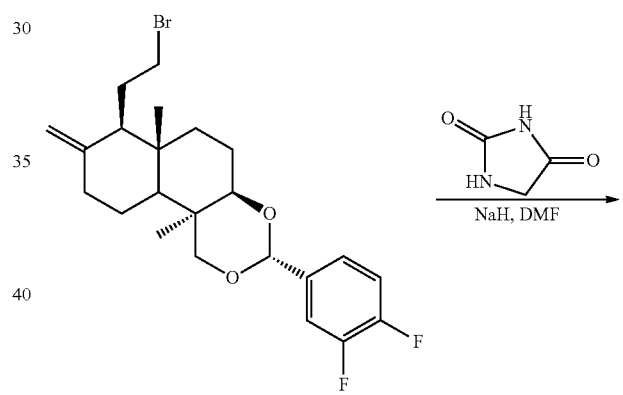

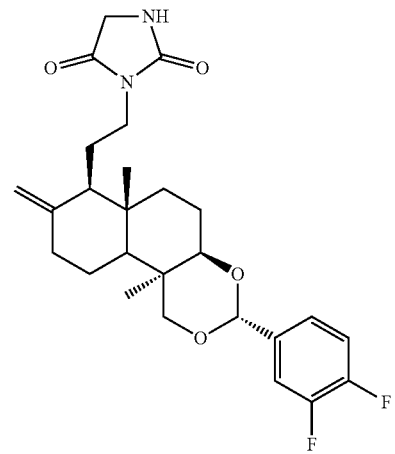

230

Step 1

3-(2-((3R,4aR,6aS,7R,10bR)-3-(3,4-difluorophenyl)-6a,10b-dimethyl-8-methylenedecahydro-1H-naphtho[2,1-d][1,3]dioxin-7-yl)ethyl)tetrahydroimidazole-2,4-dione NaH (16 mg, 0.4 mmol) was dissolved in N,N-dimethylformamide (10 mL) and tetrahydroimidazole-2,4-dione (66 mg, 0.66 mmol) was added at 0° C., and stirred at 0° C. for 15 minutes. (3R,4aR,6aS,7R,10bR)-7-(2-bromoethyl)-3-(3,4-difluorophenyl)-6a,10b-dimethyl-8-methylenedecahydro-1H-naphtho[2,1-d][1,3]dioxin (150 mg, 0.33 mmol) was added to the reaction mixture and stirred at 25° C. for 16 hours. The reaction solution was added to water (10 mL) and extracted with ethyl acetate (30 mL). The organic layer was dried over anhydrous sodium sulfate, filtered, and the filtrate was concentrated under reduced pressure and then separated by column chromatography to give 3-(2-((3R,4aR,6aS,7R,10bR)-3-(3,4-difluorophenyl)-6a,10b-dimethyl-8-methylenedecahydro-1H-naphtho[2,1-d][1,3]dioxin-7-yl)ethyl)tetrahydroimidazole-2,4-dione 230 (70 mg, yield: 44.8%).

$^1$H NMR (400 MHz, CDCl$_3$) 7.37-7.22 (m, 3H), 5.81 (s, 1H), 4.83 (s, 1H), 4.31 (d, J=11.6 Hz, 1H), 3.94 (d, J=8.4 Hz, 4H), 3.68-3.39 (m, 4H), 2.47-1.71 (m, 8H), 1.42 (s, 3H), 1.34-1.32 (m, 4H), 0.82 (s, 3H).

Compound 265

(1R,2R,4aS,5R)-1-(hydroxymethyl)-5-(2-(4-(hydroxymethyl)piperidin-1-yl)ethyl-1,4a-dimethyl-6-methylene-decahydro-naphthalenemethanol-2-ol

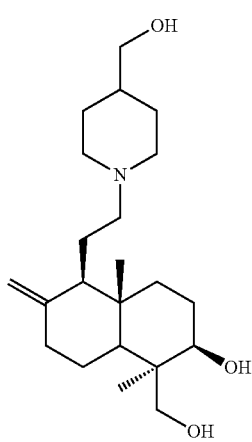

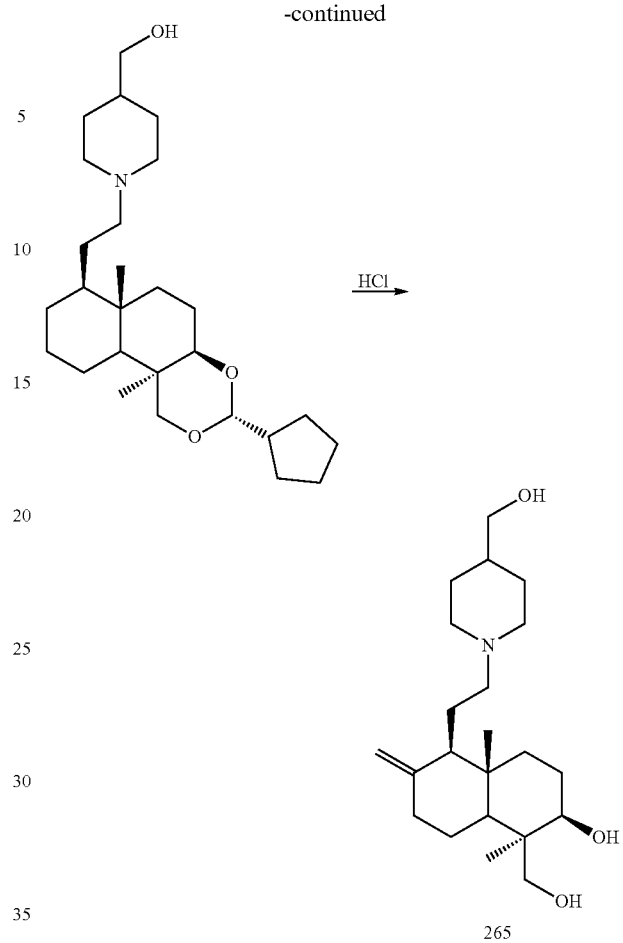

Step 1

(1R,2R,4aS,5R)-1-(hydroxymethyl)-5-(2-(4-(hydroxymethyl)piperidin-1-yl)ethyl-1,4a-dimethyl-6-methylene-decahydro-naphthalenemethanol-2-ol (1-(2-((3R,4aR,6aS,7R,10bR)-3-cyclopentyl-6a,10b-dimethyl-8-methylene-decahydro-1H-naphtho[2,1-d][1,3]dioxin-7-yl)ethyl)piperidin-4-yl)methanol (300.00 mg, 673.13 umol) was dissolved in hydrochloric acid (2.5 mL, 3M), then stirred at 70° C. under nitrogen atmosphere for 12 hours. The system was adjusted to pH=8 with sodium hydroxide solution (4M) and then separated by preparative liquid chromatography to give (1R,2R,4aS,5R)-1-(hydroxymethyl)-5-(2-(4-(hydroxymethyl)piperidin-1-yl)ethyl)-1,4a-dimethyl-6-methylene-decahydro-naphthalenemethanol-2-ol 265 (50.5 mg, yield: 20.52%).

MS m/z (ESI):366.1[M+1]

$^1$H NMR (400 MHz, CDCl3) 4.24 (d, J=11.3 Hz, 1H), 3.59-3.42 (m, 4H), 3.34 (d, J=11.3 Hz, 1H), 3.06 (br. s., 2H), 2.37 (br. s., 1H), 2.19-1.58 (m, 15H), 1.58-1.17 (m, 9H), 0.92 (s, 3H).

Test of IL-6 Release from THP-1 Cells

Experimental Purpose

The inhibitory effect of the compound on LPS-induced IL-6 release level from THP-1 cells was evaluated by measuring the level of IL-6 in the cell culture supernatant.

Experimental Materials:
Cell line: THP-1 cell line
THP-1 cell culture medium (RPMI 1640, Gibco #22400-089, 10% serum Gibco #10099-141)
LPS, 1 mg/ml (Sigma # L5293)
DPBS (Hyclone, # SH30028.01B)
Human IL-6 CBA kit, BD #558276
CBA Human Soluble Protein Master Buffer Kit, BD #558265
Dexamethasone: J&K #308890
96-well Cell Plate, Corning #
$CO_2$ incubator, Thermo #371
Centrifuge, Eppendorf #5810R
Vi-cell Cell Counter, Beckman Coulter
FACSCalibur, BD #97500540

Experimental procedures and methods:

a) Cell inoculation
1) The medium was preheated in a 37° C. water bath.
2) The suspension cells in the culture flask were blown well, transferred to a centrifuge tube and centrifuged at room temperature at 1200 rpm for 5 minutes, the supernatant was discarded, and resuspended to 10 mL by adding with culture medium;
3) 1 mL of cell resuspension was drawn and counted with Vi-cell.
4) THP-1 cells were diluted with culture medium to $5 \times 10^5$/mL and the cells were added to a 96-well plate (100 ul/well, $5 \times 10^5$ cells/well);

b) Compound adding:
1) The compound was dissolved in DMSO to 30 mM and diluted 3 times with DMSO to 4 gradients, i.e. 30 mM, 10 mM, 3 mM, 1 mM, respectively. 4 ul was taken from each above solution and added to 1ml of culture solution to make 120 uM, 40 uM, 12 uM, 4 uM. 50 ul per well was taken and added to wells with cells to give final concentrations of 30 uM, 10 uM, 3 uM, and 1 uM, respectively. Dexamethasone was added as a positive drug into an individual cell well with a final concentration of 100 nM.

c) Cell stimulation
The LPS 1 mg/ml solution was diluted to 800 ng/ml with the culture solution and added to the cell culture wells at 50 ul/well.

d) Cell incubation and detection
The cell culture plate was placed in a 37° C. incubator, and the supernatant was collected after culturing for 24 hours. The level of IL-6 in the supernatant was detected by CBA.

The experimental results are shown in Table 1:

TABLE 1

Test results of inflammatory factor IL-6 detected by CBA-inhibition rate @ 10 uM

| Test sample (Title compound) | Inhibition rate @ 10 uM |
|---|---|
| Compound 297 | A |
| Compound 420 | C |
| Compound 321 | C |
| Compound 319 | B |
| Compound 430 | B |
| Compound 357 | A |
| Compound 339 | C |
| Compound 344 | A |
| Compound 310 | A |
| Compound 443 | B |
| Compound 442 | B |

TABLE 1-continued

Test results of inflammatory factor IL-6 detected by CBA-inhibition rate @ 10 uM

| Test sample (Title compound) | Inhibition rate @ 10 uM |
|---|---|
| Compound 317 | A |
| Compound 351 | A |
| Compound 289 | A |
| Compound 422 | B |
| Compound 423 | B |
| Compound 407 | A |
| Compound 409 | C |
| Compound 441 | B |
| Compound 448 | C |
| Compound 447 | C |
| Compound 397 | A |
| Compound 410 | B |
| Compound 415 | A |
| Compound 406 | C |
| Compound 436 | C |
| Compound 431 | A |
| Compound 432 | A |
| Compound 428 | B |
| Compound 417 | C |
| Compound 349 | A |
| Compound 312 | C |
| Compound 453 | A |
| Compound 445 | C |
| Compound 452 | B |
| Compound 454 | B |
| Compound 385 | A |
| Compound 402 | A |
| Compound 416 | A |
| Compound 400 | A |
| Compound 411 | A |
| Compound 412 | A |
| Compound 429 | C |
| Compound 446 | C |
| Compound 405 | C |
| Compound 408 | C |
| Compound 399 | A |
| Compound 281 | B |
| Compound 313 | B |
| Compound 366 | A |
| Compound 482 | A |
| Compound 483 | B |
| Compound 426 | B |
| Compound 463 | A |
| Compound 484 | A |
| Compound 373 | B |
| Compound 386 | C |
| Compound 403 | C |
| Compound 404 | C |
| Compound 284 | B |
| Compound 191 | C |
| Compound 207 | B |
| Compound 345 | B |
| Compound 355 | C |
| Compound 196 | B |
| Compound 149 | B |
| Compound 163 | A |
| Compound 435 | C |
| Compound 450 | A |
| Compound 116 | B |
| Compound 455 | A |
| Compound 147 | C |
| Compound 181 | C |
| Compound 361 | B |
| Compound 123 | C |
| Compound 433 | A |
| Compound 160 | A |
| Compound 150 | B |
| Compound 451 | B |
| Compound 002 | C |
| Compound 256 | C |
| Compound 456 | A |
| Compound 457 | A |
| Compound 458 | B |
| Compound 130 | C |

TABLE 1-continued

Test results of inflammatory factor IL-6 detected by CBA-
inhibition rate @ 10 uM

| Test sample (Title compound) | Inhibition rate @ 10 uM |
| --- | --- |
| Compound 214 | A |
| Compound 212 | A |
| Compound 215 | C |
| Compound 230 | A |
| Compound 265 | C |

Note:
A > 60%;
30% < B ≤ 60%;
C ≤ 30%;

Conclusion: the compounds of the disclosure have a significant inhibitory effect on the inflammatory factor IL-6.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are to be regarded as a departure from the disclosure, and all such modifications are intended to be included within the scope of the disclosure.

What is claimed is:

1. A compound represented by formula (I), pharmaceutically acceptable salt or tautomer thereof,

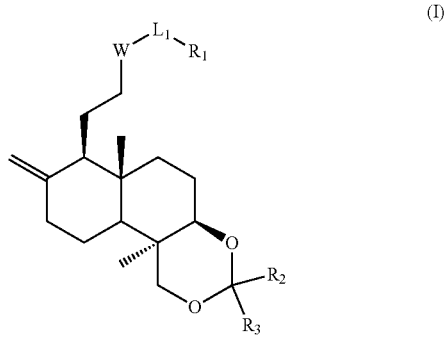
(I)

wherein,
W is O, N($R_5$) or a ring

$R_5$ is H, or a $C_{1-3}$ alkyl optionally substituted by 1, 2 or 3 halogen, OH, $NH_2$, COOH, NHMe or $N(Me)_2$;
$L_1$ is selected from a single bond and —$(CRR)_{1-3}$—;
$R_1$ is piperidinyl, which is optionally substituted with 1, 2, or 3 R or R';
$R_2$, $R_3$ are each independently selected from H, or are each independently selected from the group consisting of a $C_{1-6}$ alkyl, a $C_{1-6}$ heteroalkyl, and a $C_{3-6}$ cycloalkyl, which are optionally substituted with 1, 2, or 3 R or R';

the ring A is

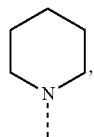

which is optionally substituted with 1, 2 or 3 R';
R is independently selected from F, Cl, Br, I, OH, $NH_2$, CN, C(=O)OH, or from the group consisting of a $C_{1-6}$ alkyl, a $C_{1-6}$ heteroalkyl, and a -L-$C_{3-6}$ cycloalkyl, which is optionally substituted with 1, 2 or 3 R';
L is a single bond, —O—, —S—, —C(=O)NH—, —NH—, —C(=O)O—, —C(=O)—, —C(=S)—, —S(=O)—, —S(=O)$_2$;
R' is independently selected from halogen, CN, OH, N(CH$_3$)$_2$, NH(CH$_3$), NH$_2$, CHO, C(=O)OH, C(=O)NH$_2$, S(=O)NH$_2$, S(=O)$_2$NH$_2$, trihalomethyl, dihalomethyl, monohalomethyl, aminomethyl, hydroxymethyl, methyl, methoxy, formyl, methoxycarbonyl, Boc, methylsulfonyl, methylsulfinyl, ethyl, n-propyl, isopropyl, and $C_{3-6}$ membered cycloalkyl;
"hetero" refers to a heteroatom or a heteroatomic group selected from the group consisting of —C(=O)N(R)—, —N(R)—, —C(=NR)—, —S(=O)$_2$N(R)—, —S(=O)N(R)—, —O—, —S—, =O, =S, —C(=O)O—, —C(=O)—, —C(=S)—, —S(=O)—, —S(=O)$_2$— and —N(R)C(=O)N(R)—;
in any of the above cases, the number of heteroatom or heteroatom group is independently selected from 1, 2 or 3.

2. The compound, pharmaceutically acceptable salt or tautomer thereof according to claim 1, wherein R' is each independently selected from the group consisting of F, Cl, Br, I, OH, NH$_2$, CN, Me, CF$_3$q, Et, N(CH$_3$)$_2$, C(=O)OH, and Boc.

3. The compound, pharmaceutically acceptable salt or tautomer thereof according to claim 1, wherein R is selected from the group consisting of F, Cl, Br, I, OH, NH$_2$, CN and C(=O)OH, or is selected from the group consisting of Me, Et, OMe, OEt,

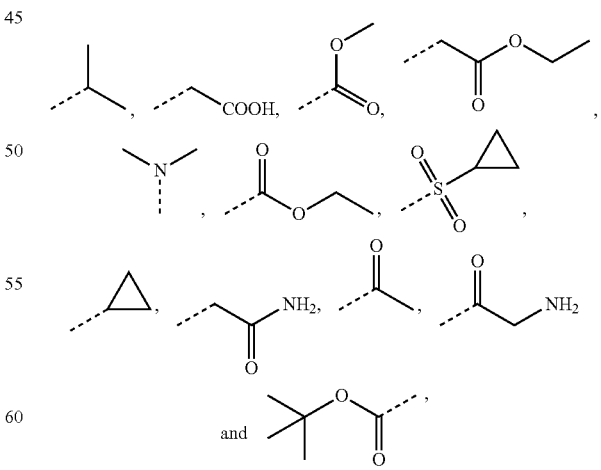

which is optionally substituted with 1, 2 or 3 R'.

4. The compound, pharmaceutically acceptable salt or tautomer thereof according to claim 1, wherein $R_5$ is selected from H,

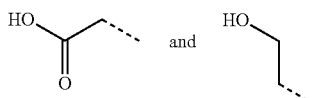

5. The compound, pharmaceutically acceptable salt or tautomer thereof according to claim 1, wherein $L_1$ is selected from a single bond and a methylene.

6. The compound, pharmaceutically acceptable salt or tautomer thereof according to claim 1, wherein $R_1$ is

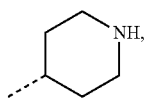

which is optionally substituted with 1, 2 or 3 R.

7. The compound, pharmaceutically acceptable salt or tautomer thereof according to claim 1, wherein $R_2$ and $R_3$ are independently selected from H, or independently selected from the group consisting of Me, Et, n-propyl,

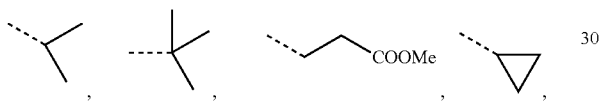

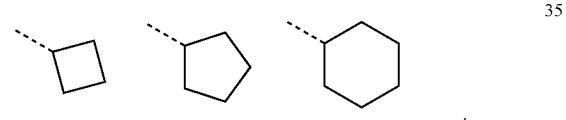

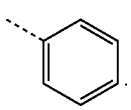

.

8. The compound, pharmaceutically acceptable salt or tautomer thereof according to claim 1, which is selected from the group consisting of

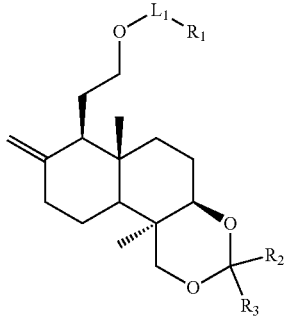
(I-1)

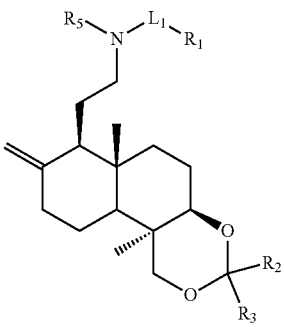
(I-2)

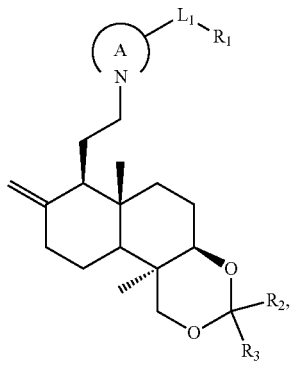
(I-3)

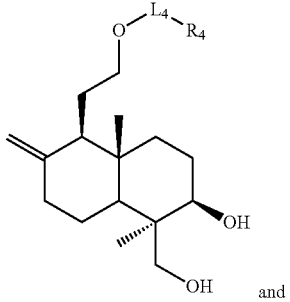
(II-1)
and

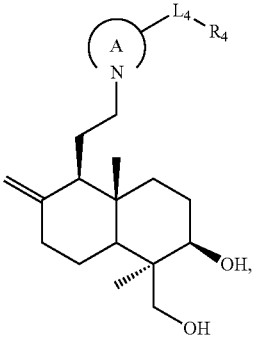
(II-2)

wherein $L_1$, $R_1$, $R_2$, $R_3$, $R_5$, and the ring A are as defined in claim 1.

9. The compound, pharmaceutically acceptable salt or tautomer thereof according to claim 1, which is selected from the group consisting of

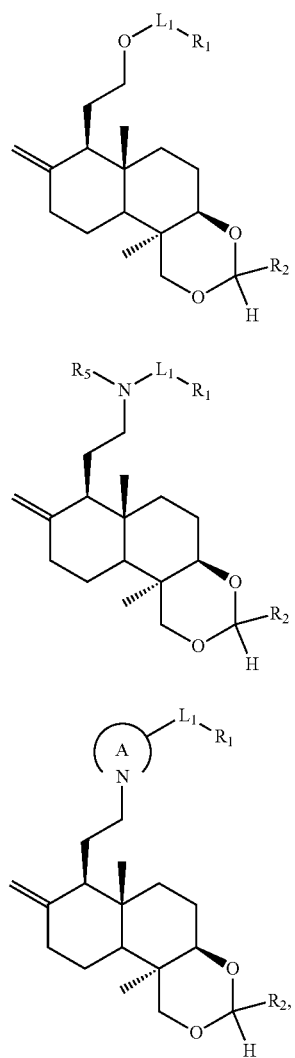
(I-4)
(I-5)
(I-6)
wherein L₁, R₁, R₂, R₅ and the ring A are as defined in claim 1.
10. The compound according to claim 1, which is selected from the group consisting of
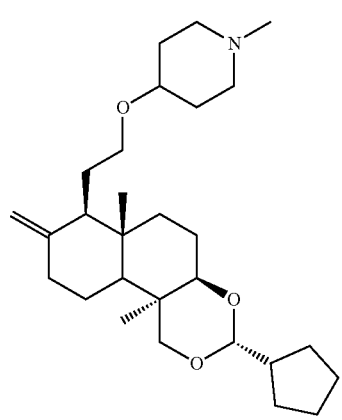
366
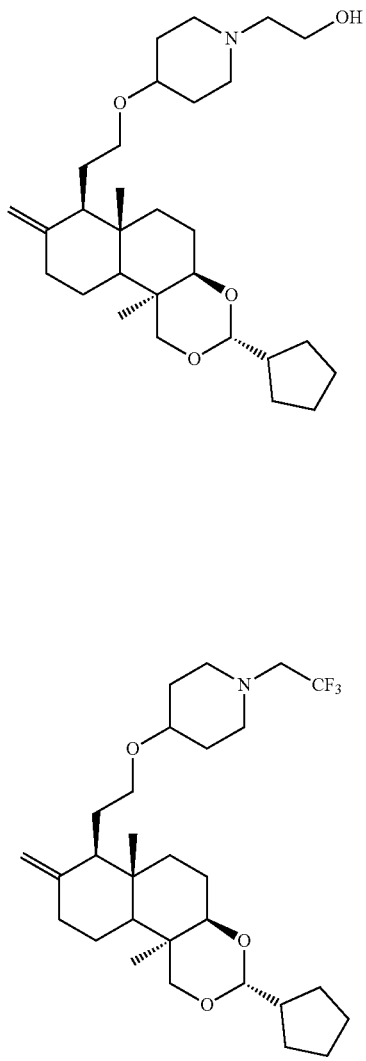
-continued
482
483
426

223
-continued
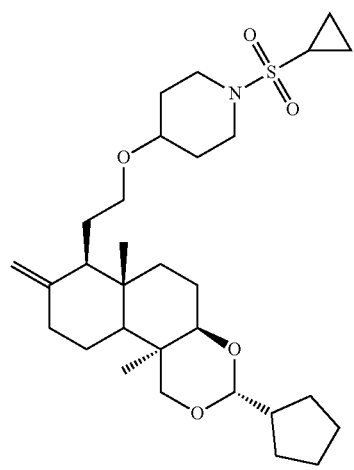
484
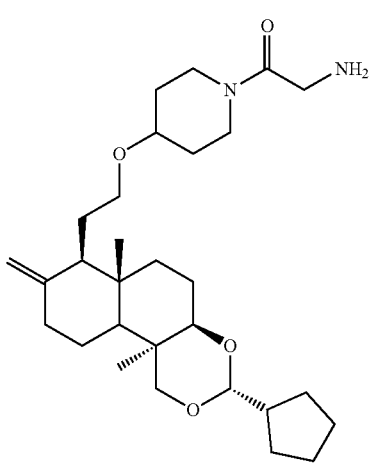
373
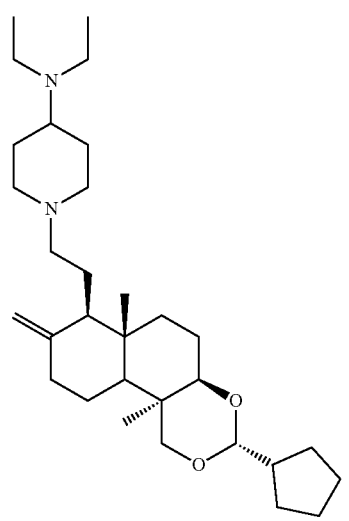
150
224
-continued
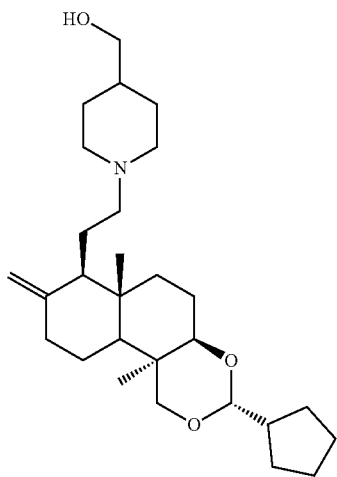
002
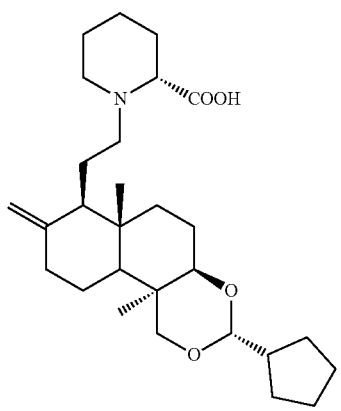
451
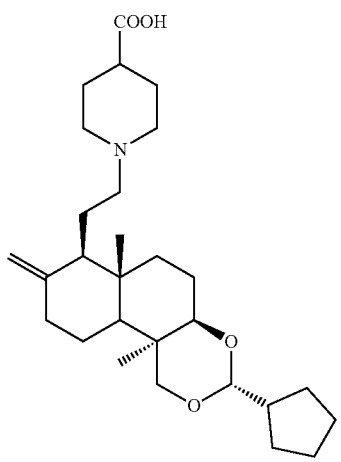
256

225

-continued

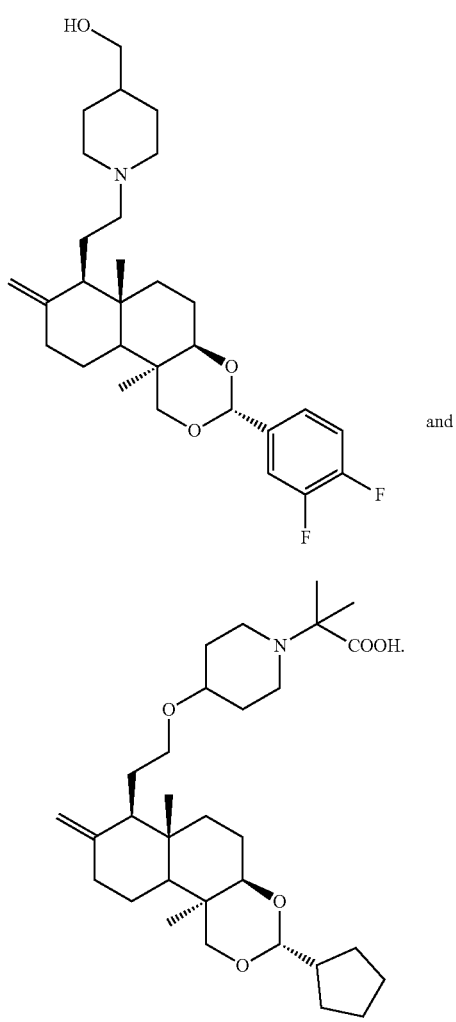

and

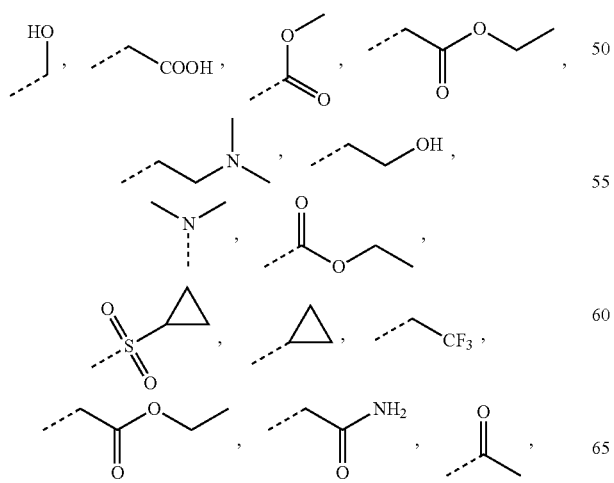

11. The compound, pharmaceutically acceptable salt or tautomer thereof according to claim 1, wherein R is selected from the group consisting of F, Cl, Br, I, OH, NH₂, CN, C(=O)OH, Me, Et, OMe,

226

-continued

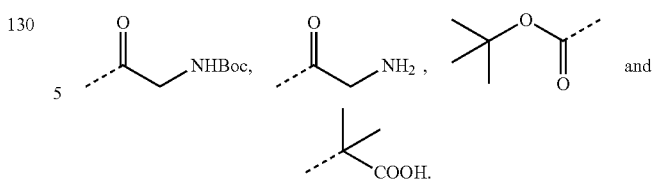

12. The compound, pharmaceutically acceptable salt or tautomer thereof according to claim 1, wherein R₁ selected from the group consisting of

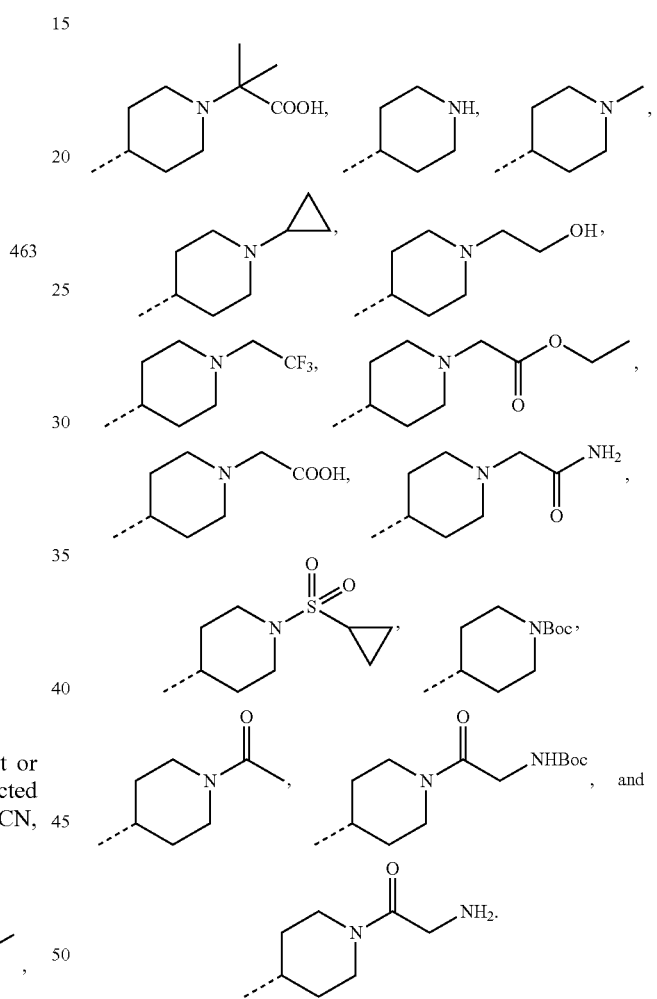

13. The compound, pharmaceutically acceptable salt or tautomer thereof according to claim 1, wherein R₂ and R₃ are independently selected from H, Me, Et,

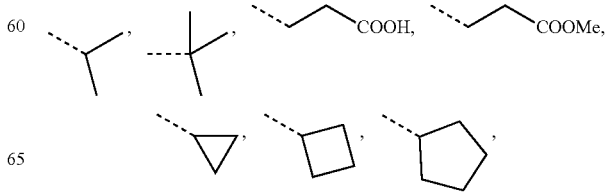

-continued
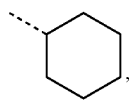, and 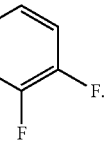.
* * * * *